US012497366B2

(12) United States Patent
Dong et al.

(10) Patent No.: US 12,497,366 B2
(45) Date of Patent: Dec. 16, 2025

(54) NITROGEN-CONTAINING HETEROCYCLIC DERIVATIVE INHIBITOR, PREPARATION METHOD THEREFOR AND USE THEREOF

(71) Applicants: SHANGHAI HANSOH BIOMEDICAL CO., LTD., Shanghai (CN); JIANGSU HANSOH PHARMACEUTICAL GROUP CO., LTD., Jiangsu (CN)

(72) Inventors: Jiaqiang Dong, Shanghai (CN); Xinxian Deng, Shanghai (CN); Wensheng Yu, Shanghai (CN); Fangfang Jin, Shanghai (CN); Zhen Gong, Shanghai (CN)

(73) Assignees: SHANGHAI HANSOH BIOMEDICAL CO., LTD., Shanghai (CN); JIANGSU HANSOH PHARMACEUTICAL GROUP CO., LTD., Jiangsu (CN)

( * ) Notice: Subject to any disclaimer, the term of this patent is extended or adjusted under 35 U.S.C. 154(b) by 0 days.

(21) Appl. No.: 19/177,721

(22) Filed: Apr. 14, 2025

(65) Prior Publication Data

US 2025/0326722 A1 Oct. 23, 2025

Related U.S. Application Data

(63) Continuation-in-part of application No. PCT/CN2023/124530, filed on Oct. 13, 2023.

(30) Foreign Application Priority Data

| | | |
|---|---|---|
| Oct. 14, 2022 | (CN) | 202211262552.0 |
| Feb. 6, 2023 | (CN) | 202310095444.7 |
| Feb. 14, 2023 | (CN) | 202310115600.1 |
| Mar. 20, 2023 | (CN) | 202310275265.1 |
| Mar. 30, 2023 | (CN) | 202310333326.5 |
| Apr. 26, 2023 | (CN) | 202310465015.4 |
| May 30, 2023 | (CN) | 202310631199.7 |
| Jul. 4, 2023 | (CN) | 202310818758.5 |
| Aug. 10, 2023 | (CN) | 202311011109.0 |

(51) Int. Cl.
*C07D 213/75* (2006.01)
*A61K 31/444* (2006.01)
(Continued)

(52) U.S. Cl.
CPC .......... *C07D 213/75* (2013.01); *A61K 31/444* (2013.01); *A61K 31/497* (2013.01); *A61K 31/4985* (2013.01); *A61K 31/501* (2013.01); *A61K 31/506* (2013.01); *A61K 31/517* (2013.01); *A61K 31/519* (2013.01); *A61K 31/52* (2013.01); *A61K 31/53* (2013.01); *A61K 31/541* (2013.01); *A61K 31/55* (2013.01);
(Continued)

(58) Field of Classification Search
CPC .. C07D 213/75; C07D 401/12; C07D 401/14; C07D 405/14; C07D 413/14; C07D 417/14; C07D 471/04; C07D 473/32; C07D 487/04; C07D 491/048; C07D 491/052; C07D 498/14; C07D 513/04; C07D 519/00; A61K 31/444; A61K 31/497; A61K 31/4985; A61K 31/501; A61K 31/506; A61K 31/517; A61K 31/519; A61K 31/52; A61K 31/53; A61K 31/541; A61K 31/55; A61K 31/551; A61K 31/553
See application file for complete search history.

(56) References Cited

U.S. PATENT DOCUMENTS

2013/0303507 A1 11/2013 Antonios-Mccrea et al.
2014/0315928 A1 10/2014 Darout et al.
(Continued)

FOREIGN PATENT DOCUMENTS

CN 103339110 10/2013
CN 105143203 12/2015
(Continued)

OTHER PUBLICATIONS

1st Office Action issued in Eurasian Patent application No. 202591064, mailed Jun. 18, 2025.
(Continued)

*Primary Examiner* — Joseph K Mckane
*Assistant Examiner* — David M Shim
(74) *Attorney, Agent, or Firm* — Pilloff Passino & Cosenza LLP; Rachel Pilloff; Sean Passino

(57) ABSTRACT

A nitrogen-containing heterocyclic derivative inhibitor, a preparation method therefor and the use thereof. Specifically disclosed are a compound as represented by general formula (I), a preparation method therefor, a pharmaceutical composition containing the compound, and the use thereof as an inhibitor in treating diseases such as cardiovascular and cerebrovascular diseases, wherein the definition of each substituent in the general formula (I) are the same as those defined in the description.

(I)

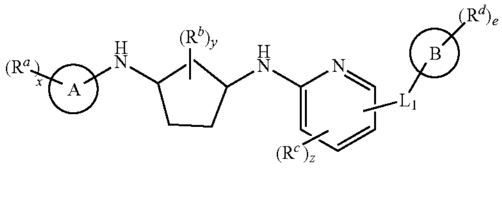

15 Claims, No Drawings

(51) Int. Cl.

| | |
|---|---|
| ***A61K 31/497*** | (2006.01) |
| ***A61K 31/4985*** | (2006.01) |
| ***A61K 31/501*** | (2006.01) |
| ***A61K 31/506*** | (2006.01) |
| ***A61K 31/517*** | (2006.01) |
| ***A61K 31/519*** | (2006.01) |
| ***A61K 31/52*** | (2006.01) |
| ***A61K 31/53*** | (2006.01) |
| ***A61K 31/541*** | (2006.01) |
| ***A61K 31/55*** | (2006.01) |
| ***A61K 31/551*** | (2006.01) |
| ***A61K 31/553*** | (2006.01) |
| ***C07D 401/12*** | (2006.01) |
| ***C07D 401/14*** | (2006.01) |
| ***C07D 405/14*** | (2006.01) |
| ***C07D 413/14*** | (2006.01) |
| ***C07D 417/14*** | (2006.01) |
| ***C07D 471/04*** | (2006.01) |
| ***C07D 473/32*** | (2006.01) |
| ***C07D 487/04*** | (2006.01) |
| ***C07D 491/048*** | (2006.01) |
| ***C07D 491/052*** | (2006.01) |
| ***C07D 498/14*** | (2006.01) |
| ***C07D 513/04*** | (2006.01) |
| ***C07D 519/00*** | (2006.01) |

(52) U.S. Cl.

CPC .......... *A61K 31/551* (2013.01); *A61K 31/553* (2013.01); *C07D 401/12* (2013.01); *C07D 401/14* (2013.01); *C07D 405/14* (2013.01); *C07D 413/14* (2013.01); *C07D 417/14* (2013.01); *C07D 471/04* (2013.01); *C07D 473/32* (2013.01); *C07D 487/04* (2013.01); *C07D 491/048* (2013.01); *C07D 491/052* (2013.01); *C07D 498/14* (2013.01); *C07D 513/04* (2013.01); *C07D 519/00* (2013.01)

(56) References Cited

U.S. PATENT DOCUMENTS

| | | | |
|---|---|---|---|
| 2016/0256467 | A1 | 9/2016 | Abdel-Meguid et al. |
| 2020/0231584 | A1 | 7/2020 | Serrano-Wu et al. |
| 2022/0220122 | A1 | 7/2022 | Serrano-Wu et al. |

FOREIGN PATENT DOCUMENTS

| | | | |
|---|---|---|---|
| CN | 105228616 | 1/2016 | |
| CN | 113412258 | 9/2021 | |
| CN | 113574055 | 10/2021 | |
| WO | WO 2020/150474 A1 * | 7/2020 | ........... C07D 401/02 |
| WO | 2022133529 | 6/2022 | |
| WO | 2023084449 | 5/2023 | |

OTHER PUBLICATIONS

International Search Report dated Nov. 23, 2023 from IA PCT/CN2023/124530.

Written Opinion of the International Searching Authority dated Nov. 23, 2023 from IA PCT/CN2023/124530.

* cited by examiner

NITROGEN-CONTAINING HETEROCYCLIC DERIVATIVE INHIBITOR, PREPARATION METHOD THEREFOR AND USE THEREOF

CROSS-REFERENCE TO RELATED APPLICATIONS

The present application is a Continuation-in-part application of International Application No. PCT/CN2023/124530, filed on Oct. 13, 2023, which claims the priority of Chinese patent application 202211262552.0 filed on Oct. 14, 2022, Chinese patent application 202310095444.7 filed on Feb. 6, 2023, Chinese patent application 202310115600.1 filed on Feb. 14, 2023, Chinese patent application 202310275265.1 filed on Mar. 20, 2023, Chinese patent application 202310333326.5 filed on Mar. 30, 2023, Chinese patent application 202310465015.4 filed on Apr. 26, 2023, Chinese patent application 202310631199.7 filed on May 30, 2023, Chinese patent application 202310818758.5 filed on Jul. 4, 2023, and Chinese patent application 202311011109.0 filed on Aug. 10, 2023. The international application and each of the above-mentioned Chinese patent applications are hereby incorporated by reference into the present application in their entireties.

TECHNICAL FIELD

The present disclosure belongs to the field of drug synthesis and specifically relates to a nitrogen-containing heterocyclic derivative inhibitor, a preparation method therefor, and the use thereof.

BACKGROUND

Cardiovascular disease (CVD) is the leading cause of death in the world, and a high level of low-density lipoprotein cholesterol (LDL-C) is the main risk factor. The accumulation of LDL-C on the inner wall of arteries leads to atherosclerosis and may cause an inflammatory response, leading to cardiovascular events such as heart attack and stroke. Statins can reduce serum LDL-C and are main lipid-lowering drugs in clinic at present. However, patients who are intolerant to statins or who fail to achieve the therapeutic goal when receiving a tolerant dose of treatment, e.g., patients with familial hypercholesterolemia, are still at risk. The discovery of PCSK9 inhibitors provides a more positive treatment method for homozygous and heterozygous patients with familial hypercholesterolemia. Non-statin Ezetimibe combined with a statin can reduce LDL-C by 15-20%, whereas a PCSK9 inhibitor combined with a statin can significantly reduce LDL-C by 54-74%. PCSK9 inhibitors can also overcome unbearable side effects of statins, e.g., symptoms such as muscle pain.

PCSK9 (Proprotein convertase subtilisin kexin type 9) is a serine protease, which is highly expressed in liver. Loss-of-function mutation in PCSK9 gene is related to a low level of LDL-C and a reduced cardiovascular risk (Cohen, J. C., 2006) and has been clinically confirmed to be a therapeutic target for hyperlipidemia. PCSK9 is synthesized as an enzyme precursor that, after synthesis, undergoes autocatalytic cleavage in a cell, and the mature PCSK9 binds to a propeptide and is secreted to the extracellular space. The binding to the propeptide blocks the catalytic activity of PCSK9.

PCSK9 is a main regulator for the level of low-density lipoprotein receptor (LDLR) on the surface of hepatocytes and can inhibit the circulating pathway of LDLR. The function of LDLR is the key to maintain cholesterol homeostasis, and it is responsible for the uptake and degradation of low-density lipoprotein. Circulating LDL binds to an N-terminal ligand binding domain of LDLR via apolipoprotein B100, and the LDL/LDLR complex is internalized by means of receptor-mediated endocytosis. A low-pH environment in the cell causes the LDLR to release LDL, the LDLR circulates back to the cell membrane, and the intracellular free LDL is sent to lysosomes and degraded. Secreted PCSK9 interferes with the circulating ability of LDLR by binding to LDLR on the surface of hepatocytes. After the PCSK9/LDLR complex migrates to acidic endosomal compartments via clathrin-coated pits, the conformational change of LDLR leads to the formation of additional binding sites with PCSK9. Therefore, PCSK9 accompanies LDLR to lysosomes for degradation, preventing LDLR circulation, thus up-regulating the LDL-C level.

Familial hypercholesterolemia (FH) is a genetic disease of low-density lipoprotein cholesterol metabolism, which affects one in every 250 people and is characterized by a significant increase in the LDL-c level. The risk of coronary heart disease (CAD) in heterozygous patients with FH is 3-4 times that in normal people, and CAD often occurs 10 years earlier than in normal people on average. Statins can reduce the low-density lipoprotein cholesterol in heterozygous patients with FH. In Besseling's research, it is believed that a high-intensity statin therapy can reduce the risk and mortality of coronary heart disease by 44%. However, in many cases, the reduction of LDL-C is considered insufficient. The compensatory mechanism of statins involves up-regulating sterol regulatory element-binding protein 2 (SREBP-2) to thus activate LDL receptor and PCSK9, increase the expression and secretion of PCSK9 which will bind to LDLR, leading to an elevated LDL-C level in blood. Therefore, although statins can reduce LDL by inhibiting HMGCoA, the effect thereof on SREPB counteracts and balances this reduction. Adding a PCSK9 inhibitor to a statin therapy can help overcome this mechanism. Considering that patients with familial hypercholesterolemia may not fully benefit from statin therapies, alternative treatment approaches such as PCSK9 inhibitors are needed.

Macromolecular PCSK9 inhibitors, Alirocumab and Evolocumab based on monoclonal antibodies, which can selectively bind to extracellular PCSK9 and prevent the interaction thereof with LDLR, have been approved by FDA for reducing the LDL-C level with good safety. Studies have shown that in heterozygous patients with FH who failed to achieve the LCL-C target after a statin therapy alone, injection of Alirocumab once every two weeks can minimize the cardiovascular risk. Alirocumab has also been shown to moderately increase "good" cholesterol (HDL-C). In addition, there is a PCSK9 siRNA drug Inclisiran currently available on the market, which can reduce lipids for an extended period with good safety by reducing the expression level of PCSK9 protein. However, the above two drugs both need to be administered by injection, and the production cost is high and expensive. To date, there has been no PCSK9 small molecule inhibitors on the market, so there is a high demand for oral PCSK9 small molecule inhibitor drugs.

PCSK9 small molecule inhibitors have been reported in patents, such as: WO 2014170786 (Pfizer), WO 2014150326 (Shifa), WO 2020150473 (AZ), and WO 2022133529 (Nyrada). At present, AZD-0780, which has the fastest progress, is in clinical phase I, while others are in preclinical development phase. There are also some polypeptides reported, with the most advanced ones in clinical phase II.

In the present disclosure, there is a need to develop an oral PCSK9 small molecule inhibitor.

BRIEF SUMMARY OF THE INVENTION

The objective of the present disclosure is to provide a compound as represented by general formula (I), or a stereoisomer or pharmaceutically acceptable salt thereof, wherein the compound as represented by general formula (T) has a structure as follows:

(I)

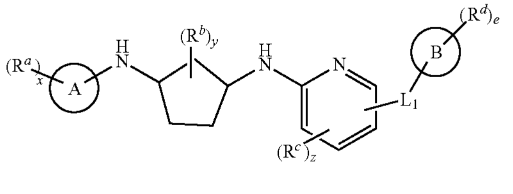

wherein ring A is selected from cycloalkyl, heterocyclyl, aryl, or heteroaryl; preferably 5-membered monoheteraryl, 5-membered fused 5-membered bicyclic heteroaryl, 5-membered fused 6-membered bicyclic heteroaryl, 6-membered monoheteraryl, 6-membered fused 5-membered bicyclic heteroaryl, or 6-membered fused 6-membered bicyclic heteroaryl;

ring B is selected from cycloalkyl, heterocyclyl, aryl, or heteroaryl; preferably $C_{3-6}$ cycloalkyl, phenyl, 3- to 8-membered heterocyclyl, 7- to 10-membered bicyclic heterocyclyl, 5-membered heteroaryl, 6-membered heteroaryl, 5-membered fused 5-membered bicyclic heteroaryl, 5-membered fused 6-membered bicyclic heteroaryl, 5-membered fused 6-membered bicyclic heterocyclyl, 6-membered fused 5-membered bicyclic heteroaryl, or 6-membered fused 6-membered bicyclic heteroaryl;

further preferably $C_{3-6}$ cycloalkyl, phenyl, 3- to 8-membered heterocyclyl, 7- to 10-membered bicyclic heterocyclyl, 5-membered heteroaryl, 6-membered heteroaryl, 5-membered fused 5-membered bicyclic heteroaryl, 5-membered fused 6-membered bicyclic heteroaryl, 6-membered fused 5-membered bicyclic heteroaryl, or 6-membered fused 6-membered bicyclic heteroaryl;

more preferably 5-membered fused 5-membered bicyclic heteroaryl, 5-membered fused 6-membered bicyclic heteroaryl, 5-membered fused 6-membered bicyclic heterocyclyl, 6-membered fused 5-membered bicyclic heteroaryl, or 6-membered fused 6-membered bicyclic heteroaryl;

ring A is preferably 5-membered fused 5-membered bicyclic heteroaryl, 5-membered fused 6-membered bicyclic heteroaryl, 6-membered monoheteraryl, 6-membered fused 5-membered bicyclic heteroaryl, or 6-membered fused 6-membered bicyclic heteroaryl; when ring A is 6-membered monoheteraryl

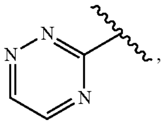 [SMILES: *c1nccnn1], ring B is not

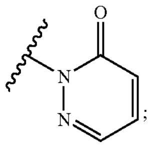 [SMILES: *n1ncccc1=O];

and when ring A is 6-membered monoheteraryl

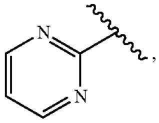 [SMILES: *c1ncccn1], ring B is selected from 5-membered fused 5-membered bicyclic heteroaryl, 5-membered fused 6-membered bicyclic heteroaryl, 5-membered fused 6-membered bicyclic heterocyclyl, 6-membered fused 5-membered bicyclic heteroaryl, or 6-membered fused 6-membered bicyclic heteroaryl; and when ring A is 6-membered fused 5-membered bicyclic heteroaryl, ring A is not

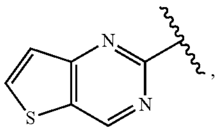, 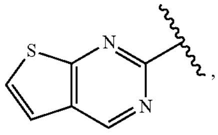, and

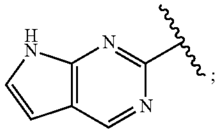;

$L_1$ is selected from a bond, —C(O)—, or —C(O)NH—;

$R^a$ is selected from hydrogen, deuterium, halogen, amino, hydroxyl, cyano, nitro, alkyl, alkenyl, alkynyl, oxo, thio, alkylthio, deuteroalkyl, haloalkyl, alkoxy, haloalkoxy, hydroxyalkyl, cyano-substituted alkyl, cycloalkyl, heterocyclyl, aryl, heteroaryl, $-(CH_2)_nR_{A1}$, $-(CH_2)_nOR_{A1}$, $-(CH_2)_nC(O)R_{A1}$, $-(CH_2)_nC(O)OR_{A1}$, $-(CH_2)_nS(O)_mR_{A1}$, $-(CH_2)_nNR_{A2}R_{A3}$, $-(CH_2)_nNR_{A2}C(O)OR_{A3}$, $-(CH_2)_nNR_{A2}C(O)(CH_2)_{n1}R_{A2}$, $-(CH_2)_nNR_{A2}C(O)NR_{A2}R_{A3}$, $-(CH_2)_nC(O)NR_{A2}(CH_2)_{n1}R_{A3}$, $-OC(R_{A1}R_{A2})(CH_2)_{n1}R_{A3}$, or $-(CH_2)_nNR_{A2}S(O)_mR_{A3}$, wherein the amino, alkyl, alkenyl, alkynyl, alkylthio, deuteroalkyl, haloalkyl, alkoxy, haloalkoxy, hydroxyalkyl, cyano-substituted alkyl, cycloalkyl, heterocyclyl, aryl, and heteroaryl can be optionally further substituted;

preferably hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, 5- to 14-membered heteroaryl, $-(CH_2)_nR_{A1}$, $-(CH_2)_nOR_{A1}$, $-(CH_2)_nC(O)R_{A1}$, $-(CH_2)_nC(O)OR_{A1}$, $-(CH_2)_nS(O)_mR_{A1}$, $-(CH_2)_nNR_{A2}R_{A3}$, $-(CH_2)_nNR_{A2}C(O)OR_{A3}$, $-(CH_2)_nNR_{A2}C(O)(CH_2)_{n1}R_{A3}$, $(CH_2)_nNR_{A2}C(O)NR_{A2}R_{A3}$, $-(CH_2)_nC(O)NR_{A2}$ $(CH_2)_{n1}R_{A3}$, —$OC(R_{A1}R_{A2})_n(CH_2)_{n1}R_{A3}$, or —$(CH_2)_nNR_{A2}S(O)_nR_{A3}$, wherein the amino, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, and 5- to 14-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl, and the amino, $C_{1-3}$ alkyl, $C_{2-4}$ alkenyl, $C_{2-4}$ alkynyl, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, $C_{3-8}$ cycloalkyl, 3- to 8-membered heterocyclyl, $C_{6-10}$ aryl, and 5- to 10-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{A1}$-$R_{A3}$ are each independently selected from hydrogen, deuterium, halogen, nitro, hydroxyl, mercapto, cyano, amino, alkyl, deuteroalkyl, haloalkyl, hydroxyalkyl, alkoxy, alkenyl, alkynyl, cycloalkyl, heterocyclyl, aryl, or heteroaryl, wherein the amino, alkyl, deuteroalkyl, haloalkyl, hydroxyalkyl, alkoxy, alkenyl, alkynyl, cycloalkyl, heterocyclyl, aryl, and heteroaryl can be optionally further substituted;

alternatively, any two adjacent or non-adjacent $R^a$ are connected to form cycloalkyl, heterocyclyl, aryl, or heteroaryl, wherein the cycloalkyl, heterocyclyl, aryl, and heteroaryl can be optionally further substituted;

$R^b$ is selected from hydrogen, deuterium, halogen, amino, hydroxyl, cyano, nitro, alkyl, alkenyl, alkynyl, oxo, thio, deuteroalkyl, haloalkyl, alkoxy, haloalkoxy, hydroxyalkyl, cyano-substituted alkyl, cycloalkyl, heterocyclyl, aryl, heteroaryl, —$(CH_2)_nR_{B1}$, —$(CH_2)_nOR_{B1}$, —$(CH_2)_nC(O)R_{B1}$, —$(CH_2)_nC(O)O$ $R_{B1}$, —$(CH_2)_nS(O)_m$ $R_{B1}$, —$(CH_2)_nNR_{B2}R_{B3}$, —$(CH_2)_nNR_{B2}C(O)OR_{B3}$, —$(CH_2)_nNR_{B2}C(O)(CH_2)_{n1}R_{B3}$, —$(CH_2)_nNR_{B2}C(O)NR_{B2}R_{B3}$, —$(CH_2)_nC(O)NR_{B2}(CH_2)_{n1}R_{B3}$, —$OC(R_{B1}R_{B2})_n(CH_2)_{n1}R_{B3}$, or —$(CH_2)_nNR_{B2}S(O)_mR_{B3}$, wherein the amino, alkyl, alkenyl, alkynyl, deuteroalkyl, haloalkyl, alkoxy, haloalkoxy, hydroxyalkyl, cyano-substituted alkyl, cycloalkyl, heterocyclyl, aryl, and heteroaryl can be optionally further substituted;

preferably hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, 5- to 14-membered heteroaryl, —$(CH_2)_nR_{A1}$, —$(CH_2)_nOR_{A1}$, —$(CH_2)_nC(O)$ $R_{A1}$, —$(CH_2)_nC(O)OR_{A1}$, —$(CH_2)_nS(O)_mR_{A1}$, —$(CH_2)_nNR_{A2}R_{A3}$, —$(CH_2)_nNR_{A2}C(O)OR_{A3}$, —$(CH_2)_nNR_{A2}C(O)(CH_2)_{n1}R_{A3}$, —$(CH_2)_nNR_{A2}C(O)NR_{A2}R_{A3}$, —$(CH_2)_nC(O)NR_{A2}(CH_2)_{n1}R_{A3}$, —$OC(R_{A1}R_{A2})_n(CH_2)_{n1}R_{A3}$, or —$(CH_2)_nNR_{A2}S(O)_mR_{A3}$, wherein the amino, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, and 5- to 14-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl, and the amino, $C_{1-3}$ alkyl, $C_{2-4}$ alkenyl, $C_{2-4}$ alkynyl, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, $C_{3-8}$ cycloalkyl, 3- to 8-membered heterocyclyl, $C_{6-10}$ aryl, and 5- to 10-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{B1}$-$R_{B3}$ are each independently selected from hydrogen, deuterium, halogen, nitro, hydroxyl, mercapto, cyano, amino, alkyl, deuteroalkyl, haloalkyl, hydroxyalkyl, alkoxy, alkenyl, alkynyl, cycloalkyl, heterocyclyl, aryl, or heteroaryl, wherein the amino, alkyl, deuteroalkyl, haloalkyl, hydroxyalkyl, alkoxy, alkenyl, alkynyl, cycloalkyl, heterocyclyl, aryl, and heteroaryl can be optionally further substituted;

alternatively, any two adjacent or non-adjacent $R^b$ are connected to form cycloalkyl, heterocyclyl, aryl, or heteroaryl, wherein the cycloalkyl, heterocyclyl, aryl, and heteroaryl can be optionally further substituted;

preferably, alternatively, any two $R^a$ and $R^b$ are connected to form heterocyclyl or heteroaryl, wherein the heterocyclyl and heteroaryl can be optionally further substituted with one or more substituents selected from deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

$R^c$ is selected from hydrogen, deuterium, halogen, amino, hydroxyl, cyano, nitro, alkyl, alkenyl, alkynyl, oxo, thio, deuteroalkyl, haloalkyl, alkoxy, haloalkoxy, hydroxyalkyl, cyano-substituted alkyl, cycloalkyl, heterocyclyl, aryl, heteroaryl, —$(CH_2)_nR_{C1}$, —$(CH_2)_nOR_{C1}$, —$(CH_2)_nC(O)$ $R_{C1}$, —$(CH_2)_nC(O)O$ $R_{C1}$, —$(CH_2)_nS(O)_m$ $R_{C1}$, —$(CH_2)_nNR_{C2}R_{C3}$, —$(CH_2)_nNR_{C2}C(O)OR_{C3}$, —$(CH_2)_nNR_{C2}C(O)(CH_2)_{n1}R_{C3}$, —$(CH_2)_nNR_{C2}C(O)NR_{C2}R_{C3}$, —$(CH_2)_nC(O)NR_{C2}(CH_2)_{n1}R_{C3}$, —$OC(R_{C1}R_{C2})_n(CH_2)_{n1}R_{C3}$, or —$(CH_2)_nNR_{C2}S(O)_mR_{C3}$, wherein the amino, alkyl, alkenyl, alkynyl, deuteroalkyl, haloalkyl, alkoxy, haloalkoxy, hydroxyalkyl, cyano-substituted alkyl, cycloalkyl, heterocyclyl, aryl, and heteroaryl can be optionally further substituted;

preferably hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, 5- to 14-membered heteroaryl, $-(CH_2)_nR_{A1}$, $-(CH_2)_nOR_{A1}$, $-(CH_2)_nC(O)\ R_{A1}$, $-(CH_2)_nC(O)OR_{A1}$, $-(CH_2)_nS(O)_mR_{A1}$, $-(CH_2)_nNR_{A2}R_{A3}$, $-(CH_2)_nNR_{A2}C(O)OR_{A3}$, $-(CH_2)_nNR_{A2}C(O)(CH_2)_{n1}R_{A3}$, $-(CH_2)_{A1}NR_{A2}C(O)NR_{A2}R_{A3}$, $-(CH_2)C(O)NR_{A2}(CH_2)_{n1}R_{A3}$, $-OC(R_{A1}R_{A2})_n(CH_2)_{n1}R_{A3}$, or $-(CH_2)_nNR_{A2}S(O)_mR_{A3}$, wherein the amino, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, and 5- to 14-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl, and the amino, $C_{1-3}$ alkyl, $C_{2-4}$ alkenyl, $C_{2-4}$ alkynyl, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, $C_{3-8}$ cycloalkyl, 3- to 8-membered heterocyclyl, $C_{6-10}$ aryl, and 5- to 10-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{C1}$-$R_{C3}$ are each independently selected from hydrogen, deuterium, halogen, nitro, hydroxyl, mercapto, cyano, amino, alkyl, deuteroalkyl, haloalkyl, hydroxyalkyl, alkoxy, alkenyl, alkynyl, cycloalkyl, heterocyclyl, aryl, or heteroaryl, wherein the amino, alkyl, deuteroalkyl, haloalkyl, hydroxyalkyl, alkoxy, alkenyl, alkynyl, cycloalkyl, heterocyclyl, aryl, and heteroaryl can be optionally further substituted;

alternatively, any two adjacent or non-adjacent $R^c$ are connected to form cycloalkyl, heterocyclyl, aryl, or heteroaryl, wherein the cycloalkyl, heterocyclyl, aryl, and heteroaryl can be optionally further substituted;

$R^d$ is selected from hydrogen, deuterium, halogen, amino, hydroxyl, cyano, nitro, alkyl, alkenyl, alkynyl, oxo, thio, deuteroalkyl, haloalkyl, alkoxy, haloalkoxy, hydroxyalkyl, cyano-substituted alkyl, cycloalkyl, heterocyclyl, aryl, heteroaryl, $-(CH_2)_nR_{D1}$, $-(CH_2)_nOR_{D1}$, $-(CH_2)_nC(O)\ R_{D1}$, $-(CH_2)_nC(O)O\ R_{D1}$, $-(CH_2)_nS(O)_m\ R_{D1}$, $-(CH_2)_nNR_{D2}R_{D3}$, $-(CH_2)_nNR_{D2}C(O)OR_{D3}$, $-(CH_2)_nNR_{D2}C(O)(CH_2)_{n1}R_{D3}$, $(CH_2)_nNR_{D2}C(O)NR_{D2}R_{D3}$, $-(CH_2)_nC(O)NR_{D2}(CH_2)_{n1}R_{D3}$, $-OC(R_{D1}R_{D2})_n(CH_2)_{n1}R_{D3}$, or $-(CH_2)_n\ NR_{D2}S(O)_mR_{D3}$, wherein the amino, alkyl, alkenyl, alkynyl, deuteroalkyl, haloalkyl, alkoxy, haloalkoxy, hydroxyalkyl, cyano-substituted alkyl, cycloalkyl, heterocyclyl, aryl, and heteroaryl can be optionally further substituted;

preferably hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, 5- to 14-membered heteroaryl, $-(CH_2)_nR_{A1}$, $-(CH_2)_nOR_{A1}$, $(CH_2)_nC(O)\ R_{A1}$, $-(CH_2)_nC(O)OR_{A1}$, $-(CH_2)S(O)_mR_{A1}$, $-(CH_2)NR_{A2}R_{A3}$, $-(CH_2)_nNR_{A2}C(O)OR_{A3}$, $-(CH_2)_nNR_{A2}C(O)(CH_2)_{n1}R_{A3}$, $-(CH_2)_nNR_{A2}C(O)NR_{A2}R_{A3}$, $-(CH_2)_nC(O)NR_{A2}(CH_2)_{n1}R_{A3}$, $-OC(R_{A1}R_{A2})_n(CH_2)_{n1}R_{A3}$, or $-(CH_2)_nNR_{A2}S(O)_mR_{A3}$, wherein the amino, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, and 5- to 14-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl, and the amino, $C_{1-3}$ alkyl, $C_{2-4}$ alkenyl, $C_{2-4}$ alkynyl, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, $C_{3-8}$ cycloalkyl, 3- to 8-membered heterocyclyl, $C_{6-10}$ aryl, and 5- to 10-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{D1}$-$R_{D3}$ are each independently selected from hydrogen, deuterium, halogen, nitro, hydroxyl, mercapto, cyano, amino, alkyl, deuteroalkyl, haloalkyl, hydroxyalkyl, alkoxy, alkenyl, alkynyl, cycloalkyl, heterocyclyl, aryl, or heteroaryl, wherein the amino, alkyl, deuteroalkyl, haloalkyl, hydroxyalkyl, alkoxy, alkenyl, alkynyl, cycloalkyl, heterocyclyl, aryl, and heteroaryl can be optionally further substituted;

alternatively, any two adjacent or non-adjacent $R^d$ are connected to form cycloalkyl, heterocyclyl, aryl, or heteroaryl, wherein the cycloalkyl, heterocyclyl, aryl, and heteroaryl can be optionally further substituted;

alternatively, any two $R^c$ and $R^d$ are connected to form cycloalkyl, heterocyclyl, aryl, or heteroaryl, wherein the cycloalkyl, heterocyclyl, aryl, and heteroaryl can be optionally further substituted;

x is 0, 1, 2, or 3;

y is 0, 1, 2, or 3;

z is 0, 1, 2, or 3;

e is 0, 1, 2, or 3;

m is 0, 1, or 2;

n is 0, 1, 2, 3, or 4;

n1 is 0, 1, 2, 3, or 4;

n2 is 0, 1, 2, 3, or 4;

n3 is 0, 1, 2, 3, or 4;

n4 is 0, 1, 2, 3, or 4; and the compound is not

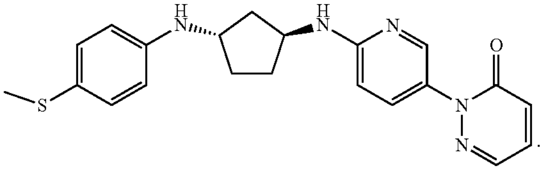 [SMILES: CSc1ccc(N[C@H]2CC[C@H](Nc3ccc(-n4ncccc4=O)cn3)C2)cc1]

In a preferred embodiment of the present disclosure, the compound is further as represented by general formula (III) or (III-1):

(III)

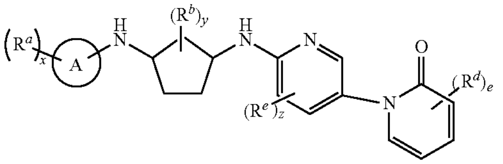

or (III-1)

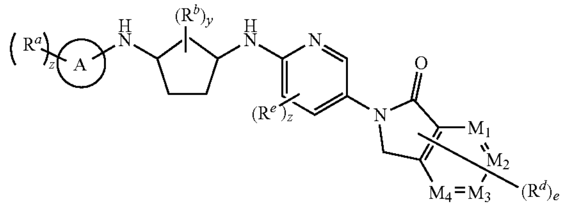

wherein $M_1$ is selected from N or CH;

$M_2$ is selected from N or CH;

$M_1$ is selected from N or CH; and $M_4$ is selected from N or CH.

In a more preferred embodiment of the present disclosure, ring A as described in the present disclosure is selected from $C_{3-12}$ cycloalkyl, 3- to 12-membered heterocyclyl, $C_{6-14}$ aryl, or 5- to 14-membered heteroaryl;

preferably, ring A is selected from $C_{6-14}$ aryl or 5- to 14-membered heteroaryl;

more preferably, ring A is selected from 5- to 12-membered monocyclic heteroaryl and 8- to 12-membered bicyclic heteroaryl;

further preferably, ring A is 5-membered monoheteraryl, 5-membered fused 5-membered bicyclic heteroaryl, 5-membered fused 6-membered bicyclic heteroaryl, 6-membered monoheterary, 6-membered fused 5-membered bicyclic heteroaryl, or 6-membered fused 6-membered bicyclic heteroaryl;

further more preferably, ring A is selected from pyrazolyl, imidazolyl, triazolyl, thiazolyl, thiadiazole, oxazolyl, pyridinyl, pyrazinyl, 1,2,4-triazinyl, 1,3,5-triazinyl, pyridazinyl,

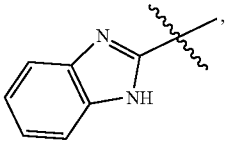,
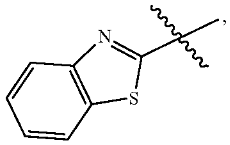,
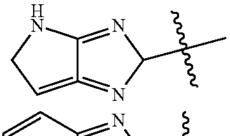,
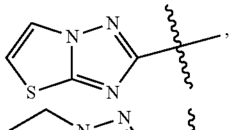,
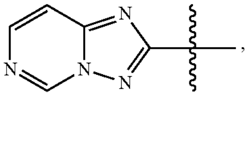,
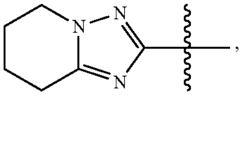,

-continued

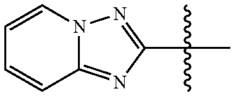
or
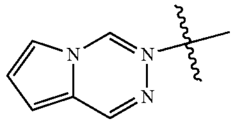;

still further preferably, ring A is selected from pyrazolyl, imidazolyl, triazolyl, thiazolyl, thiadiazole, oxazolyl, pyridinyl, pyrazinyl, 1,2,4-triazinyl, 1,3,5-triazinyl, pyridazinyl,

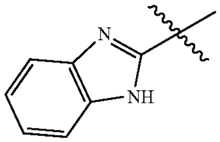,
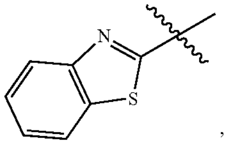,
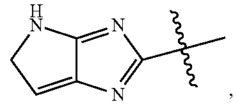,
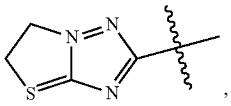,
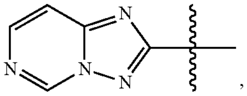,
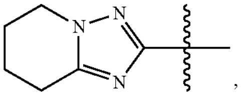,
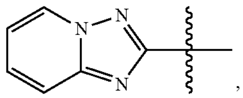,
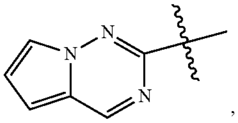,
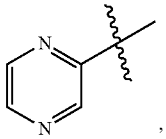,
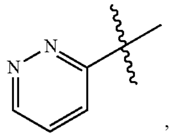,
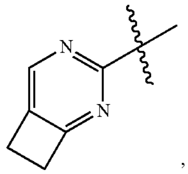,
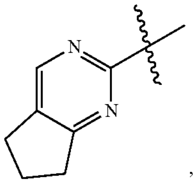,
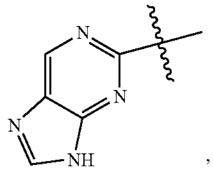,
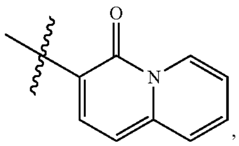,
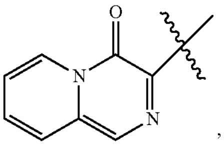,
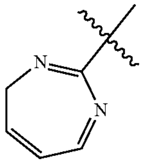
or
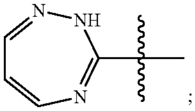;

preferably pyridinyl, pyrazinyl, 1,2,4-triazinyl, 1,3,5-triazinyl, or pyridazinyl alternatively, ring A is selected from 8- to 12-membered bicyclic heteroaryl, 8- to 12-membered heteroaryl fused aryl, 8- to 14-membered heteroaryl fused cycloalkyl, or 8- to 14-membered heteroaryl fused heterocyclyl; preferably selected from
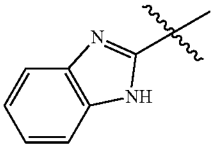,
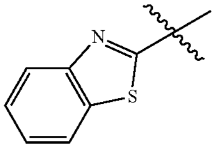,
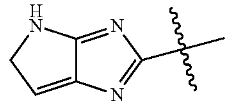,
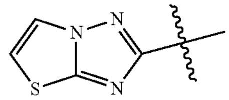,
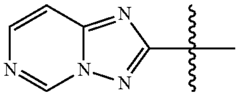,
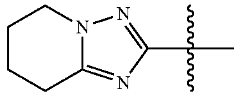,
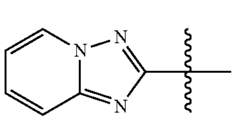,
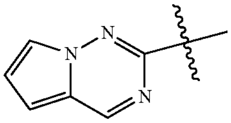,
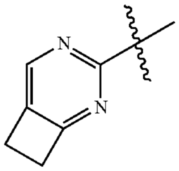,
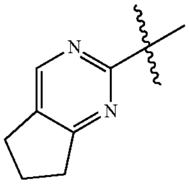,
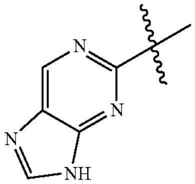,
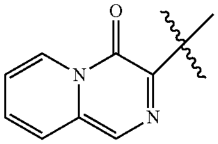,
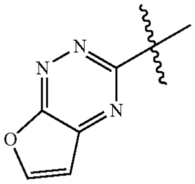,
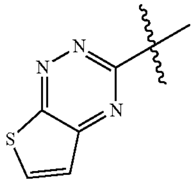,
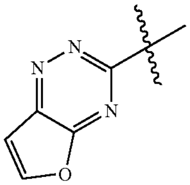,
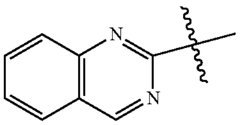,
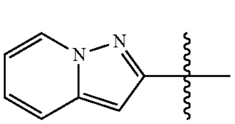,
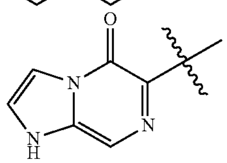
or
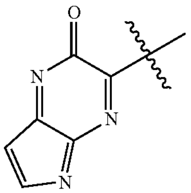;
further preferably selected from
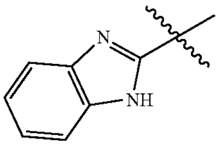,
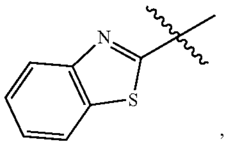,
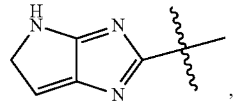,
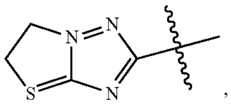,
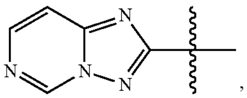,
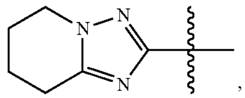,
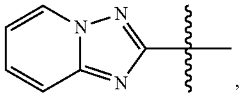,
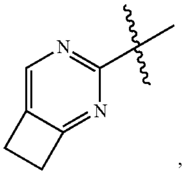,
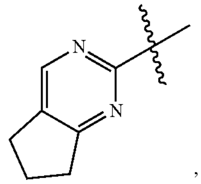,
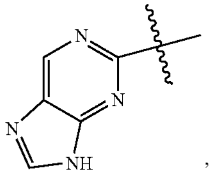,
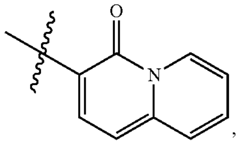,
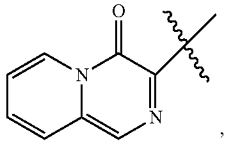,
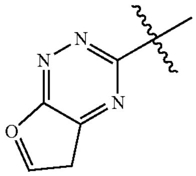,
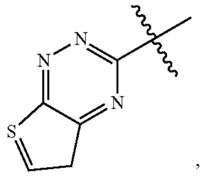,
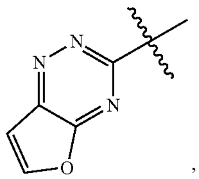,
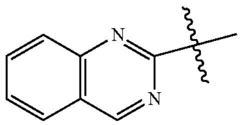
or
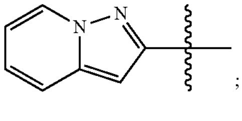;
further preferably selected from
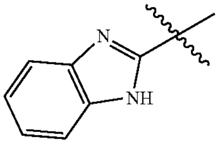,
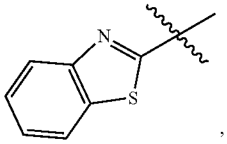,
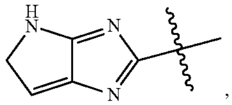,
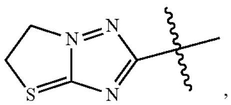, -continued

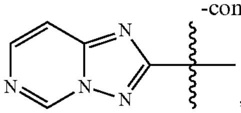
,
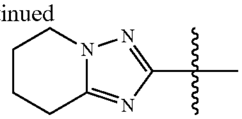
,
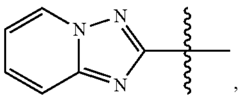
,
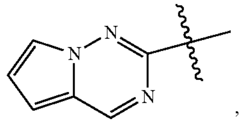
,
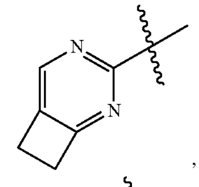
,
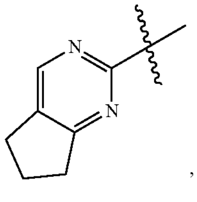
,
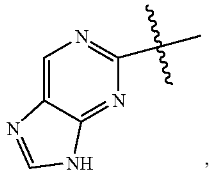
,
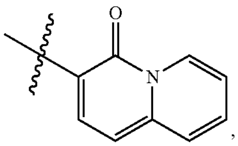
,
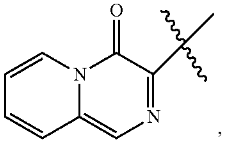
,
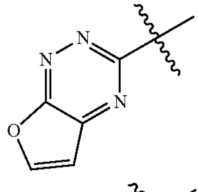
,
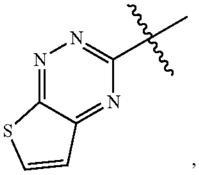
, or
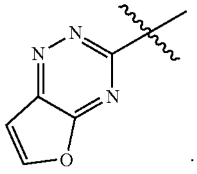
.

In a preferred embodiment of the present disclosure, the compound is further as represented by general formula (I-E):

(I-E)

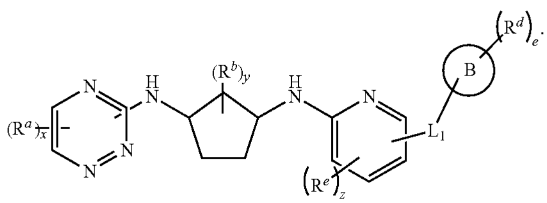

In a preferred embodiment of the present disclosure, the compound is further as represented by general formula (I-1'):

(I-1')

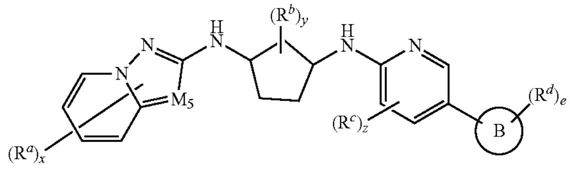

wherein ring B is selected from cycloalkyl, heterocyclyl, aryl, or heteroaryl;

$M_5$ is selected from N or $CR_5$;

$R_5$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, and 5- to 14-membered heteroaryl, wherein the amino, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, and 5- to 14-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{6-10}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R^a$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, 5- to 14-membered heteroaryl, $—(CH_2)_nR_{A1}$, $—(CH_2)_nOR_{A1}$, $—(CH_2)_nC(O)R_{A1}$, $—(CH_2)_nC(O)OR_{A1}$, $—(CH_2)_nS(O)_mR_{A1}$, $—(CH_2)_nNR_{A2}R_{A3}$, $—(CH_2)_nNR_{A2}C(O)OR_{A3}$, $—(CH_2)NR_{A2}C(O)(CH_2)_{n1}R_{A3}$, $—(CH_2)NR_{A2}C(O)NR_{A2}R_{A3}$, $—(CH_2)_nC(O)NR_{A2}(CH_2)_{n1}R_{A3}$, $—OC(R_{A1}R_{A2})_n(CH_2)_{n1}R_{A3}$, or $—(CH_2)_nNR_{A2}S(O)_nR_{A3}$, wherein the amino, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, and 5- to 14-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl, and the amino, $C_{1-3}$ alkyl, $C_{2-4}$ alkenyl, $C_{2-4}$ alkynyl, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, $C_{3-8}$ cycloalkyl, 3- to 8-membered heterocyclyl, $C_{6-10}$ aryl, and 5- to 10-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{A1}$-$R_{A3}$ are each independently selected from hydrogen, deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, or 5- to 14-membered heteroaryl, wherein the amino, $C_{1-6}$ alkyl, $C_{1-6}$ deuteroalkyl, $C_{1-6}$ haloalkyl, $C_{1-6}$ alkoxy, $C_{1-6}$ haloalkoxy, $C_{1-6}$ hydroxyalkyl, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl can be optionally further substituted with one or more substituents selected from deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

alternatively, any two adjacent or non-adjacent $R^a$ are connected to form cycloalkyl, heterocyclyl, aryl, or heteroaryl, wherein the cycloalkyl, heterocyclyl, aryl, and heteroaryl can be optionally further substituted with one or more substituents selected from deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

$R^b$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, 5- to 14-membered heteroaryl, $-(CH_2)_nR_{B1}$, $-(CH_2)_nOR_{B1}$, $-(CH_2)_nC(O)R_{B1}$, $-(CH_2)_nC(O)OR_{B1}$, $-(CH_2)_nS(O)_mR_{B1}$, $-(CH_2)_nNR_{B2}R_{B3}$, $-(CH_2)_nNR_{B2}C(O)OR_{B3}$, $-(CH_2)_nNR_{B2}C(O)(CH_2)_{n1}R_{B3}$, $-(CH_2)_nNR_{B2}C(O)NR_{B2}R_{B3}$, $-(CH_2)_nC(O)NR_{B2}(CH_2)_{n1}R_{B3}$, $-OC(R_{B1}R_{B2})_n(CH_2)_{n1}R_{B3}$, or $-(CH_2)_nNR_{B2}S(O)_nR_{B3}$, wherein the amino, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, and 5- to 14-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{B1}$-$R_{B3}$ are each independently selected from hydrogen, deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, or 5- to 14-membered heteroaryl, wherein the amino, $C_{1-6}$ alkyl, $C_{1-6}$ deuteroalkyl, $C_{1-6}$ haloalkyl, $C_{1-6}$ alkoxy, $C_{1-6}$ haloalkoxy, $C_{1-6}$ hydroxyalkyl, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl can be optionally further substituted with one or more substituents selected from deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

alternatively, any two adjacent or non-adjacent $R^b$ are connected to form cycloalkyl, heterocyclyl, aryl, or heteroaryl, wherein the cycloalkyl, heterocyclyl, aryl, and heteroaryl can be optionally further substituted with one or more substituents selected from deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

alternatively, any two $R^a$ and $R^b$ are connected to form 5- to 12-membered heterocyclyl or 5- to 12-membered heteroaryl, wherein the 5- to 12-membered heterocyclyl or 5- to 12-membered heteroaryl can be optionally further substituted with one or more substituents selected from deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

alternatively, $R_5$ and $R^b$ are connected to form 5- to 12-membered heterocyclyl or 5- to 12-membered heteroaryl, wherein the 5- to 12-membered heterocyclyl or 5- to 12-membered heteroaryl can be optionally further substituted with one or more substituents selected from deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

$R^c$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, 5- to 14-membered heteroaryl, $-(CH_2)_nR_{C1}$, $-(CH_2)_nOR_{C1}$, $-(CH_2)_nC(O)R_{C1}$, $-(CH_2)_nC(O)OR_{C1}$, $-(CH_2)_nS(O)_mR_{C1}$, $-(CH_2)_nNR_{C2}R_{C3}$, $-(CH_2)_nNR_{C2}C(O)OR_{C3}$, $-(CH_2)_nNR_{C2}C(O)(CH_2)_{n1}R_{C3}$, $-(CH_2)_nNR_{C2}C(O)NR_{C2}R_{C1}$, $-(CH_2)_nC(O)NR_{C2}(CH_2)_{n1}R_{C1}$, $-OC(R_{C1}R_{C2})_n(CH_2)_{n1}R_{C3}$, or $-(CH_2)_nNR_{C2}S(O)_nR_{C3}$, wherein the amino, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, and 5- to 14-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{C1}$-$R_{C3}$ are each independently selected from hydrogen, deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, or 5- to 14-membered heteroaryl, wherein the amino, $C_{1-6}$ alkyl, $C_{1-6}$ deuteroalkyl, $C_{1-6}$ haloalkyl, $C_{1-6}$ alkoxy, $C_{1-6}$ haloalkoxy, $C_{1-6}$ hydroxyalkyl, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl can be optionally further substituted with one or more substituents selected from deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

alternatively, any two adjacent or non-adjacent $R^c$ are connected to form cycloalkyl, heterocyclyl, aryl, or heteroaryl, wherein the cycloalkyl, heterocyclyl, aryl, and heteroaryl can be optionally further substituted with one or more substituents selected from deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

$R^d$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, 5- to 14-membered heteroaryl, $-(CH_2)_nR_{D1}$, $-(CH_2)_nOR_{D1}$, $-(CH_2)_nC(O)R_{D1}$, $-(CH_2)_nC(O)OR_{D1}$, $-(CH_2)_nS(O)_mR_{D1}$, $-(CH_2)_nNR_{D2}R_{D3}$, $-(CH_2)_nNR_{D2}C(O)OR_{D3}$, $-(CH_2)_nNR_{D2}C(O)(CH_2)_{n1}R_{D3}$, $-(CH_2)_nNR_{D2}C(O)NR_{D2}R_{D3}$, $-(CH_2)_nC(O)NR_{D2}(CH_2)_{n1}R_{D3}$, $-OC(R_{D1}R_{D2})_n(CH_2)_{n1}R_{D3}$, or $-(CH_2)_n NR_{D2}S(O)_mR_{D3}$, wherein the amino, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, and 5- to 14-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl, and the amino, $C_{1-3}$ alkyl, $C_{2-4}$ alkenyl, $C_{2-4}$ alkynyl, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, $C_{3-8}$ cycloalkyl, 3- to 8-membered heterocyclyl, $C_{6-10}$ aryl, and 5- to 10-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{D1}$-$R_{D3}$ are each independently selected from hydrogen, deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, or 5- to 14-membered heteroaryl, wherein the amino, $C_{1-6}$ alkyl, $C_{1-6}$ deuteroalkyl, $C_{1-6}$ haloalkyl, $C_{1-6}$ alkoxy, $C_{1-6}$ haloalkoxy, $C_{1-6}$ hydroxyalkyl, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl can be optionally further substituted with one or more substituents selected from deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

alternatively, any two adjacent or non-adjacent $R^d$ are connected to form cycloalkyl, heterocyclyl, aryl, or heteroaryl, wherein the cycloalkyl, heterocyclyl, aryl, and heteroaryl can be optionally further substituted with one or more substituents selected from deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

alternatively, any two $R^c$ and $R^d$ are connected to form cycloalkyl, heterocyclyl, aryl, or heteroaryl, wherein the cycloalkyl, heterocyclyl, aryl, and heteroaryl can be optionally further substituted with one or more substituents selected from deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

x is 0, 1, 2, or 3;

y is 0, 1, 2, or 3;

z is 0, 1, 2, or 3;

e is 0, 1, 2, or 3;

m is 0, 1, or 2;

n is 0, 1, 2, 3, or 4; and n1 is 0, 1, 2, 3, or 4.

In a preferred embodiment of the present disclosure, the compound is further as represented by general formula (I-1), (I-2), (I-3), (I-4), or (I-5):

(I-1)

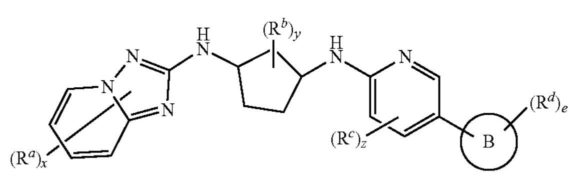

(I-2)

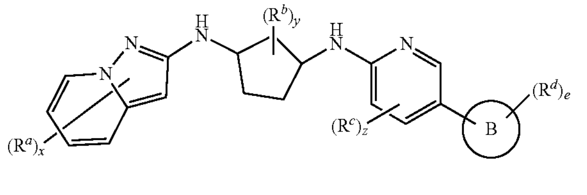

-continued (I-3)

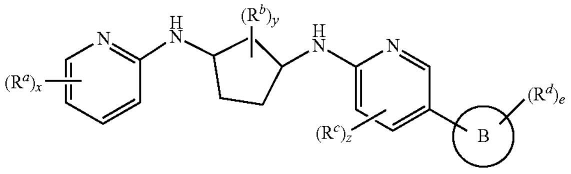

(I-4)

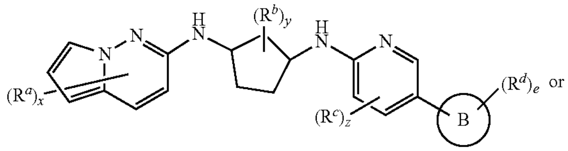 or (I-5)

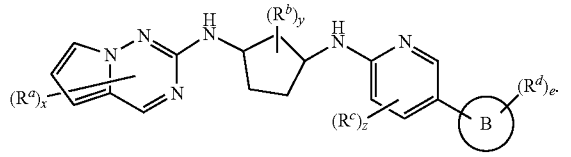

In a more preferred embodiment of the present disclosure, ring B as described in the present disclosure is selected from $C_{3-12}$ cycloalkyl, 3- to 12-membered heterocyclyl, CG-w aryl, or 5- to 14-membered heteroaryl;

preferably, ring B is selected from $C_{3-6}$ cycloalkyl, phenyl, 3- to 8-membered heterocyclyl, 7- to 10-membered bicyclic heterocyclyl, 5-membered heteroaryl, 6-membered heteroaryl, 5-membered fused 5-membered bicyclic heteroaryl, 5-membered fused 6-membered bicyclic heteroaryl, 6-membered fused 5-membered bicyclic heteroaryl, or 6-membered fused 6-membered bicyclic heteroaryl;

more preferably, ring B is selected from $C_{3-6}$ cycloalkyl, phenyl, 5-membered nitrogen-containing heterocyclyl, 6-membered nitrogen-containing heterocyclyl, 7- to 10-membered bicyclic heterocyclyl, 5-membered nitrogen-containing heteroaryl, 6-membered nitrogen-containing heteroaryl, 5-membered fused 5-membered bicyclic nitrogen-containing heteroaryl, 5-membered fused 6-membered bicyclic nitrogen-containing heteroaryl, 6-membered fused 5-membered bicyclic nitrogen-containing heteroaryl, or 6-membered fused 6-membered bicyclic nitrogen-containing heteroaryl;

further preferably, ring B is selected from pyridine, pyrimidine, pyridone, or pyrimidinone;

further more preferably, ring B is selected from pyridine, pyrimidine, benzene,

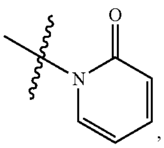, 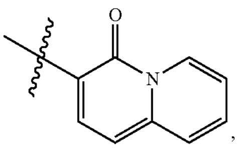,

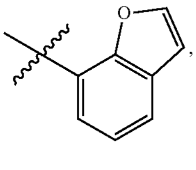, 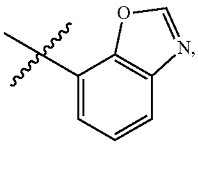

-continued

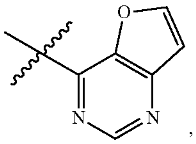, 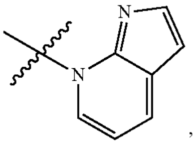,

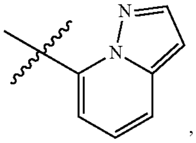, 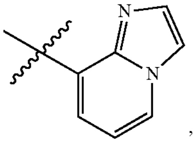,

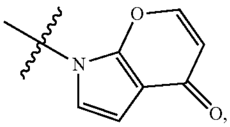 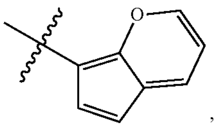,

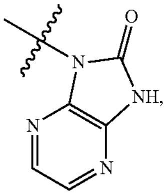 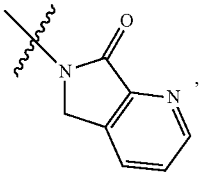,

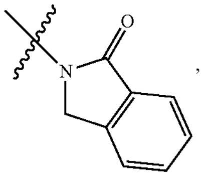, 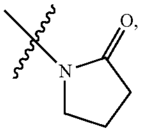

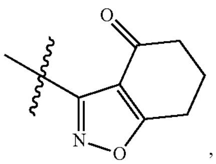, 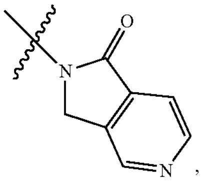,

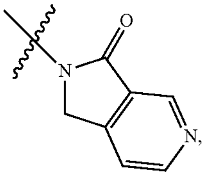 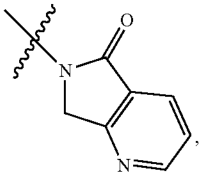,

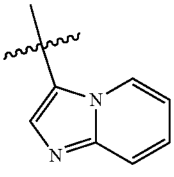, 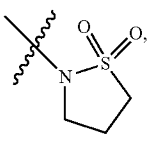 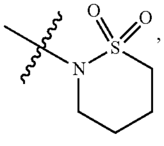,

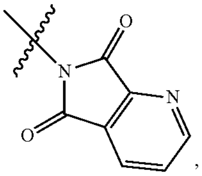, 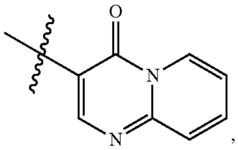,

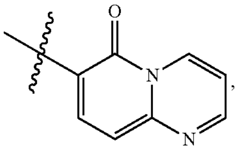, 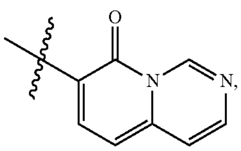 or

-continued
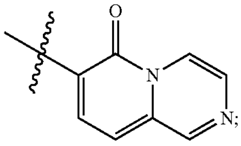;
still further preferably, ring B is selected from pyridine, pyrimidine, benzene,
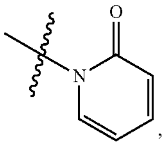, 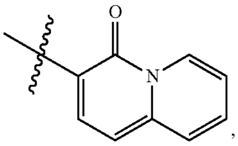,
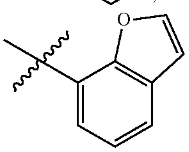, 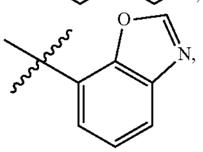,
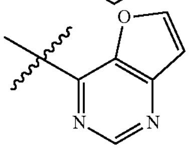, 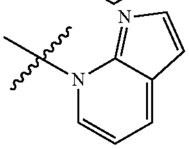,
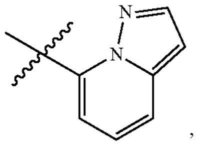, 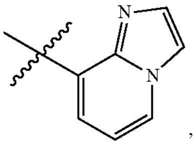,
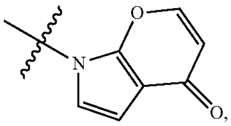, 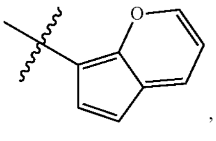,
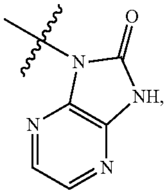, 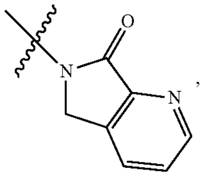,
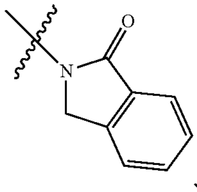, 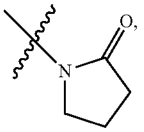,
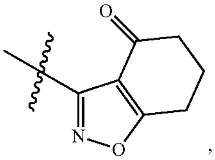, 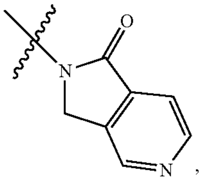,
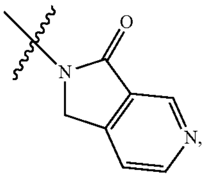, 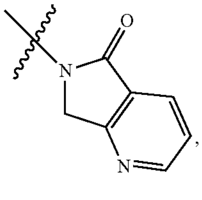,
-continued
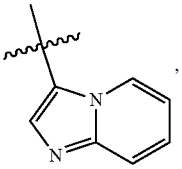, 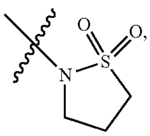, 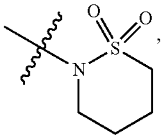,
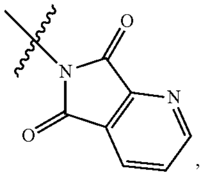, 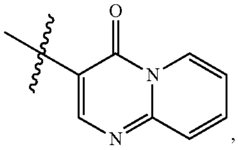,
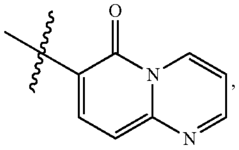, 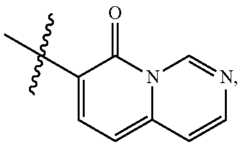, or
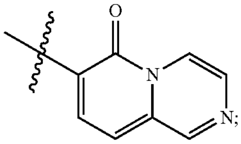;
further preferably, ring B is selected from pyridine, pyrimidine, benzene,
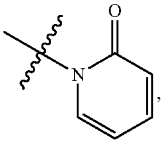, 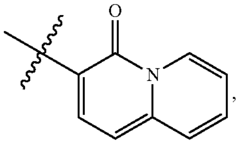,
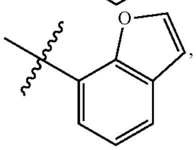, 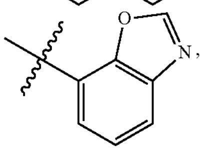,
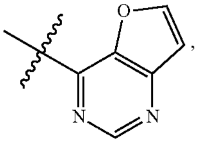, 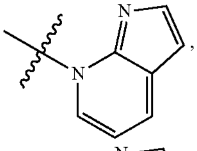,
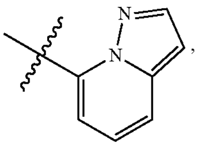, 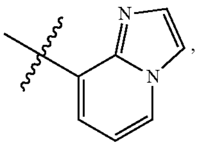,
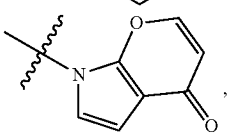, 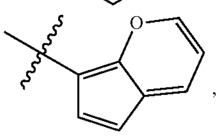,
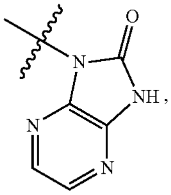, 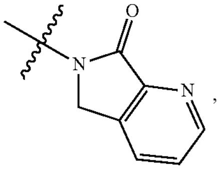, -continued
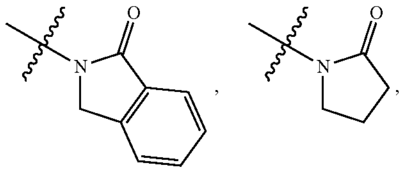
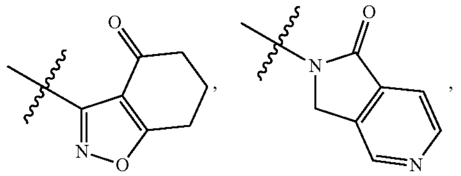
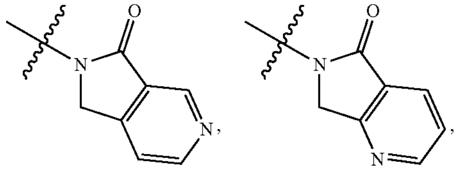
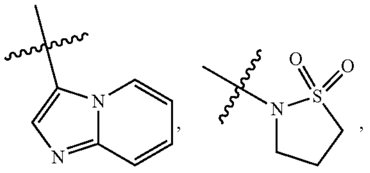
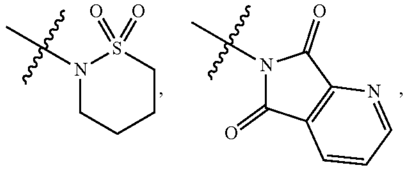
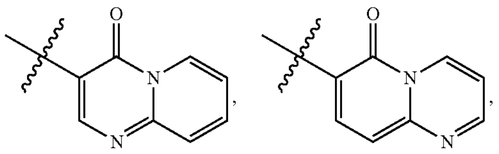
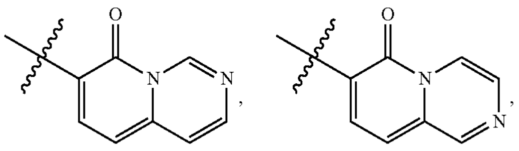
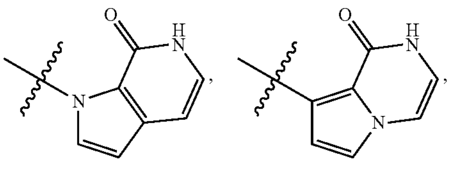
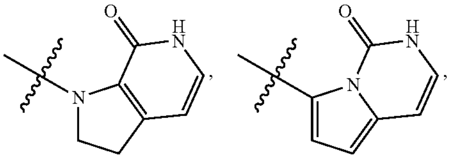
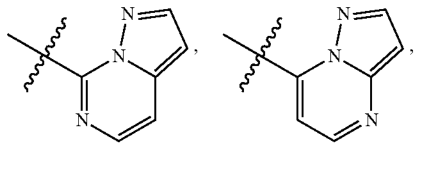
-continued
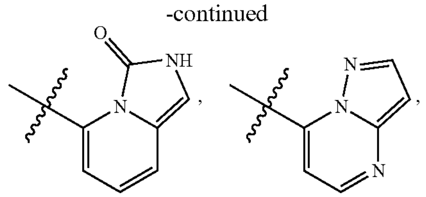
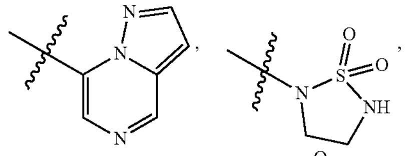
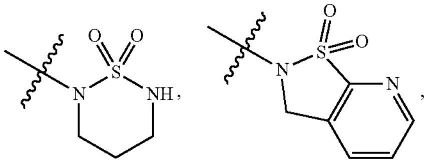
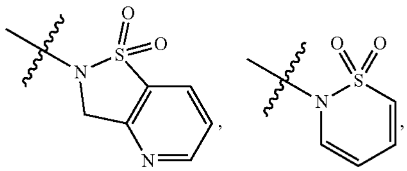
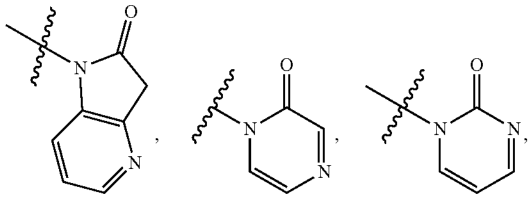
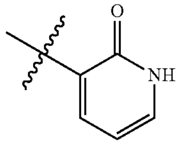
or
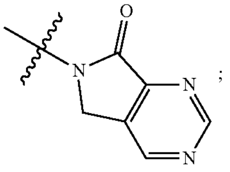
;
further preferably, ring B is selected from pyridine, pyrimidine, benzene,
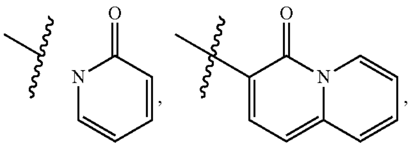
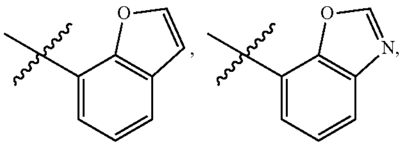
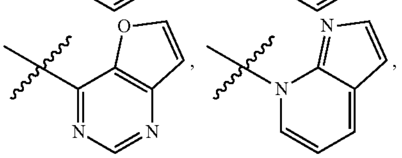
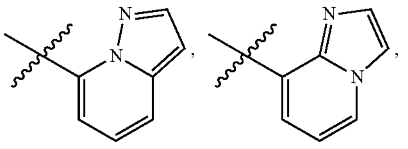

-continued
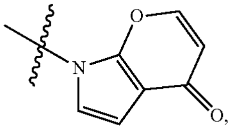,
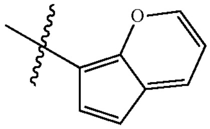,
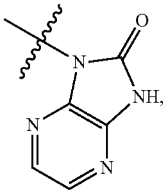,
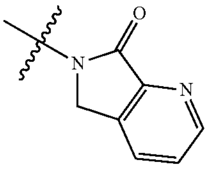,
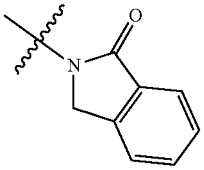,
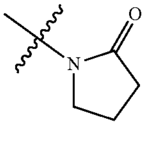,
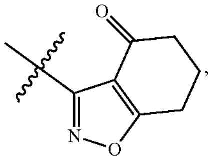,
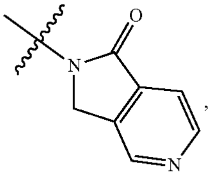,
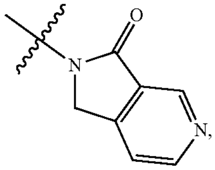,
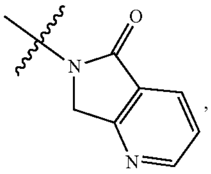,
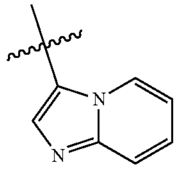,
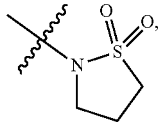,
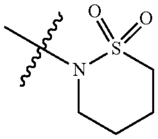,
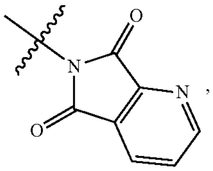,
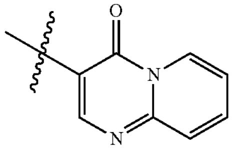,
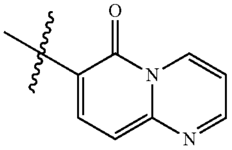,
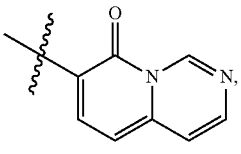,
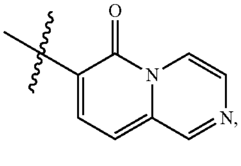,
-continued
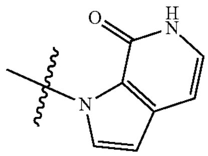,
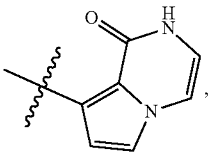,
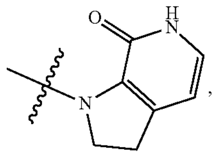,
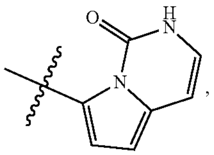,
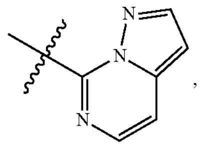,
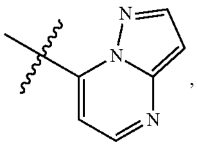,
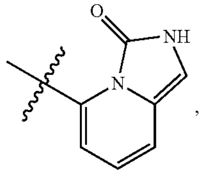,
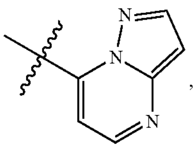,
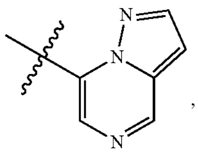,
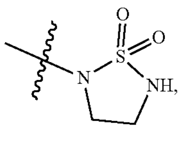,
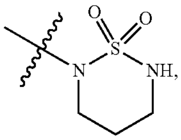,
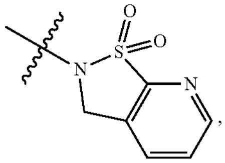,
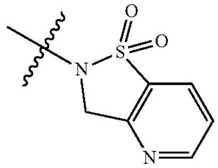 or
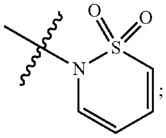;
further preferably, ring B is selected from pyridine, pyrimidine, benzene,
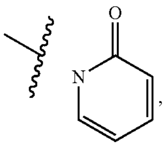,
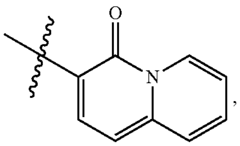,
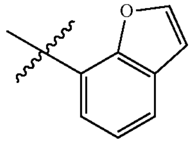,
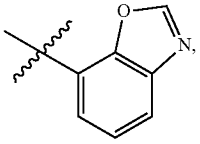,
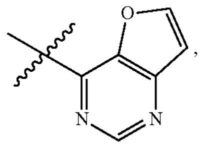,
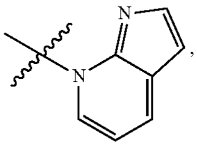, -continued
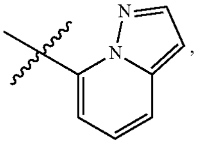, 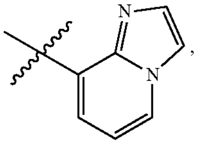,
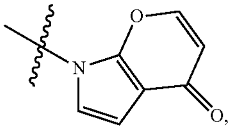, 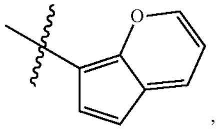,
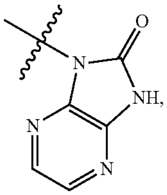, 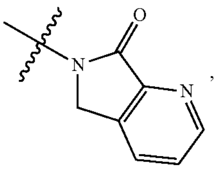,
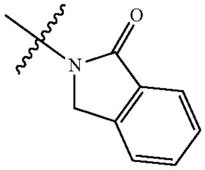, 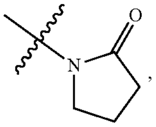,
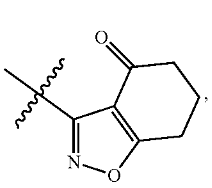, 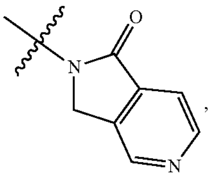,
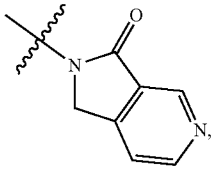, 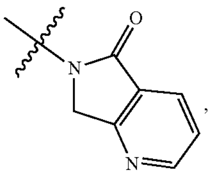,
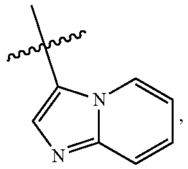, 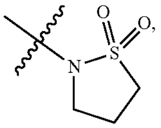
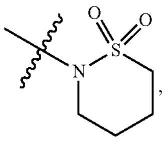, 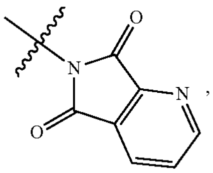,
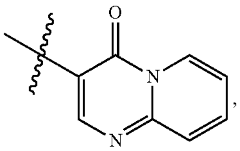, 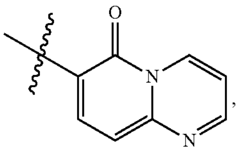,
-continued
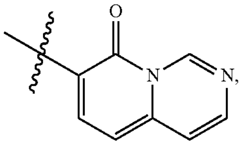, 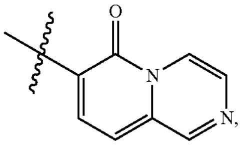
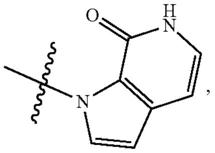, 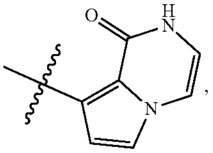,
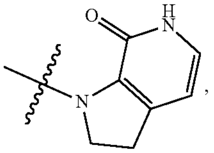, 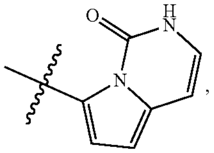,
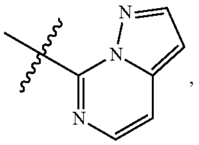, 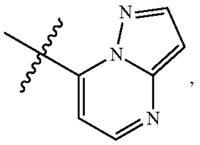,
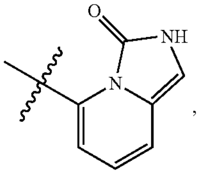, 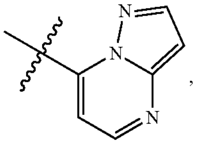,
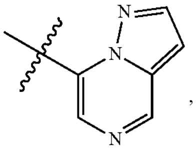, 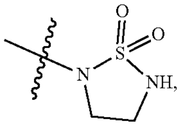, 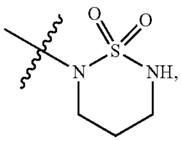
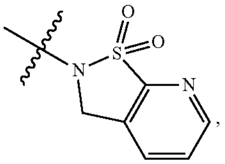, 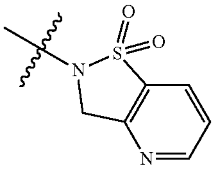 or
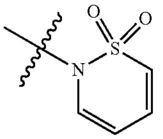 or 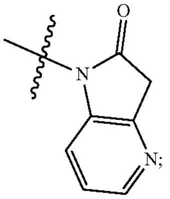
preferably, ring B may also be selected from
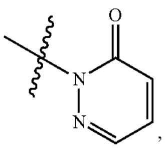, 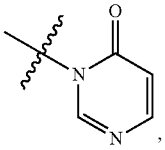, 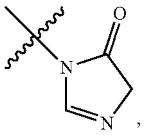, -continued

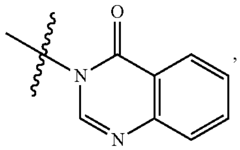

,

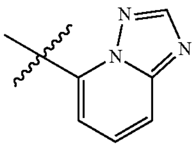

or

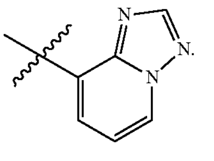

In a preferred embodiment of the present disclosure, the compound is further as represented by general formula (V):

(V)

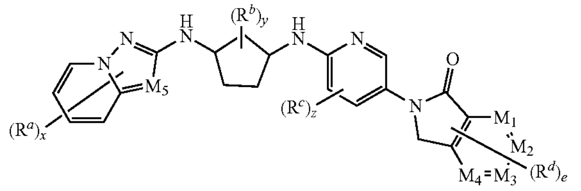

In a preferred embodiment of the present disclosure, the compound is further as represented by general formula (III-A), (III-B), (III-C), (III-D), (III-E), or (III-F):

(III-A)

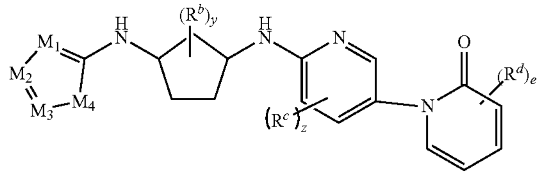

(III-B)

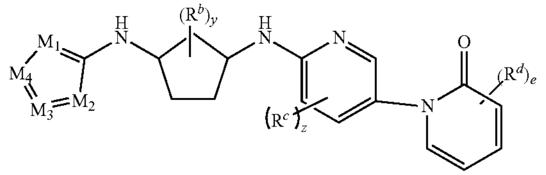

(III-C)

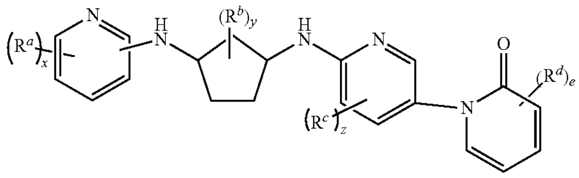

(III-D)

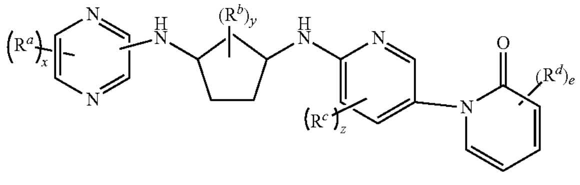

-continued (III-E)

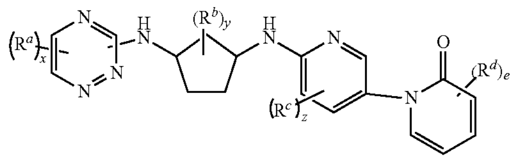

or (III-F)

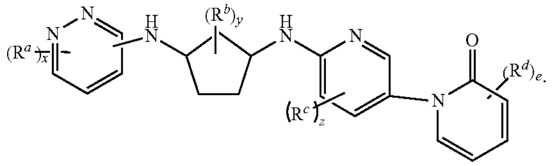

In a preferred embodiment of the present disclosure, the compound is further as represented by general formula (II'):

(II')

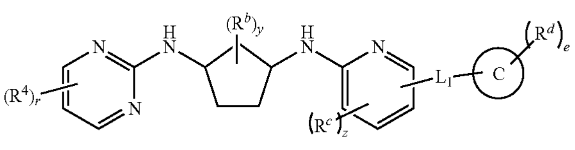

wherein ring C is selected from $C_{3-12}$ cycloalkyl, 3- to 8-membered heterocyclyl, C&12 aryl, and 5- to 14-membered heteroaryl;

preferably, ring C is selected from $C_{3-6}$ cycloalkyl, phenyl, 3- to 8-membered heterocyclyl, 7- to 10-membered bicyclic heterocyclyl, 5-membered monoheteraryl, 5-membered fused 5-membered bicyclic heteroaryl, 5-membered fused 6-membered bicyclic heteroaryl, 6-membered fused 5-membered bicyclic heteroaryl, or 6-membered fused 6-membered bicyclic heteroaryl; more preferably, $C_{3-6}$ cycloalkyl, phenyl, 5-membered nitrogen-containing heterocyclyl, 6-membered nitrogen-containing heterocyclyl, 7- to 10-membered bicyclic nitrogen-containing heterocyclyl, 5-membered nitrogen-containing heteroaryl, 5-membered fused 5-membered bicyclic nitrogen-containing heteroaryl, 5-membered fused 6-membered bicyclic nitrogen-containing heteroaryl, 6-membered fused 5-membered bicyclic nitrogen-containing heteroaryl, or 6-membered fused 6-membered bicyclic nitrogen-containing heteroaryl;

further preferably, ring C is selected from phenyl, pyrrolidinyl,

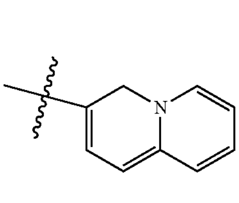

,

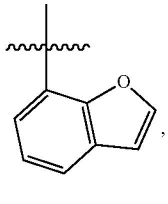

,

-continued
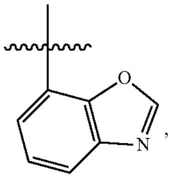
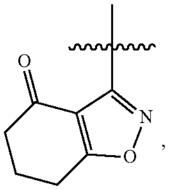
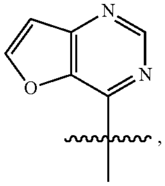
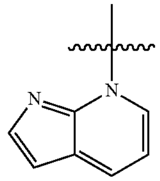
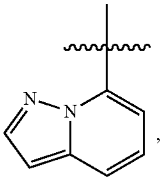
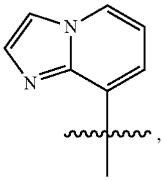
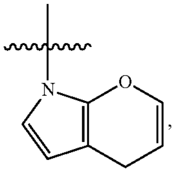
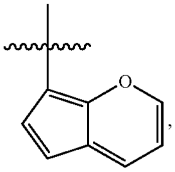
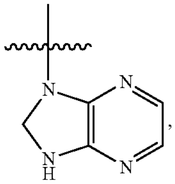
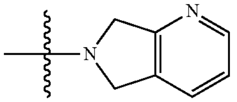
or
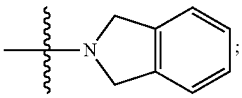
;
further more preferably, ring C is selected from pyridine, pyrimidine, benzene,
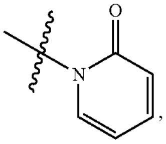
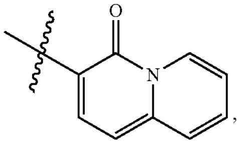
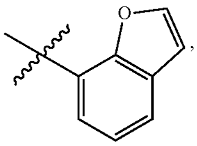
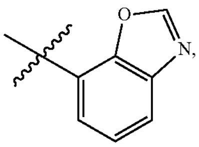
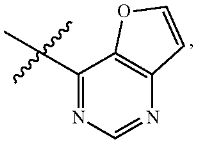
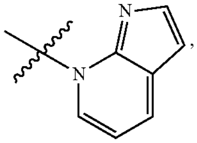
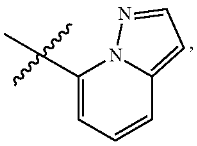
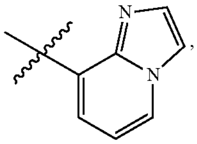
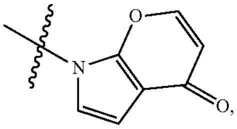
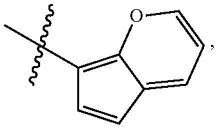
-continued
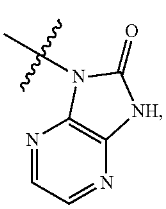
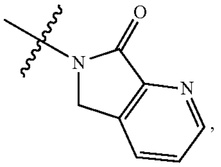
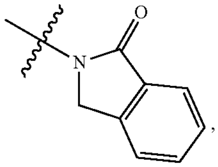
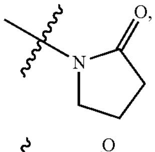
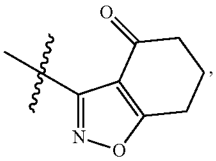
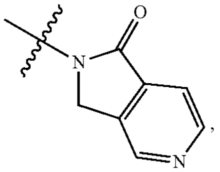
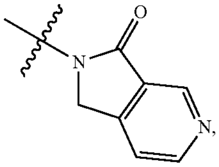
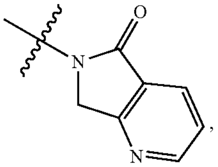
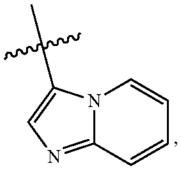
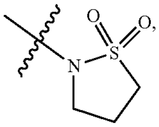
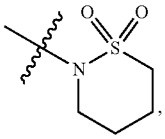
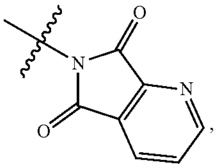
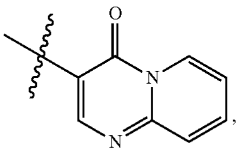
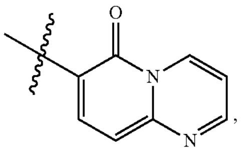
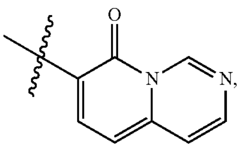
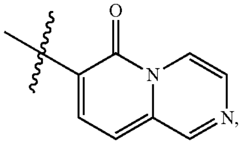

-continued
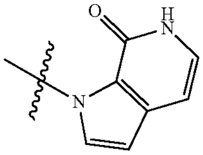, 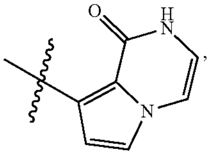, 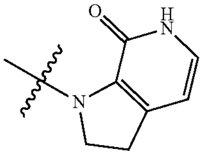, 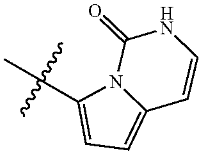, 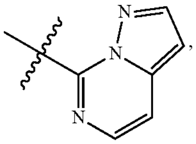, 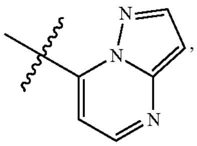, 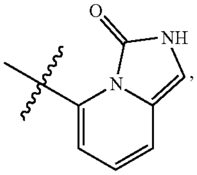, 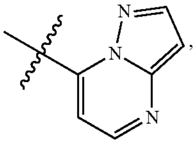, 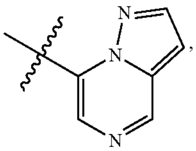, 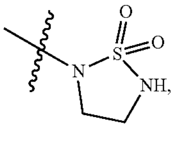 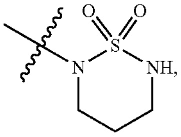 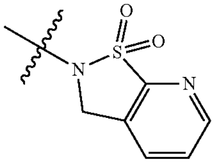, 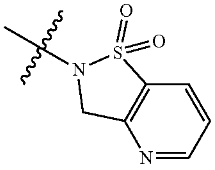, 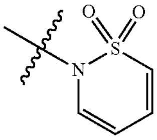 or 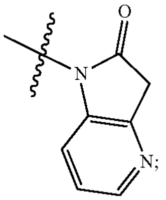
further more preferably, ring C is selected from pyridine, pyrimidine, benzene,
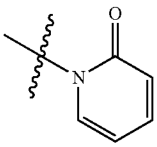, 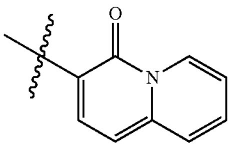,
-continued
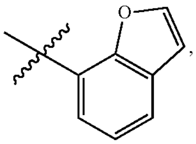, 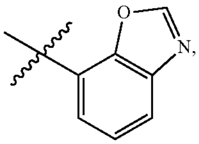 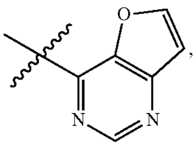, 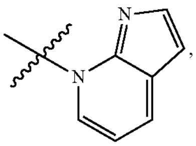, 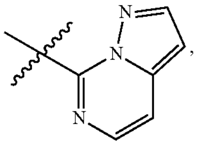, 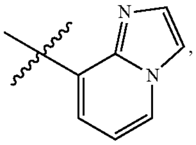, 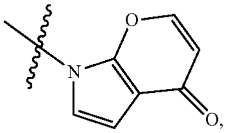 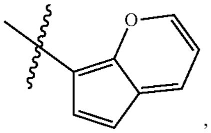, 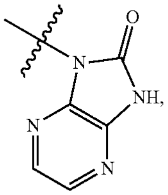 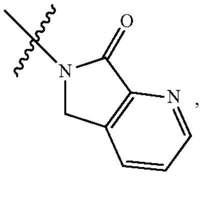, 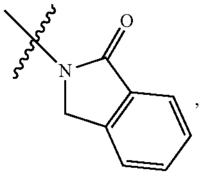, 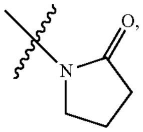 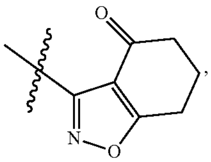, 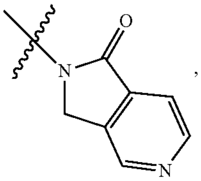, 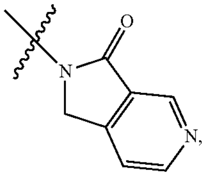 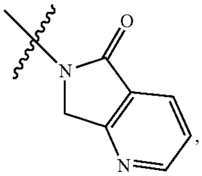, 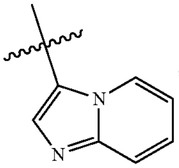, 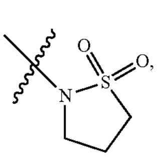 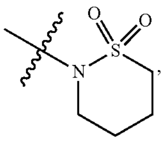 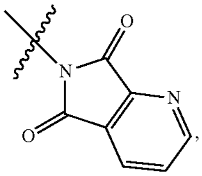 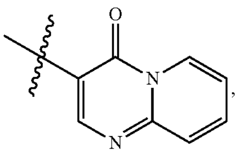, -continued

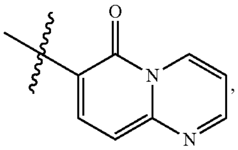
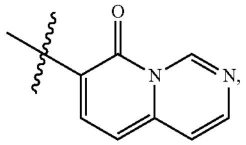
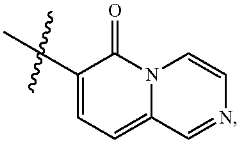
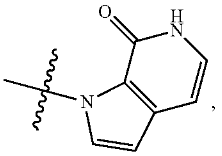
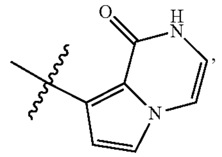
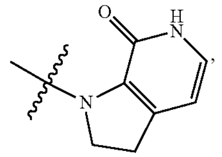
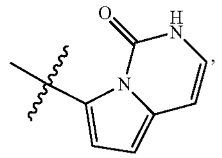
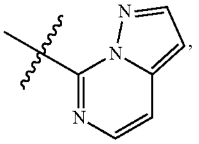
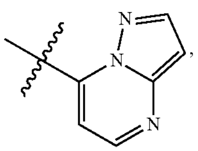
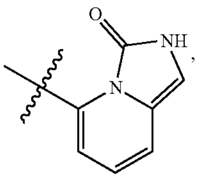
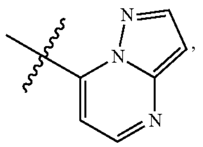
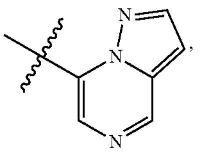
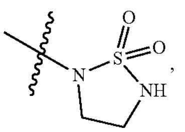
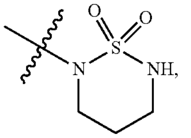
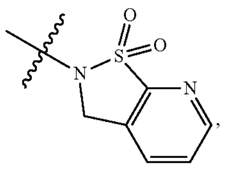
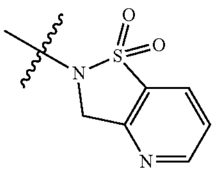

or

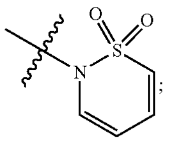 [SMILES: *N1C=CC=CS1(=O)=O]

preferably, ring C may also be selected from

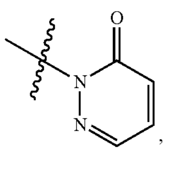
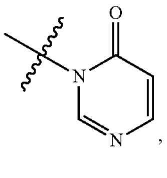
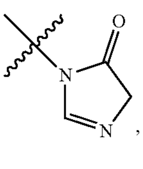

-continued

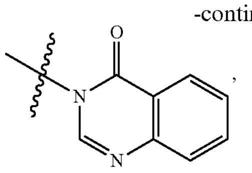
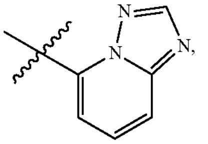

or

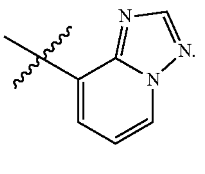

$R^b$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, 5- to 14-membered heteroaryl, $-(CH_2)_nR_{B1}$, $-(CH_2)_nOR_{B1}$, $-(CH_2)_nC(O)R_{B1}$, $-(CH_2)_nC(O)OR_{B1}$, $-(CH_2)_nS(O)_mR_{B1}$, $-(CH_2)_nNR_{B1}R_{B3}$, $-(CH_2)_nNR_{B2}C(O)OR_{B3}$, $-(CH_2)_nNR_{B2}C(O)(CH_2)_{n1}R_{B3}$, $-(CH_2)_nNR_{B2}C(O)NR_{B2}R_{B3}$, $-(CH_2)_nC(O)NR_{B2}(CH_2)_{n1}R_{B3}$, $-OC(R_{B1}R_{B2})_n(CH_2)_{n1}R_{B3}$, or $-(CH_2)_nNR_{B2}S(O)_nR_{B3}$, wherein the amino, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, and 5- to 14-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{B1}$-$R_{B3}$ are each independently selected from hydrogen, deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, or 5- to 14-membered heteroaryl, wherein the amino, $C_{1-6}$ alkyl, $C_{1-6}$ deuteroalkyl, $C_{1-6}$ haloalkyl, $C_{1-6}$ alkoxy, $C_{1-6}$ haloalkoxy, $C_{1-6}$ hydroxyalkyl, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl can be optionally further substituted with one or more substituents selected from deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

alternatively, any two adjacent or non-adjacent $R^b$ are connected to form cycloalkyl, heterocyclyl, aryl, or heteroaryl, wherein the cycloalkyl, heterocyclyl, aryl, and heteroaryl can be optionally further substituted with one or more substituents selected from deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

$R^c$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, 5- to 14-membered heteroaryl, $-(CH_2)_nR_{C1}$, $-(CH_2)_nOR_{C1}$, $-(CH_2)_nC(O)R_{C1}$, $-(CH_2)_nC(O)OR_{C1}$, $-(CH_2)_nS(O)_mR_{C1}$, $-(CH_2)_nNR_{C2}R_{C3}$, $-(CH_2)_nNR_{C2}C(O)OR_{C3}$, $-(CH_2)_nNR_{C2}C(O)(CH_2)_{n1}R_{C3}$, $-(CH_2)_nNR_{C2}C(O)NR_{C2}R_{C3}$, $-(CH_2)_nC(O)NR_{C2}(CH_2)_{n1}R_{C3}$, $-OC(R_{C1}R_{C2})_n(CH_2)_{n1}R_{C3}$, or $-(CH_2)_nNR_{C2}S(O)_mR_{C3}$, wherein the amino, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, and 5- to 14-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{C1}$-$R_{C3}$ are each independently selected from hydrogen, deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, or 5- to 14-membered heteroaryl, wherein the amino, $C_{1-6}$ alkyl, $C_{1-6}$ deuteroalkyl, $C_{1-6}$ haloalkyl, $C_{1-6}$ alkoxy, $C_{1-6}$ haloalkoxy, $C_{1-6}$ hydroxyalkyl, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl can be optionally further substituted with one or more substituents selected from deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

alternatively, any two adjacent or non-adjacent $R^c$ are connected to form cycloalkyl, heterocyclyl, aryl, or heteroaryl, wherein the cycloalkyl, heterocyclyl, aryl, and heteroaryl can be optionally further substituted with one or more substituents selected from deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

$R^d$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, 5- to 14-membered heteroaryl, $-(CH_2)_nR_{D1}$, $-(CH_2)_nOR_{D1}$, $-(CH_2)_nC(O)R_{D1}$, $-(CH_2)_nC(O)OR_{D1}$, $-(CH_2)_nS(O)_mR_{D1}$, $-(CH_2)_nNR_{D2}R_{D3}$, $-(CH_2)_nNR_{D2}C(O)OR_{D3}$, $-(CH_2)_nNR_{D2}C(O)(CH_2)_{n1}R_{D3}$, $(CH_2)_nNR_{D2}C(O)NR_{D2}R_{D3}$, $-(CH_2)_nC(O)NR_{D2}(CH_2)_{n1}R_{D3}$, $-OC(R_{D1}R_{D2})_n(CH_2)_{n1}R_{D3}$, or $-(CH_2)_nNR_{D2}S(O)_mR_{D3}$, wherein the amino, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, and 5- to 14-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl; the amino, $C_{1-3}$ alkyl, $C_{2-4}$ alkenyl, $C_{2-4}$ alkynyl, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, $C_{3-8}$ cycloalkyl, 3- to 8-membered heterocyclyl, $C_{6-10}$ aryl, and 5- to 10-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{D1}$-$R_{D3}$ are each independently selected from hydrogen, deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, or 5- to 14-membered heteroaryl, wherein the amino, $C_{1-6}$ alkyl, $C_{1-6}$ deuteroalkyl, $C_{1-6}$ haloalkyl, $C_{1-6}$ alkoxy, $C_{1-6}$ haloalkoxy, $C_{1-6}$ hydroxyalkyl, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl can be optionally further substituted with one or more substituents selected from deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

preferably, $R^d$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, 5- to 14-membered heteroaryl, $-(CH_2)_nR_{D1}$, $-(CH_2)_nOR_{D1}$, $-(CH_2)_nC(O)R_{D1}$, $-(CH_2)_nC(O)OR_{D1}$, $-(CH_2)_nS(O)_mR_{D1}$, $-(CH_2)_nNR_{D2}R_{D3}$, $-(CH_2)_nNR_{D2}C(O)OR_{D3}$, $-(CH_2)_nNR_{D2}C(O)(CH_2)_{n1}R_{D3}$, $(CH_2)_nNR_{D2}C(O)NR_{D2}R_{D3}$, $-(CH_2)_nC(O)NR_{D2}(CH_2)_{n1}R_{D3}$, $-OC(R_{D1}R_{D2})_n(CH_2)_{n1}R_{D3}$, or $-(CH_2)_nNR_{D2}S(O)_mR_{D3}$, wherein the amino, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, $C_{3-8}$ cycloalkyl, 3- to 8-membered heterocyclyl, $C_{6-12}$ aryl, and 5- to 14-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{D1}$-$R_{D3}$ are each independently selected from hydrogen, deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, or 5- to 14-membered heteroaryl, wherein the amino, $C_{1-6}$ alkyl, $C_{1-6}$ deuteroalkyl, $C_{1-6}$ haloalkyl, $C_{1-6}$ alkoxy, $C_{1-6}$ haloalkoxy, $C_{1-6}$ hydroxyalkyl, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl can be optionally further substituted with one or more substituents selected from deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

alternatively, any two adjacent or non-adjacent $R^d$ are connected to form cycloalkyl, heterocyclyl, aryl, or heteroaryl, wherein the cycloalkyl, heterocyclyl, aryl, and heteroaryl can be optionally further substituted with one or more substituents selected from deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

alternatively, any two $R^c$ and $R^d$ are connected to form cycloalkyl, heterocyclyl, aryl, or heteroaryl, wherein the cycloalkyl, heterocyclyl, aryl, and heteroaryl can be optionally further substituted with one or more substituents selected from deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl.

y is 0, 1, 2, or 3;

z is 0, 1, 2, or 3;

e is 0, 1, 2, or 3;

m is 0, 1, or 2;

n is 0, 1, 2, 3, or 4; and n1 is 0, 1, 2, 3, or 4.

In a further preferred embodiment of the present disclosure, the compound is further as represented by general formula (II'-1):

(II'-1)

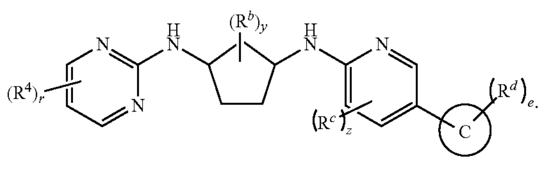

In a further preferred embodiment of the present disclosure, $R^a$ described in the present disclosure is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, 5- to 12-membered heteroaryl, $-(CH_2)_nR_{A1}$, $-(CH_2)_nOR_{A1}$, $-(CH_2)_nC(O)R_{A1}$, $-(CH_2)_nC(O)OR_{A1}$, $-(CH_2)_nS(O)_mR_{A1}$, $-(CH_2)NR_{A2}R_{A3}$, $-(CH_2)_nNR_{A2}C(O)OR_{A3}$, $-(CH_2)_nNR_{A2}C(O)(CH_2)_{n1}R_{A3}$, $-(CH_2)_nNR_{A2}C(O)NR_{A2}R_{A3}$, $-(CH_2)_nC(O)NR_{A2}(CH_2)_{n1}R_{A3}$, $-OC(R_{A1}R_{A2})_n(CH_2)_{n1}R_{A3}$, or $-(CH_2)_nNR_{A2}S(O)_mR_{A3}$, wherein the amino, $C_{1-3}$ alkyl, $C_{2-4}$ alkenyl, $C_{2-4}$ alkynyl, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, and 5- to 12-membered heteroaryl can be optionally further substituted and can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl; the amino, $C_{1-3}$ alkyl, $C_{2-4}$ alkenyl, $C_{2-4}$ alkynyl, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, $C_{3-8}$ cycloalkyl, 3- to 8-membered heterocyclyl, $C_{6-10}$ aryl, and 5- to 10-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{A1}$-$R_{A3}$ are each independently selected from hydrogen, deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, or 5- to 12-membered heteroaryl, wherein the amino, $C_{1-3}$ alkyl, $C_{1-3}$ deuteroalkyl, $C_{1-3}$ haloalkyl, $C_{1-3}$ alkoxy, $C_{1-3}$ haloalkoxy, $C_{1-3}$ hydroxyalkyl, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

preferably, $R^a$ is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, 5- to 12-membered heteroaryl, $-(CH_2)_nR_{A1}$, $-(CH_2)_nOR_{A1}$, $-(CH_2)_nC(O)R_{A1}$, $-(CH_2)_nC(O)OR_{A1}$, $-(CH_2)_nS(O)_mR_{A1}$, $-(CH_2)_nNR_{A2}R_{A3}$, $-(CH_2)_nNR_{A2}C(O)OR_{A3}$, $-(CH_2)_nNR_{A2}C(O)(CH_2)_{n1}R_{A3}$, $-(CH_2)_nNR_{A2}C(O)NR_{A2}R_{A3}$, $-(CH_2)_n$ $C(O)NR_{A2}(CH_2)_{n1}R_{A3}$, $—OC(R_{A1}R_{A2})_n(CH_2)_{n1}R_{A3}$, or $—(CH_2)_nNR_{A2}S(O)_mR_{A3}$, wherein the amino, $C_{1-3}$ alkyl, $C_{2-4}$ alkenyl, $C_{2-4}$ alkynyl, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, and 5- to 12-membered heteroaryl can be optionally further substituted and can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

$R_{A1}$-$R_{A3}$ are each independently selected from hydrogen, deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, or 5- to 12-membered heteroaryl, wherein the amino, $C_{1-3}$ alkyl, $C_{1-3}$ deuteroalkyl, $C_{1-3}$ haloalkyl, $C_{1-3}$ alkoxy, $C_{1-3}$ haloalkoxy, $C_{1-3}$ hydroxyalkyl, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl.

In a further preferred embodiment of the present disclosure, $R^b$ described in the present disclosure is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, 5- to 12-membered heteroaryl, $—(CH_2)_nR_{B1}$, $—(CH_2)_nOR_{B1}$, $—(CH_2)_nC(O)R_{B1}$, $—(CH_2)_nC(O)OR_{B1}$, $—(CH_2)_nS(O)_mR_{B1}$, $—(CH_2)_nNR_{B2}R_{B3}$, $—(CH_2)_nNR_{B2}C(O)OR_{B3}$, $—(CH_2)_nNR_{B2}C(O)(CH_2)_nR_{B1}$, $—(CH_2)_nNR_{B2}C(O)NR_{B2}R_{B3}$, $—(CH_2)_nC(O)NR_{B2}(CH_2)_{n1}R_{B3}$, $—OC(R_{B1}R_{B2})_n(CH_2)_{n1}R_{B3}$, or $—(CH_2)_nNR_{B2}S(O)_mR_{B3}$, wherein the amino, $C_{1-3}$ alkyl, $C_{2-4}$ alkenyl, $C_{2-4}$ alkynyl, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, and 5- to 12-membered heteroaryl can be optionally further substituted and can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

$R_{B1}$-$R_{B3}$ are each independently selected from hydrogen, deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, or 5- to 12-membered heteroaryl, wherein the amino, $C_{1-3}$ alkyl, $C_{1-3}$ deuteroalkyl, $C_{1-3}$ haloalkyl, $C_{1-3}$ alkoxy, $C_{1-3}$ haloalkoxy, $C_{1-3}$ hydroxyalkyl, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl.

In a further preferred embodiment of the present disclosure, $R^c$ described in the present disclosure is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, 5- to 12-membered heteroaryl, $—(CH_2)_nR_{C1}$, $—(CH_2)_nOR_{C1}$, $—(CH_2)_nC(O)R_{C1}$, $—(CH_2)_nC(O)OR_{C1}$, $—(CH_2)_nS(O)_mR_{C1}$, $—(CH_2)_nNR_{C2}R_{C3}$, $—(CH_2)_nNR_{C2}C(O)OR_{C3}$, $—(CH_2)_nNR_{C2}C(O)(CH_2)_{n1}R_{C3}$, $—(CH_2)_nNR_{C2}C(O)NR_{C2}R_{C3}$, $—(CH_2)_nC(O)NR_{C2}(CH_2)_{n1}R_{C3}$, $—OC(R_{C1}R_{C2})_n(CH_2)_{n1}R_{C3}$, or $—(CH_2)_nNR_{C2}S(O)_mR_{C3}$, wherein the amino, $C_{1-3}$ alkyl, $C_{2-4}$ alkenyl, $C_{2-4}$ alkynyl, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, and 5- to 12-membered heteroaryl can be optionally further substituted and can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

$R_{C1}$-$R_{C3}$ are each independently selected from hydrogen, deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, or 5- to 12-membered heteroaryl, wherein the amino, $C_{1-3}$ alkyl, $C_{1-3}$ deuteroalkyl, $C_{1-3}$ haloalkyl, $C_{1-3}$ alkoxy, $C_{1-3}$ haloalkoxy, $C_{1-3}$ hydroxyalkyl, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl.

In a further preferred embodiment of the present disclosure, $R^d$ described in the present disclosure is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, 5- to 12-membered heteroaryl, $—(CH_2)_nR_{D1}$, $—(CH_2)_nOR_{D1}$, $—(CH_2)_nC(O)R_{D1}$, $—(CH_2)_nC(O)OR_{D1}$, $—(CH_2)_n$ $S(O)_nR_{D1}$, $—(CH_2)_nNR_{D2}R_{D3}$, $—(CH_2)_nNR_{D2}C(O)OR_{D3}$, $—(CH_2)_nNR_{D2}C(O)(CH_2)_{n1}R_{D3}$, $—(CH_2)_nNR_{D2}C(O)NR_{D2}R_{D3}$, $—(CH_2)_nC(O)NR_{D2}(CH_2)_{n1}R_{D3}$, $—OC(R_{D1}R_{D2})_n(CH_2)_{n1}R_{D3}$, or $—(CH_2)_nNR_{D2}S(O)_mR_{D3}$, wherein the amino, $C_{1-3}$ alkyl, $C_{2-4}$ alkenyl, $C_{2-4}$ alkynyl, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, and 5- to 12-membered heteroaryl can be optionally further substituted and can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl; the amino, $C_{1-3}$ alkyl, $C_{2-4}$ alkenyl, $C_{2-4}$ alkynyl, $C_{3-8}$ deuteroalkyl, $C_{1-3}$ haloalkyl, $C_{1-3}$ alkoxy, halo $C_{1-3}$ alkoxy, $C_{1-3}$ hydroxyalkyl, $C_{3-8}$ cycloalkyl, 3- to 8-membered heterocyclyl, $C_{6-10}$ aryl, and 5- to 10-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{D1}$-$R_{D3}$ are each independently selected from hydrogen, deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, or 5- to 12-membered heteroaryl, wherein the amino, $C_{1-3}$ alkyl, $C_{1-3}$ deuteroalkyl, $C_{1-3}$ haloalkyl, $C_{1-3}$ alkoxy, $C_{1-3}$ haloalkoxy, $C_{1-3}$ hydroxyalkyl, $C_{2-4}$ alkenyl, $C_{2-4}$ alkynyl, $C_{3-9}$ cycloalkyl, 3- to 8-membered heterocyclyl, $C_{6-10}$ aryl, and 5- to 12-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

preferably, $R^d$ is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, 5- to 12-membered heteroaryl, $—(CH_2)_nR_{D1}$, $—(CH_2)_nOR_{D1}$, $—(CH_2)_nC(O)R_{D1}$, $—(CH_2)_nC(O)OR_{D1}$, $—(CH_2)_nS(O)_mR_{D1}$, $—(CH_2)_nNR_{D2}R_{D3}$, $—(CH_2)_nNR_{D2}C(O)OR_{D3}$, $—(CH_2)_nNR_{D2}C(O)(CH_2)_{n1}R_{D3}$, $—(CH_2)_nNR_{D2}C(O)NR_{D2}R_{D3}$, $—(CH_2)_nC(O)NR_{D2}(CH_2)_{n1}R_{D3}$, $—OC(R_{D1}R_{D2})_n(CH_2)_{n1}R_{D3}$, or $—(CH_2)_n NR_{D2}S(O)_mR_{D3}$, wherein the amino, $C_{1-3}$ alkyl, $C_{2-4}$ alkenyl, $C_{2-4}$ alkynyl, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, and 5- to 12-membered heteroaryl can be optionally further substituted and can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl; and $R_{D1}$-$R_{D3}$ are each independently selected from hydrogen, deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, or 5- to 12-membered heteroaryl, wherein the amino, $C_{1-3}$ alkyl, $C_{1-3}$ deuteroalkyl, $C_{1-3}$ haloalkyl, $C_{1-3}$ alkoxy, $C_{1-3}$ haloalkoxy, $C_{1-3}$ hydroxyalkyl, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl.

In a further preferred embodiment of the present disclosure, $R^{4'}$ described in the present disclosure is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, 5- to 12-membered heteroaryl, $—(CH_2)_nR_{e1}$, $—(CH_2)_nOR_{e1}$, $—(CH_2)_nC(O)R_{e1}$, $—(CH_2)_nC(O)OR_{e1}$, $—(CH_2)_nS(O)_mR_{e1}$, $—(CH_2)_nNR_{e2}R_{e3}$, $—(CH_2)_nNR_{e2}C(O)OR_{e3}$, $—(CH_2)_nNR_{e2}C(O)(CH_2)_{n1}R_{e3}$, $—(CH_2)_nNR_{e2}C(O)NR_{e2}R_{e3}$, $—(CH_2)_nC(O)NR_{e2}(CH_2)_{n1}R_{e3}$, $—OC(R_{e1}R_{e2})_n(CH_2)_{n1}R_{e3}$, or $—(CH_2)_nNR_{e2}S(O)_mR_{e3}$, wherein the amino, $C_{1-3}$ alkyl, $C_{2-4}$ alkenyl, $C_{2-4}$ alkynyl, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, and 5- to 12-membered heteroaryl can be optionally further substituted and can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl; the amino, $C_{1-3}$ alkyl, $C_{2-4}$ alkenyl, $C_{2-4}$ alkynyl, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, $C_{3-8}$ cycloalkyl, 3- to 8-membered heterocyclyl, $C_{6-10}$ aryl, and 5- to 10-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 10-membered heteroaryl;

$R_{e1}$-$R_{e3}$ are each independently selected from hydrogen, deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, or 5- to 12-membered heteroaryl, wherein the amino, $C_{1-3}$ alkyl, $C_{1-3}$ deuteroalkyl, $C_{1-3}$ haloalkyl, $C_{1-3}$ alkoxy, $C_{1-3}$ haloalkoxy, $C_{1-3}$ hydroxyalkyl, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl;

preferably, $R^{4'}$ is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, 5- to 12-membered heteroaryl, $-(CH_2)_nR_{e1}$, $-(CH_2)_nOR_{e1}$, $-(CH_2)_nC(O)R_{e1}$, $-(CH_2)_nC(O)OR_{e1}$, $-(CH_2)_nS(O)_mR_{e1}$, $-(CH_2)_nNR_{e2}R_{e3}$, $-(CH_2)_nNR_{e2}C(O)OR_{e3}$, $-(CH_2)_nNR_{e2}C(O)(CH_2)_{n1}R_{e3}$, $-(CH_2)_nNR_{e2}C(O)NR_{e2}R_{e3}$, $-(CH_2)_nC(O)NR_{e2}(CH_2)_{n1}R_{e3}$, $-OC(R_{e1}R_{e2})_n(CH_2)_{n1}R_{e3}$, or $-(CH_2)_nNR_{e2}S(O)_mR_{e3}$, wherein the amino, $C_{1-3}$ alkyl, $C_{2-4}$ alkenyl, $C_{2-4}$ alkynyl, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, $C_{3-8}$ cycloalkyl, 3- to 8-membered heterocyclyl, $C_{6-10}$ aryl, and 5- to 12-membered heteroaryl can be optionally further substituted and can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-9}$ cycloalkyl, 3- to 8-membered heterocyclyl, $C_{6-10}$ aryl, and 5- to 12-membered heteroaryl; and $R_{e1}$-$R_{e3}$ are each independently selected from hydrogen, deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, or 5- to 12-membered heteroaryl, wherein the amino, $C_{1-3}$ alkyl, $C_{1-3}$ deuteroalkyl, $C_{1-3}$ haloalkyl, $C_{1-3}$ alkoxy, $C_{1-3}$ haloalkoxy, $C_{1-3}$ hydroxyalkyl, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl can be optionally further substituted with one or more substituents selected from deuterium, halogen, nitro, hydroxyl, mercapto, cyano, amino, oxo, thio, carboxyl, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{1-3}$ deuteroalkoxy, $C_{1-3}$ haloalkoxy, $C_{2-4}$ alkenyl, $C_{2-4}$ alkynyl, $C_{3-8}$ cycloalkyl, 3- to 8-membered heterocyclyl, $C_{6-10}$ aryl, and 5- to 12-membered heteroaryl.

The present disclosure further provides a compound represented by general formula (VI) or a stereoisomer or pharmaceutically acceptable salt thereof:

(VI)

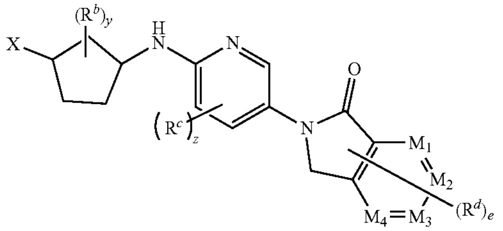

wherein

X is amino, methylthio, halogen, boronic acid, or a boronate; and the other groups are each as defined above.

The present disclosure further provides a method for a compound represented by general formula (III-1), comprising the following step:

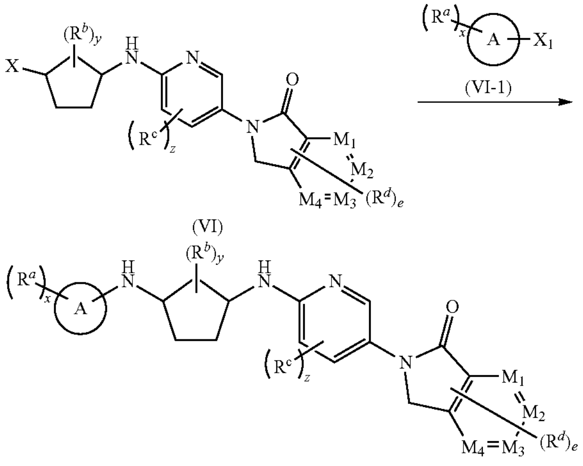

(VI) (VI-1) (III-1)

wherein $X_1$ is amino, halogen, boronic acid, or a boronate;

a compound of general formula (VI) reacts with a compound of general formula (VI-1) to obtain the compound of general formula (III-1); and the other groups are each as defined above.

The present disclosure further provides a compound represented by general formula (VI-2) or a stereoisomer or pharmaceutically acceptable salt thereof:

(VI-2)

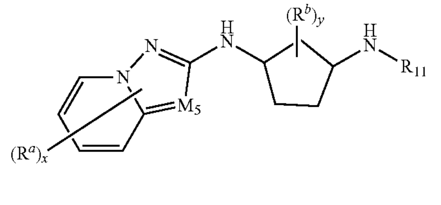

wherein $R_{11}$ is selected from hydrogen, an amino protecting group, 5- to 6-membered heteroaryl, and 5- to 6-membered heterocyclyl, wherein the 5- to 6-membered heteroaryl and 5- to 6-membered heterocyclyl are optionally further substituted with one or more substituents selected from deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, and 5- to 14-membered heteroaryl;

the amino protecting group is selected from allyloxycarbonyl, trifluoroacetyl, tert-butylsulfinyl 2,4-dimethoxybenzyl, nitrobenzenesulfonyl, triphenylmethyl, fluorenylmethoxycarbonyl, 9-fluorenylmethoxycarbonyl, benzyl, p-toluenesulfonyl, p-methoxybenzyl, formate, acetyl, benzyloxycarbonyl, phthaloyl, tert-butyloxycarbonyl, benzyl, or p-methoxyphenyl; and the general formula (VI-2) is further preferably represented by general formula (VI-3):

(VI-3)

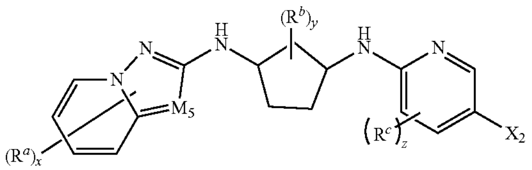

wherein $X_2$ is amino, halogen, boronic acid, or a boronate; and the other groups are each as defined above.

The present disclosure further provides a method for a compound represented by general formula (V), comprising the following step:

method I:

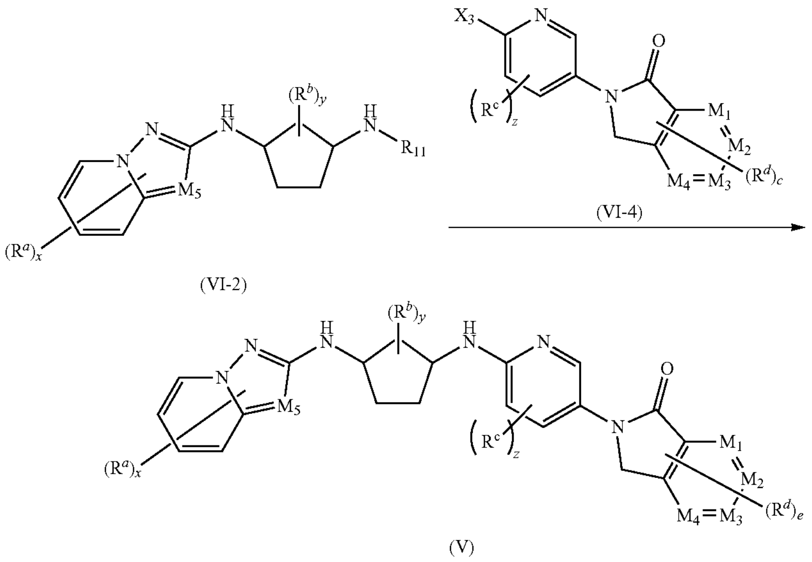

wherein $X_3$ is halogen, boronic acid, or a boronate;

a compound of general formula (VI-2) reacts with a compound of general formula (VI-4) to obtain the compound of general formula (V); and the other groups are each as defined above.

method II:

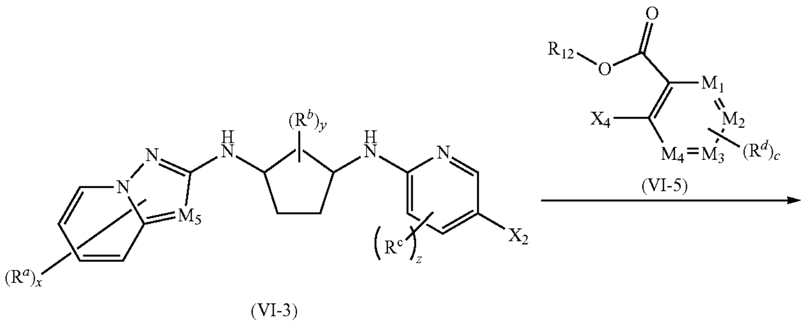

-continued

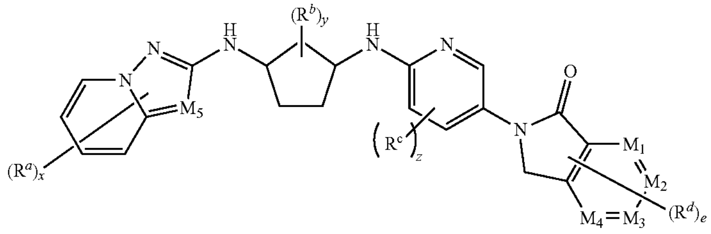

(V)

wherein $X_4$ is formaldehyde group, hydroxymethyl, or halomethyl;

$R_{12}$ is selected from $C_{1-6}$ alkyl, $C_{1-6}$ deuteroalkyl, or $C_{1-6}$ haloalkyl;

a compound of general formula (VI-3) reacts with a compound of general formula (VI-5) to obtain the compound of general formula (V); and the other groups are each as defined above.

The present disclosure further relates to a pharmaceutical composition comprising a therapeutically effective dose of any compound represented by general formula (I) and a stereoisomer or pharmaceutically acceptable salt thereof and one or more pharmaceutically acceptable carriers, diluents or excipients.

In certain embodiments of the present disclosure, the weight percentage of the compound or the stereoisomer or pharmaceutically acceptable salt thereof in the pharmaceutical composition is 0.1-95%, preferably 5-70%, e.g., 70%, 65%, 60%, 55%, 50%, 45%, 40%, 35%, 30%, 25%, 20%, 15%, 10%, or 5% on a free base basis.

In certain embodiments of the present disclosure, the pharmaceutical composition is selected from tablets, capsules, a liquid preparation, or an injection, and preferably, it further comprises a filler and optionally also a disintegrant, or further comprises one or more glidants or lubricants.

In certain embodiments of the present disclosure, the pharmaceutical composition is a fast-release preparation or a slow-release preparation.

In certain embodiments of the present disclosure, the unit dose of the compound or the stereoisomer or pharmaceutically acceptable salt thereof in the pharmaceutical composition is 1-1000 mg, preferably 1-500 mg, or preferably 1 mg, 2 mg, 3 mg, 5 mg, 10 mg, 20 mg, 40 mg, 50 mg, 60 mg, 80 mg, 100 mg, 200 mg, 300 mg, 400 mg, or 500 mg on a free base basis.

In certain embodiments of the present disclosure, the compound or the stereoisomer or pharmaceutically acceptable salt thereof can be administered by any convenient method, for example, by oral, parenteral, oral cavity, sublingual, nasal cavity, rectal, intrathecal, or transdermal administration, and as pharmaceutical compositions adjusted accordingly.

In certain embodiments of the present disclosure, the compound or the stereoisomer or pharmaceutically acceptable salt thereof can be prepared into a liquid or solid preparation, such as a syrup, a suspension, an emulsion, tablets, capsules, a powder, granules, or a lozenge.

The present disclosure further relates to the use of any compound represented by general formula (I) and a stereoisomer or pharmaceutically acceptable salt thereof or the pharmaceutical composition in the preparation of a PCSK9 inhibitor drug.

The present disclosure further relates to the use of any compound represented by general formula (I) and a stereoisomer or pharmaceutically acceptable salt thereof or the pharmaceutical composition in the preparation of an LDL-lowering drug.

The present disclosure further relates to the use of the general formula (I) and the stereoisomer or pharmaceutically acceptable salt thereof or the pharmaceutical composition in the preparation of a drug for treating a cardiovascular disease, a cerebrovascular disease, atherosclerosis and/or a related disease thereof or a symptom thereof; preferably in the preparation of a drug for stroke, hypercholesterolemia, hyperlipidemia, hyperlipoproteinemia, hypertriglyceridemia, dyslipidemia, abnormal lipoproteinemia, atherosclerosis, hepatic steatosis, metabolic syndrome and/or coronary artery disease.

The present disclosure further relates to the use of the general formula (I) and the stereoisomer or pharmaceutically acceptable salt thereof or the pharmaceutical composition in the preparation of a method for treating a cardiovascular disease, a cerebrovascular disease, atherosclerosis and/or a related disease thereof or a symptom thereof; preferably in the preparation for treating stroke, hypercholesterolemia, hyperlipidemia, hyperlipoproteinemia, hypertriglyceridemia, dyslipidemia, abnormal lipoproteinemia, atherosclerosis, hepatic steatosis, metabolic syndrome and/or coronary artery disease.

The present disclosure further relates to a method for preventing and/or treating stroke, hypercholesterolemia, hyperlipidemia, hyperlipoproteinemia, hypertriglyceridemia, dyslipidemia, abnormal lipoproteinemia, atherosclerosis, hepatic steatosis, metabolic syndrome and/or coronary artery disease, comprising administering a therapeutically effective dose of the compound or the stereoisomer or pharmaceutically acceptable salt thereof, or the pharmaceutical composition thereof according to the present disclosure to a patient.

The present disclosure further provides a method for treating a disease condition with the compound or pharmaceutical composition of the present disclosure. The disease condition includes, but is not limited to, conditions related to PCSK9.

The present disclosure further relates to a method for treating stroke, hypercholesterolemia, hyperlipidemia, hyperlipoproteinemia, hypertriglyceridemia, dyslipidemia, abnormal lipoproteinemia, atherosclerosis, hepatic steatosis, metabolic syndrome and/or coronary artery disease condition in a mammal, comprising administering a therapeutically effective amount of the compound or pharmaceutically acceptable salt, ester, prodrug, solvate, hydrate or derivative according to the present disclosure to the mammal.

DETAILED DESCRIPTION OF THE INVENTION

Unless stated to the contrary, the terms used in the description and claims have the following meanings.

The term “alkyl” refers to a saturated aliphatic hydrocarbon group, which is a linear or branched group containing 1 to 20 carbon atoms, preferably alkyl containing 1 to 8 carbon atoms, more preferably alkyl containing 1 to 6 carbon atoms, and most preferably alkyl containing 1 to 3 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof, etc. More preferably, the alkyl is a lower alkyl group containing 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc. Alkyl can be substituted or unsubstituted, and when substituted, the substituent can be substituted at any available connection point, and the substituent is preferably one or more of groups independently selected from alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, oxo, carboxyl or a carboxylate group. In the present disclosure, alkyl is preferably methyl, ethyl, isopropyl, tert-butyl, haloalkyl, deuteroalkyl, alkoxy-substituted alkyl and hydroxyl-substituted alkyl.

The term “alkylene” refers to one hydrogen atom of alkyl being further substituted, for example: “methylene” refers to $-CH_2-$, “ethylene” refers to $-(CH_2)_2-$, “propylene” refers to $-(CH_2)_3-$, and “butylene” refers to $-(CH_2)_4-$, etc. The term “alkenyl” refers to an alkyl group as defined above consisting of at least two carbon atoms and at least one carbon-carbon double bond, such as ethenyl, 1-propenyl, 2-propenyl, 1-, 2- or 3-butenyl, etc. Alkenyl can be substituted or unsubstituted. When the alkenyl is substituted, the substituent is preferably one or more of groups independently selected from alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, or heterocycloalkylthio.

The term “cycloalkyl” refers to a saturated or partially unsaturated monocyclic or polycyclic cyclic hydrocarbon substituent. The cycloalkyl ring contains 3 to 20 carbon atoms, preferably 3 to 12 carbon atoms, and more preferably 3 to 6 carbon atoms. Non-limiting examples of monocyclic cycloalkyl include cyclopropyl, cyclobutyl, cyclopentyl, cyclopentenyl, cyclopentenyl, cyclohexyl, cyclohexenyl, cyclohexadienyl, cycloheptyl, cycloheptatrienyl, cyclooctyl, etc.; and polycyclic cycloalkyl includes spiro, fused and bridged cycloalkyl, preferably cyclopropyl, cyclobutyl, cyclohexyl, cyclopentyl, and cycloheptyl.

The term “fused cycloalkyl” refers to a 5- to 20-membered all-carbon polycyclic group in which each ring in the system shares an adjacent pair of carbon atoms with other rings in the system, one or more ring of which may contain one or more double bonds, but no ring has a fully conjugated π electron system. Preferably, the bridged heterocyclyl is 6- to 14-membered, and more preferably 7- to 10-membered. According to the number of constituent rings, it can be divided into bicyclic, tricyclic, tetracyclic or polycyclic fused cycloalkyl, preferably bicyclic or tricyclic, and more preferably 5-membered/5-membered or 5-membered/6-membered bicyclic cycloalkyl. Non-limiting examples of fused cycloalkyl include:

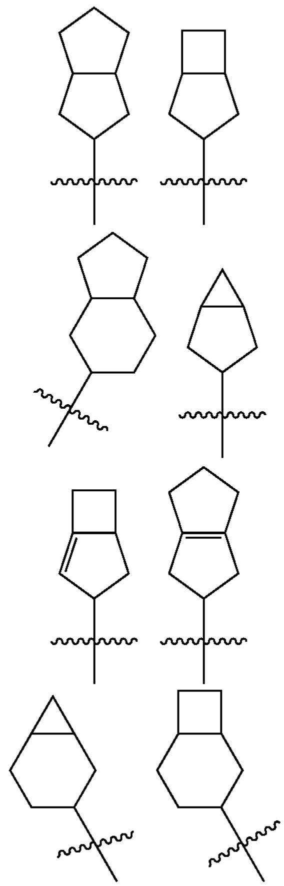

,

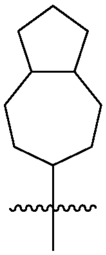

, etc.

The cycloalkyl ring can be fused to an aryl, heteroaryl or heterocycloalkyl ring, wherein the ring connected to the parent structure is cycloalkyl, and non-limiting examples include indanyl, tetrahydronaphthyl, benzocycloheptanyl, etc. Cycloalkyl can be optionally substituted or unsubstituted. When the cycloalkyl is substituted, the substituent is preferably one or more of groups independently selected from alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, oxo, carboxyl or a carboxylate group.

The term "heterocyclyl" refers to a saturated or partially unsaturated monocyclic or polycyclic cyclic hydrocarbon substituent, which comprises 3 to 20 ring atoms, wherein one or more ring atoms are heteroatoms selected from nitrogen, oxygen or $S(O)_m$ (wherein m is an integer of 0 to 2), but excluding ring moieties of —O—O—, —O—S— or —S—S—, and the remaining ring atoms are carbon. Preferably, the heterocyclyl comprises 3 to 12 ring atoms, among which 1-4 are heteroatoms; more preferably, the heterocyclyl comprises 3 to 8 ring atoms; most preferably, the heterocyclyl comprises 3 to 8 ring atoms; further preferably, the heterocyclyl is 3-membered, 4-membered, 5-membered, 6-membered, 7-membered, or 8-membered heterocyclyl comprising 1-3 nitrogen atoms, optionally substituted with 1-2 oxygen atoms, sulfur atoms, or oxo, including nitrogen-containing monocyclic heterocyclyl, nitrogen-containing spiro heterocyclyl, or nitrogen-containing fused heterocyclyl; alternatively, preferably, the heterocyclyl comprises 5 to 12 ring atoms, among which 1-4 are heteroatoms and is further preferably 5-membered, 6-membered, 7-membered, 8-membered, 9-membered, 10-membered, 11-membered, or 12-membered heterocyclyl comprising 1-3 nitrogen and/or oxygen atoms.

Non-limiting examples of monocyclic heterocyclyl include pyrrolidinyl, imidazolidinyl, tetrahydrofuryl, tetrahydrothienyl, dihydroimidazolyl, dihydrofuryl, dihydropyrazolyl, dihydropyrrolyl, piperidinyl, piperazinyl, morpholinyl, thiomorpholinyl, homopiperazinyl, azepinyl, 1,4-diazacycloheptyl, pyranyl, etc., preferably pyrrolidinyl, morpholinyl, piperidinyl, azepinyl, 1,4-diazacycloheptyl and piperazinyl. Polycyclic heterocyclyl includes spiro, fused and bridged heterocyclyl, wherein the spiro, fused and bridged heterocyclyl groups are optionally connected to other groups through a single bond, or further fused to other cycloalkyl, heterocyclyl, aryl and heteroaryl through any two or more atoms on the ring.

The term "fused heterocyclyl" refers to a 5- to 20-membered polycyclic heterocyclyl with each ring in the system sharing a pair of atoms neighboring other rings in the system, and one or more rings may contain one or more double bonds, but no ring has a fully conjugated n electron system, wherein one or more ring atoms are heteroatoms selected from nitrogen, oxygen, or $S(O)_m$ (wherein m is an integer of 0 to 2), and the remaining ring atoms are carbon. Preferably, the bridged heterocyclyl is 6- to 14-membered, and more preferably 7- to 10-membered. According to the number of constituent rings, it can be divided into bicyclic, tricyclic, tetracyclic or polycyclic fused heterocyclyl, preferably bicyclic or tricyclic, more preferably 5-membered fused 5-membered or 5-membered fused 6-membered bicyclic heterocyclyl. Non-limiting examples of fused heterocyclyl include:

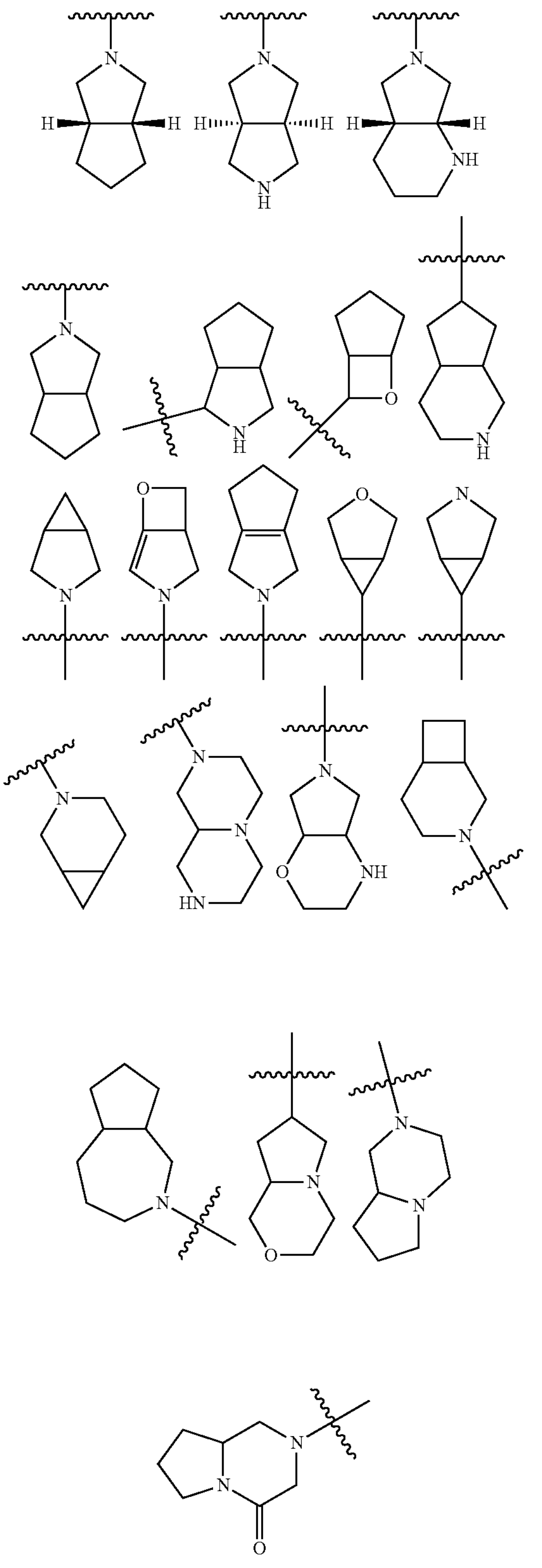

etc.

The heterocyclyl ring can be fused to an aryl, heteroaryl or cycloalkyl ring, wherein the ring connected to the parent structure is heterocyclyl, and the non-limiting examples thereof include:

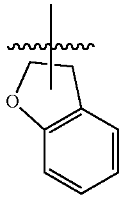
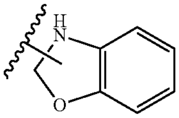
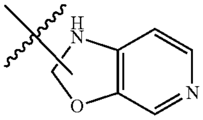
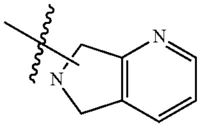
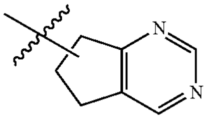
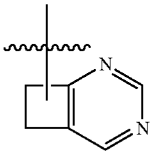
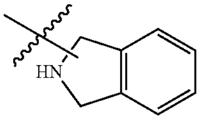
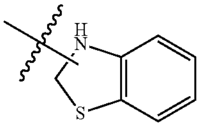

etc.

Heterocyclyl can be optionally substituted or unsubstituted. When the heterocyclyl is substituted, the substituent is preferably one or more of groups independently selected from alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, oxo, carboxyl or a carboxylate group.

The term "aryl" refers to a 6- to 14-membered all-carbon monocyclic or fused polycyclic (i.e., rings sharing an adjacent pair of carbon atoms) group having a conjugated n electron system, preferably 6- to 12-membered aryl, such as phenyl and naphthyl, and more preferably phenyl. The aryl ring can be fused to heteroaryl, heterocyclyl or cycloalkyl ring, including benzo 5- to 10-membered heteroaryl, benzo 3- to 8-membered cycloalkyl and benzo 3- to 8-membered heteroalkyl, preferably benzo 5- to 6-membered heteroaryl, benzo 3- to 6-membered cycloalkyl and benzo 3- to 6-membered heteroalkyl, wherein the heterocyclyl is heterocyclyl containing 1-3 nitrogen atoms, oxygen atoms, or sulfur atoms; or further including a three-membered nitrogen-containing fused ring containing a benzene ring, wherein the ring connected to the parent structure is aryl ring, and the non-limiting examples thereof include:

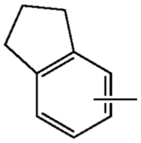
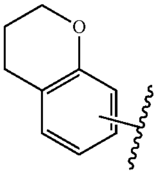
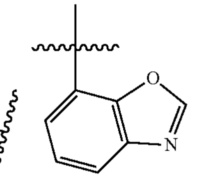
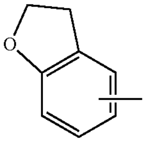
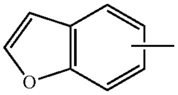
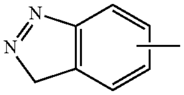

-continued

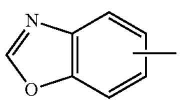
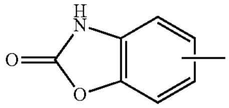
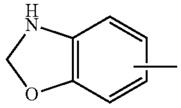
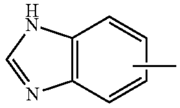
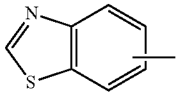
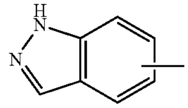
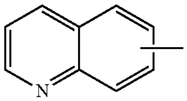
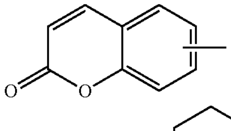
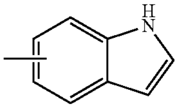
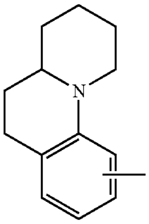

etc.

Aryl can be substituted or unsubstituted. When the aryl is substituted, the substituent is preferably one or more of groups independently selected from alkyl, alkenyl, alkynyl, alkoxy, alkylthio, alkylamino, halogen, mercapto, hydroxyl, nitro, cyano, cycloalkyl, oxo, heterocycloalkyl, aryl, heteroaryl, cycloalkoxy, heterocycloalkoxy, cycloalkylthio, heterocycloalkylthio, carboxyl or a carboxylate group.

The term "heteroaryl" refers to a heteroaromatic system containing 1 to 4 heteroatoms and 5 to 14 ring atoms, wherein the heteroatoms are selected from oxygen, sulfur and nitrogen. The heteroaryl is preferably 5- to 12-membered, more preferably 5-membered or 6-membered monocyclic heteroaryl or 8- to 12-membered bicyclic heteroaryl, such as imidazolyl, furyl, thienyl, thiazolyl, pyrazolyl, oxazolyl, oxadiazolyl, pyrrolyl, triazolyl, tetrazolyl, pyridinyl, pyrimidinyl, thiadiazole, pyrazinyl, triazinyl, pyridazinyl, etc., preferably triazolyl, thienyl, imidazolyl, pyrazolyl, oxazolyl, pyrimidinyl, or thiazolyl; more preferably, pyrazolyl, pyrrolyl and oxazolyl.

The bicyclic heteroaryl is preferably 5-membered fused 5-membered bicyclic heteroaryl, 5-membered fused 6-membered bicyclic heteroaryl, 6-membered fused 5-membered bicyclic heteroaryl, or 6-membered fused 6-membered bicyclic heteroaryl, and non-limiting examples thereof include:

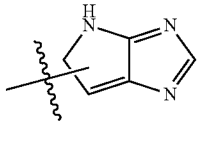
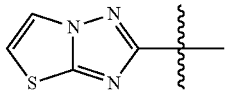
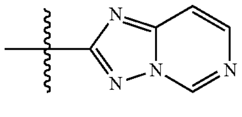
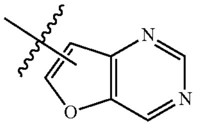

-continued
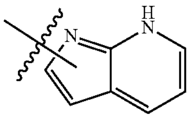
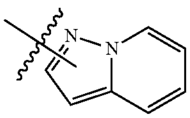
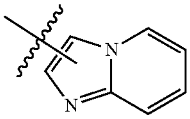
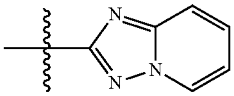
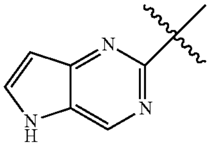
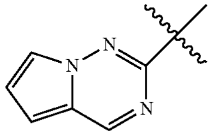
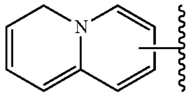
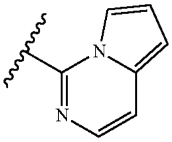
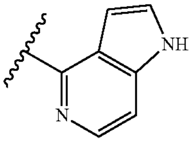
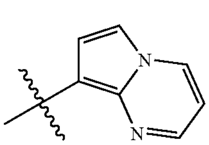
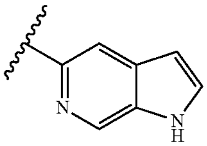
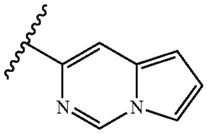
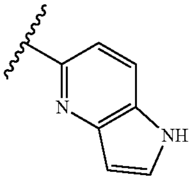
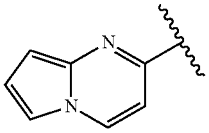
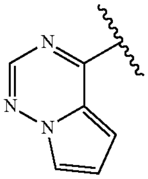
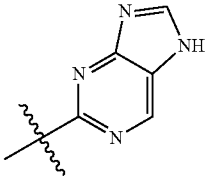
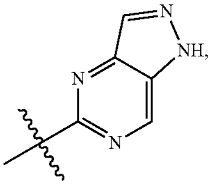
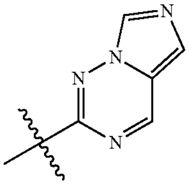
,
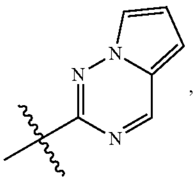
,
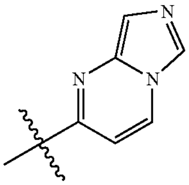
,
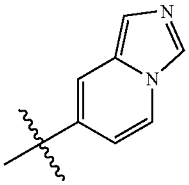
,
-continued
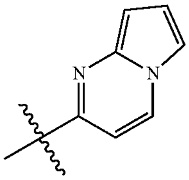
,
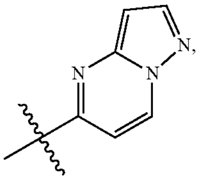
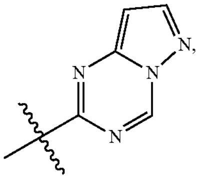
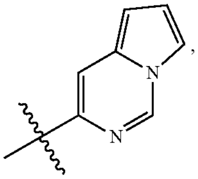
,
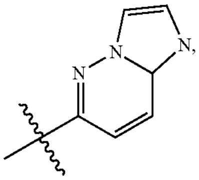
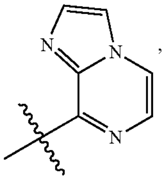
,
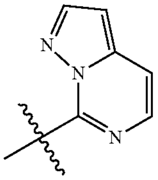
,
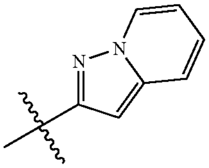
,
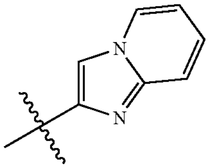
,
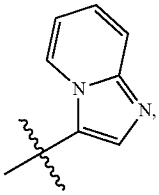
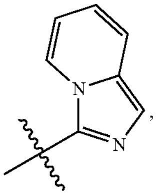
,
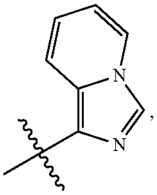
,
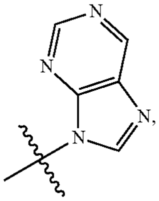
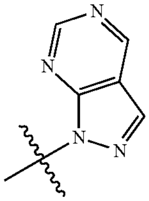
or
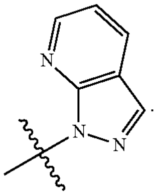
.
The heteroaryl ring can be fused to an aryl, heterocyclyl or cycloalkyl ring, wherein the ring connected to the parent structure is heteroaryl ring, and the non-limiting examples thereof include:
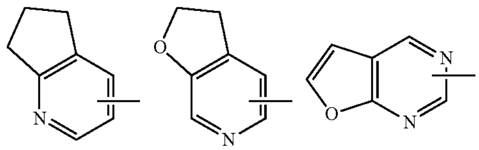
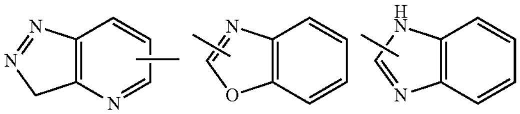
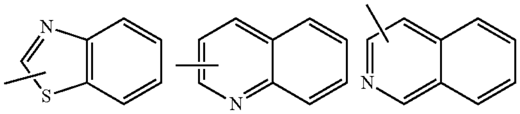

-continued

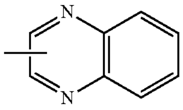
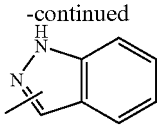
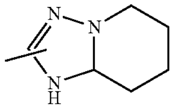
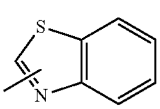
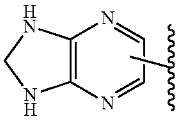
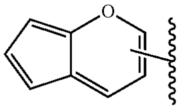
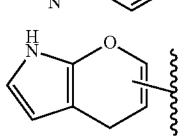
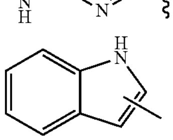
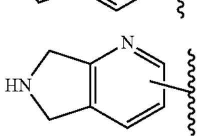
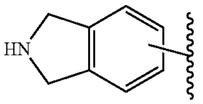
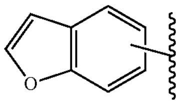
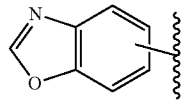

etc.

Heteroaryl can be optionally substituted or unsubstituted. When the heterocyclyl is substituted, the substituent is preferably one or more of groups independently selected from alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl, oxo, or a carboxylate group.

The term "alkoxy" refers to —O-(alkyl) and —O-(unsubstituted cycloalkyl), where the alkyl is as defined above. Non-limiting examples of alkoxy include: methoxy, ethoxy, propoxy, butoxy, cyclopropoxy, cyclobutoxy, cyclopentoxy, and cyclohexoxy. Alkoxy can be optionally substituted or unsubstituted. When the alkoxy is substituted, the substituent is preferably one or more of groups independently selected from alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl or a carboxylate group.

"Haloalkyl" refers to alkyl substituted with one or more halogen, wherein alkyl is defined as above.

"Haloalkoxy" refers to alkoxy substituted with one or more halogen, wherein alkoxy is defined as above.

"Hydroxyalkyl" refers to alkyl substituted with hydroxyl, wherein alkyl is defined as above.

"Alkenyl" is also known as alkylene, wherein the alkenyl can be further substituted with other related groups, such as: alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl or a carboxylate group.

"Alkynyl" refers to (CH≡C—), wherein the alkynyl can be further substituted with other related groups, such as: alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl or a carboxylate group.

The term "alkenylcarbonyl" refers to —C(O)-(alkenyl), wherein alkenyl is defined as above. Non-limiting examples of alkenylcarbonyl include: ethenylcarbonyl, propenylcarbonyl, and butenylcarbonyl. Alkenylcarbonyl can be optionally substituted or unsubstituted. When the alkenylcarbonyl is substituted, the substituent is preferably one or more of groups independently selected from alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl or a carboxylate group.

Different terms such as "X is selected from A, B, or C", "X is selected from A, B and C", "X is A, B or C", and "X is A, B and C" all express the same meaning, i.e., X can be any one or more of A, B, and C.

The hydrogen atoms of the present disclosure can be replaced with its isotope deuterium, and any hydrogen atom in the example compounds involved in the present disclosure can also be replaced with a deuterium atom.

"Optional" or "optionally" means that the event or circumstance subsequently described may but need not to occur, and the description includes the occasion where the event or circumstance occurs or does not occur. For example, "heterocyclic group optionally substituted with alkyl" means the alkyl may but need not be present, and the description includes the case where the heterocyclic group is substituted with alkyl and the case where the heterocyclic group is not substituted with alkyl.

"Substituted" means that one or more hydrogen atoms, preferably at most 5, more preferably 1-3 hydrogen atoms in the group are each independently substituted with a corresponding number of substituents. It goes without saying, the substituents may be only in their possible chemical positions, a person skilled in the art can determine the possible or impossible substitutions (by experiment or theory) without paying too much effort. For example, the amino group having a free hydrogen or a hydroxyl group may be unstable when combined the carbon atoms having an unsaturated (e.g., olefinic) bond.

"Pharmaceutical composition" denotes a mixture containing one or more compounds described herein or physiologically/pharmaceutically acceptable salts or prodrug thereof and other chemical components, as well as other components, such as physiologically/pharmaceutically acceptable carriers and excipients. The purpose of pharmaceutical compositions is to facilitate administration to living organisms and facilitate the absorption of active ingredients to exert biological activity.

"Pharmaceutically acceptable salts" refer to salts of the compounds of the present disclosure, which are safe and effective when used in mammals, and have appropriate biological activity.

DETAILED DESCRIPTION OF EMBODIMENTS

The present disclosure will be further described below in conjunction with examples, but these examples are not meant to limit the scope of the present disclosure.

EXAMPLES

The structure of the compound of the present disclosure is determined by nuclear magnetic resonance (NMR) or/and liquid chromatography-mass spectrometry (LC-MS). NMR chemical shift (S) is given in parts per million (ppm). NMR was determined using Bruker AVANCE-400 nuclear magnetic instrument. The solvent for the determination is deuterated dimethyl sulfoxide ($DMSO-d_6$), deuterated methanol ($CD_3OD$), deuterated chloroform ($CDCl_3$), or deuterium water ($D_2O$), and the internal standard, if any, is tetramethylsilane (TMS).

Agilent 1200 Infinity Series mass spectrometer is used for measurement by liquid chromatography-mass chromatography (LC-MS). For determination by HPLC, Agilent 1200DAD high-pressure liquid chromatograph (Sunfire C18 150×4.6 mm chromatographic column) and Waters 2695-2996 high-pressure liquid chromatograph (Gimini $C_{18}$ 150×4.6 mm chromatographic column) are used.

Yantai Huanghai HSGF254 or Qingdao GF254 silica gel plate is used as a thin layer chromatography silica plate, and TLC is of the specification of 0.15-0.20 mm, and the specification when separating and purifying a product by thin layer chromatography is 0.4-0.5 mm. For column chromatography, Yantai Huanghai silica gel of 200-300 mesh silica gel is generally used as a carrier.

The starting materials in the examples of the present disclosure are known and can be purchased on the market, or can be synthesized using or according to methods known in the art.

Unless otherwise specified, all reactions in the present disclosure are carried out under continuous magnetic stirring in a dry nitrogen or argon atmosphere, the solvent is a dry solvent, and the reaction temperature unit is degrees Celsius.

Eluent systems for silica gel column chromatography and developer systems for thin layer chromatography, which are used for the purification of compounds in the intermediates and examples, include: A: dichloromethane and methanol system, B: n-hexane and ethyl acetate system, and C: dichloromethane and acetone system, wherein the volume ratio between the solvents could be adjusted depending on the polarity of the compound, or could also be adjusted by adding a small amount of basic or acidic reagents such as triethylamine and acetic acid.

Unless otherwise specified, in the examples of the present disclosure, ratios in mobile phases in HPLC chiral resolution conditions and HPLC chiral analysis conditions were volume ratios.

Intermediate 1

(1S,3S)—N1-(5-(difluoromethoxy)pyrimidin-2-yl) cyclopentane-1,3-diamine

By reference to the preparation method of patent WO 2020150473 A2, intermediate 1 was synthesized.

MS m/z (ESI): 245.1 [M+H]$^+$.

Intermediate 1 could also be obtained by the following method:

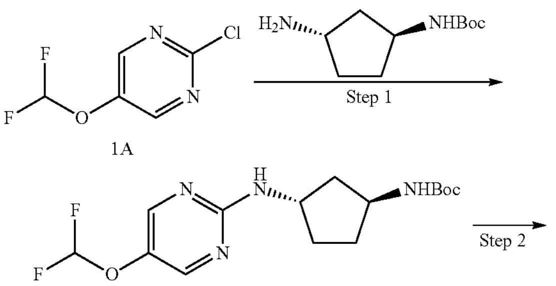

1A

1B

-continued

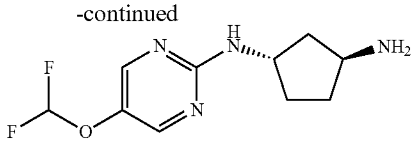

Intermediate 1

Step 1

2-Chloro-5-(difluoromethoxy)pyrimidine 1A (2.0 g, 11.1 mmol), tert-butyl (1S,3S)-3-aminocyclopentylcarbamate (2.44 g, 12.2 mmol), and diisopropylethylamine (2.86 g, 14.08 mmol) were dissolved in dimethyl sulfoxide (10 mL), and the reaction was heated to 100° C. and stirred for 5 hours. The reaction liquid was cooled to room temperature and poured into water (50 mL), and the aqueous phase was extracted with ethyl acetate (100 mL×2). The organic phases were combined, washed successively with water (50 mL) and a saturated sodium chloride solution (50 mL), dried, and concentrated, and the residue was purified by silica gel chromatography (elution system B) to separate tert-butyl (1S,3S)-3-((5-(difluoromethoxy)pyrimidin-2-yl)amino)cyclopentylcarboxylate 1B (2.1 g), yield: 55.1%.

MS m/z (ESI): 345.2 [M+H]$^+$.

Step 2

1B (2.1 g, 6.1 mmol) was dissolved in methanol (10 mL), a solution of hydrochloric acid in dioxane (4M, 20 mL) was added, and the reaction was stirred at room temperature for 2 hours. The reaction liquid was concentrated, and the pH was adjusted to weak alkalinity by adding an ammonia methanol solution (7M, 10 mL). After concentration again, the residue was purified by silica gel chromatography (elution system A) to separate intermediate 1, (1 S,3S)—$N^1$-(5-(difluoromethoxy)pyrimidin-2-yl)cyclopentane-1,3-diamine (1.3 g), yield: 87.3%.

MS m/z (ESI): 245.1 [M+H]$^+$.

Intermediate 2

6'-(((1S,3S)-3-aminocyclopentyl)amino)-2H-[1,3'-bipyridinyl]-2-one

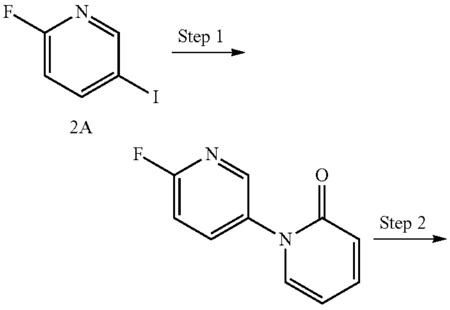

2A

2B

-continued

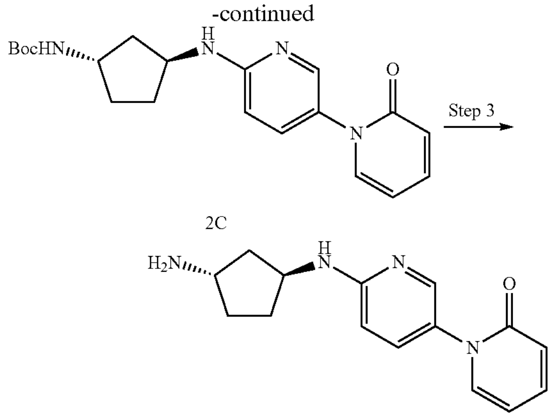

2C

Intermediate 2

Step 1

2-Fluoro-5-iodopyridine 2A (5 g, 22.4 mmol), 2-hydroxy-pyridine (2.35 g, 24.7 mmol), cuprous iodide (427 mg, 2.24 mmol), trans-(1R,2R)—N,N-dimethyl 1,2-cyclohexanediamine (159 mg, 1.12 mmol), and cesium carbonate (9.5 g, 29.2 mmol) were dissolved in 1,4-dioxane (75 mL), and the reaction was heated to 100° C. and stirred for 16 hours. The reaction liquid was cooled to room temperature and poured into 100 mL of water, and the aqueous phase was extracted with ethyl acetate (100 mL×2). The organic phases were combined, washed successively with water (100 mL) and a saturated sodium chloride solution (100 mL), dried, and concentrated, and the residue was purified by silica gel chromatography (elution system B) to obtain 6'-fluoro-2H-[1,3'-bipyridinyl]-2-one 2B (3.1 g), yield: 72.7%.

MS m/z (ESI): 191.1 $[M+H]^+$.

Step 2

Tert-butyl (1S,3S)-3-aminocyclopentylcarbamate (2.0 g, 9.99 mmol), 6'-fluoro-2H-[1,3'-bipyridinyl]-2-one 2B (2.85 g, 14.9 mmol), and N,N-diisopropylethylamine (3.87 g, 30.0 mmol) were dissolved in dimethyl sulfoxide (30 mL), and the reaction was heated to 130° C. and stirred for 16 hours. The reaction liquid was cooled to room temperature and poured into water (100 mL), and the aqueous phase was extracted with ethyl acetate (100 mL×2). The organic phases were combined, washed successively with water (100 mL) and a saturated sodium chloride solution (100 mL), dried, and concentrated, and the residue was purified by silica gel chromatography (elution system B) to obtain tert-butyl ((1S,3S)-3-((2-carbonyl-2H-[1,3'-bipyridinyl]-6'-yl)amino)cyclopentyl)carbamate 2C (2.9 g), yield: 78.4%.

MS m/z (ESI): 371.2 $[M+H]^+$.

Step 3

Tert-butyl ((1S,3S)-3-((2-carbonyl-2H-[1,3'-bipyridinyl]-6'-yl)amino)cyclopentyl) carbamate 2C (2.9 g, 7.83 mmol) was dissolved in a solution of 4 M hydrochloric acid in dioxane (30 mL), and the reaction was stirred at room temperature for 3 hours. The reaction liquid was concentrated, and the residue was purified by a reversed-phase chromatographic column (eluent system C) to obtain intermediate 2, 6'-(((1S,3S)-3-aminocyclopentyl)amino)-2H-[1,3'-bipyridinyl]-2-one (1.5 g), yield: 70.9%.

MS m/z (ESI): 271.2 $[M+H]^+$.

Example 1

6'-(((1S,3S)-3-((5-(difluoromethoxy)-3-fluoropyridin-2-yl)amino)cyclopentyl)amino)-2H-[1,3'-bipyridinyl]-2-one Example 1 could also be obtained by the following method:

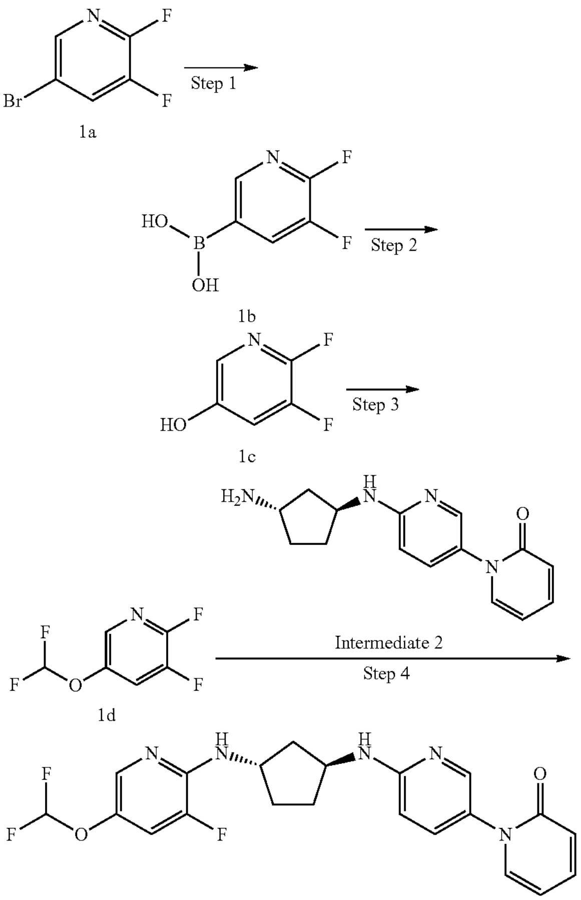

1a

1b

1c

1d

1

Step 1

Under nitrogen protection, la (10.00 g, 51.55 mmol), bis(pinacolato)diboron (19.64 g, 77.33 mmol), 1,1-bis(diphenylphosphino)ferrocene dichloropalladium (3.79 g, 5.16 mmol), and potassium acetate (10.10 g, 103.11 mmol) were dissolved in 1,4-dioxane (200 mL), heated to 90° C., and stirred for 3 hours. The reaction liquid was filtered, and the organic phase was concentrated to obtain crude (5,6-difluoro-3-pyridinyl)boronic acid 1b (7.60 g), which was directly used in the next reaction without purification.

MS m/z (ESI): 160.0 $[M+H]^+$.

Step 2

1b (6.00 g, 37.76 mmol) and hydrogen peroxide (12.84 g, 113.28 mmol, 30% aqueous solution) were dissolved in 1,4-dioxane (100 mL) and stirred at room temperature for 3 hours. The reaction liquid was diluted with ethyl acetate (200 mL), and the organic phase was washed with water (100 mL) and saturated sodium chloride (100 mL). The organic phase was dried and concentrated, and the residue was separated by silica gel column chromatography (eluent system A) to obtain 5,6-difluoro-3-hydroxypyridine 1c (3.20 g), yield: 64.6%.

MS m/z (ESI): 132.0 $[M+H]^+$.

Step 3

At room temperature, 1c (5.00 g, 38.14 mmol) and cesium carbonate (18.60 g, 57.22 mmol) were dissolved in N,N-dimethylformamide (30 mL) and stirred for 30 minutes. Under nitrogen protection, sodium 2-chloro-2,2-difluoroacetate (11.90 g, 76.29 mmol) was added to the reaction liquid, heated to 90° C., and stirred for 3 hours. The reaction liquid was diluted with ethyl acetate (200 mL) and concentrated, and the filtrate was washed with water (50 mL) and saturated sodium chloride (50 mL). The organic phase was concentrated, and the residue was separated by silica gel column chromatography (eluent system A) to obtain 5-(difluoromethoxy)-2,3-difluoropyridine Id (2.60 g), yield: 37.6%.

MS m/z (ESI): 182.0 $[M+H]^+$.

Step 4

By reference to the synthesis method of step 1 for intermediate 1, 6'-(((1S,3S)-3-((5-(difluoromethoxy)-3-fluoropyridin-2-yl)amino)cyclopentyl)amino)-2H-[1,3'-bipyridinyl]-2-one 1 was synthesized.

MS m/z (ESI): 432.2 $[M+H]^+$.

$^1$H NMR (400 MHz, DMSO-$d_6$) δ 7.92 (d, 1H), 7.80 (d, 1H), 7.60 (m, 1H), 7.42 (m, 3H), 7.04 (t, 1H), 6.93 (d, 1H), 6.72 (m, 1H), 6.53 (d, 1H), 6.44 (m, 1H), 6.27 (m, 1H), 4.45 (m, 1H), 4.33 (m, 1H), 2.11 (m, 2H), 1.93 (m, 2H), 1.52 (m, 2H).

Example 4

6'-(((1S,3S)-3-((6-(difluoromethoxy)-1,2,4-triazin-3-yl)amino)cyclopentyl)amino)-2H-[1,3'-bipyridinyl]-2-one

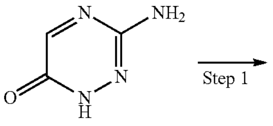

4a

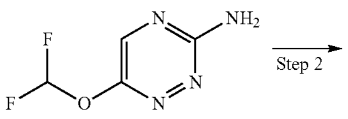

4b

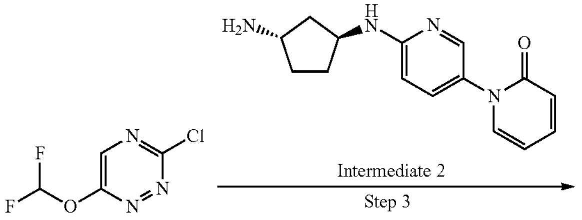

4c

-continued

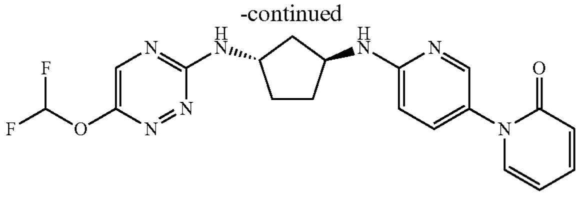

4

Step 1

3-Amino-1,2,4-triazin-6(1H)-one 4a (1 g, 8.92 mmol), trimethylsilyl 2-(fluorosulfonyl)difluoroacetate (3.35 g, 13.4 mmol), and 1,4-diazabicyclo[2.2.2]octane (2.0 g, 17.8 mmol) were dissolved in anhydrous toluene (15 mL), and the reaction was heated to 80° C. and stirred for 2 hours. The reaction liquid was cooled to room temperature, washed successively with water (30 mL) and a saturated sodium chloride solution (30 mL), dried, and concentrated, and the residue was purified by silica gel chromatography (elution system B) to obtain 6-(difluoromethoxy)-1,2,4-triazinyl-3-amine 4b (430 mg), yield: 29.7%.

MS m/z (ESI): 163.0 $[M+H]^+$.

Step 2

Under nitrogen protection, 6-(difluoromethoxy)-1,2,4-triazinyl-3-amine 4b (430 mg, 2.65 mmol), tert-butyl nitrite (410 mg, 3.98 mmol), and cuprous chloride (341 mg, 3.45 mmol) were dissolved in anhydrous acetonitrile (6 mL), and the reaction was heated to 70° C. and stirred for 2 hours. The reaction liquid was cooled to room temperature and concentrated, and the residue was purified by silica gel chromatography (elution system B) to obtain 3-chloro-6-(difluoromethoxy)-1,2,4-triazine 4c (260 mg), yield: 54.0%.

MS m/z (ESI): 182.0 $[M+H]^+$.

Step 3

Under nitrogen protection, intermediate 2 (80 mg, 0.256 mmol), 3-chloro-6-(difluoromethoxy)-1,2,4-triazine 4c (54 mg, 0.256 mmol), and N,N-diisopropylethylamine (115 mg, 0.888 mmol) were dissolved in dimethyl sulfoxide (2 mL), and the reaction was heated to 80° C. and stirred for 3 hours. The reaction liquid was cooled to room temperature, and ethyl acetate (30 mL) was added. The organic phase was washed successively with water (30 mL) and a saturated sodium chloride solution (30 mL), dried, and concentrated, and the residue was purified by a reversed-phase chromatographic column (ammonium bicarbonate system) to obtain 6'-(((S,3S)-3-((6-(difluoromethoxy)-1,2,4-triazin-3-yl) amino)cyclopentyl) amino)-2H-[1,3'-bipyridinyl]-2-one 4 (37 mg), yield: 30.1%.

MS m/z (ESI): 416.2 $[M+H]^+$.

Example 12

6'-(((1S,3S)-3-((1-cyclopropyl-1H-1,2,4-triazol-3-yl) amino)cyclopentyl)amino)-2H-[1,3'-bipyridinyl]-2-one

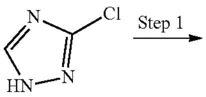

12a

-continued

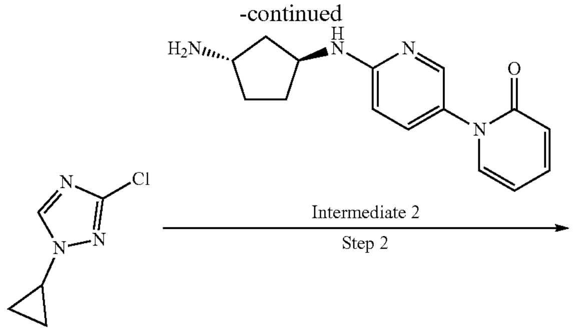

12b

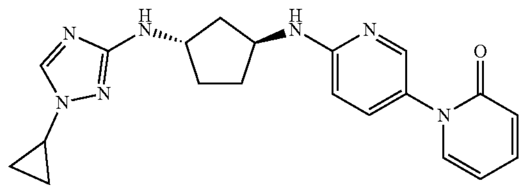

12

Step 1

3-Chloro-1,2,4-triazole 12a (1 g, 9.66 mmol), cyclopropylboronic acid (1.66 g, 19.3 mmol), copper acetate (2.63 g, 14.5 mmol), 2,2'-bipyridinyl (2.26 g, 14.5 mmol), and sodium carbonate (2.05 g, 19.3 mmol) were dissolved in 1,2-dichloroethane (20 mL), and the reaction was heated to 80° C. and stirred for 3 hours. The reaction liquid was cooled to room temperature and filtered, the filtrate was washed successively with water (30 mL) and a saturated sodium chloride solution (30 mL), dried, and concentrated, and the residue was purified by silica gel chromatography (elution system B) to obtain 3-chloro-1-cyclopropyl-1H-1,2,4-triazole 12b (340 mg), yield: 24.5%.

MS m/z (ESI): 144.0 $[M+H]^+$.

Step 2

By reference to the synthesis method of Example 4, the target compound 6'-(((1S,3S)-3-((1-cyclopropyl-1H-1,2,4-triazol-3-yl)amino)cyclopentyl)amino)-2H-[1,3'-bipyridinyl]-2-one 12 was synthesized.

MS m/z (ESI): 378.2 $[M+H]^+$.

$^1H$ NMR (400 MHz, $CD_3OD$) δ 8.02 (s, 1H), 7.94 (d, 1H), 7.64-7.56 (m, 2H), 7.44 (dd, 1H), 6.67-6.57 (m, 2H), 6.46 (t, 1H), 4.34-4.29 (m, 1H), 4.13-4.05 (m, 1H), 3.52-3.44 (m, 1H), 2.28-2.17 (m, 2H), 2.03-1.95 (m, 2H), 1.65-1.52 (m, 2H), 1.14-0.97 (m, 4H).

Example 15

6'-(((1S,3S)-3-((5-(difluoromethoxy)-1,2,4-thiadiazol-3-yl)amino)cyclopentyl)amino)-2H-[1,3'-bipyridinyl]-2-one

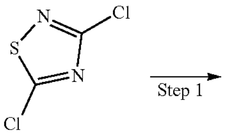

15a

-continued

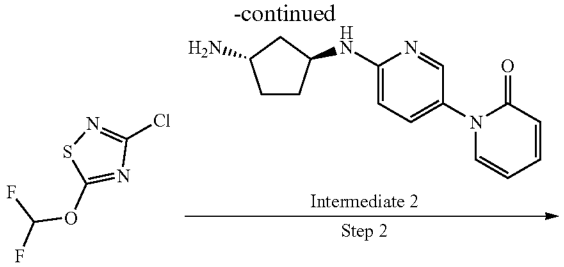

15b

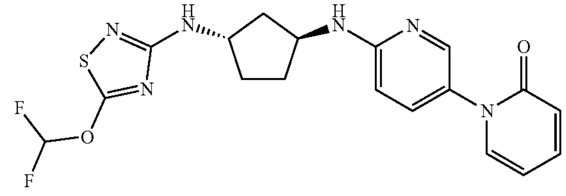

15

Step 1

Under nitrogen protection, 3-bromo-5-chloro-1,2,4-thiadiazole 15a (400 mg, 2.01 mmol), difluoromethyl trifluoromethanesulfonate (803 mg, 4.02 mmol), tris(dibenzylideneindeneacetone)dipalladium (184 mg, 0.201 mmol), 2-di-tert-butylphosphino-2',4',6'-triisopropylbiphenyl (170 mg, 0.401 mmol), and potassium hydroxide (169 mg, 3.01 mmol) were dissolved in 1,4-dioxane (6 mL), and the reaction was heated to 100° C. and reacted for 6 hours. The reaction liquid was cooled to room temperature, and ethyl acetate (50 mL) was added. The organic phase was washed successively with water (30 mL) and a saturated sodium chloride solution (30 mL), dried, and concentrated, and the residue was purified by silica gel chromatography (elution system B) to obtain 3-chloro-5-(difluoromethoxy)-1,2,4-thiadiazole 15b (130 mg), yield: 28.1%.

MS m/z (ESI): 187.0 $[M+H]^+$.

Step 2

By reference to the synthesis method of Example 4, the target compound 6'-(((1S,3S)-3-((5-(difluoromethoxy)-1,2,4-thiadiazol-3-yl)amino)cyclopentyl) amino)-2H-[1,3'-bipyridinyl]-2-one 15 was synthesized.

MS m/z (ESI): 421.1 $[M+H]^+$.

Example 20

6'-(((1S,3S)-3-(pyrrolo[2,1-f][1,2,4]triazin-2-ylamino)cyclopentyl)amino)-2H-[1,3'-bipyridinyl]-2-one

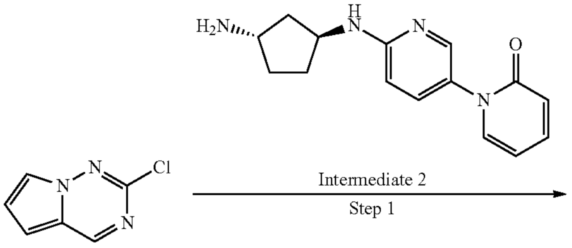

20a

-continued

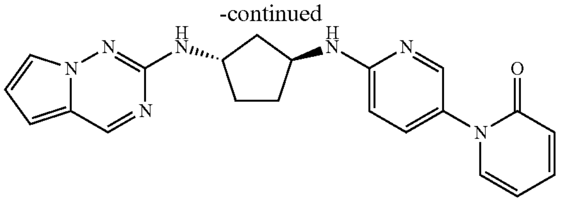

20

Step 1

2-Chloropyrrolo[2,1-f][1,2,4]triazine 20a (50 mg, 0.326 mmol), intermediate 2 (88 mg, 0.326 mmol), and diisopropylethylamine (84 mg, 0.651 mmol) were dissolved in dimethyl sulfoxide (3 mL), and the reaction was heated to 110° C. and stirred for 16 hours. The reaction was brought back to room temperature, and a saturated sodium chloride solution (10 mL) was added to the reaction liquid. The aqueous phase was extracted with ethyl acetate (10 mL×3), the organic phases were combined, dried, and concentrated, and the residue was separated by silica gel column chromatography (eluent system A) to obtain 6'-(((1S,3S)-3-(pyrrolo[2,1-f][1,2,4]triazin-2-ylamino)cyclopentyl)amino)-2H-[1,3'-bipyridinyl]-2-one 20 (85 mg), yield: 67.4%.

MS m/z (ESI): 388.2 $[M+H]^+$.

$^1H$ NMR (400 MHz, $CD_3OD$) δ 8.67 (s, 1H), 7.98 (s, 1H), 7.63-7.57 (m, 2H), 7.51 (dd, 1H), 7.45 (d, 1H), 6.71 (m, 2H), 6.61 (dt, 2H), 6.46 (td, 1H), 4.39-4.26 (m, 2H), 2.34-2.17 (m, 2H), 2.13-1.98 (m, 2H), 1.71-1.57 (m, 2H).

Example 22

6'-(((1S,3S)-3-((5-(2,2-difluorocyclopropyl)-1,2,4-oxadiazol-3-yl)amino)cyclopentyl)amino)-2H-[1,3'-bipyridinyl]-2-one Example 22 could also be synthesized by the following method:

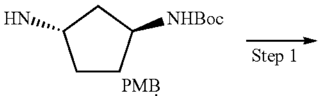

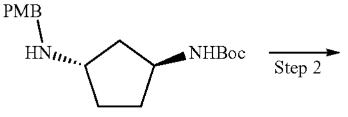

22a

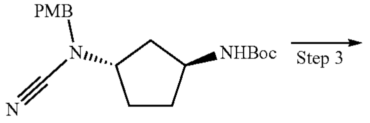

22b

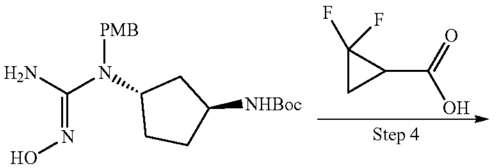

22c

-continued

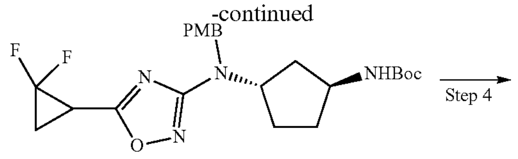

22d

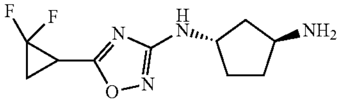

22e

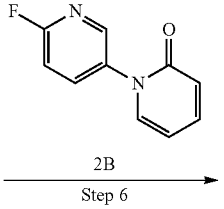

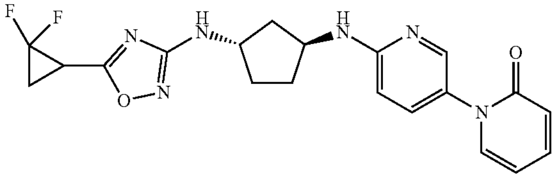

22

Step 1

Tert-butyl ((1S,3S)-3-aminocyclopentyl)carbamate (1.0 g, 4.99 mmol) and 4-methoxybenzaldehyde (816 mg, 5.99 mmol) were dissolved in methanol (10 mL), and acetic acid (300 mg, 4.99 mmol) was added under stirring. The reaction was stirred at 17° C. for 16 hours. Sodium cyanoborohydride (941 mg, 14.98 mmol) was added to the reaction liquid, and the reaction was stirred for 1 hour. The reaction liquid was concentrated, and the residue was purified by silica gel column chromatography (elution system C) to obtain tert-butyl ((1S,3S)-3-((4-methoxybenzyl)amino)cyclopentyl) carbamate 22a (1.2 g), yield: 75%.

MS m/z (ESI): 321.3 $[M+H]^+$.

Step 2

22a (1.3 g, 4.06 mmol), cyanogen bromide (645 mg, 6.09 mmol), and N,N-diisopropylethylamine (1.0 g, 8.11 mmol) were dissolved in tetrahydrofuran (10 mL), stirred, and added. The reaction was stirred at 18° C. for 16 hours. The reaction liquid was concentrated, and the residue was purified by silica gel column chromatography (elution system C) to obtain tert-butyl ((1S,3S)-3-(N-(4-methoxybenzyl)cyanamino)cyclopentyl)carbamate 22b (1.2 g), yield: 85.6%.

MS m/z (ESI): 346.1 $[M+H]^+$.

Step 3

Under nitrogen protection, 22b (1.15 g, 3.33 mmol), hydroxylamine hydrochloride (578.4 mg, 8.32 mmol), and triethylamine (1.35 g, 13.32 mmol) were dissolved in isopropanol (10 mL), heated to 90° C., and stirred for 16 hours. The reaction liquid was concentrated, and the residue was purified by silica gel column chromatography (elution system C) to obtain tert-butyl ((1S,3S)-3-((E)-2-hydroxy-1-(4-methoxybenzyl)guanidino)cyclopentyl)carbamate 22c (1.0 g), yield: 79.4%.

MS m/z (ESI): 379.2 $[M+H]^+$.

Step 4

At room temperature, 2,2-difluorocyclopropane-1-carboxylic acid (419 mg, 3.43 mmol) and carbonyldiimidazole (557 mg, 3.43 mmol) were dissolved in N,N-dimethylformamide (10 mL) and stirred for 0.5 hours. 22c (1.0 g, 2.64 mmol) was dissolved in N,N-dimethylformamide (2 mL) and dropwise added to the reaction liquid. The reaction was stirred at room temperature for 1 hour, then heated to 100° C., and stirred for 1 hour. The reaction liquid was diluted with ethyl acetate (100 mL), and the organic phase was washed with saturated sodium chloride (60 mL×3), dried, and concentrated. The residue was purified by silica gel column chromatography (elution system C) to obtain tert-butyl ((1S,3S)-3-((5-(2,2-difluorocyclopropyl)-1,2,4-oxadiazol-3-yl)(4-methoxybenzyl)amino)cyclopentyl)carbamate 22d (390 mg), yield 31.8%.

MS m/z (ESI): 465.3 $[M+H]^+$.

Step 5

22d (390 mg, 0.84 mmol) was dissolved in trifluoroacetic acid (10 mL), and the reaction was stirred at 18° C. for 1 hour. The reaction liquid was concentrated and adjusted to pH=8 by adding an ammonia methanol solution (7M) to the residue. The reaction liquid was concentrated, and the residue was purified by reversed-phase chromatography (aqueous ammonia system) to obtain (1S,3S)—N1-(5-(2,2-difluorocyclopropyl)-1,2,4-oxadiazol-3-yl)cyclopentane-1,3-diamine 22e (70 mg), yield 34.1%.

MS m/z (ESI): 245.2 $[M+H]^+$.

Step 6

22e (60 mg, 0.24 mmol), 2B (60 mg, 0.32 mmol), and N,N-diisopropylethylamine (95 mg, 0.74 mmol) were dissolved in dimethyl sulfoxide (2 mL), and the reaction was heated to 130° C. and stirred for 16 hours. The reaction liquid was filtered, and the filtrate was purified by preparative HPLC (ammonium carbonate system) to obtain 6'-(((1S,3S)-3-((5-(2,2-difluorocyclopropyl)-1,2,4-oxadiazol-3-yl)amino)cyclopentyl)amino)-2H-[1,3'-bipyridinyl]-2-one 22 (13.5 mg), yield 13.1%.

MS m/z (ESI): 415.1 $[M+H]^+$.

$^1$H NMR (400 MHz, $CDCl_3$) δ 7.97 (s, 1H), 7.45 (dd, 1H), 7.35-7.28 (m, 1H), 7.22 (dd, 1H), 6.58 (d, 1H), 6.37 (d, 1H), 6.16 (t, 1H), 4.67 (d, 1H), 4.32 (d, 1H), 4.25-4.15 (m, 1H), 4.05-3.95 (m, 1H), 2.85-2.75 (m, 1H), 2.33-1.86 (m, 8H).

Example 26

6'-(((1S,3S)-3-((5,6,7,8-tetrahydro-[1,2,4]triazolo[1,5-a]pyridin-2-yl)amino)cyclopentyl)amino)-2H-[1,3'-bipyridinyl]-2-one Example 26 could also be synthesized by reference to the following preparation method:

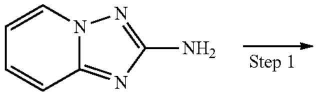

26a

-continued

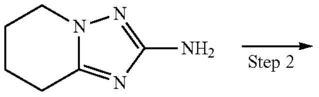

26b

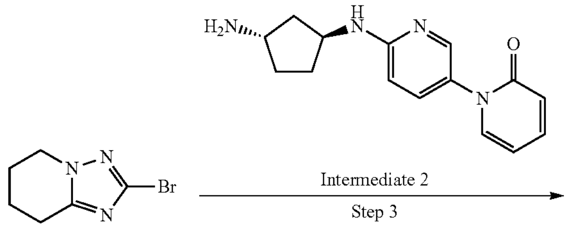

26c

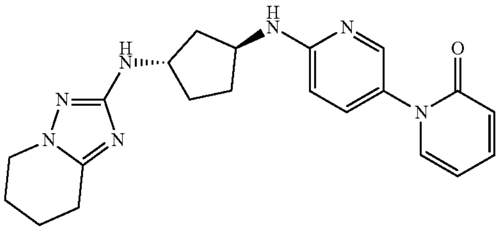

26

Step 1

In a hydrogen atmosphere at 25° C., [1,2,4]triazolo[1,5-a]pyridine-2-amine 26a (2.7 g, 20.13 mmol) and platinum dioxide (914 mg, 4.03 mmol) were dissolved in a mixed liquid of hydrochloric acid (12 M, 3 mL) and methanol (3 mL) and stirred for 48 hours. The reaction liquid was filtered, and the filtrate was concentrated. The residue was neutralized to pH=10 with a saturated sodium bicarbonate solution. The mixture was extracted five times with a mixed liquid of dichloromethane/isopropanol (3:1). The organic phase was dried, filtered, and concentrated to obtain 5,6,7,8-tetrahydro-[1,2,4]triazolo[1,5-a]pyridine-2-amine 26b (2.5 g), yield: 89.9%.

MS m/z (ESI): 139.2 $[M+H]^+$.

Step 2

Copper bromide (711.0 mg, 3.18 mmol) and tert-butyl nitrite (820.9 mg, 7.96 mmol) were dissolved in acetonitrile (6 mL), and 26b (220 mg, 1.59 mmol) was added under stirring. The reaction liquid was stirred at room temperature for 0.5 hours, then heated to 60° C., and stirred for 1 hour. The reaction liquid was concentrated, and the residue was diluted with ethyl acetate (50 mL) and filtered. The organic phase was washed with water (30 mL), dried, filtered, and concentrated. The residue was purified by silica gel column chromatography (elution system C) to obtain 2-bromo-5,6,7,8-tetrahydro-[1,2,4]triazolo[1,5-a]pyridine 26c (200 mg), yield: 62.2%.

MS m/z (ESI): 204.0 $[M+H]^+$.

Step 3

Under nitrogen protection, 26c (597.9 mg, 2.96 mmol), intermediate 2 (200 mg, 0.74 mmol), sodium tert-butoxide (213.3 mg, 2.22 mmol), tris(dibenzylideneacetone)palladium (135.5 mg, 0.15 mmol), and Xantphos (171.2 mg, 0.3 mmol) were dissolved in 1'4-dioxane (8 mL), heated to 130° C. by microwave, and stirred for 4 hours. The reaction liquid was diluted with ethyl acetate (20 mL), and the organic phase was washed with water and a saturated sodium chloride aqueous solution, dried, filtered, and concentrated. The residue was purified by preparative HPLC (formic acid system) to obtain 6'-(((1S,3S)-3-((5,6,7,8-tetrahydro-[1,2,4]triazolo[1,5-a]pyridin-2-yl)amino)cyclopentyl)amino)-2H-[1,3'-bipyridinyl]-2-one 26 (9.5 mg), yield: 2.9%.

MS m/z (ESI): 392.2 [M+H]$^+$.

$^1$H NMR (400 MHz, DMSO-$d_6$) δ 7.91 (d, 1H), 7.60 (dd, 1H), 7.48 (t, 1H), 7.38 (dd, 1H), 6.87 (d, 1H), 6.51 (d, 1H), 6.44 (d, 1H), 6.27 (t, 1H), 5.69 (d, 1H), 4.27 (q, 1H), 3.95 (q, 1H), 3.83 (t, 2H), 2.62 (t, 2H), 2.19-1.70 (m, 8H), 1.53-1.39 (m, 2H).

Example 27

6'-((3-(((1S,3S)-7-fluoro-[1,2,4]triazolo[1,5-a]pyridin-2-yl)amino)cyclopentyl)amino)-2H-[1,3'-bipyridinyl]-2-one

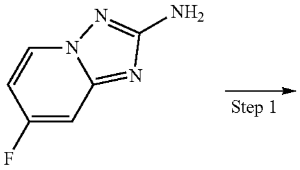

27a

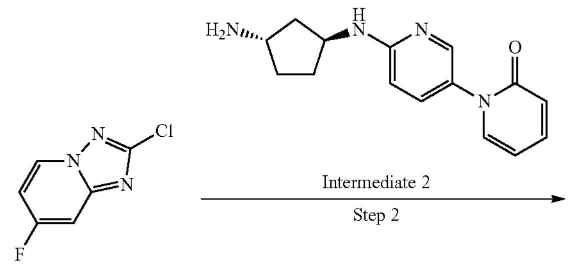

27b

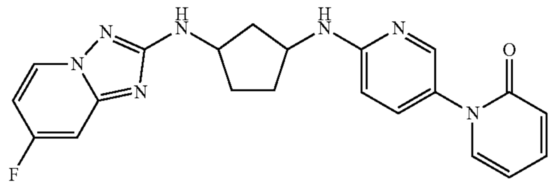

27

Step 1

In an ice bath, 7-fluoro-[1,2,4]triazolo[1,5-a]pyridine-2-amine 27a (100 mg, 0.657 mmol) was dissolved in acetonitrile and stirred, sodium nitrite (91 mg, 1.31 mmol) was added to the reaction liquid, and stirring was continued for 1 minute. Hydrochloric acid (4 M, 0.41 mL) was dropwise added to the reaction liquid, the reaction was heated to room temperature and continued to be stirred, and the completion of the reaction was detected by a thin layer chromatography plate. A saturated sodium bicarbonate solution was dropwise added to the reaction liquid until pH=7. The reaction liquid was extracted with dichloromethane (10 mL×3). The organic phase was dried and concentrated, and the residue was separated by silica gel column chromatography (eluent system A) to obtain 2-chloro-7-fluoro-[1,2,4]triazolo[1,5-a]pyridine 27b (65 mg), yield: 77.5%.

MS m/z (ESI): 172.1 [M+H]$^+$.

Step 2

By reference to the synthesis method of step 1 of Example 20, the target compound 6'-((3-(((1S,3S)-7-fluoro-[1,2,4]triazolo[1,5-a]pyridin-2-yl)amino)cyclopentyl)amino)-2H-[1,3'-bipyridinyl]-2-one 27 was synthesized.

Step 2 could also be synthesized by reference to the following method:

Under nitrogen protection, 27b (80 mg, 0.37 mmol), 27c (100 mg, 0.37 mmol), cesium carbonate (241.3 mg, 0.74 mmol), $Pd_2dba_3$ (67.8 mg, 0.074 mmol), and xantphos (85.7 mg, 0.15 mmol) were dissolved in 1'4-dioxane (2 mL). The reaction liquid was heated to 130° C. and reacted for 2 hours by microwave. The reaction liquid was heated to 130° C. under nitrogen protection and reacted for 16 hours. The reaction liquid was filtered and concentrated. The residue was purified by preparative HPLC (basic system) to obtain 6'-(((1S,3S)-3-((7-fluoro-[1,2,4]triazolo[1,5-a]pyridin-2-yl)amino)cyclopentyl)amino)-2H-[1,3'-bipyridinyl]-2-one 27 (6.6 mg), yield 4.08%.

MS m/z (ESI): 406.2 [M+H]$^+$.

$^1$H NMR (400 MHz, DMSO-$d_6$) δ 8.69-6.59 (m, 1H), 7.92 (d, 1H), 7.60 (dd, 1H), 7.51-7.35 (m, 2H), 7.27 (dd, 1H), 6.97-6.82 (m, 2H), 6.74 (d, 1H), 6.52 (d, 1H), 6.44 (d, 1H), 6.26 (t, 1H), 4.35-4.28 (m, 1H), 4.20-4.10 (m, 1H), 2.20-2.07 (m, 2H), 2.00-1.82 (m, 2H), 1.60-1.42 (m, 2H).

Example 38

6'-(((1S,3S)-3-((5-(2-hydroxyprop-2-yl)pyridin-2-yl)amino)cyclopentyl)amino)-2H-[1,3'-bipyridinyl]-2-one Example 38 could also be synthesized by the following method:

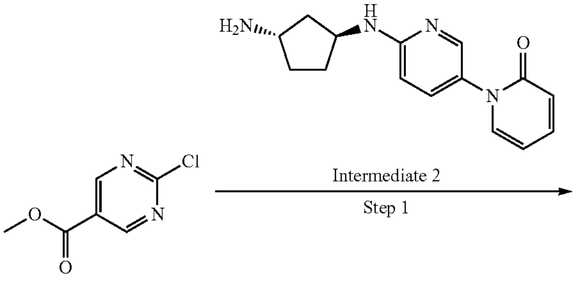

38a

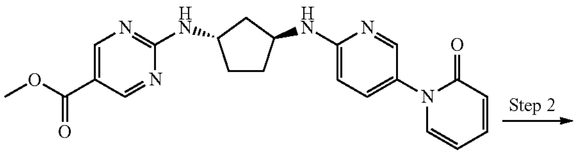

38b

-continued

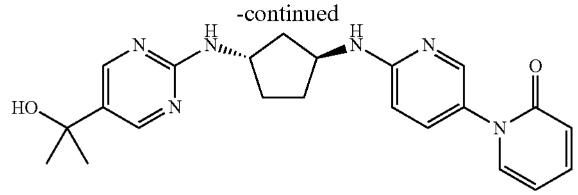

38

Step 1

By reference to the synthesis method of Example 20, with methyl 2-chloropyrimidine-5-carboxylate 38a as a starting raw material, methyl 2-(((1S,3S)-3-((2-one-2H-[1,3'-bi-pyridinyl]-6-yl)amino)cyclopentyl)amino)pyridine-5-carboxylate 38b was synthesized.

MS m/z (ESI): 407.2 $[M+H]^+$.

Step 2

Under nitrogen protection at 0° C., 38b (35 mg, 0.086 mmol) was dissolved in anhydrous tetrahydrofuran (2 mL), a solution of methylmagnesium bromide in tetrahydrofuran (1M, 2 mL) was dropwise added to the reaction liquid, and the reaction liquid was heated to room temperature and stirred for 1 hour. The reaction was quenched with methanol and concentrated, and the residue was purified by preparative HPLC (ammonium bicarbonate system) to obtain the target compound (9 mg), yield: 25.7%.

MS m/z (ESI): 407.2 $[M+H]^+$.

$^1$H NMR (400 MHz, DMSO-$d_6$) δ 8.33 (s, 2H), 7.92 (d, 1H), 7.60 (dd, 1H), 7.48 (ddd, 1H), 7.39 (dd, 1H), 7.09 (d, 1H), 6.93 (d, 1H), 6.53 (d, 1H), 6.44 (d, 1H), 6.27 (td, 1H), 5.01 (s, 1H), 4.37-4.27 (m, 2H), 2.16-2.07 (m, 2H), 1.93-1.81 (m, 2H), 1.54-1.43 (m, 2H), 1.39 (s, 6H).

Example 47

3-(6-(((1S,3S)-3-((5-(difluoromethoxy)pyrimidin-2-yl)amino)cyclopentyl)amino)pyridin-3-yl)-4H-quinolin-4-one

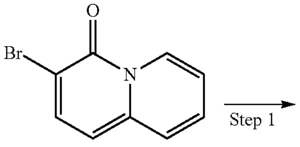

47a

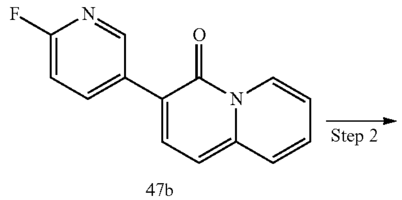

47b

-continued

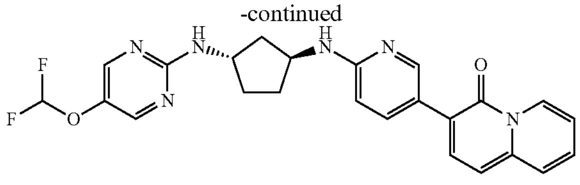

47

Step 1

Under nitrogen protection, 3-bromo-4H-quinolizin-4-one 47a (1.0 g, 4.46 mmol), (6-fluoropyridin-3-yl)boronic acid (755 mg, 5.36 mmol), bis(diphenylphosphino)ferrocene dichloropalladium (162 mg, 0.223 mmol), and potassium carbonate (1.54 g, 11.5 mmol) were dissolved in a mixed liquid of dioxane (20 mL) and water (2 mL), and the reaction was heated to 90° C. and stirred for 16 hours. The reaction liquid was filtered, the filtrate was concentrated, and the residue was separated by silica gel column chromatography (eluent system A) to obtain 3-(6-fluoropyridin-3-yl)-4H-quinolizin-4-one 47b (360 mg), yield: 34%.

MS m/z (ESI): 241.1 $[M+H]^+$.

Step 2

3-(6-Fluoropyridin-3-yl)-4H-quinolizin-4-one 47b (100 mg, 0.416 mmol), intermediate 1 (102 mg, 0.416 mmol), and N,N-diisopropylethylamine (207 μL, 1.25 mmol) were dissolved in dimethyl sulfoxide (2 mL), and the reaction was heated to 130° C. and stirred for 24 hours. The reaction liquid was purified by preparative HPLC (formic acid system) to obtain the target compound 3-(6-(((1S,3S)-3-((5-(difluoromethoxy)pyrimidin-2-yl)amino)cyclopentyl) amino) pyridin-3-yl)-4H-quinolin-4-one 47 (47 mg), yield: 24%.

MS m/z (ESI): 465.2 $[M+H]^+$.

$^1$H NMR (400 MHz, DMSO-$d_6$) δ 9.07 (d, 1H), 8.54 (s, 1H), 8.24 (s, 2H), 8.00 (d, 2H), 7.78 (d, 1H), 7.56-7.44 (m, 2H), 7.25-7.17 (m, 1H), 7.03 (t, 1H), 6.95 (d, 1H), 6.60 (d 1H), 4.32 (h, 2H), 2.23-2.08 (m, 2H), 1.90 (dp, 2H), 1.54 (ddt, 2H).

Example 47 could also be obtained by the following synthesis method:

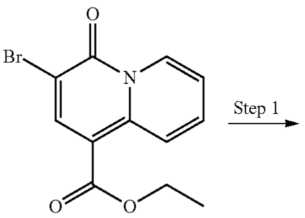

47c

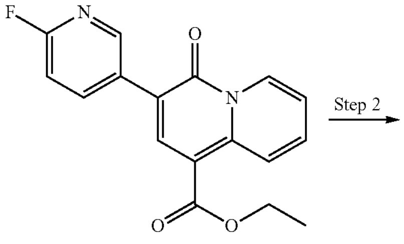

47d

-continued

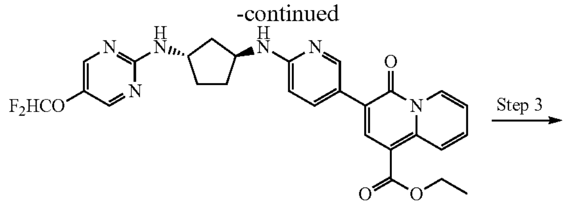

47e

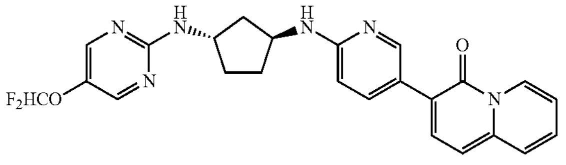

47

Step 1

47c (120 mg, 0.405 mmol), (6-fluoropyridin-3-yl)boronic acid (103 mg, 0.729 mmol), bis(diphenylphosphino)ferrocene dichloropalladium (29 mg, 0.041 mmol), and potassium carbonate (140 mg, 1.01 mmol) were dissolved in a mixed liquid of dioxane (1.5 mL) and water (0.15 mL), and the reaction was heated to 90° C. and stirred for 16 hours. The reaction liquid was filtered, the filtrate was concentrated, and the residue was separated by silica gel column chromatography (eluent system A) to obtain ethyl 3-(6-fluoropyridin-3-yl)-4-oxo-4H-quinoline-1-carboxylate 47d (110 mg), yield: 87%.

MS m/z (ESI): 313.1 $[M+H]^+$.

Step 2

47d (102 mg, 0.328 mmol), intermediate 1 (80 mg, 0.328 mmol), and N,N-diisopropylethylamine (143 μL, 0.819 mmol) were dissolved in dimethyl sulfoxide (2 mL), and the reaction was heated to 130° C. and stirred for 24 hours. The reaction liquid was purified by preparative HPLC (formic acid system) to obtain ethyl 3-(6-(((1S,3S)-3-((5-(difluoromethoxy)pyrimidin-2-yl)amino)cyclopentyl)amino-amino) pyridin-3-yl)-4-oxo-4H-quinoline-1-carboxylate 47e (53 mg), yield: 30%.

MS m/z (ESI): 537.2 $[M+H]^+$.

Step 3

47e (35 mg, 0.065 mmol) was dissolved in hydrochloric acid (12 M, 5 mL), and the reaction was heated to 100° C. and stirred for 1.5 hours. The reaction liquid was purified by preparative HPLC (formic acid system) to obtain the target compound 3-(6-(((1S,3S)-3-((5-(difluoromethoxy)pyrimidin-2-yl)amino)cyclopentyl)amino) pyridin-3-yl)-4H-quinolin-4-one 47 (21 mg), yield: 69%.

MS m/z (ESI): 465.2 $[M+H]^+$.

$^1$H NMR (400 MHz, DMSO-$d_6$) δ 9.07 (d, 1H), 8.54 (s, 1H), 8.24 (s, 2H), 8.00 (d, 2H), 7.78 (d, 1H), 7.56-7.44 (m, 2H), 7.25-7.17 (m, 1H), 7.03 (t, 1H), 6.95 (d, 1H), 6.60 (d 1H), 4.32 (h, 2H), 2.23-2.08 (m, 2H), 1.90 (dp, 2H), 1.54 (ddt, 2H).

Example 52

(1S,3S)—$N^1$-(5-(difluoromethoxy)pyrimidin-2-yl)-$N^3$-(5-(pyrazolo[1,5-a]pyridin-7-yl)pyridin-2-yl) cyclopentane-1,3-diamine Example 52 could also be synthesized by the following method:

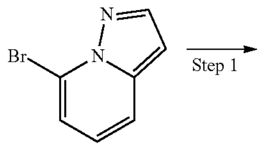

52a

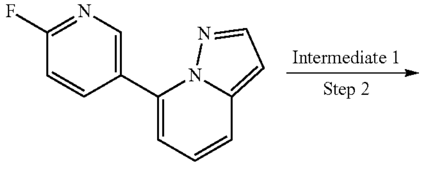

52b

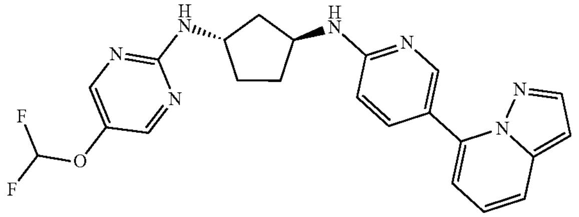

52

Step 1

Under nitrogen protection, 7-bromopyrazolo[1,5-a]pyridine 52a (150 mg, 0.76 mmol), (6-fluoropyridin-3-yl)boronic acid (139 mg, 0.99 mmol), 1,1-bis(diphenylphosphino)ferrocene dichloropalladium (56 mg, 0.08 mmol), and cesium carbonate (496 mg, 1.52 mmol) were dissolved in 1,4-dioxane (2 mL), and the reaction was heated to 100° C. and stirred for 16 hours. The reaction liquid was cooled to room temperature, and the organic phase was separated. The aqueous phase was extracted with ethyl acetate (2 mL). The organic phases were combined, dried, and concentrated, and the residue was separated by silica gel column chromatography (elution system B) to obtain 7-(6-fluoropyridin-3-yl) pyrazolo[1,5-a]pyridine 52b (155 mg), yield: 95.49%.

MS m/z (ESI): 214.1 $[M+H]^+$.

Step 2

Intermediate 1 (60 mg, 0.25 mmol), 52b (105 mg, 0.49 mmol), and N,N-dimethylethylamine (79 mg, 0.61 mmol) were dissolved in dimethyl sulfoxide (1 mL), and the reaction was heated to 130° C. and stirred for 16 hours. The reaction liquid was filtered, and the filtrate was subjected to reversed-phase HPLC (ammonium bicarbonate system) to prepare (1S,3S)—$N^1$-(5-(difluoromethoxy) pyrimidin-2-yl)-$N^3$-(5-(pyrazolo[1,5-a]pyridin-7-yl)pyridin-2-yl)cyclopentane-1,3-diamine 52 (42.3 mg), yield: 39.36%.

MS m/z (ESI): 438.2 $[M+H]^+$.

$^1$H NMR (400 MHz, DMSO-$d_6$) δ 8.56 (d, 1H), 8.24 (s, 2H), 8.07-7.97 (m, 2H), 7.63 (d, 1H), 7.51 (d, 1H), 7.29-7.23 (m, 1H), 7.07 (d, 1H), 7.22-6.85 (m, 1H), 6.95 (d, 1H), 6.68 (d, 1H), 6.59 (d, 1H), 4.47-4.23 (m, 2H), 2.24-2.05 (m, 2H), 1.99-1.84 (m, 2H), 1.63-1.45 (m, 2H).

Example 53

(1S,3S)—$N^1$-(5-(difluoromethoxy)pyrimidin-2-yl)-$N^3$-(5-(imidazolo[1,2-a]pyridin-8-yl)pyridin-2-yl] cyclopentane-1,3-diamine

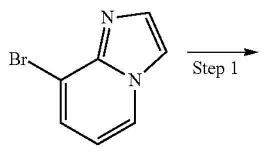

53a

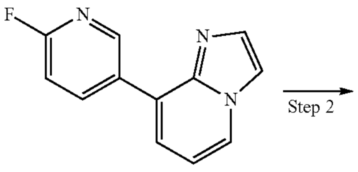

53b

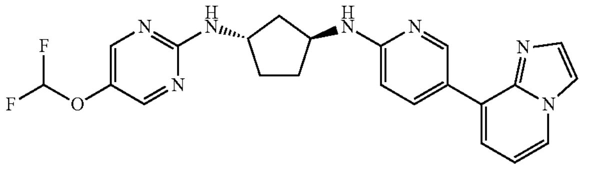

53

Step 1

Under nitrogen protection, 8-bromoimidazolo[1,2-a]pyridine 53a (1.0 g, 5.08 mmol), (6-fluoropyridin-3-yl)boronic acid (858 mg, 6.09 mmol), bis(diphenylphosphino)ferrocene dichloropalladium (184 mg, 0.254 mmol), and potassium carbonate (1.75 g, 12.7 mmol) were dissolved in a mixed liquid of dioxane (20 mL) and water (2 mL), and the reaction was heated to 90° C. and stirred for 16 hours. The reaction liquid was filtered through diatomite and concentrated, and the residue was separated by silica gel column chromatography (eluent system A) to obtain 8-(6-fluoropyridin-3-yl) imidazolo[1,2-a]pyridine 53b (415 mg), yield: 38%.

MS m/z (ESI): 214.1 $[M+H]^+$.

Step 2

By reference to the synthesis method of step 2 of Example 47, the target compound (1S,3S)—$N^1$-(5-(difluoromethoxy) pyrimidin-2-yl)-$N^3$-(5-(imidazolo[1,2-a]pyridin-8-yl)pyridin-2-yl]cyclopentane-1,3-diamine 53 was synthesized.

MS m/z (ESI): 438.2 $[M+H]^+$.

$^1$H NMR (400 MHz, DMSO-$d_6$) δ 8.81 (d, 1H), 8.46 (d, 1H), 8.25-8.18 (m, 3H), 7.99 (d, 1H), 7.59 (d, 1H), 7.51 (d, 1H), 7.36 (d, 1H), 7.03 (t, 1H), 6.93 (t, 1H), 6.88-6.81 (m, 1H), 6.56 (d, 1H), 4.33 (dq, 2H), 2.22-2.07 (m, 2H), 2.00-1.85 (m, 2H), 1.53 (ddd, 2H).

Example 56

1-(6-(((1S,3S)-3-((5-(difluoromethoxy)pyrimidin-2-yl)amino)cyclopentyl)amino)pyridin-3-yl)-3-methyl-1,3-dihydro-2H-imidazolo[4,5-b]pyrazin-2-one

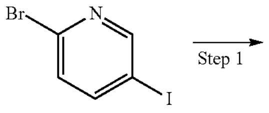

56a

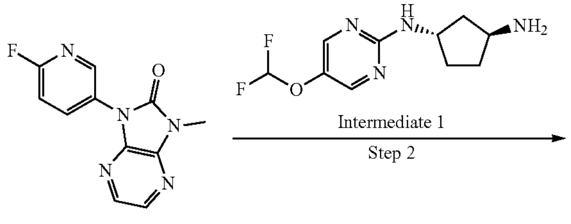

56b

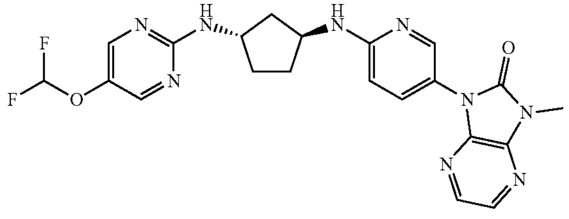

56

Step 1

Under nitrogen protection, 2-fluoro-5-iodopyridine 56a (2.2 g, 9.87 mmol), 1-methyl-1H-imidazo[4,5-b]pyrazin-2 (3H)-one (1.78 g, 11.84 mmol), cuprous iodide (188 mg, 0.99 mmol), N,N-dimethyl-1,2-cyclohexanediamine (281 mg, 1.97 mmol), and potassium phosphate (4.19 g, 19.73 mmol) were dissolved in dimethyl sulfoxide (40 mL), and the reaction was heated to 100° C. and stirred for 3 hours. The reaction liquid was brought back to room temperature, and a saturated sodium chloride solution (120 mL) was added to the reaction liquid. The aqueous phase was extracted with ethyl acetate (40 mL/3). The organic phases were combined, dried, and concentrated, and the residue was separated by silica gel column chromatography to obtain 1-(6-fluoropyridin-3-yl)-3-methyl-1,3-dihydro-2H-imidazolo[4,5-b]pyrazin-2-one 56b (1.4 g, light yellow solid), yield: 57.87%.

MS m/z (ESI): 246.1 $[M+H]^+$.

Step 2

Intermediate 1 (70 mg, 0.29 mmol), 1-(6-fluoropyridin-3-yl)-3-methyl-1,3-dihydro-2H-imidazolo[4,5-b]pyrazin-2-one 56b (77 mg, 0.32 mmol), and cesium carbonate (280 mg, 0.86 mmol) were dissolved in dimethyl sulfoxide (3 mL), and the reaction was heated to 130° C. and stirred for 48 hours. The reaction liquid was cooled to room temperature and filtered, and the filtrate was subjected to preparative separation by reversed-phase HPLC (ammonium bicarbonate system) to obtain 1-(6-(((1S,3S)-3-((5-(difluoromethoxy)pyrimidin-2-yl)amino)cyclopentyl)amino) pyridin-3-yl)-3-methyl-1,3-dihydro-2H-imidazolo[4,5-b]pyrazin-2-one 56 (41 mg, white solid), yield: 30.47%.

MS m/z (ESI): 470.1 [M+H]$^+$.

$^1$H NMR (400 MHz, DMSO-$d_6$) δ 8.24 (s, 2H), 8.11 (d, 1H), 8.01 (d, 1H), 7.91 (d, 1H), 7.57-7.45 (m, 2H), 7.26-6.82 (m, 1H), 6.97 (d, 1H), 6.59 (d, 1H), 4.42-4.19 (m, 2H), 3.40 (s, 3H), 2.22-2.05 (m, 2H), 1.95-1.82 (m, 2H), 1.61-1.42 (m, 2H).

Example 57

6-(6-(((1S,3S)-3-((5-(difluoromethoxy)pyrimidin-2-yl)amino)cyclopentyl)amino)pyridin-3-yl)-5,6-dihydro-7H-pyrrolo[3,4-b]pyridin-7-one

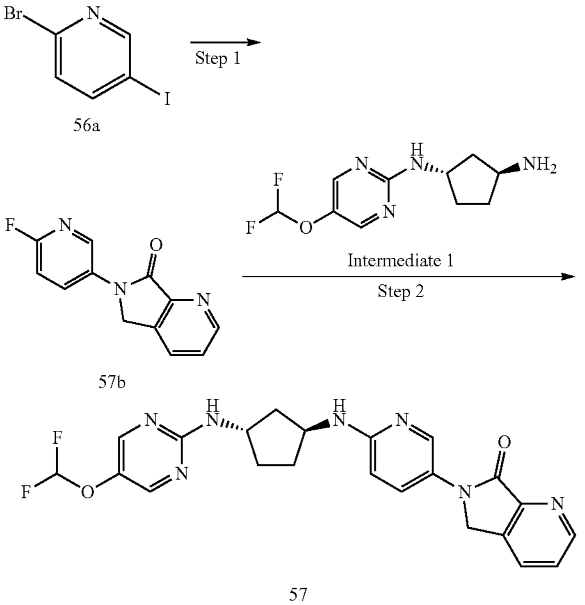

Step 1

Under nitrogen protection, 2-fluoro-5-iodopyridine 56a (2.2 g, 9.87 mmol), 5,6-dihydro-7H-pyrrolo[3,4-b]pyridin-7-one (1.59 g, 11.84 mmol), cuprous iodide (188 mg, 0.99 mmol), N,N-dimethyl-1,2-cyclohexanediamine (281 mg, 1.97 mmol), and potassium phosphate (4.19 g, 19.73 mmol) were dissolved in dimethyl sulfoxide (40 mL), and the reaction was heated to 100° C. and stirred for 3 hours. The reaction liquid was brought back to room temperature, and a saturated sodium chloride solution (120 mL) was added to the reaction liquid. The aqueous phase was extracted with ethyl acetate (40 mL×3). The organic phases were combined, dried, and concentrated, and the residue was separated by silica gel column chromatography (eluent system A) to obtain 6-(6-fluoropyridin-3-yl)-5,6-dihydro-7H-pyrrolo[3,4-b]pyridin-7-one 57b (1.3 g), yield: 57.49%.

MS m/z (ESI): 230.1 [M+H]$^+$.

Step 2

Intermediate 1 (70 mg, 0.29 mmol), 6-(6-fluoropyridin-3-yl)-5,6-dihydro-7H-pyrrolo[3,4-b]pyridin-7-one 57b (72 mg, 0.32 mmol), and cesium carbonate (280 mg, 0.86 mmol) were dissolved in dimethyl sulfoxide (3 mL), and the reaction was heated to 130° C. and stirred for 48 hours. The reaction liquid was cooled to room temperature and filtered, and the filtrate was subjected to preparative separation by reversed-phase HPLC (formic acid system) to obtain 6-(6-(((1S,3S)-3-((5-(difluoromethoxy)pyrimidin-2-yl)amino)cyclopentyl)amino)pyridin-3-yl)-5,6-dihydro-7H-pyrrolo[3,4-b]pyridin-7-one 57 (46 mg), yield: 35.4%.

MS m/z (ESI): 454.1 [M+H]$^+$.

$^1$H NMR (400 MHz, DMSO-$d_6$) δ 8.76 (d, 1H), 8.35 (d, 1H), 8.24 (s, 2H), 8.11 (d, 1H), 7.88 (d, 1H), 7.66-7.57 (m, 1H), 7.48 (d, 1H), 7.25-6.82 (m, 1H), 6.71 (s, 1H), 6.57 (d, 1H), 4.93 (s, 2H), 4.37-4.19 (m, 2H), 2.22-2.04 (m, 2H), 1.96-1.80 (m, 2H), 1.60-1.41 (m, 2H).

Example 63

6'-(((1S,3S)-3-((6-cyclopropyl-1,2,4-triazin-3-yl)amino)cyclopentyl)amino)-2H-[1,3'-bipyridinyl]-2-one Example 63 could also be synthesized by the following method:

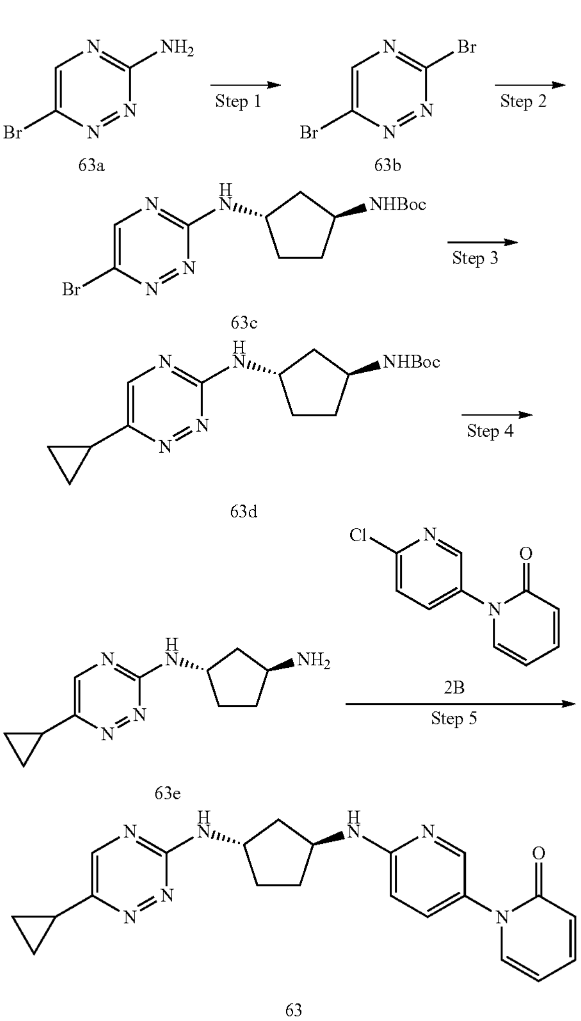

Step 1

63a (3.5 g, 20 mmol) was dissolved in acetonitrile (50 mL), and tert-butyl nitrite (3.09 g, 30 mmol) was added. The mixture was stirred at room temperature for 30 minutes, and copper bromide (6.7 g, 30 mmol) was then added. After the mixture was stirred at room temperature for 1 hour, the reaction was heated to 50° C. and stirred for 1 hour. The reaction liquid was filtered and concentrated, and the residue was separated by silica gel column chromatography (eluent system B) to obtain 3,6-dibromo-1,2,4-triazine 63b (1.3 g), yield: 27.3%.

MS m/z (ESI): 237.9 [M+H]$^+$.

Step 2

63b (1.3 g, 5.44 mmol), tert-butyl (1S,3S)-3-aminocyclopentylcarbamate (1.2 g, 5.99 mmol), and diisopropylethylamine (1.41 g, 10.88 mmol) were dissolved in dioxane (20 mL), and the reaction was heated to 80° C. and stirred for 2 hours. Ethyl acetate (100 mL) was added to the reaction liquid. The organic phase was washed with water (30 mL×3) and saturated sodium chloride, dried, and concentrated, and the residue was separated by silica gel column chromatography (eluent system B) to obtain tert-butyl ((1S,3S)-3-((6-bromo-1,2,4-triazin-3-yl)amino)cyclopentane) carbamate 63c (1.5 g), yield: 76.9%.

MS m/z (ESI): 358.1 [M+H]$^+$.

Step 3

63c (1.5 g, 4.19 mmol), cyclopropylboronic acid (719 mg, 8.38 mmol), 1,1'-bis(diphenylphosphino)ferrocene dichloropalladium (306.4 mg, 0.42 mmol), and sodium carbonate (1.33 g, 12.56 mmol) were dissolved in dioxane (20 mL) and water (5 mL), and the reaction was heated to 120° C. and stirred for 16 hours. The reaction liquid was filtered, and ethyl acetate (100 mL) was added. The organic phase was washed with water (30 mL×3) and saturated sodium chloride, dried, and concentrated, and the residue was separated by silica gel column chromatography (eluent system B) to obtain tert-butyl ((1S,3S)-3-((6-cyclopropyl-1,2,4-triazin-3-yl)amino)cyclopentane)carbamate 63d (400 mg), yield: 29.9%.

MS m/z (ESI): 320.2 [M+H]$^+$.

Step 4

63d (400 mg, 1.25 mmol) was dissolved in methanol (5 mL), a solution of 4 M hydrochloric acid in dioxane (5 mL) was added, and the reaction was stirred at room temperature for 2 hours. The reaction liquid was concentrated, and the pH was adjusted to weak alkalinity by adding an ammonia methanol solution. After concentration again, the residue was separated by silica gel column chromatography (eluent system A) to obtain ((1S,3S)—N$^1$-((6-cyclopropyl-1,2,4-triazin-3-yl)cyclopentane-1,3-diamine 63e (120 mg), yield: 43.6%.

MS m/z (ESI): 220.2 [M+H]$^+$.

Step 5

63e (100 mg, 0.456 mmol), 2B (141.3 mg, 0.684 mmol), tris(dibenzylideneacetone)dipalladium (41.76 mg, 0.0456 mmol), 2-dicyclohexylphosphino-2',6'-diisopropylbiphenyl (42.56 mg, 0.091 mmol), and sodium tert-butoxide (131.5 mg, 1.37 mmol) were dissolved in dioxane (10 mL), and the reaction was heated to 100° C. and stirred for 15 hours. Ethyl acetate (30 mL) was added to the reaction liquid. The organic phase was washed with water (10 mL×3) and saturated sodium chloride, dried, and concentrated, and the residue was purified by preparative HPLC (ammonium bicarbonate system) to obtain the target compound 6'-(((1S,3S)-3-((6-cyclopropyl-1,2,4-triazin-3-yl)amino)cyclopentyl) amino)-2H-[1,3'-bipyridinyl]-2-one 63 (26 mg), yield: 14.6%.

MS m/z (ESI): 390.2 [M+H]$^+$.

$^1$H NMR (400 MHz, DMSO-$d_6$) δ 8.18 (s, 1H), 7.92 (d, 1H), 7.60 (dd, 1H), 7.54 (s, 1H), 7.47 (td, 1H), 7.38 (dd, 1H), 6.93 (d, 1H), 6.53 (d, 1H), 6.44 (d, 1H), 6.27 (t, 1H), 4.34 (m, 2H), 2.18-2.10 (m, 2H), 2.08-2.02 (m, 1H), 1.98-1.85 (m, 2H), 1.60-1.39 (m, 2H), 1.00-0.86 (m, 4H).

Example 64

6'-(((1S,3S)-3-((5-(difluoromethoxy)pyrimidin-2-yl) amino)cyclopentyl)amino]-3-(2-hydroxyprop-2-yl)-2H-[1,3'-bipyridinyl]-2-one Example 64 could also be synthesized by the following method:

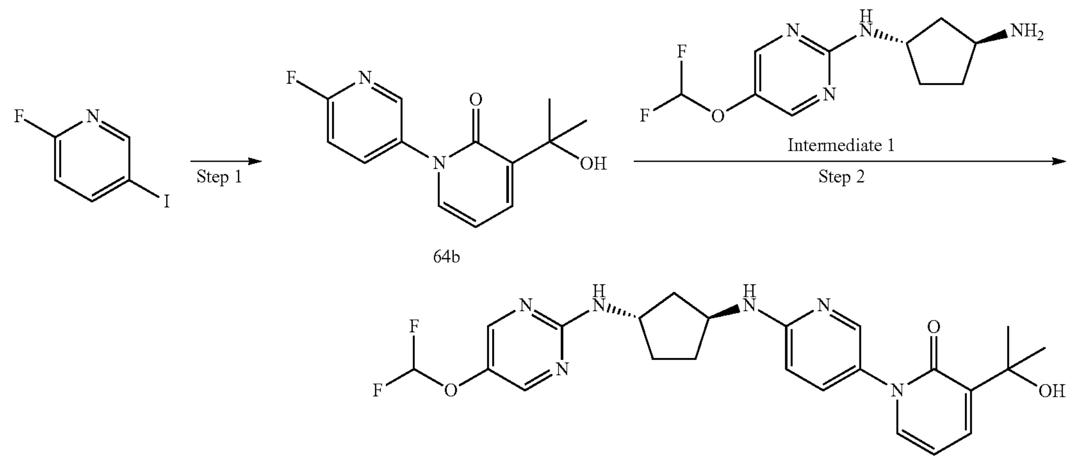

64b

64

Step 1

By reference to the synthesis method of step 1 for intermediate 2, the target compound 6'-fluoro-3-(2-hydroxy-prop-2-yl)-2H-[1,3'-bipyridinyl]-2-one 64b was synthesized.

MS m/z (ESI): 249.1 $[M+H]^+$.

Step 2

64b (150 mg, 0.604 mmol), intermediate 1 (98 mg, 0.403 mmol), and N,N-diisopropylethylamine (104 mg, 0.806 mmol) were dissolved in dimethyl sulfoxide (2 mL), and the reaction was heated to 130° C. and stirred for 24 hours. The reaction liquid was purified by preparative HPLC (formic acid system) to obtain 6'-(((1S,3S)-3-((5-(difluoromethoxy)pyrimidin-2-yl)amino)cyclopentyl)amino]-3-(2-hydroxy-prop-2-yl)-2H-[1,3'-bipyridinyl]-2-one 64 (62 mg), yield: 32.6%.

MS m/z (ESI): 473.2 $[M+H]^+$.

$^1$H NMR (400 MHz, $CDCl_3$) δ 8.18 (s, 2H), 8.03 (d, 1H), 7.55 (dd, 1H), 7.41 (dd, 1H), 7.29 (dd, 1H), 6.47 (d, 1H), 6.41 (t, 1H) 6.31 (t, 1H), 5.89 (s, 1H), 5.22 (d, 1H), 5.00 (s, 1H), 4.41 (d, 1H), 4.26 (d, 1H), 2.33 (m, 2H), 2.05 (m, 2H), 1.77 (s, 2H), 1.58 (s, 6H).

Example 68

6'-(((1S,3S)-3-((7-fluoropyrrolo[2,1-f][1,2,4]triazin-2-ylamino)cyclopentyl)amino)-2H-[1,3'-bipyridinyl]-2-one Example 68 could also be synthesized by the following method:

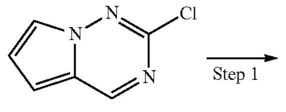

68a

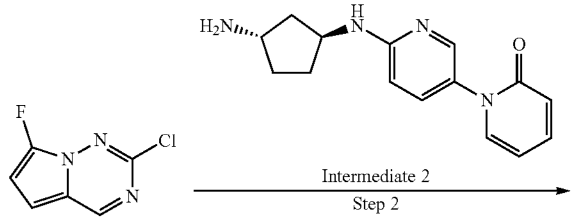

68b

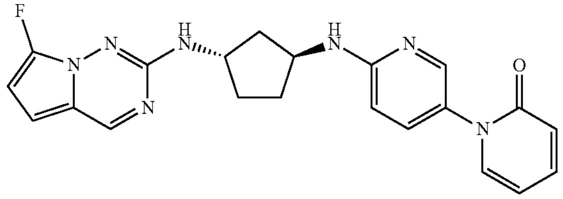

68

Step 1

2-Chloropyrrolo[2,1-f][1,2,4]triazine 68a (50 mg, 0.325 mmol) and 1-chloromethyl-4-fluoro-1,4-diazoniabicyclo[2.2.2]octane bis(tetrafluoroboronate) (173 mg, 0.488 mmol) were dissolved in acetonitrile (3 mL), and the reaction was heated to 80° C. by microwave and stirred for 1 hour. The reaction liquid was concentrated, and the residue was separated by silica gel column chromatography (eluent system B) to obtain 2-chloro-7-fluoropyrrolo[2,1-f][1,2,4]triazine 68b (25 mg), yield: 44.7%.

MS m/z (ESI): 172.0 $[M+H]^+$.

Step 2

68b (25 mg, 0.146 mmol), intermediate 2 (39.4 mg, 0.146 mmol), and cesium carbonate (95.0 g, 0.291 mmol) were dissolved in N,N-dimethylformamide (3 mL), and the reaction was heated to 100° C. and stirred for 2 hours. The reaction liquid was filtered, and the filtrate was purified by preparative HPLC (ammonium bicarbonate system) to obtain 6'-(((1S,3S)-3-((7-fluoropyrrolo[2,1-f][1,2,4]triazin-2-ylamino)cyclopentyl)amino)-2H-[1,3'-bipyridinyl]-2-one 68 (27 mg), yield: 45.7%.

MS m/z (ESI): 406.2 $[M+H]^+$.

$^1$H NMR (400 MHz, DMSO-$d_6$) δ 8.73 (d, 1H), 7.92 (d, 1H), 7.61 (dd, 1H), 7.48 (td, 1H), 7.40 (dd, J H), 7.16 (d, 11H), 6.96 (d, 1H), 6.67 (t, 1H), 6.53 (d, 1H), 6.44 (d, 1H), 6.37 (t, 1H), 6.27 (t, 1H), 4.34-4.19 (m, 2H), 2.21-2.11 (m, 2H), 2.03-1.85 (m, 2H), 1.62-1.46 (m, 2H).

Example 75

2-(6-(((1S,3S)-3-((5-(difluoromethoxy)pyrimidin-2-yl)amino)cyclopentyl)amino)pyridin-3-yl)-1,2-dihydro-3H-pyrrolo[3,4-c]pyridin-3-one Example 75 could also be synthesized by the following method:

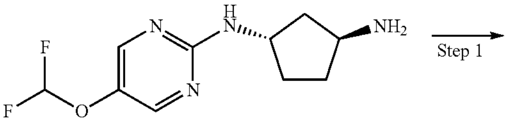

Intermediate 1

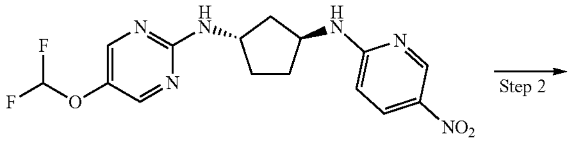

75a

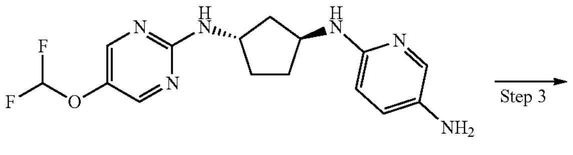

75b

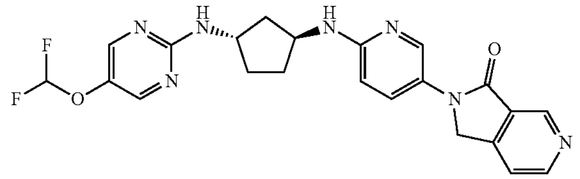

75

Step 1

Under nitrogen protection, intermediate 1 (1.2 g, 4.91 mmol), 2-fluoro-5-nitro-pyridine (768 mg, 5.40 mmol), and cesium carbonate (2.24 g, 6.88 mmol) were dissolved in acetonitrile (15 mL), and the reaction was heated to 80° C. and stirred for 16 hours. A saturated sodium chloride solution was added to the reaction liquid. The reaction liquid was extracted with ethyl acetate (30 mL×2). The organic phases were combined, dried, and concentrated to obtain crude (1S,3S)—N1-(5-(difluoromethoxy)pyrimidin-2-yl)-N3-(5-nitropyridin-2-yl)cyclopentane-1,3-diamine 75a (1.79 g), yield: 99.45%, which was directly used in the next reaction without further purification.

MS m/z (ESI): 367.1 $[M+H]^+$.

Step 2

In a hydrogen atmosphere, 75a (1.79 g, 4.89 mmol) and palladium on carbon (593 mg, 0.49 mmol, 10% content) were dissolved in a mixed solvent of methanol (15 mL) and tetrahydrofuran (5 mL) and stirred at 20° C. for 5 hours. The reaction liquid was filtered, and the filtrate was concentrated to obtain crude N2-((1S,3S)-3-((5-(difluoromethoxy)pyrimidin-2-yl)amino)cyclopentyl)pyridine-2,5-diamine 75b (1.42 g), yield: 86.40%, which was directly used in the next reaction without further purification.

MS m/z (ESI): 337.2 $[M+H]^+$.

Step 3

Under nitrogen protection, 75b (439 mg, 1.30 mmol) and potassium carbonate (481 mg, 3.48 mmol) were dissolved in N,N-dimethylformamide (7 mL) and stirred at 20° C. for 1 hour, and the reaction was then heated to 55° C. and stirred for 48 hours. A saturated sodium chloride solution was added to the reaction liquid, and the reaction liquid was extracted with ethyl acetate. The organic phases were combined, washed, and concentrated, and the residue was separated by silica gel column chromatography to obtain a crude product, which was further subjected to reversed-phase HPLC to prepare 2-(6-(((1S,3S)-3-((5-(difluoromethoxy)pyrimidin-2-yl)amino)cyclopentyl)amino)pyridin-3-yl)-1,2-dihydro-3H-pyrrolo[3,4-c]pyridin-3-one 75 (45.2 mg), yield: 25.88%.

MS m/z (ESI): 454.1 $[M+H]^+$.

$^1$H NMR (400 MHz, DMSO-$d_6$) δ 8.95 (s, 1H), 8.79 (d, 1H), 8.31 (d, 1H), 8.23 (s, 2H), 7.87-7.78 (m, 1H), 7.73 (d, 1H), 7.49 (d, 11H), 7.26-6.81 (m, 11H), 6.70 (d, 1H), 6.55 (d, 1H), 5.00 (s, 2H), 4.36-4.22 (m, 2H), 2.19-2.03 (m, 2H), 1.97-1.79 (m, 2H), 1.60-1.40 (m, 2H).

Example 76

2-(6-(((1S,3S)-3-((5-(difluoromethoxy)pyrimidin-2-yl)amino)cyclopentyl)amino)pyridin-3-yl)-2,3-dihydro-1H-pyrrolo[3,4-c]pyridin-1-one

76

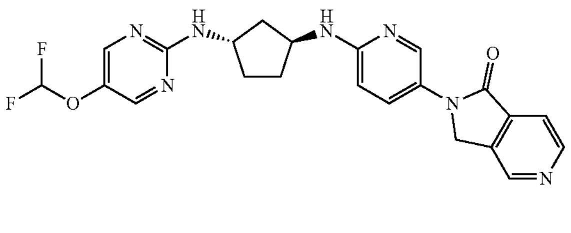

Example 76 could also be synthesized by the following method:

By reference to the synthesis method of Example 75, the target compound 2-(6-(((0S,3S)-3-((5-(difluoromethoxy)pyrimidin-2-yl)amino)cyclopentyl)amino) pyridin-3-yl)-2,3-dihydro-1H-pyrrolo[3,4-c]pyridin-1-one 76 was synthesized.

MS m/z (ESI): 454.1 $[M+H]^+$.

$^1$H NMR (400 MHz, DMSO-$d_6$) δ 8.96 (s, 1H), 8.77 (d, 1H), 8.35 (d, J H), 8.23 (s, 2H), 7.89-7.80 (m, 1H), 7.76-7.69 (m, 1H), 7.47 (d, 1H), 7.26-6.82 (m, 1H), 6.71 (d, 1H), 6.55 (d, 1H), 5.03 (s, 2H), 4.38-4.22 (m, 2H), 2.22-2.02 (m, 2H), 1.98-1.78 (m, 2H), 1.62-1.41 (m, 2H).

Example 77

6-(6-(((1S,3S)-3-((5-(difluoromethoxy)pyrimidin-2-yl)amino)cyclopentyl)amino)pyridin-3-yl)-6,7-dihydro-5H-pyrrolo[3,4-b]pyridin-5-one

77

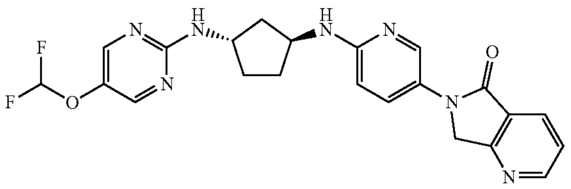

Example 77 could also be synthesized by the following method:

By reference to the synthesis method of Example 75, the target compound 6-(6-(((1S,3S)-3-((5-(difluoromethoxy)pyrimidin-2-yl)amino)cyclopentyl)amino) pyridin-3-yl)-6,7-dihydro-5H-pyrrolo[3,4-b]pyridin-5-one 77 was synthesized.

MS m/z (ESI): 454.1 $[M+H]^+$.

$^1$H NMR (400 MHz, DMSO-$d_6$) δ 8.83-8.77 (m, 1H), 8.36 (d, 1H), 8.23 (s, 2H), 8.18-8.10 (m, 1H), 7.90-7.83 (m, 1H), 7.59-7.53 (m, 1H), 7.48 (d, 1H), 7.25-6.81 (m, 1H), 6.67 (d, 1H), 6.54 (d, 1H), 4.97 (s, 2H), 4.36-4.22 (m, 2H), 2.19-2.05 (m, 2H), 1.97-1.81 (m, 2H), 1.58-1.42 (m, 2H).

Example 78

6'-(((1S,3S)-3-((5-cyclopropyl-1,2,4-thiadiazol-3-yl)amino)cyclopentyl)amino)-2H-[1,3'-bipyridinyl]-2-one Example 78 could also be synthesized by the following method:

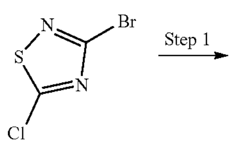

-continued

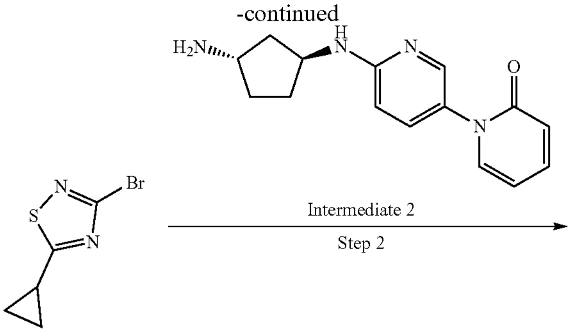

78a

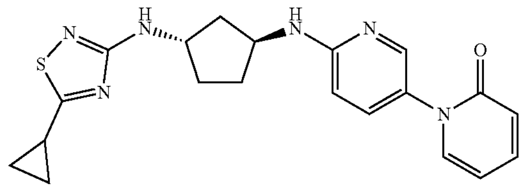

78

Step 1

Under nitrogen protection, 3-bromo-5-chloro-1,2,4-thiadiazole (900 mg, 4.51 mmol), cyclopropylboronic acid (775 mg, 9.02 mmol), 1,1-bis(diphenylphosphino)ferrocene dichloropalladium(II) (164 mg, 0.226 mmol), and potassium carbonate (1.56 g, 11.28 mmol) were dissolved in a mixed liquid of toluene (15 mL), water (5 mL), and ethanol (5 mL), heated to 90° C., and stirred for 8 hours. The reaction liquid was cooled to room temperature and filtered, and the filter cake was washed with ethyl acetate (50 mL). The organic phases were combined, washed successively with water (30 mL) and saturated sodium chloride (30 mL), dried, filtered, and concentrated, and the residue was purified by silica gel chromatography (elution system B) to obtain 3-bromo-5-cyclopropyl-1,2,4-thiadiazole 78a (120 mg), yield: 13.0%.

$^1$H NMR (400 MHz, $CDCl_3$) δ 2.41 (m, 1H), 1.32 (m, 2H), 1.29 (m, 2H).

Step 2

By reference to the synthesis method of Example 4, the target compound 6'-(((1S,3S)-3-((5-cyclopropyl-1,2,4-thiadiazol-3-yl)amino)cyclopentyl)amino)-2H-[1,3'-bipyridinyl]-2-one 78 was synthesized.

MS m/z (ESI): 395.1 $[M+H]^+$.

$^1$H NMR (400 MHz, DMSO-$d_6$) δ 7.91 (d, 1H), 7.60 (dd, 1H), 7.47 (m, 1H), 7.41-7.31 (m, 2H), 6.89 (d, 1H), 6.51 (d, 1H), 6.44 (d, 1H), 6.27 (m, 1H), 4.30-4.25 (m, 1H), 4.15 (m, 1H), 2.46-2.41 (m, 1H), 2.13-2.06 (m, 2H), 1.93-1.89 (m, 1H), 1.85-1.81 (m, 1H), 1.55-1.44 (m, 2H), 1.22-1.17 (m, 2H), 1.02-0.98 (m, 2H).

Example 82

N-((1 S,3S)-3-((5-(difluoromethoxy)pyrimidin-2-yl)amino)cyclopentyl)-2-((2-oxopyridin-1(2H)-yl)methyl)benzamide Example 82 could also be synthesized by the following method:

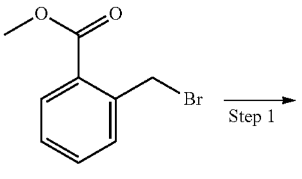

82a

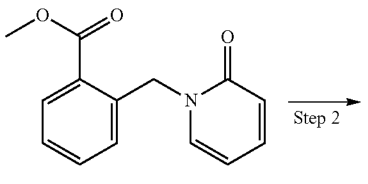

82b

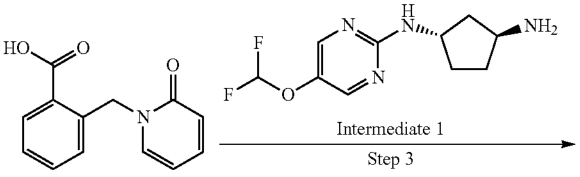

82c

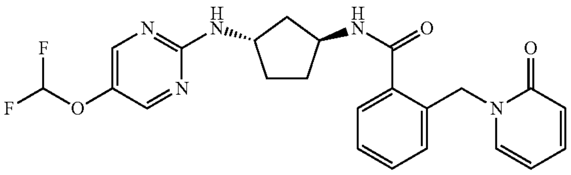

82

Step 1

At 0° C., pyridin-2(1H)-one (150 mg, 1.58 mmol) was dissolved in a mixed solution of tetrahydrofuran (3 mL) and N,N-dimethylformamide (3 mL), and sodium hydride (69 mg, 1.74 mmol, 60% in mineral oil) was added to the reaction liquid under stirring. After the reaction was stirred for 10 minutes, methyl 2-(bromomethyl)benzoate 82a (361 mg, 1.58 mmol) was added to the reaction liquid, and the reaction was stirred at room temperature for 6 hours. The reaction liquid was quenched with formic acid (1 mL) and concentrated, and the residue was separated by silica gel column chromatography (eluent system A) to obtain methyl 2-((2-oxopyridin-1(2H)-yl)methyl)benzoate 82b (310 mg), yield: 80.8%.

MS m/z (ESI): 244.1 $[M+H]^+$.

Step 2

At room temperature, 82b (310 mg, 1.27 mmol) and lithium hydroxide (61 mg, 2.55 mmol) were dissolved in a mixed liquid of methanol (3 mL) and water (1 mL) and stirred for 3 hours. The reaction liquid was filtered, the filtrate was concentrated, and the residue was separated by preparative HPLC (formic acid system) to obtain the title product 2-(2-oxopyridin-1(2H)-yl)methyl)benzoic acid 82c (190 mg), yield: 65.0%.

MS m/z (ESI): 230.1 $[M+H]^+$.

Step 3

At room temperature, 82c (40 mg, 0.18 mmol), (1S,3S)—N1-(5-(difluoromethoxy)pyrimidin-2-yl)cyclopentane-1,3-diamine (50 mg, 0.18 mmol), triethylamine (54 mg, 0.54 mmol), and O-(7-azabentriazol-1-yl)-N,N,N',N'-tetramethyluronium hexafluorophosphate (80 mg, 0.21 mmol) were dissolved in N,N-dimethylformamide (3 mL) and stirred for 16 hours. The reaction liquid was concentrated, and the residue was separated by preparative HPLC (formic acid system) to obtain the product N-((1S,3S)-3-((5-(difluoromethoxy)pyrimidin-2-yl)amino)cyclopentyl)-2-((2-oxopyridin-1(2H)-yl)methyl)benzamide 82 (40 mg), yield: 49.3%.

MS m/z (ESI): 456.2 [M+H]$^+$.

$^1$H NMR (400 MHz, DMSO-$d_6$) δ 8.66 (d, 1H), 8.23 (s, 2H), 7.75 (d, 1H), 7.41 (m, 5H), 7.03 (s, 1H), 7.01 (t, 1H), 6.42 (d, 1H), 6.25 (d, 1H), 5.21 (s, 2H), 4.31 (m, 2H), 2.09 (m, 2H), 1.91 (t, 2H), 1.50 (m, 2H).

Example 84

6'-(((1S,3S)-3-((5-cyclopropyl-1,2,4-thiadiazol-3-yl)amino)cyclopentyl)amino)-2H-[1,3'-bipyridinyl]-2-one Example 84 could also be synthesized by the following method:

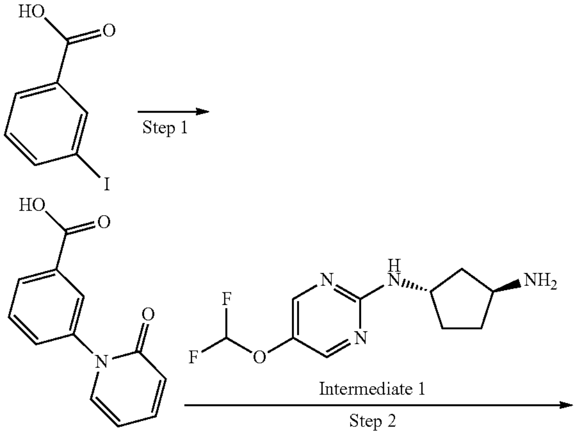

84a

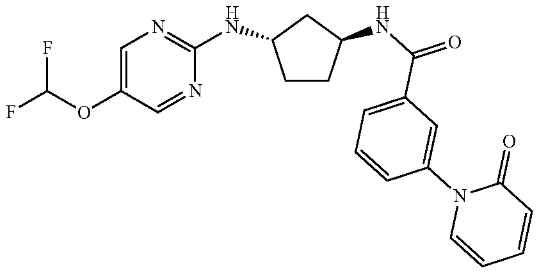

84

Step 1

Under nitrogen protection, 3-iodobenzoic acid (1.5 g, 6.05 mmol), 2-hydroxypyridine (1.15 g, 12.10 mmol), cuprous iodide (576 mg, 3.02 mmol), trans-(1R,2R)—N,N'-dimethyl 1,2-cyclohexanediamine (86 mg, 0.605 mmol), and cesium carbonate (3.94 g, 12.10 mmol) were dissolved in 1'4-dioxane (30 mL), heated to 100° C., and stirred for 6 hours. The reaction liquid was cooled to room temperature and filtered, the filtrate was concentrated, and the residue was purified by silica gel chromatography (elution system A) to obtain the compound 3-(2-oxo-1-pyridinyl)benzoic acid 84a (1.2 g), yield: 92.2%.

MS m/z (ESI): 216.1 [M+H]$^+$.

Step 2

Under nitrogen protection, intermediate 1 (70 mg, 0.287 mmol), 84a (93 mg, 0.43 mmol), N,N,N',N'-tetramethylchloroformamidinium hexafluorophosphate (121 mg, 0.43 mmol), and N-methylmorpholine (58 mg, 0.573 mmol) were dissolved in acetonitrile (2 mL), and the reaction was stirred at room temperature for 4 hours. The reaction liquid was poured into water (50 mL), and the aqueous phase was extracted with ethyl acetate (30 mL×2). The organic phases were combined, washed successively with water (30 mL) and a saturated sodium chloride solution (30 mL), dried, and concentrated. The filtrate was concentrated, and the residue was purified by reverse C18 chromatography (elution system C) to obtain 6'-(((0S,3S)-3-((5-cyclopropyl-1,2,4-thiadiazol-3-yl)amino)cyclopentyl)amino)-2H-[1,3'-bipyridinyl]-2-one 84 (79.1 mg), yield: 61.8%.

MS m/z (ESI): 442.1 [M+H]$^+$.

$^1$H NMR (400 MHz, DMSO-$d_6$) δ 8.47 (d, 1H), 8.23 (s, 2H), 7.93 (dt, 1H), 7.89-7.87 (m, 1H), 7.70 (dd, 1H), 7.62-7.52 (m, 3H), 7.48 (d, 1H), 7.03 (dd, 1H), 6.51 (d, 1H), 6.35 (td, 1H), 4.47-4.42 (m, 1H), 4.35-4.30 (m, 1H), 2.14-2.06 (m, 2H), 1.95-1.87 (m, 2H), 1.60-1.50 (m, 2H).

Example 87

6'-(((1S,3S)-3-((7-methyl-[1,2,4]triazolo[1,5-a]pyridin-2-yl)amino)cyclopentyl)amino)-2H-[1,3'-bipyridinyl]-2-one Example 87 could also be synthesized by the following method:

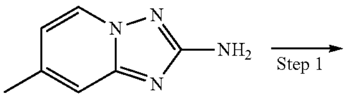

87a

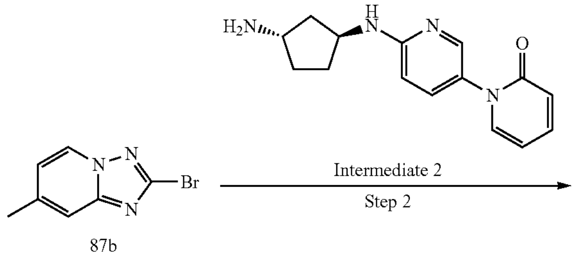

87b

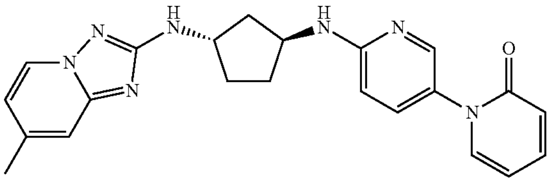

87

Step 1

Copper bromide (1.13 g, 5.06 mmol) and tert-butyl nitrite (1.74 g, 16.87 mmol) were dissolved in acetonitrile (5 mL), and 7-methyl-[1,2,4]triazolo[1,5-a]pyridine-2-amine 87a (500 mg, 3.37 mmol) was added to the reaction liquid under stirring. The reaction liquid was stirred at room temperature for 0.5 hours, then heated to 60° C., and stirred for 0.5 hour. The reaction liquid was concentrated, and the residue was diluted with ethyl acetate (30 mL) and filtered. The organic phase was washed with water (30 mL). The organic phase was concentrated, and the residue was purified by silica gel column chromatography (elution system C) to obtain 2-bromo-7-methyl-[1,2,4]triazolo[1,5-a]pyridine 87b (530 mg), yield: 74.1%.

MS m/z (ESI): 214.0 $[M+H]^+$.

Step 2

Under nitrogen protection, 87b (211.8 mg, 1.0 mmol), intermediate 2 (90 mg, 0.33 mmol), sodium tert-butoxide (96.0 mg, 1.0 mmol), tris(dibenzylideneacetone)palladium (61.0 mg, 0.07 mmol), and Ruphos (46.6 mg, 0.1 mmol) were dissolved in 1'4-dioxane (8 mL), heated to 130° C., and stirred for 16 hours. The reaction liquid was filtered and concentrated. The residue was purified by preparative HPLC (ammonium bicarbonate system) to obtain 6'-(((1S,3S)-3-((7-methyl-[1,2,4]triazolo[1,5-a]pyridin-2-yl)amino)cyclopentyl)amino)-2H-[1,3'-bipyridinyl]-2-one 87 (30 mg), yield 22.2%.

MS m/z (ESI): 402.2 $[M+H]^+$.

$^1H$ NMR (400 MHz, DMSO-$d_6$) δ 8.43 (d, 1H), 7.91 (d, 1H), 7.60 (dd, 1H), 7.47 (t, 1H), 7.39 (dd, 1H), 7.16 (s, 1H), 6.91 (d, 1H), 6.69 (d, 1H), 6.56-6.50 (m, 2H), 6.44 (d, 1H), 6.26 (t, 1H), 4.34-4.29 (m, 1H), 4.20-4.10 (m, 1H), 2.34 (s, 3H), 2.25-2.08 (m, 2H), 2.01-1.81 (m, 2H), 1.64-1.41 (m, 2H).

Example 88

6'-(((1S,3S)-3-((6-fluoro-[1,2,4]triazolo[1,5-a]pyridin-2-yl)amino)cyclopentyl)amino)-2H-[1,3'-bipyridinyl]-2-one Example 88 could also be synthesized by the following method:

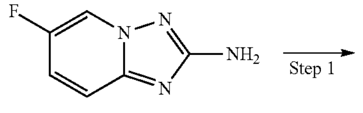

88a

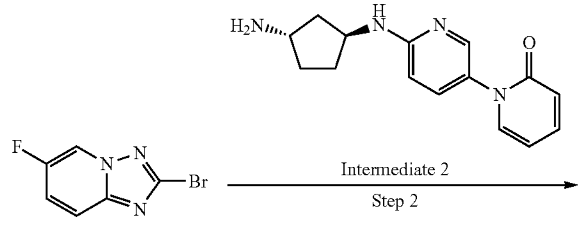

88b

-continued

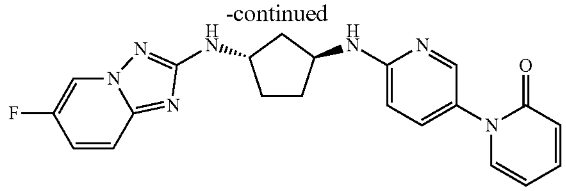

88

Step 1

Copper bromide (1.10 g, 4.93 mmol) and tert-butyl nitrite (1.69 g, 16.43 mmol) were dissolved in acetonitrile (5 mL), and 6-fluoro-[1,2,4]triazolo[1,5-a]pyridine-2-amine 88a (500.00 mg, 3.29 mmol) was added to the reaction liquid under stirring. The reaction was stirred at room temperature for 0.5 hours, then heated to 60° C., and stirred for 0.5 hours. The reaction liquid was concentrated, and the residue was diluted with ethyl acetate (100 mL) and filtered. The organic phase was washed with water (100 mL) and concentrated, and the residue was diluted with ethyl acetate (30 mL) and filtered. The organic phase was washed with water (30 mL), dried, and concentrated, and the residue was purified by silica gel column chromatography (elution system C) to obtain 2-bromo-6-fluoro-[1,2,4]triazolo[1,5-a]pyridine 88b (490 mg), yield: 69.0%.

MS m/z (ESI): 215.9 $[M+H]^+$.

Step 2

Under nitrogen protection, 88b (215.8 mg, 1.0 mmol), intermediate 2 (90 mg, 0.33 mmol), sodium tert-butoxide (96.0 mg, 1.0 mmol), tris(dibenzylideneacetone)palladium (61.0 mg, 0.07 mmol), and Ruphos (46.6 mg, 0.1 mmol) were dissolved in 1'4-dioxane (8 mL), heated to 130° C., and stirred for 16 hours. The reaction liquid was filtered and concentrated. The residue was purified by preparative HPLC (ammonium bicarbonate system) to obtain 6'-(((1S,3S)-3-((6-fluoro-[1,2,4]triazolo[1,5-a]pyridin-2-yl)amino)cyclopentyl)amino)-2H-[1,3'-bipyridinyl]-2-one 88 (10.5 mg), yield 7.23%.

MS m/z (ESI): 406.1 $[M+H]^+$.

$^1H$ NMR (400 MHz, DMSO-$d_6$) δ 8.96-8.90 (m, 1H), 7.91 (d, 1H), 7.59 (d, 1H), 7.54-7.44 (m, 2H), 7.43-7.37 (m, 2H), 6.91 (d, 1H), 6.71 (d, 1H), 6.60-6.40 (m, 2H), 6.27 (t, 1H), 4.38-4.26 (m, 1H), 4.23-4.10 (m, 1H), 2.25-2.05 (m, 2H), 2.01-1.81 (m, 2H), 1.65-1.40 (m, 2H).

Example 91

2-(6-(((1S,3S)-3-((5-(difluoromethoxy)pyrimidin-2-yl)amino)cyclopentyl)amino)pyridin-3-yl)-1,1-dioxoisothiazolane Example 91 could also be synthesized by the following method:

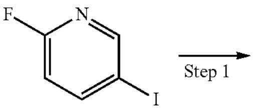

91a

-continued

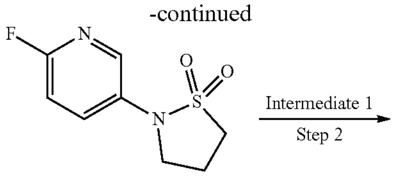

91b

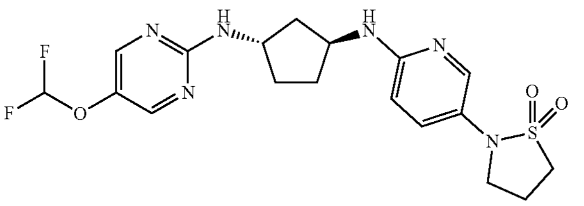

91

Step 1

Under nitrogen protection, 2-fluoro-5-iodopyridine 91a (300 mg, 1.35 mmol), 1,1-dioxoisothiazolidine (326 mg, 2.69 mmol), cuprous iodide (51 mg, 0.27 mmol), dimethyl ethylenediamine (24 mg, 0.27 mmol), and potassium carbonate (558 mg, 4.04 mmol) were dissolved in 1,4-dioxane (5 mL), heated to 130° C. by microwave, and stirred for 1 hour. A saturated sodium chloride solution was added to the reaction liquid. The aqueous phase was extracted with ethyl acetate (25 mL×2). The organic phases were combined, dried, and concentrated, and the residue was separated by silica gel column chromatography (elution system B) to obtain 2-(6-fluoropyridin-3-yl)-1,1-dioxoisothiazolidine 91b (269 mg), yield: 92.47%.

MS m/z (ESI): 217.1 $[M+H]^+$.

Step 2

Under nitrogen protection, intermediate 1 (75 mg, 0.31 mmol), 91b (133 mg, 0.62 mmol), and diisopropylethylamine (80 mg, 0.62 mmol) were dissolved in dimethyl sulfoxide (1 mL), and the reaction was heated to 125° C. and stirred for 48 hours. The reaction liquid was filtered, and the filtrate was subjected to reversed-phase HPLC (ammonium bicarbonate system) to prepare 2-(6-(((1S,3S)-3-((5-(difluoromethoxy)pyrimidin-2-yl)amino)cyclopentyl)amino)pyridin-3-yl)-1,1-dioxoisothiazolidine 91 (17.1 mg), yield: 12.59%.

MS m/z (ESI): 441.1 $[M+H]^+$.

$^1$H NMR (400 MHz, DMSO-$d_6$) δ 8.23 (s, 2H), 7.87 (d, 1H), 7.49 (d, 1H), 7.41-7.31 (m, 1H), 7.25-6.80 (m, 1H), 6.74 (d, 1H), 6.48 (d, 1H), 4.36-4.16 (m, 2H), 3.59 (t, 2H), 3.42-3.36 (m, 2H), 2.40-2.29 (m, 2H), 2.16-2.04 (m, 2H), 1.93-1.76 (m, 2H), 1.59-1.38 (m, 2H).

Example 92

2-(6-(((1S,3S)-3-((5-(difluoromethoxy)pyrimidin-2-yl)amino)cyclopentyl)amino)pyridin-3-yl)-1,4-butanesulfolactam

92

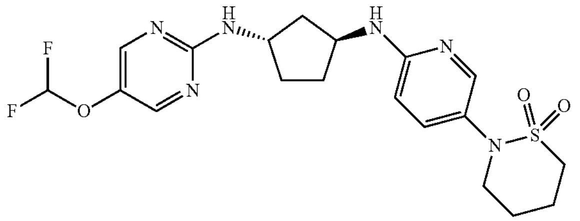

Example 92 could also be synthesized by the following method:

By reference to the synthesis method of Example 91, the target compound 2-(6-(((1S,3S)-3-((5-(difluoromethoxy)pyrimidin-2-yl)amino)cyclopentyl)amino) pyridin-3-yl)-1,4-butanesulfolactam 92 was synthesized.

MS m/z (ESI): 455.2 $[M+H]^+$.

$^1$H NMR (400 MHz, DMSO-$d_6$) δ 8.23 (s, 2H), 7.88 (d, 1H), 7.46 (d, 1H), 7.36-7.28 (m, 1H), 7.23-6.81 (m, 1H), 6.76 (d, 1H), 6.44 (d, 1H), 4.35-4.18 (m, 2H), 3.57-3.46 (m, 2H), 3.28-3.18 (m, 2H), 2.18-2.03 (m, 4H), 1.95-1.69 (m, 4H), 1.59-1.38 (m, 2H).

Example 93

6-(6-(((1S,3S)-3-((5-(difluoromethoxy)pyrimidin-2-yl)amino)cyclopentyl)amino)pyridin-3-yl)-5,5-dimethyl-5,6-dihydro-7H-pyrrolo[3,4-b]pyridin-7-one Example 93 could also be synthesized by the following method:

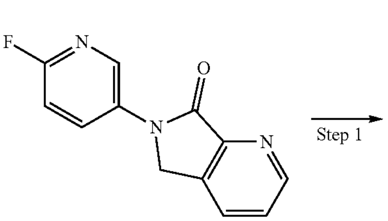

57b

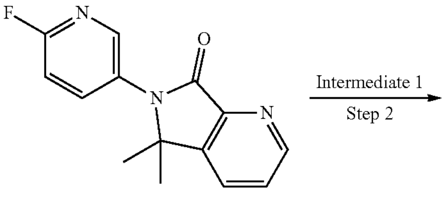

93a

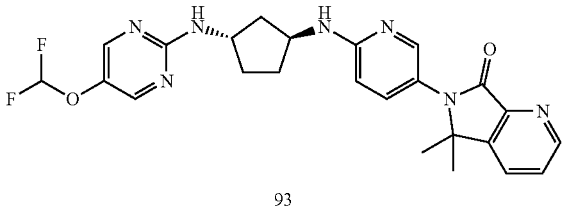

93

Step 1

At 0° C., lithium bis(trimethylsilyl)amide (1 M, 3.6 mL) was added to a solution of 57b (167 mg, 0.73 mmol) and iodomethane (517 mg, 3.64 mmol) in tetrahydrofuran (3 mL), and the reaction was heated to room temperature and stirred for 3 hours. At 0° C., a saturated ammonium chloride solution was added to the reaction liquid. The aqueous phase was extracted with ethyl acetate (20 mL×2). The organic phases were combined, dried, and concentrated, and the residue was separated by silica gel column chromatography to obtain 6-(6-fluoropyridin-3-yl)-5,5-dimethyl-5,6-dihydro-7H-pyrrolo[3,4-b]pyridin-7-one 93a (110 mg), yield: 58.69%.

MS m/z (ESI): 258.1 $[M+H]^+$.

Step 2

Under nitrogen protection, intermediate 1 (100 mg, 0.41 mmol), 93a (70 mg, 0.27 mmol), and diisopropylethylamine (106 mg, 0.82 mmol) were dissolved in dimethyl sulfoxide (1.5 mL), and the reaction was heated to 130° C. and stirred for 48 hours. A saturated sodium chloride solution was added to the reaction liquid. The aqueous phase was extracted with ethyl acetate (15 mL×2). The organic phases were combined, dried, and concentrated, and the residue was subjected to reversed-phase HPLC to prepare 6-(6-(((1S,3S)-3-((5-(difluoromethoxy)pyrimidin-2-yl)amino)cyclopentyl)amino)pyridin-3-yl)-5,5-dimethyl-5,6-dihydro-7H-pyrrolo[3,4-b]pyridin-7-one 93 (32.1 mg), yield: 24.50%.

MS m/z (ESI): 482.3 $[M+H]^+$.

$^1$H NMR (400 MHz, DMSO-$d_6$) δ 8.79-8.69 (m, 1H), 8.29-8.19 (m, 3H), 7.86 (d, 1H), 7.68-7.59 (m, 1H), 7.49 (d, 1H), 7.32-7.26 (m, 1H), 7.23-6.82 (m, 1H), 6.90 (d, 1H), 6.57 (d, 1H), 4.42-4.20 (m, 2H), 2.23-2.03 (m, 2H), 2.01-1.78 (m, 2H), 1.64-1.34 (m, 8H).

Example 95

6-(6-(((1S,3S)-3-((5-(difluoromethoxy)pyrimidin-2-yl)amino)cyclopentyl)amino)pyridin-3-yl)-5H-pyrrolo[3,4-b]pyridine-5,7(6H)-dione Example 95 could also be synthesized by the following method:

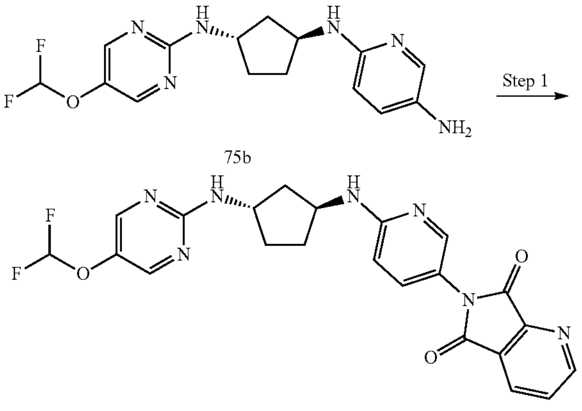

75b

95

Step 1

75b (75 mg, 0.22 mmol), 2,3-pyridinedicarboxylic anhydride (33 mg, 0.22 mmol), and 4-dimethylaminopyridine (3 mg, 0.02 mmol) were dissolved in tetrahydrofuran (2 mL) and stirred at 50° C. for 1 hour, and acetic anhydride (46 mg, 0.45 mmol) was added to the above reaction liquid. The reaction was heated to 70° C. and stirred for 1 hour. The reaction liquid was filtered, and the filtrate was subjected to reversed-phase HPLC to prepare 6-(6-(((1S,3S)-3-((5-(difluoromethoxy)pyrimidin-2-yl)amino)cyclopentyl)amino)pyridin-3-yl)-5H-pyrrolo[3,4-b]pyridine-5,7(6H)-dione 95 (21.3 mg), yield: 20.44%.

MS m/z (ESI): 468.2 $[M+H]^+$.

$^1$H NMR (400 MHz, DMSO-$d_6$) δ 9.07-8.99 (m, 1H), 8.42-8.33 (m, 1H), 8.24 (s, 2H), 7.98 (d, 1H), 7.89-7.79 (m, 1H), 7.51 (d, 1H), 7.44-7.38 (m, 1H), 7.26-6.81 (m, 1H), 6.98 (d, 1H), 6.57 (d, 1H), 4.38-4.26 (m, 2H), 2.2-2.07 (m, 2H), 1.95-1.83 (m, 2H), 1.60-1.44 (m, 2H).

Example 97

1-Cyclopropyl-3-(6-(((1S,3S)-3-((5-(difluoromethoxy)pyrimidin-2-yl)amino)cyclopentyl)amino)pyridin-3-yl)-1,3-dihydro-2H-imidazo[4,5-b]pyrazin-2-one

97

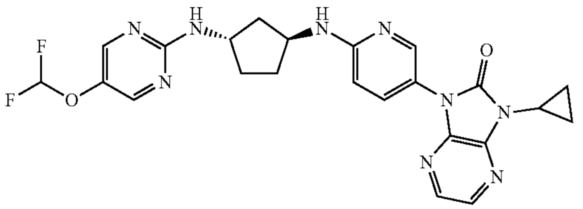

Example 97 could also be synthesized by the following method:

By reference to the synthesis method of Example 56, the target compound 1-cyclopropyl-3-(6-(((1S,3S)-3-((5-(difluoromethoxy)pyrimidin-2-yl)amino)cyclopentyl)amino)pyridin-3-yl)-1,3-dihydro-2H-imidazo[4,5-b]pyrazin-2-one 97 was synthesized.

MS m/z (ESI): 496.2 $[M+H]^+$.

$^1$H NMR (400 MHz, DMSO-$d_6$) δ 8.24 (s, 2H), 8.09 (d, 1H), 8.00 (d, 1H), 7.90 (d, 1H), 7.56-7.45 (m, 2H), 7.26-6.80 (m, 1H), 6.96 (d, 1H), 6.58 (d, 1H), 4.40-4.21 (m, 2H), 3.10-2.96 (m, 1H), 2.22-2.03 (m, 2H), 2.00-1.81 (m, 2H), 1.61-1.42 (m, 2H), 1.16-0.95 (m, 4H).

Example 99

7-(6-(((1S,3S)-3-((5-(difluoromethoxy)pyrimidin-2-yl)amino)cyclopentyl)amino)-3-yl)pyrazolo[1,5-a]pyridine-3-carbonitrile Example 99 could also be synthesized by the following method:

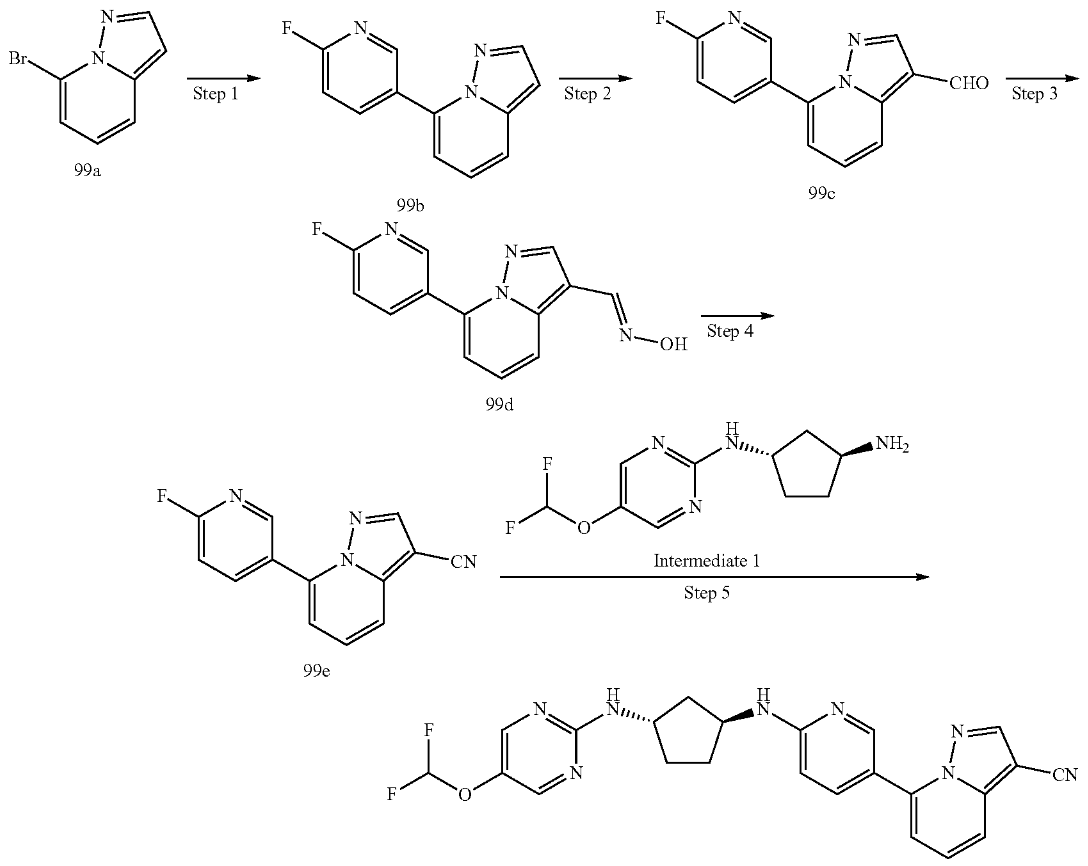

99a
99b
99c
99d
99e
99

Step 1

Under nitrogen protection, 7-bromopyrazolo[1,5-a]pyridine 99a (650 mg, 3.3 mmol), (6-fluoropyridin-3-yl)boronic acid (604 mg, 4.29 mmol), bis(diphenylphosphino)ferrocene dichloropalladium (241 mg, 0.33 mmol), and potassium carbonate (1.14 g, 8.25 mmol) were dissolved in a mixed solution of 1,4-dioxane (16 mL) and water (4 mL), and the reaction was heated to 100° C. and stirred for 10 hours. The reaction liquid was filtered through diatomite and concentrated, and the residue was separated by silica gel column chromatography (eluent system B) to obtain 7-(6-fluoropyridin-3-yl)pyrazolo[1,5-a]pyridine 99b (640 mg), yield: 91.0%.

MS m/z (ESI): 214.1 $[M+H]^+$.

Step 2

99b (300 mg, 1.41 mmol) was dissolved in N,N-dimethylformamide (5 mL) and placed in an ice-water bath, and under nitrogen protection, phosphorus oxychloride (1 mL) was added. The reaction was stirred at room temperature for 1 hour. The reaction liquid was poured into ice water (20 mL), and the pH was adjusted to weak alkalinity by adding a sodium hydroxide aqueous solution. The reaction liquid was extracted with ethyl acetate (30 mL×3). The combined organic phases were washed with saturated sodium chloride (30 mL), dried, and concentrated, and the residue was separated by silica gel column chromatography (eluent system B) to obtain 7-(6-fluoropyridin-3-yl)pyrazolo[1,5-a]pyridine-3-carbaldehyde 99c (310 mg), yield: 91.3%.

MS m/z (ESI): 242.1 $[M+H]^+$.

Step 3

99c (200 mg, 0.83 mmol) and hydroxylamine hydrochloride (86 mg, 1.24 mmol) were dissolved in a mixed solution of ethanol (15 mL) and water (5 mL), and the reaction was heated to 50° C. and stirred for 2 hours. The reaction liquid was concentrated, a saturated sodium bicarbonate aqueous solution (10 mL) was added, and the mixture was filtered. The filter cake was washed with water and dried to obtain 7-(6-fluoropyridin-3-yl)pyrazolo[1,5-a]pyridine-3-carbaldehydeoxime 99d (150 mg), yield: 70.6%.

MS m/z (ESI): 257.1 $[M+H]^+$.

Step 4

99d (60 mg, 0.234 mmol) was dissolved in acetic anhydride (5 mL), and the reaction was heated to 130° C. and stirred for 2 hours. The reaction liquid was cooled to room temperature and filtered, and the filter cake was washed with a saturated sodium bicarbonate aqueous solution and an aqueous solution, respectively, and dried to obtain 7-(6-fluoropyridin-3-yl)pyrazolo[1,5-a]pyridine-3-carbonitrile 99e (30 mg), yield: 53.8%.

MS m/z (ESI): 239.1 $[M+H]^+$.

Step 5

99e (35 mg, 0.147 mmol), intermediate 2 (36 mg, 0.147 mmol), and diisopropylethylamine (40 mg, 0.294 mmol) were dissolved in dimethyl sulfoxide (2 mL), and the reaction was heated to 130° C. and stirred for 16 hours. The reaction liquid was filtered, and the filtrate was purified by preparative HPLC (ammonium bicarbonate system) to obtain 7-(6-(((1S,3S)-3-((5-(difluoromethoxy)pyrimidin-2-yl)amino)cyclopentyl)amino)pyridin-3-yl)pyrazolo[1,5-a]pyridine-3-carbonitrile 99 (32 mg), yield: 47.1%.

MS m/z (ESI): 463.2 $[M+H]^+$.

$^1$H NMR (400 MHz, DMSO-$d_6$) δ 8.65 (s, 1H), 8.55 (d, 1H), 8.24 (s, 2H), 8.00 (dd, 1H), 7.82 (dd, 1H), 7.67 (dd, 1H), 7.50 (d, 1H), 7.30 (dd, 1H), 7.21 (s, 1H), 7.03 (t, 1H), 6.60 (d, 1H), 4.42-4.29 (m, 2H), 2.21-2.07 (m, 2H), 2.03-1.86 (m, 2H), 1.60-1.46 (m, 2H).

Example 102

(1S,3S)—$N^1$-(5-(difluoromethoxy)pyrimidin-2-yl)-$N^3$-(5-(3-fluoropyrazolo[1,5-a]pyridin-7-yl)pyridin-2-yl)cyclopentane-1,3-diamine Example 102 could also be synthesized by the following method:

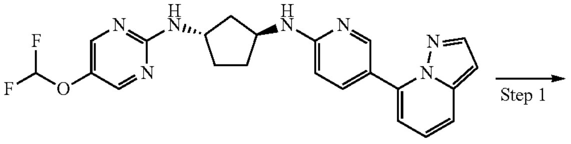

52

-continued

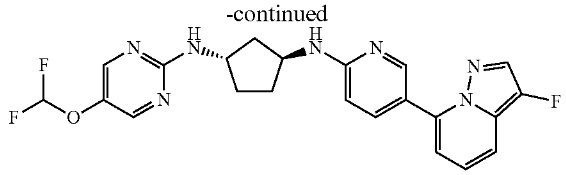

102

Step 1

(1S,3S)—$N^1$-(5-difluoromethoxy)pyrimidin-2-yl)-$N^3$-(5-(pyrazolo[1,5-a]pyridin-7-yl)pyridin-2-yl)cyclopentane-1,3-diamine 52 (30 mg, 0.068 mmol) and 1-chloromethyl-4-fluoro-1,4-diazoniabicyclo[2.2.2]octane bis(tetrafluoroboronate) (24 mg, 0.068 mmol) were dissolved in acetonitrile (2 mL), and the reaction was stirred at room temperature for 1 hour. The reaction liquid was filtered, and the filtrate was purified by preparative HPLC (ammonium bicarbonate system) to obtain the target compound (1S,3S)—$N^1$-(5-difluoromethoxy)pyrimidin-2-yl)-1-(5-(3-fluoropyrazolo[1,5-a]pyridin-7-yl)pyridin-2-yl)cyclopentane-1,3-diamine 102 (7 mg), yield: 22.4%.

MS m/z (ESI): 456.2 $[M+H]^+$.

$^1$H NMR (400 MHz, DMSO-$d_6$) δ 8.53 (d, 1H), 8.24 (s, 2H), 8.11 (d, 1H), 7.98 (dd, 1H), 7.60 (dd, 1H), 7.49 (d, 1H), 7.27 (dd, 1H), 7.10 (d, 1H), 7.03 (t, 1H), 6.98 (dd, 1H), 6.58 (d, 1H), 4.40-4.28 (m, 2H), 2.22-2.07 (m, 2H), 2.03-1.85 (m, 2H), 1.60-1.46 (m, 2H).

Example 108

3-(6-(((1S,3S)-3-((5-(difluoromethoxy)pyrimidin-2-yl)amino)cyclopentyl)amino)pyridin-3-yl)-4H-pyrido[1,2-a]pyrimidin-4-one Example 108 could also be prepared according to the following method:

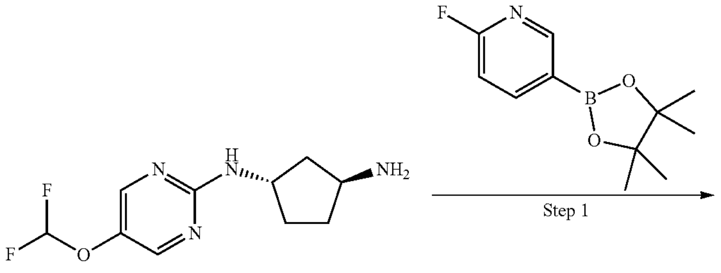

Intermediate 1

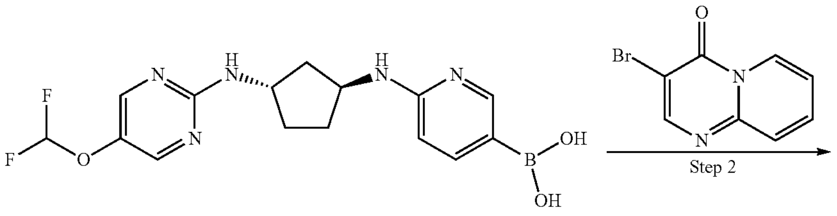

108a

-continued

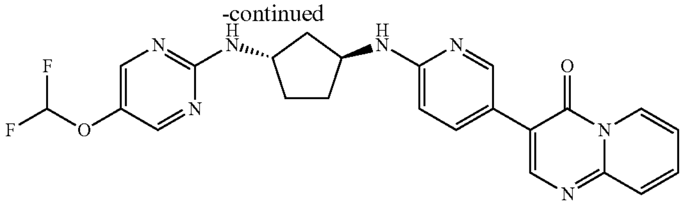

108

Step 1

Under nitrogen protection, intermediate 1 (300 mg, 1.23 mmol), 2-fluoro-5-(4,4,5,5-tetramethyl-1,3,2-dioxaborolan-2-yl)pyridine (301.4 mg, 1.35 mmol), and N,N-diisopropylethylamine (476.3 mg, 3.68 mmol) were dissolved in dimethyl sulfoxide (3 mL), heated to 130° C., and stirred for 16 hours. The reaction liquid was filtered, and the filtrate was purified by preparative HPLC (formic acid system) to obtain (6-(((1S,3S)-3-((5-(difluoromethoxy)pyrimidin-2-yl)amino) cyclopentyl) amino)pyridin-3-yl)boronic acid 108a (250 mg), yield: 55.7%.

MS m/z (ESI): 366.2 $[M+H]^+$.

Step 2

Under nitrogen protection, 108a (80 mg, 0.22 mmol), 3-bromo-4H-pyridino[1,2-a]pyrimidin-4-one (98.6 mg, 0.44 mmol), [1,1'-bis(di-tert-butylphosphino)ferrocene]dichloropalladium (15.9 mg, 0.024 mmol), and sodium carbonate (71.0 mg, 0.66 mmol) were dissolved in a mixed liquid of 1'4-dioxane (5 mL) and water (0.5 mL), heated to 100° C., and stirred for 16 hours. The reaction liquid was filtered, and the filtrate was concentrated. The residue was purified by silica gel column chromatography (elution system A) to obtain 3-(6-(((1S,3S)-3-((5-(difluoromethoxy)pyrimidin-2-yl)amino)cyclopentyl)amino)pyridin-3-yl)-4H-pyridino[1,2-a]pyrimidin-4-one 108 (39 mg), yield: 37.1%.

MS m/z (ESI): 466.2 $[M+H]^+$.

$^1$H NMR (400 MHz, DMSO-$d_6$) δ 9.07 (d, 1H), 8.56 (s, 1H), 8.46 (d, 1H), 8.24 (s, 2H), 7.95-7.84 (m, 2H), 7.72 (d, 1H), 7.49 (d, 1H), 7.39 (t, 1H), 7.03 (s, 1H), 6.79 (s, 1H), 6.55 (d, 1H), 4.40-4.26 (m, 2H), 2.22-2.04 (m, 2H), 1.97-1.82 (m, 2H), 1.59-1.45 (m, 2H).

Example 112

6'-(((1S,3S)-3-((7-chloro-[1,2,4]triazolo[1,5-a]pyridin-2-yl)amino)cyclopentyl)amino)-2H-[1,3'-bipyridinyl]-2-one

112

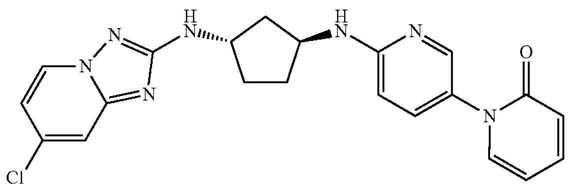

By reference to the synthesis method of Example 27, 6'-(((1S,3S)-3-((7-chloro-[1,2,4]triazolo[1,5-a]pyridin-2-yl) amino)cyclopentyl)amino)-2H-[1,3'-bipyridinyl]-2-one 112 was synthesized.

MS m/z (ESI): 422.1 $[M+H]^+$.

$^1$H NMR (400 MHz, DMSO-$d_6$) δ 8.62 (d, 1H), 7.91 (d, 1H), 7.59 (dd, 1H), 7.54 (d, 1H), 7.50-7.43 (m, 1H), 7.39 (dd, 1H), 6.96-6.88 (m, 2H), 6.83 (d, 1H), 6.52 (d, 1H), 6.44 (d, 1H), 6.27 (t, 1H), 4.39-4.26 (m, 1H), 4.21-4.09 (m, 1H), 2.23-2.06 (m, 2H), 2.00-1.81 (m, 2H), 1.62-1.43 (m, 2H).

Example 113

6'-(((1S,3S)-3-((7-(trifluoromethyl)-[1,2,4]triazolo[1,5-a]pyridin-2-yl)amino)cyclopentyl)amino)-2H-[1,3'-bipyridinyl]-2-one

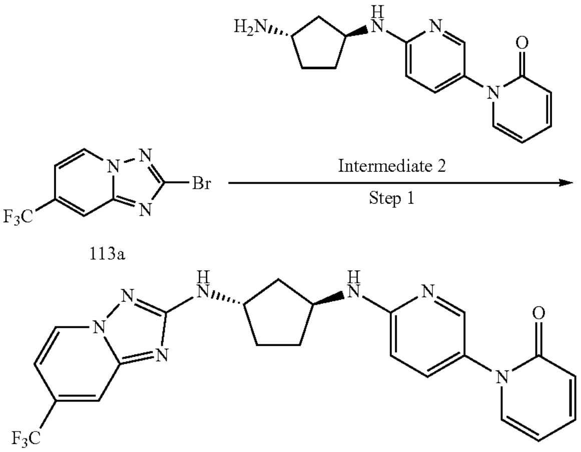

113a

113

Under nitrogen protection, 2-bromo-7-(trifluoromethyl)-[1,2,4]triazolo[1,5-a]pyridine 113a (77 mg, 0.29 mmol), intermediate 2 (60 mg, 0.22 mmol), sodium tert-butoxide (64 mg, 0.67 mmol), tris(dibenzylideneacetone)dipalladium (41 mg, 0.04 mmol), and 2-dicyclohexylphosphino-2',6'-diisopropoxy-1,1'-biphenyl (41 mg, 0.09 mmol) were dissolved in 1,4-dioxane (2 mL), heated to 130° C. by microwave, and stirred for 2 hours. The reaction liquid was filtered, and the filtrate was concentrated. The residue was purified by preparative HPLC (ammonium bicarbonate system) to obtain 6'-(((1S,3S)-3-((7-(trifluoromethyl)-[1,2,4] triazolo[1,5-a]pyridin-2-yl)amino)cyclopentyl)amino)-2H-[1,3'-bipyridinyl]-2-one 113 (31.7 mg), yield: 31.4%.

MS m/z (ESI): 456.2 $[M+H]^+$.

$^1$H NMR (400 MHz, DMSO-$d_6$) δ 8.83 (d, 1H), 7.92 (s, 1H), 7.86 (s, 1H), 7.60 (d, 1H), 7.52-7.44 (m, 1H), 7.40 (d, 1H), 7.15 (d, 1H), 7.05 (d, 1H), 6.94 (d, 1H), 6.53 (d, 1H), 6.44 (d, 1H), 6.27 (t, 1H), 4.40-4.29 (m, 1H), 4.27-4.12 (m, 1H), 2.22-2.09 (m, 2H), 2.03-1.82 (m, 2H), 1.66-1.43 (m, 2H).

Example 114

6'-(((1S,3S)-3-((6-(trifluoromethyl)-1,2,4-triazin-3-yl)amino)cyclopentyl)amino)-2H-[1,3'-bipyridinyl]-2-one Example 114 could also be prepared by reference to the following method.

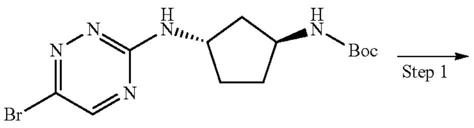

63c

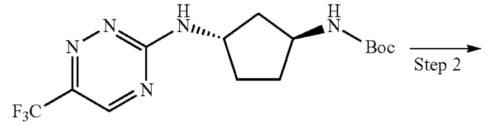

114a

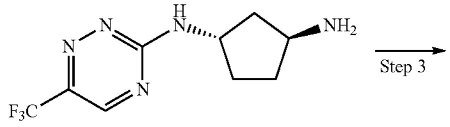

114b

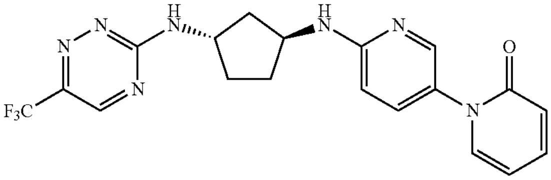

114

Step 1

Under nitrogen protection, 63c (241 mg, 0.67 mmol), methyl 2,2-difluoro-2-fluorosulfonylacetate (259 mg, 1.35 mmol), and cuprous iodide (192 mg, 1.01 mmol) were dissolved in N,N-dimethylformamide (3 mL), heated to 90° C. by microwave, and stirred for 3 hours. The reaction liquid was diluted with ethyl acetate (50 mL), and the organic phase was washed with water (20 mL) and saturated sodium chloride (20 mL). The organic phase was dried and concentrated, and the residue was separated by silica gel column chromatography (eluent system A) to obtain the title product tert-butyl (1S,3S)-3-(((6-(trifluoromethyl)-1,2,4-triazin-3-yl)amino)cyclopentyl)carbamate 114a (160 mg), yield: 68.5%.

MS m/z (ESI): 348.2 $[M+H]^+$.

Step 2

By reference to the synthesis method of step 4 of Example 63, the target compound (1S,3S)—N1-(6-(trifluoromethyl)-1,2,4-triazin-3-yl)cyclopentane-1,3-diamine 114b was synthesized.

MS m/z (ESI): 296.2 $[M+H]^+$.

Step 3

By reference to the synthesis method of step 5 of Example 63, the target compound 6'-(((1S,3S)-3-((6-(trifluoromethyl)-1,2,4-triazin-3-yl)amino)cyclopentyl)amino)-2H-[1,3'-bipyridinyl]-2-one 114 was synthesized.

MS m/z (ESI): 418.2 $[M+H]^+$.

$^1$H NMR (400 MHz, $CD_3OD$) δ 8.52 (s, 1H), 7.95 (d, 1H), 7.60 (m, 2H), 7.45 (m, 1H), 6.62 (m, 2H), 6.46 (m, 1H), 4.62 (d, 1H), 4.39 (m, 1H), 2.29 (m, 2H), 2.11 (m, 2H), 1.68 (m, 2H)

Example 115

2-(6-(((1S,3S)-3-((5-(difluoromethoxy)pyrimidin-2-yl)amino)cyclopentyl)amino)-3-yl)-4-methyl-2,3-dihydro-1H-pyrrolo[3,4-c]pyridin-1-one

115

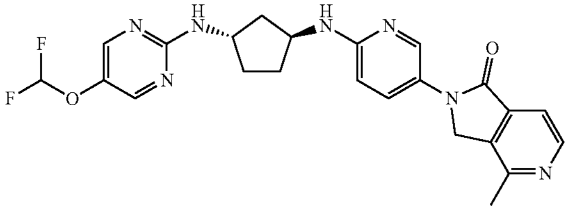

By reference to the synthesis method of Example 75, the target compound 2-(6-(((1S,3S)-3-((5-(difluoromethoxy)pyrimidin-2-yl)amino)cyclopentyl)amino) pyridin-3-yl)-4-methyl-2,3-dihydro-1H-pyrrolo[3,4-c]pyridin-1-one was synthesized.

MS m/z (ESI): 468.2 $[M+H]^+$.

$^1$H NMR (400 MHz, DMSO-$d_6$) δ 8.64 (d, 1H), 8.37 (d, 1H), 8.23 (s, 2H), 7.86 (dd, 1H), 7.55 (d, 1H), 7.48 (d, 1H), 7.03 (t, 1H), 6.71 (d, 1H), 6.55 (d, 1H), 4.98 (s, 2H), 4.33-4.26 (m, 2H), 2.57 (s, 3H), 2.18-2.08 (m, 2H), 1.95-1.82 (m, 2H), 1.58-1.44 (m, 2H).

Example 116

2-(6-(((1S,3S)-3-((5-(difluoromethoxy)pyrimidin-2-yl)amino)cyclopentyl)amino)-3-yl)-6-methyl-2,3-dihydro-1H-pyrrolo[3,4-c]pyridin-1-one

116

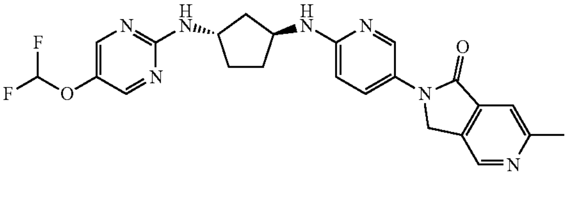

By reference to the synthesis method of Example 75, the target compound 2-(6-(((1S,3S)-3-((5-(difluoromethoxy)pyrimidin-2-yl)amino)cyclopentyl)amino) pyridin-3-yl)-6-methyl-2,3-dihydro-1H-pyrrolo[3,4-c]pyridin-1-one was synthesized.

MS m/z (ESI): 468.2 $[M+H]^+$.

$^1$H NMR (400 MHz, DMSO-$d_6$) δ 8.80 (s, 1H), 8.34 (d, 1H), 8.23 (s, 2H), 7.85 (dd, 1H), 7.59 (s, 1H), 7.49 (d, 1H), 7.03 (t, 1H), 6.72 (d, 1H), 6.54 (d, 1H), 4.97 (s, 2H), 4.33-4.26 (m, 2H), 2.60 (s, 3H), 2.18-2.08 (m, 2H), 1.95-1.82 (m, 2H), 1.58-1.45 (m, 2H).

Example 117

(1S,3S)—N[1]-(5-(difluoromethoxy)pyrimidin-2-yl)-N*-(5-(3-methylpyrazolo[1,5-a]pyridin-7-yl)pyridin-2-yl)cyclopentane-1,3-diamine Example 117 could also be prepared by reference to the following method:

Step 2

117a (50 mg, 0.206 mmol), phenyl chlorothioformate (35.5 mg, 0.206 mmol), and 4-dimethylaminopyridine (50.2 mg, 0.412 mmol) were dissolved in acetonitrile (5 mL), and the reaction was stirred at room temperature for 2 hours. The reaction liquid was concentrated, and the residue was separated by silica gel column chromatography (eluent system B) to obtain O-phenyl O-((7-(6-fluoropyridin-3-yl)pyrazolo[1,5-a]pyridin-3-yl)methyl) thiocarbonate 117b (30 mg), yield: 64.1%.

MS m/z (ESI): 380.1 [M+H]$^+$.

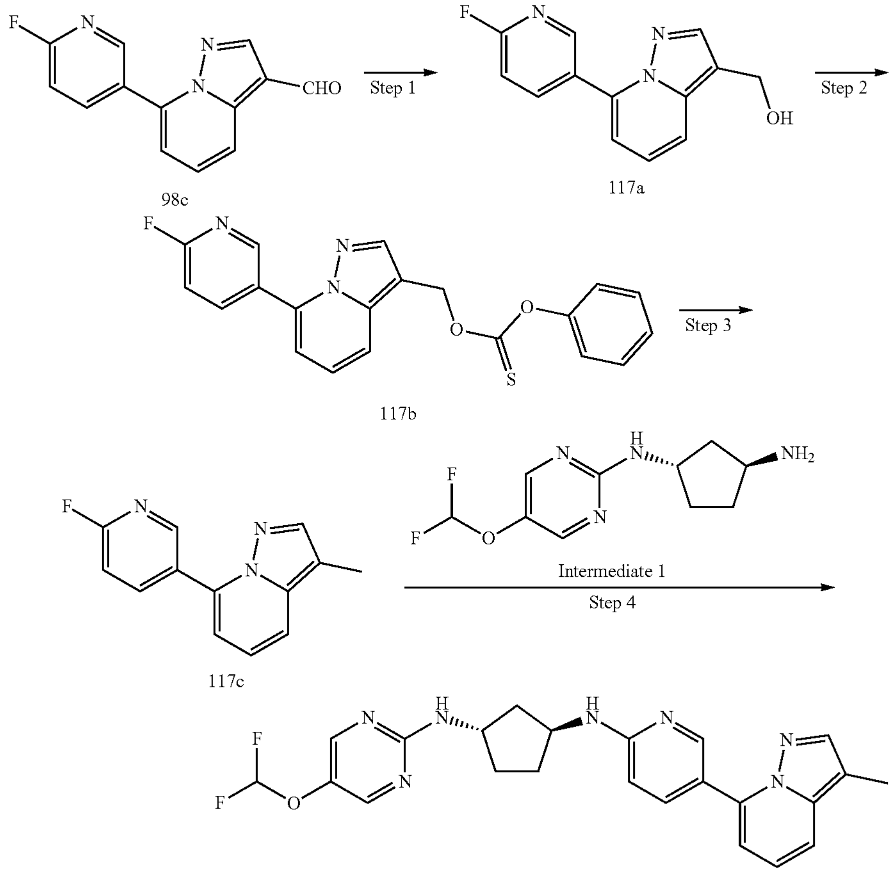

98c

117a

117b

117c

117

Step 1

In an ice bath, 99c (300 mg, 1.24 mmol) was dissolved in methanol (10 mL), sodium borohydride (47 mg, 1.24 mmol) was added to the reaction liquid under stirring, and the reaction was heated to room temperature and stirred for 2 hours. The reaction liquid was quenched by adding hydrochloric acid (1 M). The reaction liquid was concentrated, and the residue was separated by silica gel column chromatography (eluent system B) to obtain (7-(6-fluoropyridin-3-yl)pyrazolo[1,5-a]pyridin-3-yl)methanol 117a (240 mg), yield: 79.3%.

MS m/z (ESI): 244.1 [M+H]$^+$.

Step 3

Under nitrogen protection, 117b (50 mg, 0.132 mmol), azodiisobutyronitrile (4.3 mg, 0.026 mmol), and tributyltin hydride (4.3 mg, 0.026 mmol) were dissolved in toluene (3 mL), heated to 130° C., and stirred for 1 hour. The reaction liquid was concentrated, and the residue was separated by silica gel column chromatography (eluent system B) to obtain 7-(6-fluoropyridin-3-yl)-3-methylpyrazolo[1,5-a]pyridine 117c (20 mg), yield: 66.8%.

Step 4

117c (20 mg, 0.088 mmol), intermediate 2 (21.5 mg, 0.088 mmol), and diisopropylethylamine (22.7 mg, 0.176 mmol) were dissolved in dimethyl sulfoxide (2 mL), heated to 130° C., and stirred for 16 hours. The reaction liquid was filtered, and the filtrate was purified by preparative HPLC (ammonium bicarbonate system) to obtain the target compound (1S,3S)—$N^1$-(5-difluoromethoxy)pyrimidin-2-yl)-$N^3$-(5-(3-methylpyrazolo[1,5-a]pyridin-7-yl)pyridin-2-yl) cyclopentane-1,3-diamine 117 (12 mg), yield: 30.2%.

MS m/z (ESI): 452.2 $[M+H]^+$.

$^1$H NMR (400 MHz, DMSO-$d_6$) δ 8.55 (d, 1H), 8.24 (s, 2H), 8.02 (dd, 1H), 7.83 (s, 1H), 7.54 (dd, 1H), 7.50 (d, 1H), 7.21 (dd, 1H), 7.05 (t, 1H), 7.03 (s, 1H), 6.90 (dd, 1H), 6.57 (d, 1H), 4.40-4.30 (m, 2H), 2.30 (s, 3H), 2.18-2.10 (m, 2H), 1.97-1.85 (m, 2H), 1.58-1.49 (m, 2H).

Example 118

7-(6-(((1S,3S)-3-((5-(difluoromethoxy)pyrimidin-2-yl)amino)cyclopentyl)amino)pyridin-3-yl)pyrazolo [1,5-a]pyrimidine-3-carbonitrile

118

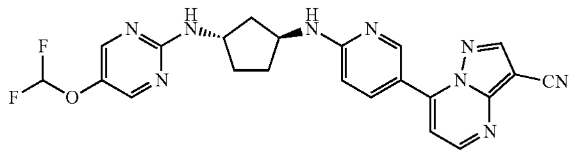

By reference to the synthesis method of Example 99, the target compound 7-(6-(((1S,3S)-3-((5-(difluoromethoxy)pyrimidin-2-yl)amino)cyclopentyl)amino) pyridin-3-yl)pyrazolo[1,5-a]pyrimidine-3-carbonitrile was synthesized.

MS m/z (ESI): 464.2 $[M+H]^+$.

$^1$H NMR (400 MHz, DMSO-$d_6$) δ 8.95 (d, 1H), 8.84 (s, 1H), 8.76 (d, 1H), 8.27 (dd, 1H), 8.24 (s, 2H), 7.62 (d, 1H), 7.56 (d, 1H), 7.52 (d, 1H), 7.04 (t, 1H), 6.65 (d, 1H), 4.44-4.30 (m, 2H), 2.23-2.08 (m, 2H), 1.99-1.86 (m, 2H), 1.59-1.51 (m, 2H).

Example 119

2-(6-(((1S,3S)-3-((5-((difluoromethoxy)pyrimidin-2-yl)amino)cyclopentyl)oxypyridin-3-yl)-5,5-dimethylisothiazolidine-1,1-dioxide Example 119 could also be prepared by reference to the following method.

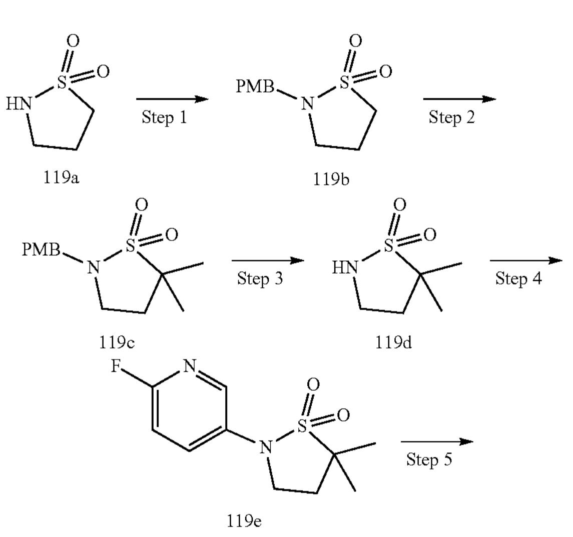

-continued

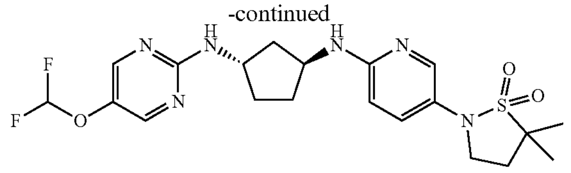

119

Step 1

Under nitrogen protection at 0° C., 1,2-thiazolidine-1,1-dioxide (2 g, 16.5 mmol) and 4-methoxychlorobenzyl (3.10 g, 19.8 mmol) were dissolved in tetrahydrofuran (35 mL), and sodium hydride (792 mg, 19.8 mmol, content: 60%) was added to the reaction liquid in portions under stirring. The reaction was gradually heated to room temperature and stirred for 16 hours. A saturated ammonium chloride solution was added to the reaction liquid. The aqueous phase was extracted with ethyl acetate (20 mL×3). The organic phases were washed with a saturated sodium chloride aqueous solution, dried, and concentrated, and the residue was separated by silica gel column chromatography (eluent system A) to obtain 2-(4-methoxybenzyl)isothiazolidine 1,1-dioxide 119b (1.52 g), yield: 38%.

MS m/z (ESI): 505.1 $[2M+Na]^+$.

Step 2

119b (1 g, 4.14 mmol) was dissolved in tetrahydrofuran (35 mL), and at −78° C., butyl lithium (2.5 M, 4.14 mL) was dropwise added to the reaction liquid. After the reaction continued to be maintained at −78° C. and was stirred for 1 hour, iodomethane (3.53 g, 24.9 mmol) was dropwise added to the reaction liquid. The reaction continued to be maintained at −78° C. with stirring for 2 hours and then transferred to room temperature with stirring for 1 hour. The reaction liquid was purified by preparative HPLC (formic acid system) to obtain 2-(4-methoxybenzyl)-5,5-dimethylisothiazolidine 1,1-dioxide 119c (586 mg), yield: 52%.

MS m/z (ESI): 539.2 $[2M+H]^+$.

Step 3

119c (0.32 g, 1.19 mmol) was dissolved in dichloromethane (10 mL), and trifluoroacetic acid (3 mL) was dropwise added to the reaction liquid under stirring and stirred at room temperature for 4 hours. The reaction liquid was concentrated and then diluted with ethyl acetate, and the organic phase was washed with a saturated sodium chloride aqueous solution, dried, and concentrated to obtain 5,5-dimethylisothiazolidine 1,1-dioxide 119d (165 mg). The product could be directly used in the next reaction without purification.

MS m/z (ESI): 150.1 $[M+H]^+$.

Step 4

By reference to the synthesis method of step 1 of Example 91, 2-(6-fluoropyridin-3-yl)-5,5-dimethylisothiazolidine 1,1-dioxide 119e (154 mg) was synthesized, yield: 56%.

MS m/z (ESI): 245.1 $[M+H]^+$.

Step 5

By reference to the synthesis method of step 2 of Example 91, the target compound 2-(6-(((1S,3S)-3-((5-((difluoromethoxy)pyrimidin-2-yl)amino)cyclopentyl) aminopyridin-3-yl)-5,5-dimethylisothiazolidine-1,1-dioxide 119 (21 mg) was synthesized, yield: 14%.

MS m/z (ESI): 469.2 [M+H]$^+$.

$^1$H NMR (400 MHz, DMSO-$d_6$) δ 8.23 (s, 2H), 7.88 (d, 1H), 7.46 (d, 1H), 7.35 (dd, 1H), 7.03 (t, 1H), 6.72 (d, 1H), 6.48 (d, 1H), 4.26 (dp, 2H), 3.53 (t, 2H), 2.21 (t, 2H), 2.10 (dtd, 2H), 1.85 (qt, 2H), 1.58-1.42 (m, 2H), 1.39 (s, 6H).

Example 120

2-(6-(((1S,3S)-3-((5-(difluoromethoxy)pyrimidin-2-yl)amino)cyclopentylamino)pyridin-3-yl)-6,6-dimethyl-1,2-thiazane-1,1-dioxide

120

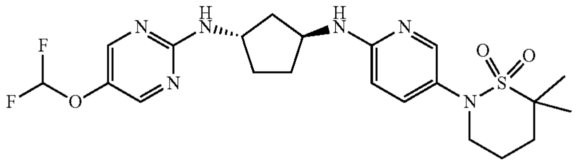

By reference to the synthesis method of Example 91, the target compound 2-(6-(((1S,3S)-3-((5-(difluoromethoxy)pyrimidin-2-yl)amino)cyclopentylamino) pyridin-3-yl)-6,6-dimethyl-1,2-thiazane-1,1-dioxide 120 was synthesized.

MS m/z (ESI): 483.2 [M+H]$^+$.

$^1$H NMR (400 MHz, DMSO-$d_6$) δ 8.23 (s, 2H), 7.85 (d, 1H), 7.47 (d, 1H), 7.28 (dd, 1H), 7.03 (t, 1H), 6.74 (d, 1H), 6.43 (d, 1H), 4.27 (dp, 2H), 3.50 (t, 2H), 2.10 (pd, 2H), 2.05-1.96 (m, 2H), 1.88-1.76 (m, 4H), 1.49 (ddd, 2H), 1.39 (s, 6H).

Example 121

2-(6-(((1S,3S)-3-((5-(difluoromethoxy)pyrimidin-2-yl)amino)cyclopentylamino)pyridin-3-yl)-2,3-dihydroisothiazolo[5,4-b]pyridine 1,1-dioxide Example 121 could also be obtained by the following method:

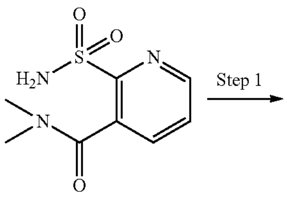

121a

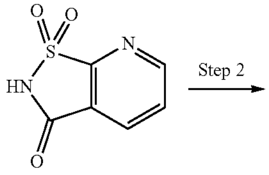

121b

-continued

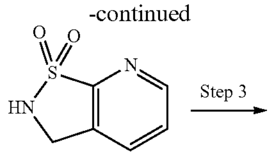

121c

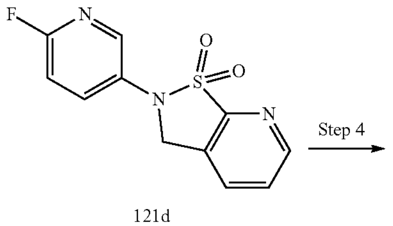

121d

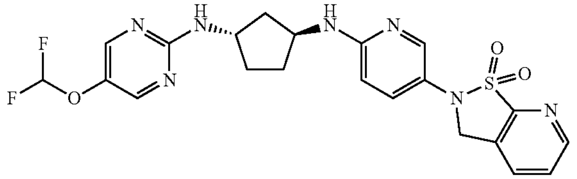

121

Step 1

2-Aminosulfonyl-N,N-dimethylnicotinamide (4 g, 17.45 mmol), benzyltriethylammonium chloride (40 mg, 0.174 mmol), and sodium carbonate (1.85 g, 17.45 mmol) were dissolved in pure water (2 mL), heated to 60° C. and stirred for 5 hours. The reaction liquid was concentrated by 1/2 volume and then poured into dilute hydrochloric acid (1N, 100 mL), whereupon a large amount of solid precipitated, which was filtered and dried to obtain isothiazolo[5,4-b]pyridine-3(2H)-one 1,1-dioxide 121a (1.27 g), yield: 40%.

MS m/z (ESI): 185.1 [M+H]$^+$.

$^1$H NMR (400 MHz, DMSO-$d_6$) δ 9.04 (dd, 1H), 8.45 (dd, 1H), 7.93 (dd, 1H).

Step 2

Under nitrogen protection, 121a (194 mg, 1.05 mmol) was dissolved in tetrahydrofuran (4 mL), and at 0° C., a solution of lithium aluminum hydride (88 mg, 2.32 mmol) in tetrahydrofuran (2 mL) was dropwise added to the reaction liquid. The reaction was transferred to room temperature and stirred for 2 hours. After the reaction liquid was diluted with ethyl acetate (25 mL), the organic phase was washed with saturated ammonium chloride (10 mL), dried, and concentrated to obtain 2,3-dihydroisothiazolo[5,4-b]pyridine 1,1-dioxide 121b (150 mg). The product was directly brought to the next reaction without further purification.

MS m/z (ESI): 171.0 [M+H]$^+$.

Step 3

Under nitrogen protection, 2-fluoro-5-iodopyridine (120 mg, 0.54 mmol), 121b (92 mg, 0.54 mmol), cuprous iodide (123 mg, 0.65 mmol), trans-(1R,2R)—N,N-dimethyl1,2-cyclohexanediamine (92 mg, 0.65 mmol), and potassium carbonate (260 mg, 1.88 mmol) were dissolved in dioxane (2 mL), and the reaction was heated to 100° C. and stirred for 4 hours. After the reaction liquid was filtered, the filtrate was diluted with ethyl acetate (25 mL) and water (10 mL). The organic phase was separated. The aqueous phase was extracted with ethyl acetate (25 mL×2). The organic phases were combined, washed with saturated sodium chloride (25 mL), dried, and concentrated, and the residue was purified by silica gel column chromatography (elution system A) to obtain 2-(6-fluoropyridin-3-yl)-2,3-dihydroisothiazolo[5,4-b]pyridine 1,1-dioxide 121c (36 mg), yield: 25%.

MS m/z (ESI): 266.1 $[M+H]^+$.

Step 4

Intermediate 1 (32 mg, 0.13 mmol), 121c (35 mg, 0.13 mmol), and N,N-diisopropylethylamine (51 mg, 0.39 mmol) were dissolved in dimethyl sulfoxide (1 mL), heated to 125° C., and stirred for 16 hours. The reaction liquid was purified by preparative HPLC (formic acid system) to obtain 2-(6-(((1S,3S)-3-((5-(difluoromethoxy)pyrimidin-2-yl)amino)cyclopentylamino)pyridin-3-yl)-2,3-dihydroisothiazolo[5,4-b]pyridine 1,1-dioxide 121 (6 mg), yield: 9%.

MS m/z (ESI): 490.1 $[M+H]^+$.

$^1H$ NMR (400 MHz, $CDCl_3$) δ 8.87-8.77 (m, 1H), 8.18 (q, 3H), 7.90-7.83 (m, 1H), 7.67 (dd, 1H), 7.59 (dd, 1H), 6.41 (t, 1H), 6.47 (d, 1H), 5.26 (d, 1H), 5.04 (s, 1H), 4.74 (s, 2H), 4.43 (p, 1H), 4.25 (s, 1H), 2.42-2.28 (m, 2H), 2.12-2.02 (m, 2H), 1.58-1.47 (m, 2H).

Examples 122 and 123

6-(6-(((1S,3S)-3-((5-(trifluoromethoxy)pyrimidin-2-yl)amino)cyclopentylamino)pyridin-3-yl)-6,7-dihydro-5H-pyrrolo[3,4-b]pyridin-5-one and 6-(6-(((1S,3S)-3-((5-(bromodifluoromethoxy)pyrimidin-2-yl)amino)cyclopentyl)amino)pyridin-3-yl)-6,7-dihydro-5H-pyrrolo[3,4-b]pyridin-5-one

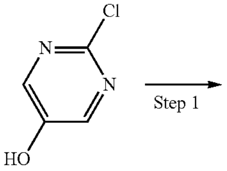

122a

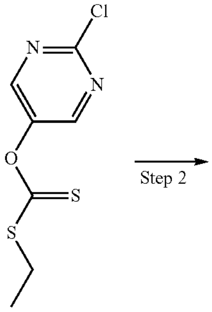

122b

-continued

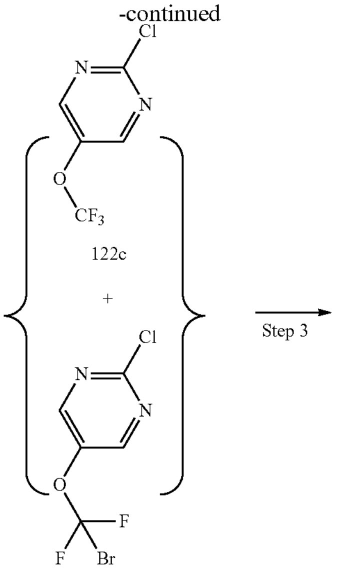

122c

123a

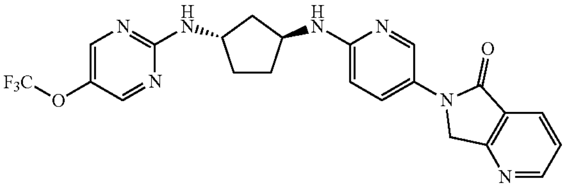

122

+

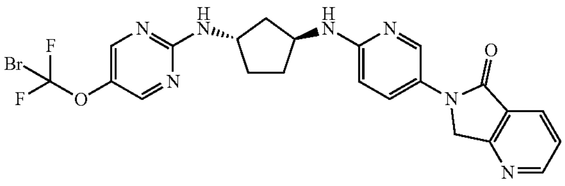

123

Step 1

In an ice bath, thiophosgene (6.61 g, 57.46 mmol) was added to a solution of 2-chloro-5-hydroxypyrimidine 122a (5.00 g, 38.30 mmol) and diisopropylethylamine (7.43 g, 57.46 mmol) in dichloromethane (100 mL), and the reaction liquid was heated to room temperature and stirred for 1 hour. The reaction liquid was cooled in an ice bath, sodium thioethylate (6.44 g, 76.61 mmol) was added to the reaction liquid, and the reaction was stirred in the ice bath for 1 hour. The reaction liquid was filtered. The organic phase was concentrated, and the residue was separated by silica gel column chromatography (eluent system A) to obtain the title product 0-(2-chloropyrimidin-5-yl) S-ethyl thiocarbonate 122b (4.20 g), yield: 46.7%.

MS m/z (ESI): 235.0 $[M+H]^+$.

Step 2

At −78° C., a hydrogen fluoride pyridine solution (40 mL, containing 70% of hydrofluoric acid) was dropwise added to a solution of 1,3-dibromo-5,5-dimethylimidazolidine-2,4-dione (4.87 g, 17.04 mmol) in dichloromethane (100 mL), and the reaction was stirred for 30 minutes. A solution of 122b (1.00 g, 4.26 mmol) in dichloromethane (5 mL) was dropwise added to the reaction liquid, and the reaction was heated to 0° C. and stirred for 2 hours. The reaction liquid was adjusted to a pH value of 9 with a sodium carbonate aqueous solution. The organic phase was separated and concentrated, and the residue was separated by silica gel column chromatography (eluent system B) to obtain the products 2-chloro-5-(trifluoromethoxy)pyrimidine 122c and 5-(bromodifluoromethoxy)-2-chloropyrimidine 123a as a mixture (160 mg).

122c MS m/z (ESI): 199.0 $[M+H]^+$.

123a MS m/z (ESI): 259.0 $[M+H]^+$.

Step 3

6-[6-[[(1S,3S)-3-aminocyclopentyl]amino]-3-pyridinyl]-7H-pyrrolo[3,4-b]pyridin-5-one (31 mg, 0.10 mmol, referring to Example 75 for the synthesis method therefor), the mixture of 122c and 123a (40 mg), and diisopropylethylamine (26 mg, 0.20 mmol) were dissolved in N,N-dimethylformamide (2 mL), and the reaction was heated to 60° C. and stirred for 16 hours. The reaction liquid was concentrated, and the residue was purified by preparative HPLC (ammonium bicarbonate system) to obtain 6-(6-(((1S,3S)-3-((5-(trifluoromethoxy)pyrimidin-2-yl)amino)cyclopentylamino)pyridin-3-yl)-6,7-dihydro-5H-pyrrolo[3,4-b]pyridin-5-one 122 (6 mg), yield: 12.6%.

MS m/z (ESI): 472.2 $[M+H]^+$.

$^1H$ NMR (400 MHz, $CD_3OD$) δ 8.78 (dd, 1H), 8.36 (d, 1H), 8.25 (s, 2H), 8.21 (dd, 1H), 7.85 (d, 1H), 7.59 (dd, 1H), 6.63 (d, 1H), 4.96 (s, 2H), 4.40 (m, 1H), 4.32 (t, 1H), 2.28 (m, 2H), 2.00 (m, 2H), 1.61 (m, 2H).

6-(6-(((1S,3S)-3-((5-(bromodifluoromethoxy)pyrimidin-2-yl)amino)cyclopentyl) amino)pyridin-3-yl)-6,7-dihydro-5H-pyrrolo[3,4-b]pyridin-5-one 123 (16 mg) was obtained, yield: 29.8%.

MS m/z (ESI): 532.1 $[M+H]^+$.

$^1H$ NMR (400 MHz, $CD_3OD$) δ 8.78 (dd, 1H), 8.36 (d, 1H), 8.25 (s, 2H), 8.21 (dd, 1H), 7.84 (dd, 1H), 7.59 (dd, 1H), 6.63 (d, 1H), 4.96 (s, 2H), 4.41 (m, 1H), 4.30 (m, 1H), 2.27 (dd, 2H), 2.02 (m, 2H), 1.60 (m, 2H)

Example 124

6-(6-(((1S,3S)-3-((5-(2,2,2-trifluoroethoxyl)pyrimidin-2-yl)amino)cyclopentylamino)pyridin-3-yl)-6,7-dihydro-5H-pyrrolo[3,4-b]pyridin-5-one

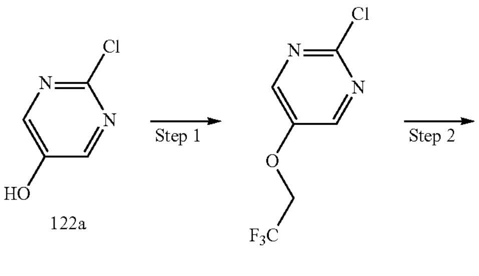

122a

-continued

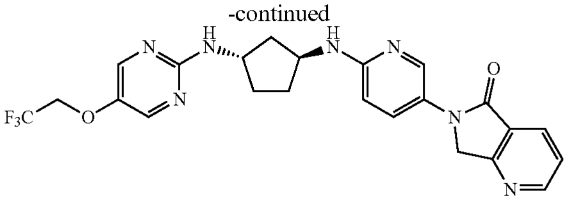

124

Step 1

At room temperature, 122a (1.00 g, 7.66 mmol), cesium carbonate (3.24 g, 9.96 mmol), and 2,2,2-trifluoroethyl trifluoromethanesulfonate (2.31 g, 9.96 mmol) were dissolved in N,N-dimethylformamide (8 mL) and stirred for 16 hours. Ethyl acetate (160 mL) was added to the reaction liquid. The organic phase was washed with water (25 mL) and saturated sodium chloride (25 mL), dried, and concentrated, and the residue was separated by silica gel column chromatography (eluent system B) to obtain 2-chloro-5-(2,2,2-trifluoroethoxyl)pyrimidine 124a (1.20 g), yield: 73.7%.

MS m/z (ESI): 213.0 $[M+H]^+$.

Step 2

By reference to the synthesis method of step 3 of Example 122, 6-(6-(((1S,3S)-3-((5-(2,2,2-trifluoroethoxyl)pyrimidin-2-yl)amino)cyclopentylamino)pyridin-3-yl)-6,7-dihydro-5H-pyrrolo[3,4-b]pyridin-5-one 124 was synthesized.

MS m/z (ESI): 486.2 $[M+H]^+$.

$^1H$ NMR (400 MHz, DMSO-$d_6$) δ 8.80 (dd, 1H), 8.36 (d, 1H), 8.20 (s, 2H), 8.15 (dd, 1H), 7.87 (dd, 1H), 7.56 (dd, 1H), 7.10 (d, 1H), 6.67 (d, 1H), 6.54 (d, 1H), 4.97 (s, 2H), 4.71 (q, 2H), 4.28 (q, 2H), 2.12 (m, 2H), 1.91 (m, 2H), 1.49 (m, 2H).

Example 125

6-(6-(((1S,3S)-3-((5-(2,2,2-trifluoroethoxyl)pyrimidin-2-yl)amino)cyclopentyl)amino]pyridin-3-yl)-5,6-dihydro-7H-pyrrolo[3,4-b]pyridin-7-one

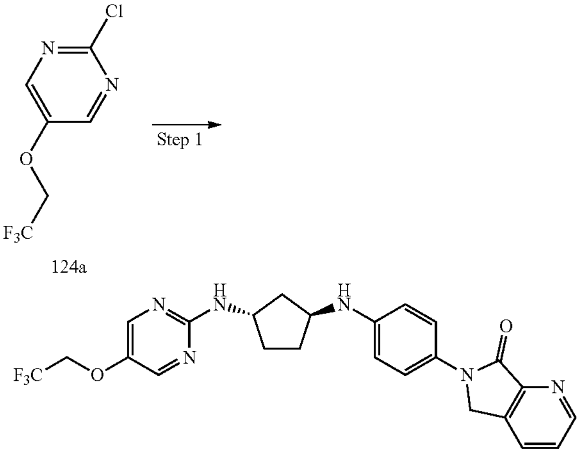

124a

125

Step 1

By reference to the synthesis method of step 3 of Example 122, 6-(6-(((1S,3S)-3-((5-(2,2,2-trifluoroethoxyl)pyrimidin-2-yl)amino)cyclopentyl)amino]pyridin-3-yl)-5,6-dihydro-7H-pyrrolo[3,4-b]pyridin-7-one 125 was synthesized.

MS m/z (ESI): 486.2 $[M+H]^+$.

$^1H$ NMR (400 MHz, DMSO-$d_6$) δ 8.75 (dd, 1H), 8.35 (d, 1H), 8.20 (s, 2H), 8.11 (dd, 1H), 7.87 (dd, 1H), 7.62 (dd, 1H), 7.10 (d, 1H), 6.69 (d, 1H), 6.55 (d, 1H), 4.93 (s, 2H), 4.71 (q, 2H), 4.28 (d, 2H), 2.11 (d, 2H), 1.90 (m, 2H), 1.49 (m, 2H).

Example 126

6-(6-(((1S,3S)-3-((6-cyclopropyl-1,2,4-triazin-3-yl)amino)cyclopentyl)amino)pyridin-3-yl)-5,6-dihydro-7H-pyrrolo[3,4-b]pyridin-7-one

126

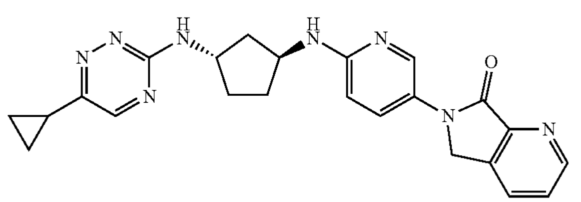

By reference to the synthesis method of Example 75, the target compound 6-(6-(((1 S,3S)-3-((6-cyclopropyl-1,2,4-triazin-3-yl)amino)cyclopentyl)amino) pyridin-3-yl)-5,6-dihydro-7H-pyrrolo[3,4-b]pyridin-7-one 126 was synthesized.

MS m/z (ESI): 429.2 $[M+H]^+$.

$^1H$ NMR (400 MHz, DMSO-$d_6$) δ 8.75 (d, 1H), 8.35 (d, 1H), 8.18 (s, 1H), 8.11 (d, 1H), 7.88 (dd, 1H), 7.62 (dd, 1H), 7.54 (s, 1H), 6.71 (d, 1H), 6.56 (d, 1H), 4.93 (s, 2H), 4.36-4.28 (m, 2H), 2.17-2.12 (m, 2H), 2.08-1.85 (m, 3H), 1.59-1.47 (m, 2H), 0.98-0.84 (m, 4H).

Example 127

6-(6-(((1S,3S)-3-((5-cyclopropylpyrimidin-2-yl)amino)cyclopentylamino)pyridin-3-yl)-5,6-dihydro-7H-pyrrolo[3,4-b]pyridin-7-one

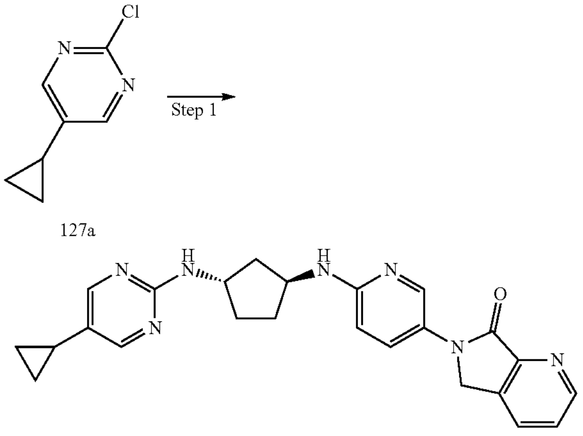

127a

127

Step 1

By reference to the synthesis method of step 3 of Example 122, 6-(6-(((1S,3S)-3-((5-cyclopropylpyrimidin-2-yl)amino)cyclopentylamino)pyridin-3-yl)-5,6-dihydro-7H-pyrrolo[3,4-b]pyridin-7-one 127 was synthesized.

MS m/z (ESI): 428.2 $[M+H]^+$.

$^1H$ NMR (400 MHz, DMSO-$d_6$) δ 8.75 (dd, 1H), 8.34 (d, 1H), 8.11 (dd, 1H), 8.07 (s, 2H), 7.87 (dd, 1H), 7.62 (dd, 1H), 7.01 (d, 1H), 6.68 (d, 1H), 6.55 (d, 1H), 4.93 (s, 2H), 4.29 (dd, 2H), 2.10 (m, 2H), 1.90 (m, 2H), 1.73 (m, 1H), 1.50 (m, 2H), 0.83 (m, 2H), 0.59 (m, 2H).

Example 128

6-(6-(((1S,3S)-3-((5-cyclopropylpyrimidin-2-yl)amino)cyclopentylamino)pyridin-3-yl)-6,7-dihydro-5H-pyrrolo[3,4-b]pyridin-5-one

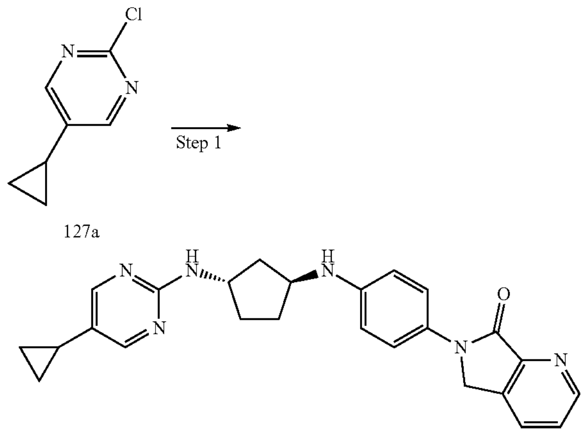

127a

128

Step 1

By reference to the synthesis method of step 3 of Example 122, 6-(6-(((1S,3S)-3-((5-cyclopropylpyrimidin-2-yl)amino)cyclopentylamino)pyridin-3-yl)-6,7-dihydro-5H-pyrrolo[3,4-b]pyridin-5-one 128 was synthesized.

MS m/z (ESI): 428.2 $[M+H]^+$.

$^1H$ NMR (400 MHz, DMSO-$d_6$) δ 8.80 (dd, 1H), 8.36 (d, 1H), 8.14 (dd, 1H), 8.06 (s, 2H), 7.87 (dd, 1H), 7.56 (dd, 1H), 7.00 (d, 1H), 6.65 (d, 1H), 6.54 (d, 1H), 4.97 (s, 2H), 4.29 (m, 2H), 2.07 (m, 2H), 1.86 (m, 2H), 1.72 (m, 1H), 1.49 (m, 2H), 0.82 (m, 2H), 0.59 (m, 2H).

Example 129

6-(6-(((1S,3S)-3-((7-fluoro-[1,2,4]triazolo[1,5-a]pyridin-2-yl)amino)cyclopentyl)amino)pyridin-3-yl)-5,6-dihydro-7H-pyrrolo[3,4-b]pyridin-7-one

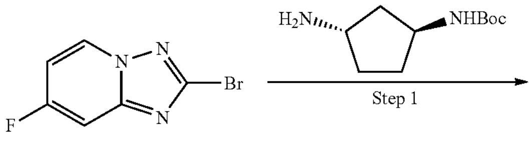

129a

-continued

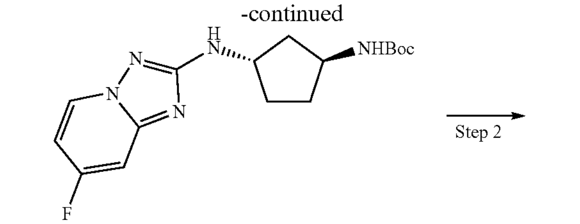

129b

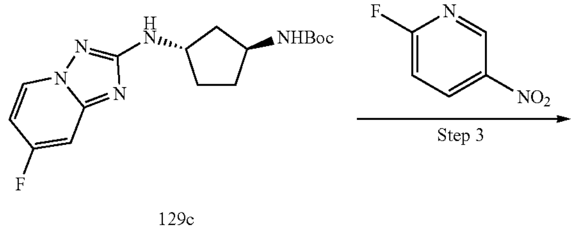

129c

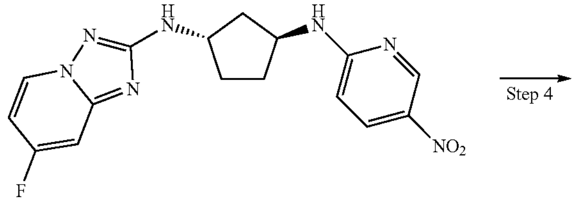

129d

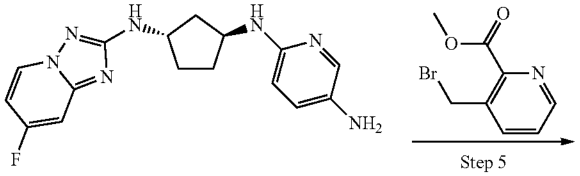

129e

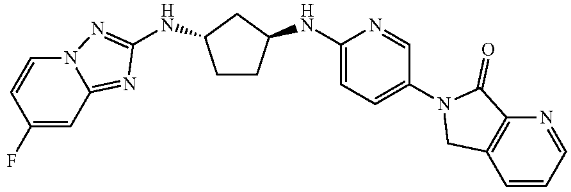

129

Step 1

Under nitrogen protection, 2-bromo-7-fluoro-[1,2,4]triazolo[1,5-a]pyridine 129a (500 mg, 2.31 mmol), tert-butyl N-[(1S,3S)-3-aminocyclopentyl]carbamate (510 mg, 2.55 mmol), cesium carbonate (1.51 g, 4.63 mmol), tris(dibenzylideneacetone)dipalladium (424 mg, 0.46 mmol), and 4,5-bis(diphenylphosphino)-9,9-dimethylxanthene (536 mg, 0.92 mmol) were dissolved in 1,4-dioxane (15 mL), heated to 130° C. by microwave, and stirred for 2 hours. The reaction liquid was filtered, and the filtrate was concentrated. The residue was purified by silica gel column chromatography (elution system B) and preparative HPLC (formic acid system) to obtain tert-butyl N-[(1S,3S)-3-[(7-fluoro-[1,2,4]triazolo[1,5-a]pyridin-2-yl)amino]cyclopentyl]carbamate 129b (240 mg), yield: 30.9%.

MS m/z (ESI): 336.0 $[M+H]^+$.

Step 2

At room temperature, 129b (202 mg, 0.60 mmol) was dissolved in methanol (2 mL) and stirred, and a solution of hydrochloric acid in 1,4-dioxane (4 M, 5 mL) was added to the reaction liquid. The reaction liquid was stirred at room temperature for 1 hour. The reaction liquid was concentrated, and the residue was purified by preparative HPLC (aqueous ammonia system) to obtain (1S,3S)—N1-(7-fluoro-[1,2,4]triazolo[1,5-a]pyridin-2-yl)cyclopentane-1,3-diamine 129c (140 mg), yield: 98.6%.

MS m/z (ESI): 236.2 $[M+H]^+$.

Step 3

129c (150 mg, 0.64 mmol), 2-fluoro-5-nitro-pyridine (91 mg, 0.64 mmol), and cesium carbonate (416 mg, 1.28 mmol) were dissolved in acetonitrile (2 mL), and the reaction was heated to 80° C. and stirred for 16 hours. The reaction liquid was filtered, the filtrate was concentrated, and the residue was purified by silica gel column chromatography (elution system B) to obtain (1S,3S)—N1-(7-fluoro-[1,2,4]triazolo[1,5-a]pyridin-2-yl)-N3-(5-nitropyridin-2-yl)cyclopentane-1,3-diamine 129d (190 mg), yield: 83.4%.

MS m/z (ESI): 358.1 $[M+H]^+$.

Step 4

In a hydrogen atmosphere at room temperature, 129d (190 mg, 0.53 mmol) and palladium on carbon (28 mg, 0.026 mmol, content: 10%) were dissolved in methanol (5 mL) and stirred for 1 hour. The reaction liquid was filtered, and the filtrate was concentrated to obtain N2-((1S,3S)-3-((7-fluoro-[1,2,4]triazolo[1,5-a]pyridin-2-yl)amino)cyclopentyl)pyridine-2,5-diamine 129e (170 mg), yield: 97.7%.

MS m/z (ESI): 328.1 $[M+H]^+$.

Step 5

At room temperature, 129e (80 mg, 0.24 mmol), methyl 3-(bromomethyl)picolinate (62 mg, 0.27 mmol), and potassium carbonate (101.2 mg, 0.73 mmol) were dissolved in N,N-dimethylformamide (2 mL), stirred for 1 hour, then heated to 50° C., and stirred for 4 hours. The reaction liquid was filtered, and the filtrate was purified by preparative HPLC (ammonium bicarbonate system) to obtain 6-(6-(((1S,3S)-3-((7-fluoro-[1,2,4]triazolo[1,5-a]pyridin-2-yl)amino)cyclopentyl) amino)pyridin-3-yl)-5,6-dihydro-7H-pyrrolo[3,4-b]pyridin-7-one 129 (24.3 mg), yield: 22.4%.

MS m/z (ESI): 445.2 $[M+H]^+$.

$^1$H NMR (400 MHz, DMSO-$d_6$) δ 8.75 (d, 1H), 8.66 (t, 1H), 8.35 (d, 1H), 8.11 (d, 1H), 7.88 (dd, 1H), 7.62 (dd, 1H), 7.27 (dd, 1H), 6.86 (td, 1H), 6.75 (d, 1H), 6.70 (d, 1H), 6.56 (d, 1H), 4.93 (s, 2H), 4.38-4.24 (m, 1H), 4.22-4.09 (m, 1H), 2.24-2.10 (m, 2H), 2.03-1.82 (m, 2H), 1.66-1.39 (m, 2H).

Example 130

6-(6-(((1S,3S)-3-((7-methyl-[1,2,4]triazolo[1,5-a]pyridin-2-yl)amino)cyclopentyl)amino)pyridin-3-yl)-5,6-dihydro-7H-pyrrolo[3,4-b]pyridin-7-one

130

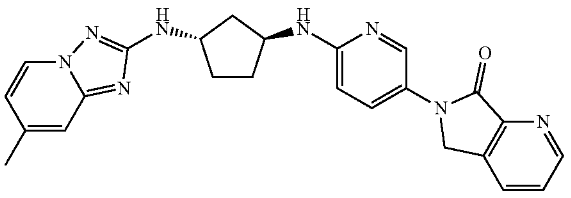

By reference to the synthesis method of Example 129, 6-(6-(((1S,3S)-3-((7-methyl-[1,2,4]triazolo[1,5-a]pyridin-2-yl)amino)cyclopentyl)amino)pyridin-3-yl)-5,6-dihydro-7H-pyrrolo[3,4-b]pyridin-7-one 130 was synthesized.

MS m/z (ESI): 441.2 $[M+H]^+$.

$^1H$ NMR (400 MHz, DMSO-$d_6$) δ 8.76 (d, 1H), 8.44 (d, 1H), 8.35 (d, 1H), 8.14-8.08 (m, 1H), 7.88 (dd, 1H), 7.61 (dd, 1H), 7.16 (dd, 1H), 6.69 (dd, 2H), 6.54 (t, 2H), 4.93 (s, 2H), 4.34-4.22 (m, 1H), 4.20-4.07 (m, 1H), 2.34 (s, 3H), 2.21-2.06 (m, 2H), 2.00-1.81 (m, 2H), 1.63-1.39 (m, 2H).

Example 131

6-(6-(((1S,3S)-3-((4-methylquinazolin-2-yl)amino)cyclopentyl)amino)pyridin-3-yl)-5,6-dihydro-7H-pyrrolo[3,4-b]pyridin-7-one

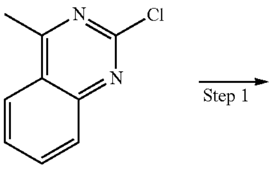

131a

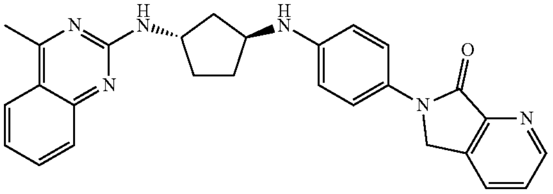

131

Step 1

By reference to the synthesis method of step 3 of Example 122, the target compound 6-(6-(((1S,3S)-3-((4-methylquinazolin-2-yl)amino)cyclopentyl)amino) pyridin-3-yl)-5,6-dihydro-7H-pyrrolo[3,4-b]pyridin-7-one 131 was synthesized.

MS m/z (ESI): 452.2 $[M+H]^+$.

$^1H$ NMR (400 MHz, DMSO-$d_6$) δ 8.75 (d, 1H), 8.35 (d, 1H), 8.11 (d, 1H), 7.89 (m, 2H), 7.62 (dd, 2H), 7.40 (dd, 2H), 7.19 (d, 1H), 6.72 (d, 1H), 6.57 (d, 1H), 4.93 (s, 2H), 4.50 (m 1H), 4.31 (m, 1H), 2.70 (s, 3H), 2.16 (m, 2H), 1.94 (m, 2H), 1.54 (m, 2H).

Example 132

6-(6-(((1S,3S)-3-((5-(difluoromethoxy)pyrimidin-2-yl)amino)cyclopentyl)amino)pyridin-3-yl)-5,6-dihydro-7H-pyrrolo[3,4-d]pyrimidin-7-one Example 132 could also be prepared by reference to the following method.

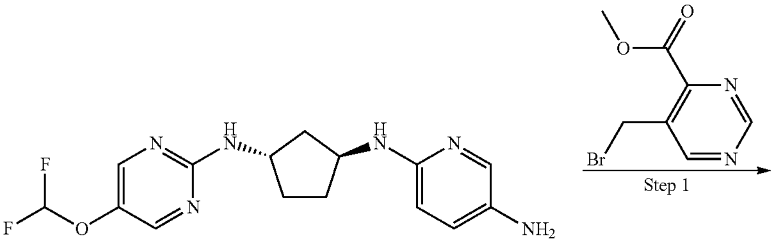

75b

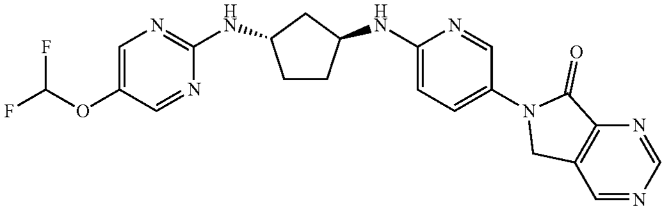

132

Step 1

At room temperature, 75b (57.7 mg, 0.25 mmol) and potassium carbonate (73.9 mg, 0.53 mmol) were dissolved in N,N-dimethylformamide (3 mL), stirred for 1 hour, then heated to 60° C., and stirred for 4 hours. The reaction liquid was filtered, and the filtrate was purified by preparative HPLC (ammonium bicarbonate system) to obtain 6-(6-(((1S, 3S)-3-((5-(difluoromethoxy)pyrimidin-2-yl)amino)cyclopentyl) amino)pyridin-3-yl)-5,6-dihydro-7H-pyrrolo[3,4-d] pyrimidin-7-one 132 (21 mg), yield: 25.9%.

MS m/z (ESI): 455.2 $[M+H]^+$.

$^1H$ NMR (400 MHz, DMSO-$d_6$) δ 8.89-8.75 (m, 2H), 8.40 (d, 1H), 8.23 (s, 2H), 7.91 (dd, 1H), 7.48 (d, 1H), 7.03 (t, 1H), 6.74 (d, 1H), 6.56 (d, 1H), 5.02 (s, 2H), 4.36-4.23 (m, 2H), 2.21-2.05 (m, 2H), 1.98-1.81 (m, 2H), 1.62-1.43 (m, 2H).

Example 133

6-(6-(((1S,3S)-3-((5-(trifluoromethyl)pyrimidin-2-yl)amino)cyclopentyl)amino)-3-yl)-6,7-dihydro-5H-pyrrolo[3,4-b]pyridin-5-one

133

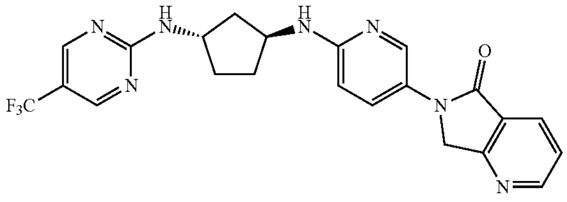

By reference to the synthesis method of Example 75, 6-(6-(((1S,3S)-3-((5-(trifluoromethyl)pyrimidin-2-yl) amino)cyclopentyl)amino)pyridin-3-yl)-6,7-dihydro-5H-pyrrolo[3,4-b]pyridin-5-one 133 was synthesized.

MS m/z (ESI): 456.2 $[M+H]^+$.

$^1H$ NMR (400 MHz, DMSO-dr) δ 8.80 (d, 1H), 8.61 (d, 2H), 8.37 (d, 1H), 8.20 (d, 1H), 8.15 (d, 1H), 7.88 (dd, 1H), 7.56 (dd, 1H), 6.70 (d, 1H), 6.56 (d, 1H), 4.97 (s, 2H), 4.47-4.28 (m, 2H), 2.18-2.10 (m, 2H), 1.98-1.85 (m, 2H), 1.62-1.48 (m, 2H).

Example 134

6-(6-(((1S,3S)-3-((5-(trifluoromethyl)pyrimidin-2-yl)amino)cyclopentyl)amino)-3-yl)-5,6-dihydro-7H-pyrrolo[3,4-b]pyridin-7-one

134

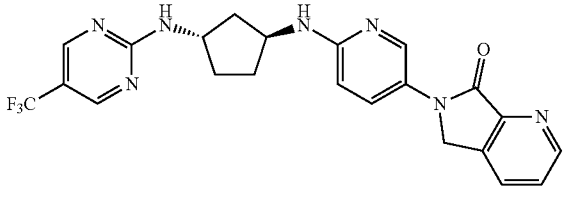

By reference to the synthesis method of Example 75, 6-(6-(((1S,3S)-3-((5-(trifluoromethyl)pyrimidin-2-yl) amino)cyclopentyl)amino)pyridin-3-yl)-5,6-dihydro-7H-pyrrolo[3,4-b]pyridin-7-one 134 was synthesized.

MS m/z (ESI): 456.2 $[M+H]^+$.

$^1H$ NMR (400 MHz, DMSO-$d_6$) δ 8.76 (d, 1H), 8.61 (d, 2H), 8.35 (d, 1H), 8.21 (d, 1H), 8.11 (d, 1H), 7.88 (dd, 1H), 7.62 (dd, 1H), 6.72 (d, 1H), 6.56 (d, 1H), 4.93 (s, 2H), 4.45-4.28 (m, 2H), 2.18-2.10 (m, 2H), 1.98-1.85 (m, 2H), 1.62-1.48 (m, 2H).

Example 135

6'-(((1S,3S)-3-((7-cyclopropyl-[1,2,4]triazolo[1,5-a] pyridin-2-yl)amino)cyclopentyl)amino)-2H-[1,3'-bipyridinyl]-2-one

135

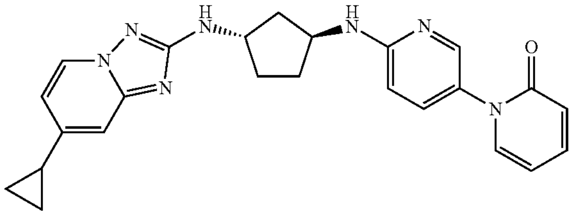

By reference to the synthesis method of Example 27, 6'-(((1S,3S)-3-((7-cyclopropyl-[1,2,4]triazolo[1,5-a]pyridin-2-yl)amino)cyclopentyl)amino)-2H-[1,3'-bipyridinyl]-2-one 135 was synthesized.

MS m/z (ESI): 428.2 $[M+H]^+$.

$^1H$ NMR (400 MHz, DMSO-$d_6$) δ 8.40 (d, 1H), 7.91 (d, 1H), 7.60 (dd, 1H), 7.47 (ddd, 1H), 7.39 (dd, 1H), 7.07 (d, 1H), 6.91 (d, 1H), 6.59-6.49 (m, 3H), 6.44 (dt, 1H), 6.26 (td, 1H), 4.36-4.25 (m, 1H), 4.20-4.08 (m, 1H), 2.20-2.07 (m, 2H), 2.02-1.81 (m, 3H), 1.61-1.42 (m, 2H), 1.07-0.98 (m, 2H), 0.84-0.74 (m, 2H).

Example 136

6-(6-(((1S,3S)-3-((5-(difluoromethoxy)pyrimidin-2-yl)amino)cyclopentyl)aminopyridin-3-yl)-3-fluoro-5, 6-dihydro-7H-pyrrolo[3,4-b]pyridin-7-one

136

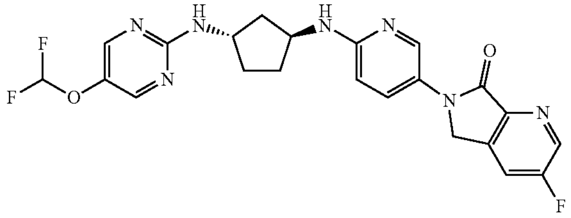

By reference to the synthesis method of Example 75, the target compound 6-(6-(((1 S,3S)-3-((5-(difluoromethoxy) pyrimidin-2-yl)amino)cyclopentyl) aminopyridin-3-yl)-3-fluoro-5,6-dihydro-7H-pyrrolo[3,4-b]pyridin-7-one 136 was synthesized.

MS m/z (ESI): 472.1 $[M+H]^+$.

$^1$H NMR (400 MHz, DMSO-$d_6$) δ 8.76 (s, 1H), 8.32 (d, 1H), 8.23 (s, 2H), 8.09 (dd, 1H), 7.84 (dd, 1H), 7.48 (d, 1H), 7.03 (dd, 1H), 6.71 (d, 1H), 6.55 (d, 1H), 4.93 (s, 2H), 4.26-4.33 (m, 2H), 2.07-2.17 (m, 2H), 1.83-1.93 (m, 2H), 1.46-1.56 (m, 2H).

Example 137

6-(6-(((1S,3S)-3-((5-(difluoromethoxy)pyrimidin-2-yl)amino)cyclopentyl)aminopyridin-3-yl)-3-fluoro-6,7-dihydro-5H-pyrrolo[3,4-b]pyridin-5-one

137

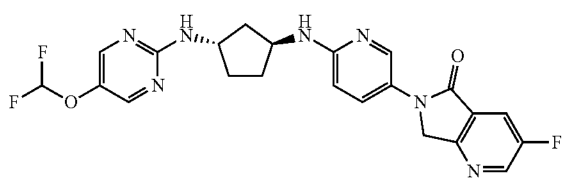

By reference to the synthesis method of Example 75, the target compound 6-(6-(((1 S,3S)-3-((5-(difluoromethoxy)pyrimidin-2-yl)amino)cyclopentyl)aminopyridin-3-yl)-3-fluoro-6,7-dihydro-5H-pyrrolo[3,4-b]pyridin-5-one 137 was synthesized.

MS m/z (ESI): 472.1 $[M+H]^+$.

$^1$H NMR (400 MHz, DMSO-$d_6$) δ 8.82 (dd, 1H), 8.36 (d, 1H), 8.23 (s, 2H), 8.11 (dd, 1H), 7.86 (dd, 1H), 7.48 (d, 1H), 7.03 (dd, 1H), 6.70 (d, 1H), 6.55 (d, 1H), 4.96 (s, 2H), 4.26-4.33 (m, 2H), 2.07-2.15 (m, 2H), 1.83-1.93 (m, 2H), 1.47-1.56 (m, 2H).

Example 138

2-(6-(((1S,3S)-3-((5-(difluoromethoxy)pyrimidin-2-yl)amino)cyclopentyl)amino)pyridin-3-yl)-6-trifluoromethyl-2,3-dihydro-1H-pyrrolo[3,4-c]pyridin-1-one

138

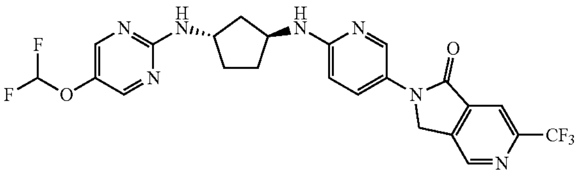

By reference to the synthesis method of Example 75, the target compound 2-(6-(((1 S,3S)-3-((5-(difluoromethoxy)pyrimidin-2-yl)amino)cyclopentyl)amino)pyridin-3-yl)-6-trifluoromethyl-2,3-dihydro-1H-pyrrolo[3,4-c]pyridin-1-one 138 was synthesized.

MS m/z (ESI): 522.2 $[M+H]^+$.

$^1$H NMR (400 MHz, DMSO-$d_6$) δ 9.15 (s, 1H), 8.36 (d, 1H), 8.23 (s, 2H), 8.16 (d, 1H), 7.86 (dd, 1H), 7.48 (d, 1H), 7.03 (t, 1H), 6.77 (d, 1H), 6.57 (d, 1H), 5.13 (s, 2H), 4.33-4.27 (m, 2H), 2.19-2.05 (m, 2H), 1.97-1.81 (m, 2H), 1.56-1.46 (m, 2H).

Example 139

(1S,3S)—N1-(5-([1,2,4]triazolo[1,5-a]pyridin-5-yl)pyridin-2-yl)-N3-(5-(difluoromethoxy)pyrimidin-2-yl)cyclopentane-1,3-diamine

139

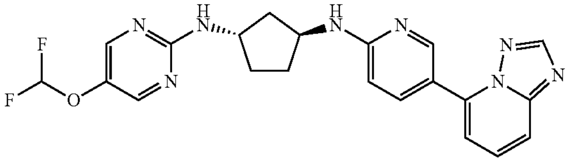

By reference to the synthesis method of Example 52, (1S,3S)—N1-(5-([1,2,4]triazolo[1,5-a]pyridin-5-yl)pyridin-2-yl)-N3-(5-(difluoromethoxy)pyrimidin-2-yl)cyclopentane-1,3-diamine 139 was synthesized.

MS m/z (ESI): 439.2 $[M+H]^+$.

$^1$H NMR (400 MHz, DMSO-$d_6$) δ 8.88-8.80 (m, 2H), 8.53 (s, 1H), 8.23 (s, 2H), 8.21-8.16 (m, 1H), 7.83 (dd, 1H), 7.49 (d, 1H), 7.26-7.21 (m, 1H), 7.03 (t, 1H), 6.98 (d, 1H), 6.60 (dd, 1H), 4.41-4.26 (m, 2H), 2.24-2.07 (m, 2H), 2.01-1.82 (m, 2H), 1.62-1.44 (m, 2H).

Example 140

(1S,3S)—N1-(5-([1,2,4]triazolo[1,5-a]pyridin-8-yl)pyridin-2-yl)-N3-(5-(difluoromethoxy)pyrimidin-2-yl)cyclopentane-1,3-diamine

140

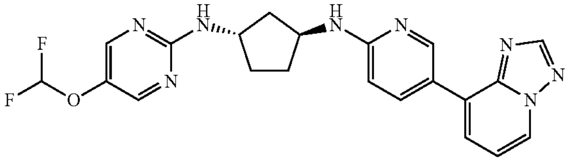

By reference to the synthesis method of Example 52, (1S,3S)—N1-(5-([1,2,4]triazolo[1,5-a]pyridin-8-yl)pyridin-2-yl)-N3-(5-(difluoromethoxy)pyrimidin-2-yl)cyclopentane-1,3-diamine 140 was synthesized.

MS m/z (ESI): 439.2 $[M+H]^+$.

$^1$H NMR (400 MHz, DMSO-$d_6$) δ 8.66 (d, 1H), 8.51 (s, 1H), 8.24 (s, 2H), 8.08 (dd, 1H), 7.77-7.66 (m, 2H), 7.50 (d, 1H), 7.31 (dd, 1H), 7.21 (d, 1H), 7.03 (t, 1H), 6.61 (d, 1H), 4.45-4.26 (m, 2H), 2.23-2.08 (m, 2H), 2.00-1.84 (m, 2H), 1.62-1.44 (m, 2H).

Example 142

6-(6-(((1S,3S)-3-((5-(trifluoromethoxy)pyrimidin-2-yl)amino)cyclopentyl)amino)pyridin-3-yl)-5,6-dihydro-7H-pyrrolo[3,4-b]pyridin-7-one

142

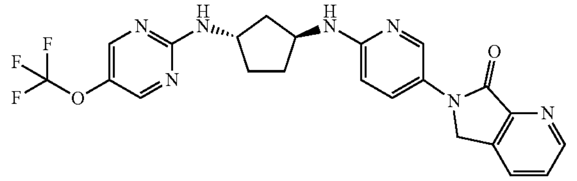

By reference to the synthesis method of Example 122, 6-(6-(((1S,3S)-3-((5-(trifluoromethoxy)pyrimidin-2-yl) amino)cyclopentyl)amino)pyridin-3-yl)-5,6-dihydro-7H-pyrrolo[3,4-b]pyridin-7-one 142 was synthesized.

MS m/z (ESI): 532.1 $[M+H]^+$.

$^1H$ NMR (400 MHz, DMSO-$d_6$) δ 8.75 (d, 1H), 8.40 (s, 2H), 8.35 (d, 1H), 8.11 (dd, 1H), 7.87 (dd, 1H), 7.74 (dd, 1H), 7.61 (dd, 1H), 6.69 (d, 1H), 6.55 (d, 1H), 4.93 (s, 2H), 4.33-4.30 (m, 2H), 2.16-2.10 (m, 2H), 1.93-1.86 (m, 2H), 1.56-1.51 (m, 2H).

Example 143

6-(6-(((1S,3S)-3-((7-(trifluoromethyl)-[1,2,4]triazolo[1,5-a]pyridin-2-yl)amino)cyclopentyl)amino)pyridin-3-yl)-5,6-dihydro-7H-pyrrolo[3,4-b]pyridin-7-one

143

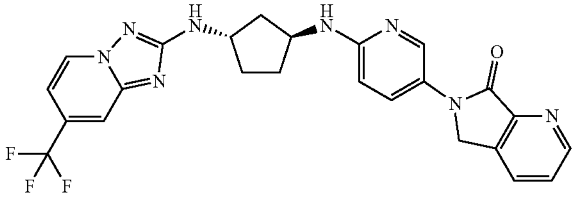

By reference to the synthesis method of Example 129, 6-(6-(((1S,3S)-3-((7-(trifluoromethyl)-[1,2,4]triazolo[1,5-a] pyridin-2-yl)amino)cyclopentyl)amino) pyridin-3-yl)-5,6-dihydro-7H-pyrrolo[3,4-b]pyridin-7-one 143 was synthesized.

MS m/z (ESI): 495.2 $[M+H]^+$.

$^1H$ NMR (400 MHz, DMSO-$d_6$) δ 8.83 (d, 1H), 8.75 (dd, 1H), 8.35 (d, 1H), 8.15-8.06 (m, 1H), 7.88 (dd, 1H), 7.86 (s, 1H), 7.62 (dd, 1H), 7.15 (dd, 1H), 7.04 (d, 1H), 6.71 (s, 1H), 6.57 (d, 1H), 4.93 (s, 2H), 4.36-4.15 (m, 2H), 2.23-2.10 (m, 2H), 2.05-1.83 (m, 2H), 1.65-1.42 (m, 2H).

Example 144

6-(6-(((1S,3S)-3-((6-(trifluoromethyl)-1,2,4-triazin-3-yl)amino)cyclopentylamino)pyridin-3-yl)-5,6-dihydro-7H-pyrrolo[3,4-b]pyridin-7-one Example 144 could also be prepared by reference to the following method:

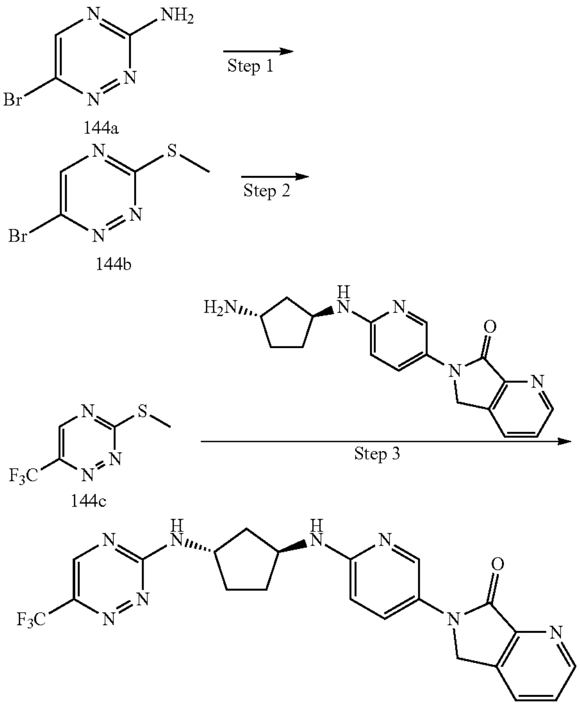

144a

144b

144c

144

Step 1

At room temperature, tert-butyl nitrite (14.73 g, 142.87 mmol) was dropwise added to a solution of 6-bromo-1,2,4-triazinyl-3-amine 144a (5.00 g, 28.57 mmol) in acetonitrile (50 mL) and dimethyl disulfide (10 mL) and stirred for 3 hours. The reaction liquid was quenched with methanol (515 mL). The organic phase was concentrated, and the residue was separated by silica gel column chromatography (eluent system A) to obtain the title product 6-bromo-3-(methylthio)-1,2,4-triazine 144b (4.60 g), yield: 78.1%.

MS m/z (ESI): 205.9 $[M+H]^+$.

Step 2

Under nitrogen protection, 144b (2.00 g, 9.71 mmol), methyl 2,2-difluoro-2-fluorosulfonylacetate (5.59 g, 29.17 mmol), and cuprous iodide (5.55 g, 29.12 mmol) were dissolved in N,N-dimethylformamide (15 mL), heated to 90° C., and stirred for 3 hours. The reaction liquid was diluted with ethyl acetate (180 mL), and the organic phase was washed with water (100 mL) and saturated sodium chloride (100 mL). The organic phase was dried and concentrated, and the residue was separated by silica gel column chromatography (eluent system A) to obtain the title product 3-(methylthio)-6-(trifluoromethyl)-1,2,4-triazine 144c (710 mg), yield: 37.5%.

MS m/z (ESI): 196.0 $[M+H]^+$.

Step 3

By reference to the synthesis method of step 3 of Example 122, 6-(6-(((1S,3S)-3-((6-(trifluoromethyl)-1,2,4-triazin-3-yl)amino)cyclopentylamino)pyridin-3-yl)-5,6-dihydro-7H-pyrrolo[3,4-b]pyridin-7-one 144 was synthesized.

MS m/z (ESI): 457.2 $[M+H]^+$.

$^1$H NMR (400 MHz, DMSO-$d_6$) δ 9.10, 8.60 (d, 1H), 8.75 (m, 1H), 8.70 (s, 1H), 8.36 (d, 1H), 8.11 (m, 1H), 7.88 (m, 1H), 7.62 (m, 1H), 6.74 (m, 1H), 6.57 (d, 1H), 4.93 (s, 2H), 4.61, 4.35 (m, 1H), 4.36 (m, 1H), 2.17 (m, 2H), 2.00 (m, 2H), 1.61 (m, 2H).

Example 145

6-(6-(((1S,3S)-3-((6-(trifluoromethyl)-1,2,4-triazin-3-yl)amino)cyclopentylamino)pyridin-3-yl)-6,7-dihydro-5H-pyrrolo[3,4-b]pyridin-5-one Example 145 could also be prepared by reference to the following method:

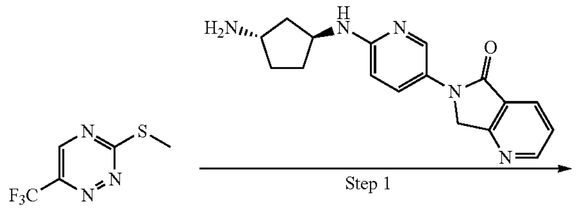

144c

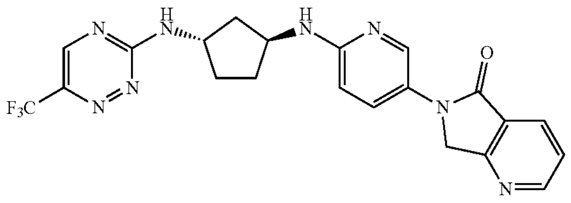

145

Step 1

By reference to the synthesis method of step 3 of Example 122, 6-(6-(((1S,3S)-3-((6-(trifluoromethyl)-1,2,4-triazin-3-yl)amino)cyclopentylamino)pyridin-3-yl)-6,7-dihydro-5H-pyrrolo[3,4-b]pyridin-5-one 145 was synthesized.

MS m/z (ESI): 457.2 $[M+H]^+$.

$^1$H NMR (400 MHz, DMSO-$d_6$) δ 9.10, 8.61 (d, 1H), 8.80 (m, 1H), 8.70 (s, 1H), 8.36 (d, 1H), 8.15 (m, 1H), 7.88 (m, 1H), 7.56 (m, 1H), 6.73 (m, 1H), 6.56 (d, 1H), 4.96 (s, 2H), 4.61, 4.33 (m, 1H), 4.35 (m, 1H), 2.18 (m, 2H), 2.00 (m, 2H), 1.63 (m, 2H).

Example 146

5,5-Dimethyl-6-(6-(((1S,3S)-3-((6-(trifluoromethyl)-1,2,4-triazin-3-yl)amino)cyclopentyl)amino)pyridin-3-yl)-5,6-dihydro-7H-pyrrolo[3,4-b]pyridin-7-one Example 146 could also be prepared by reference to the following method:

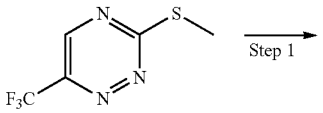

144c

-continued

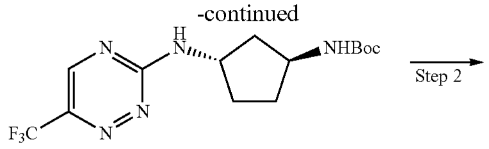

146a

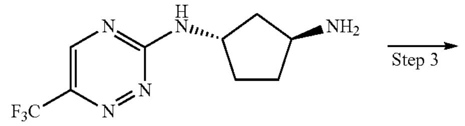

146b

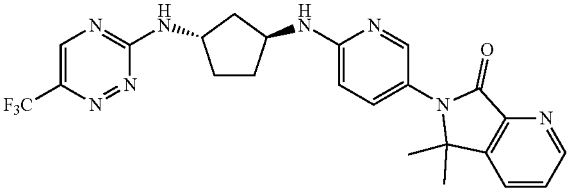

146

Step 1

3-(Methylthio)-6-(trifluoromethyl)-1,2,4-triazine 144c (390 mg, 2.00 mmol), tert-butyl ((1S,3S)-3-aminocyclopentyl)carbamate (420 mg, 2.10 mmol), and diisopropylethylamine (258 mg, 2.00 mmol) were dissolved in N-methylpyrrolidone (5 mL), and the reaction was heated to 90° C. and stirred for 2 hours. Ethyl acetate (25 mL) and water (10 mL) were added to the reaction liquid. The organic phases were washed with a saturated sodium chloride aqueous solution. The organic phase was concentrated, and the residue was separated by silica gel column chromatography (elution system A) to obtain tert-butyl ((1S,3S)-3-((6-(trifluoromethyl)-1,2,4-triazin-3-yl)amino)cyclopentyl)carbamate 146a (410 mg), yield: 59.07%.

MS m/z (ESI): 348.2 $[M+H]^+$.

Step 2

146a (410 mg, 1.18 mmol) was dissolved in methanol (3 mL), and hydrochloric acid in 1,4-dioxane (4 M, 3 mL) was added to the reaction liquid and stirred at room temperature for 2 hours. The reaction liquid was concentrated, and the residue was dissolved with a small amount of methanol. The pH was adjusted to alkalinity by adding aqueous ammonia, and after further concentration, the residue was separated by silica gel column chromatography (elution system A) to obtain (1S,3S)—N1-(6-(trifluoromethyl)-1,2,4-triazin-3-yl)cyclopentane-1,3-diamine 146b (280 mg), yield: 95.95%.

MS m/z (ESI): 248.2 $[M+H]^+$.

Step 3

Under nitrogen protection, 146b (43 mg, 0.17 mmol), 93a (63 mg, 0.24 mmol), and diisopropylethylamine (56 mg, 0.43 mmol) were dissolved in dimethyl sulfoxide (1.5 mL), and the reaction was heated to 130° C. and stirred for 48 hours. The reaction liquid was filtered, and the filtrate was subjected to reversed-phase HPLC (formic acid system) to prepare 5-dimethyl-6-(6-(((1S,3S)-3-((6-(trifluoromethyl)-1,2,4-triazin-3-yl)amino)cyclopentyl)amino)pyridin-3-yl)-5,6-dihydro-7H-pyrrolo[3,4-b]pyridin-7-one 146 (28 mg), yield: 33.23%.

MS m/z (ESI): 485.2 $[M+H]^+$.

$^1H$ NMR (400 MHz, DMSO-$d_6$) δ 9.17-8.60 (m, 1H), 8.77-8.74 (m, 1H), 8.71 (d, 1H), 8.24 (d, 1H), 7.87 (d, 1H), 7.70-7.61 (m, 1H), 7.35-7.27 (m, 1H), 7.00-6.90 (m, J H), 6.58 (d, 1H), 4.71-4.24 (m, 2H), 2.27-2.11 (m, 2H), 2.08-1.87 (m, 2H), 1.73-1.52 (m, 2H), 1.45 (s, 6H).

Example 147

2-(6-(((1S,3S)-3-((7-fluoro-[1,2,4]triazolo[1,5-a]pyridin-2-yl)amino)cyclopentyl)amino)pyridin-3-yl)-6-methyl-2,3-dihydro-1H-pyrrolo[3,4-c]pyridin-1-one

147

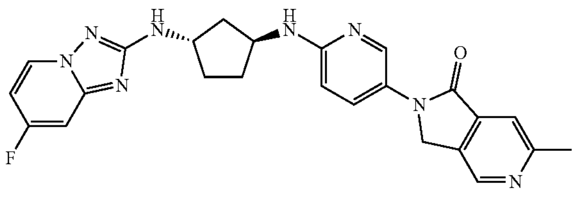

By reference to the synthesis method of Example 129, 2-(6-(((I S,3S)-3-((7-fluoro-[1,2,4]triazolo[1,5-a]pyridin-2-yl)amino)cyclopentyl)amino)pyridin-3-yl)-6-methyl-2,3-dihydro-1H-pyrrolo[3,4-c]pyridin-1-one 147 was synthesized.

MS m/z (ESI): 459.2 $[M+H]^+$.

$^1H$ NMR (400 MHz, DMSO-$d_6$) δ 8.80 (s, 1H), 8.66 (dd, 1H), 8.34 (d, 1H), 7.85 (dd, 1H), 7.59 (s, 1H), 7.27 (dd, 1H), 6.86 (td, 1H), 6.73 (dd, 2H), 6.55 (d, 1H), 4.97 (s, 2H), 4.29 (q, 1H), 4.15 (q, 1H), 2.60 (s, 3H), 2.19-2.08 (m, 2H), 1.99-1.83 (m, 2H), 1.59-1.46 (m, 2H).

Example 148

6-Methyl-2-(6-(((1S,3S)-3-((6-(trifluoromethyl)-1,2,4-triazin-3-yl)amino)cyclopentyl)amino)pyridin-3-yl)-2,3-dihydro-1H-pyrrolo[3,4-c]pyridin-1-one

148

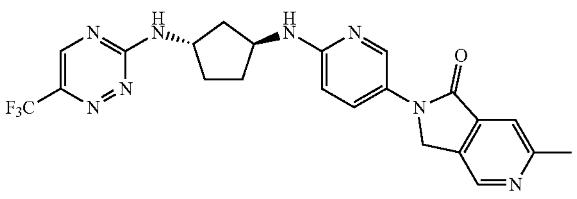

By reference to the synthesis method of Example 144, 6-methyl-2-(6-(((1S,3S)-3-((6-(trifluoromethyl)-1,2,4-triazin-3-yl)amino)cyclopentyl)amino)pyridin-3-yl)-2,3-dihydro-1H-pyrrolo[3,4-c]pyridin-1-one 148 was synthesized.

MS m/z (ESI): 471.2 $[M+H]^+$.

$^1H$ NMR (400 MHz, DMSO-$d_6$) δ 9.11 (d, 1H), 8.80 (s, 1H), 8.70 (s, 1H), 8.35 (d, 1H), 7.86 (dd, 1H), 7.59 (s, 1H), 6.76 (d, 1H), 6.56 (d, 1H), 4.98 (s, 2H), 4.61 (d, 1H), 4.33 (d, 1H), 2.60 (s, 3H), 2.23-2.13 (m, 2H), 1.99 (d, 2H), 1.59 (d, 2H).

Example 149

2-(6-(((1S,3S)-3-((7-fluoro-[1,2,4]triazolo[1,5-a]pyridin-2-yl)amino)cyclopentyl)amino)pyridin-3-yl)-4-methyl-2,3-dihydro-1H-pyrrolo[3,4-c]pyridin-1-one

149

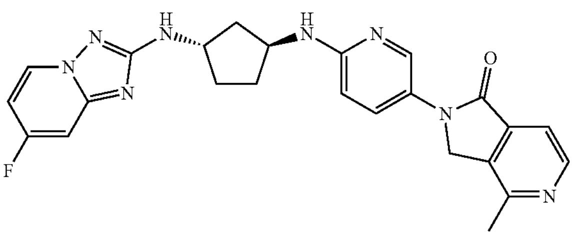

By reference to the synthesis method of Example 129, 2-(6-(((1 S,3S)-3-((7-fluoro-[1,2,4]triazolo[1,5-a]pyridin-2-yl)amino)cyclopentyl)amino)pyridin-3-yl)-4-methyl-2,3-dihydro-1H-pyrrolo[3,4-c]pyridin-1-one 149 was synthesized.

MS m/z (ESI): 459.2 $[M+H]^+$.

$^1H$ NMR (400 MHz, DMSO-$d_6$) δ 8.69-8.59 (m, 2H), 8.37 (d, 1H), 7.86 (dd, 1H), 7.55 (d, 1H), 7.27 (dd, 1H), 6.86 (td, 1H), 6.73 (dd, 2H), 6.55 (d, 1H), 4.98 (s, 2H), 4.29 (q, 1H), 4.15 (q, 1H), 2.57 (s, 3H), 2.21-2.09 (m, 2H), 2.03-1.90 (m, 2H), 1.59-1.44 (m, 2H).

Example 151

2-(6-(((1S,3S)-3-((7-fluoro-[1,2,4]triazolo[1,5-a]pyridin-2-yl)amino)cyclopentyl)amino)pyridin-3-yl)-6-(trifluoromethyl)-2,3-dihydro-1H-pyrrolo[3,4-c]pyridin-1-one

151

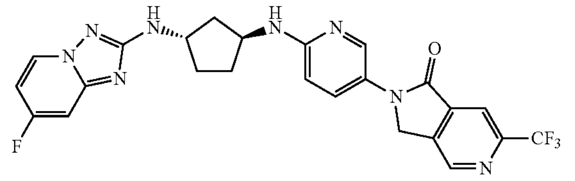

By reference to the synthesis method of Example 129, 2-(6-(((1 S,3S)-3-((7-fluoro-[1,2,4]triazolo[1,5-a]pyridin-2-yl)amino)cyclopentyl)amino)pyridin-3-yl)-6-(trifluoromethyl)-2,3-dihydro-1H-pyrrolo[3,4-c]pyridin-1-one 151 was synthesized.

MS m/z (ESI): 513.2 $[M+H]^+$.

$^1H$ NMR (400 MHz, DMSO-$d_6$) δ 9.15 (s, 1H), 8.66 (t, 1H), 8.36 (d, 1H), 8.16 (s, 1H), 7.86 (dd, 1H), 7.27 (dd, 1H), 6.86 (td, 1H), 6.76 (dd, 2H), 6.57 (d, 1H), 5.13 (s, 2H), 4.30 (q, 1H), 4.15 (q, 1H), 2.23-2.07 (m, 2H), 2.03-1.84 (m, 2H), 1.59-1.44 (m, 2H).

Example 152

6-(Trifluoromethyl)-2-(6-(((1S,3S)-3-((6-(trifluoromethyl)-1,2,4-triazin-3-yl)amino)cyclopentyl)amino)pyridin-3-yl)-2,3-dihydro-1H-pyrrolo[3,4-c]pyridin-1-one

152

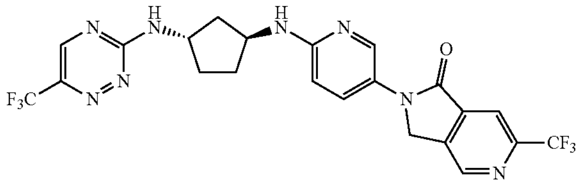

By reference to the synthesis method of Example 144, 6-(trifluoromethyl)-2-(6-(((I S,3S)-3-((6-(trifluoromethyl)-1,2,4-triazin-3-yl)amino)cyclopentyl)amino) pyridin-3-yl)-2,3-dihydro-1H-pyrrolo[3,4-c]pyridin-1-one 152 was synthesized.

MS m/z (ESI): 525.2 $[M+H]^+$.

$^1H$ NMR (400 MHz, DMSO-$d_6$) δ 9.15 (s, 1H), 9.10 (d, 1H), 8.86 (dd, 1H), 8.37 (d, 1H), 8.16 (s, 1H), 7.87 (dd, 1H), 6.82 (d, 1H), 6.58 (d, 1H), 5.14 (s, 2H), 4.42-4.28 (m, 2H), 2.28-2.09 (m, 2H), 2.05-1.97 (m, 2H), 1.75-1.49 (m, 2H).

Example 153

3-Fluoro-6-(6-(((1S,3S)-3-((6-(trifluoromethyl)-1,2,4-triazin-3-yl)amino)cyclopentyl)amino)pyridin-3-yl)-5,6-dihydro-7H-pyrrolo[3,4-b]pyridin-7-one

153

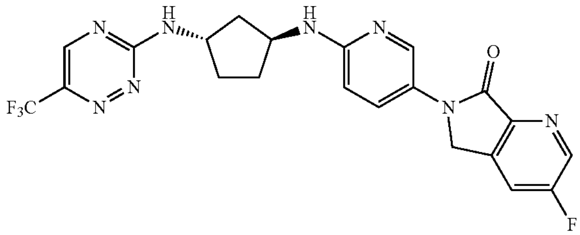

By reference to the synthesis method of Example 144, 3-fluoro-6-(6-(((1S,3S)-3-((6-(trifluoromethyl)-1,2,4-triazin-3-yl)amino)cyclopentyl)amino)pyridin-3-yl)-5,6-dihydro-7H-pyrrolo[3,4-b]pyridin-7-one 153 was synthesized.

MS m/z (ESI): 475.2 $[M+H]^+$.

$^1H$ NMR (400 MHz, DMSO-$d_6$) δ 9.11 (d, 1H), 8.76 (s, 1H), 8.70 (s, 1H), 8.34 (d, 1H), 8.10 (dd, 1H), 7.86 (dd, 1H), 6.78-6.73 (m, 1H), 6.56 (d, 1H), 4.94 (s, 2H), 4.36-4.32 (m, 2H), 2.23-2.13 (m, 2H), 2.02-1.91 (m, 2H), 1.69-1.62 (m, 1H), 1.57-1.51 (m, 1H).

Example 154

2-(6-(((1S,3S)-3-((6-(trifluoromethyl)-1,2,4-triazin-3-yl)amino)cyclopentyl)amino)pyridin-3-yl)-2,3-dihydroisothiazolo[5,4-b]pyridine 1,1-dioxide

154

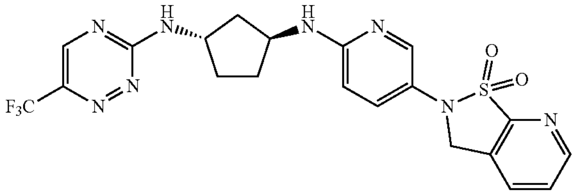

By reference to the synthesis method of Example 121, 2-(6-(((1S,3S)-3-((6-(trifluoromethyl)-1,2,4-triazin-3-yl)amino)cyclopentyl)amino)pyridin-3-yl)-2,3-dihydroisothiazolo[5,4-b]pyridine 1,1-dioxide 154 was synthesized.

MS m/z (ESI): 493.1 $[M+H]^+$.

Example 155

6-(6-(((1S,3S)-3-((7-fluoro-[1,2,4]triazolo[1,5-a]pyridin-2-yl)amino)cyclopentyl)amino)pyridin-3-yl)-2-(trifluoromethyl)-5,6-dihydro-7H-pyrrolo[3,4-b]pyridin-7-one

155

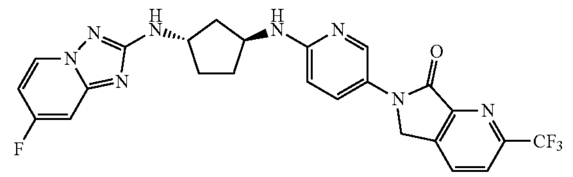

By reference to the synthesis method of Example 129, 6-(6-((1S,3S)-3-((7-fluoro-[1,2,4]triazolo[1,5-a]pyridin-2-yl)amino)cyclopentyl)amino)pyridin-3-yl)-2-(trifluoromethyl)-5,6-dihydro-7H-pyrrolo[3,4-b]pyridin-7-one 155 was synthesized.

MS m/z (ESI): 513.2 $[M+H]^+$.

$^1H$ NMR (400 MHz, DMSO-$d_6$) δ 8.66 (dd, 1H), 8.41 (d, 1H), 8.36 (d, 1H), 8.14 (d, 1H), 7.88 (dd, 1H), 7.27 (dd, 1H), 6.86 (td, 1H), 6.75 (dd, 2H), 6.57 (d, 1H), 5.04 (s, 2H), 4.30 (q, 1H), 4.16 (q, 1H), 2.21-2.10 (m, 2H), 2.03-1.84 (m, 2H), 1.60-1.47 (m, 2H).

Example 156

6-Methyl-2-(6-(((1S,3S)-3-((7-(trifluoromethyl)-[1,2,4]triazolo[1,5-a]pyridin-2-yl)amino)cyclopentyl)amino)pyridin-3-yl)-2,3-dihydro-1H-pyrrolo[3,4-c]pyridin-1-one

156

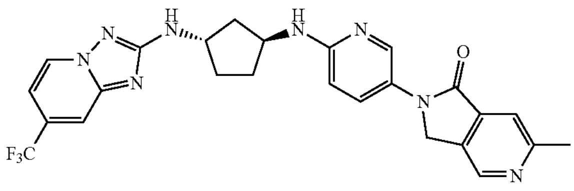

By reference to the synthesis method of Example 143, 6-methyl-2-(6-(((1S,3S)-3-((7-(trifluoromethyl)-[1,2,4]triazolo[1,5-a]pyridin-2-yl)amino)cyclopentyl)amino)pyridin-3-yl)-2,3-dihydro-1H-pyrrolo[3,4-c]pyridin-1-one 156 was synthesized.

MS m/z (ESI): 509.2 $[M+H]^+$.

$^1H$ NMR (400 MHz, DMSO-$d_6$) δ 8.82 (d, 1H), 8.80 (s, 1H), 8.34 (d, 1H), 7.85 (d, 2H), 7.59 (s, 1H), 7.15 (dd, 1H), 7.03 (dd, 1H), 6.72 (d, 1H), 6.55 (d, 1H), 4.97 (s, 2H), 4.31 (q, 1H), 4.20 (q, 1H), 2.60 (s, 3H), 2.22-2.13 (m, 2H), 2.01-1.86 (m, 2H), 1.61-1.47 (m, 2H).

Example 157

7-(Trifluoromethyl)-2-(6-(((1S,3S)-3-((6-(trifluoromethyl)-1,2,4-triazin-3-yl)amino)cyclopentyl)amino)pyridin-3-yl)isoindolin-1-one

157

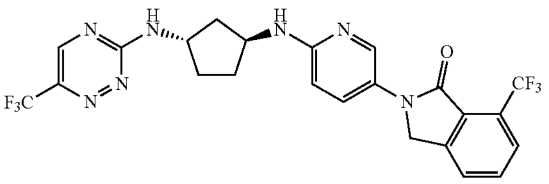

By reference to the synthesis method of Example 144, 7-(trifluoromethyl)-2-(6-(((1S,3S)-3-((6-(trifluoromethyl)-1,2,4-triazin-3-yl)amino)cyclopentyl) amino)pyridin-3-yl) isoindolin-1-one 157 was synthesized.

MS m/z (ESI): 524.2 $[M+H]^+$.

$^1H$ NMR (400 MHz, DMSO-$d_6$) δ 9.12-8.63 (m, 1H), 8.70 (d, 1H), 8.38 (d, 1H), 8.05 (d, 1H), 8.01 (d, 1H), 7.84 (dd, 1H), 7.78 (t, 1H), 6.74 (d, 1H), 6.55 (d, 1H), 5.11 (s, 2H), 4.61-4.33 (m, 2H), 2.24-2.12 (m, 2H), 1.96 (d, 2H), 1.69-1.50 (m, 2H).

Example 158

4-(Trifluoromethyl)-2-(6-(((1S,3S)-3-((6-(trifluoromethyl)-1,2,4-triazin-3-yl)amino)cyclopentyl)amino)pyridin-3-yl)isoindolin-1-one

158

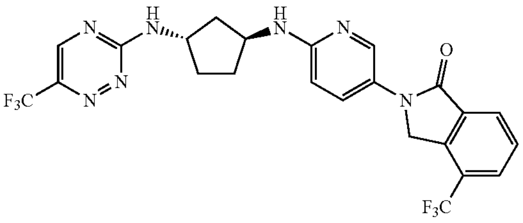

By reference to the synthesis method of Example 144, 4-(trifluoromethyl)-2-(6-(((1S,3S)-3-((6-(trifluoromethyl)-1,2,4-triazin-3-yl)amino)cyclopentyl)amino) pyridin-3-yl) isoindolin-1-one 158 was synthesized.

MS m/z (ESI): 524.2 $[M+H]^+$.

$^1H$ NMR (400 MHz, DMSO-$d_6$) δ 8.80 (s, 1H), 8.34 (d, 1H), 8.18 (s, 1H), 7.85 (dd, 1H), 7.59 (s, 1H), 7.54 (s, 1H), 6.72 (d, 1H), 6.55 (d, 1H), 4.97 (s, 2H), 4.32 (d, 2H), 2.60 (s, 3H), 2.17-2.02 (m, 3H), 1.90 (dt, 2H), 1.52 (dd, 2H), 0.98-0.87 (m, 4H).

Example 159

6-(6-(((1S,3S)-3-((6-cyclopropyl-1,2,4-triazin-3-yl)amino)cyclopentyl)amino)pyridin-3-yl)-2-(trifluoromethyl)-5,6-dihydro-7H-pyrrolo[3,4-b]pyridin-7-one

159

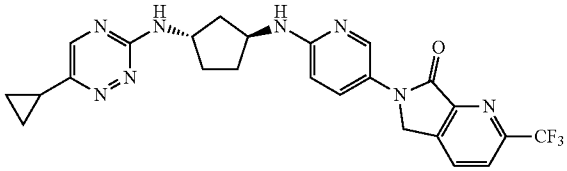

By reference to the synthesis method of Example 144, 6-(6-(((1S,3S)-3-((6-cyclopropyl-1,2,4-triazin-3-yl)amino)cyclopentyl)amino)pyridin-3-yl)-2-(trifluoromethyl)-5,6-dihydro-7H-pyrrolo[3,4-b]pyridin-7-one 159 was synthesized.

MS m/z (ESI): 497.2 $[M+H]^+$.

Example 161

2-(6-(((1S,3S)-3-((7-fluoro-[1,2,4]triazolo[1,5-a]pyridin-2-yl)amino)cyclopentylamino)pyridin-3-yl)-7-(trifluoromethyl)isoindol-1-one

161

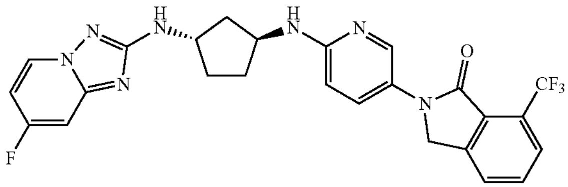

By reference to the synthesis method of Example 129, 2-(6-((1S,3S)-3-((7-fluoro-[1,2,4]triazolo[1,5-a]pyridin-2-yl)amino)cyclopentylamino)pyridin-3-yl)-7-(trifluoromethyl)isoindol-1-one 161 was synthesized.

MS m/z (ESI): 512.2 $[M+H]^+$.

$^1$H NMR (400 MHz, DMSO-$d_6$) δ 8.66 (dd, 1H), 8.30 (d, 1H), 7.95 (d, 1H), 7.90-7.77 (m, 3H), 7.27 (dd, 1H), 6.86 (t, 1H), 6.75 (d, 1H), 6.68 (d, 1H), 6.54 (d, 1H), 4.98 (s, 2H), 4.29 (q, 1H), 4.15 (q, 1H), 2.15 (dd, 2H), 2.01-1.84 (m, 2H), 1.61-1.44 (m, 2H).

Example 162

2-(6-(((1S,3S)-3-((7-fluoro-[1,2,4]triazolo[1,5-a]pyridin-2-yl)amino)cyclopentylamino)pyridin-3-yl)-4-(trifluoromethyl)isoindol-1-one

162

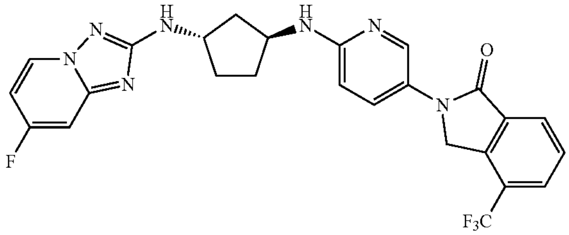

By reference to the synthesis method of Example 129, 2-(6-(((1S,3S)-3-((7-fluoro-[1,2,4]triazolo[1,5-a]pyridin-2-yl)amino)cyclopentylamino)pyridin-3-yl)-4-(trifluoromethyl)isoindol-1-one 162 was synthesized.

MS m/z (ESI): 512.1 $[M+H]^+$.

$^1$H NMR (400 MHz, DMSO-$d_6$) δ 8.66 (dd, 1H), 8.36 (d, 1H), 8.03 (dd, 2H), 7.89-7.70 (m, 2H), 7.27 (dd, 1H), 6.86 (t, 1H), 6.72 (dd, 2H), 6.54 (d, 1H), 5.10 (d, 2H), 4.22 (d, 2H), 2.21-2.06 (m, 2H), 2.00-1.81 (m, 2H), 1.64-1.42 (m, 2H).

Example 163

3-Fluoro-6-(6-(((1S,3S)-3-((7-(trifluoromethyl)-[1,2,4]triazolo[1,5-a]pyridin-2-yl)amino)cyclopentyl)amino)pyridin-3-yl)-5,6-dihydro-7H-pyrrolo[3,4-b]pyridin-7-one

163

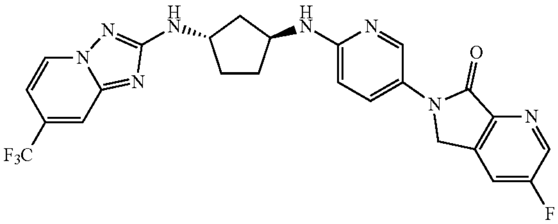

By reference to the synthesis method of Example 143, 3-fluoro-6-(6-(((1S,3S)-3-((7-(trifluoromethyl)-[1,2,4]triazolo[1,5-a]pyridin-2-yl)amino)cyclopentyl) amino)pyridin-3-yl)-5,6-dihydro-7H-pyrrolo[3,4-b]pyridin-7-one 163 was synthesized.

MS m/z (ESI): 513.2 $[M+H]^+$.

$^1$H NMR (400 MHz, DMSO-dt) δ 8.82 (d, 1H), 8.75 (s, 1H), 8.33 (d, 1H), 8.09 (dd, 1H), 7.87-7.83 (m, 2H), 7.15 (dd, 1H), 7.04 (d, 1H), 6.72 (d, 1H), 6.56 (d, 1H), 4.93 (s, 2H), 4.35-4.29 (m, 1H), 4.25-4.17 (m, 1H), 2.20-2.13 (m, 2H), 2.00-1.86 (m, 2H), 1.62-1.48 (m, 2H).

Example 164

2-(Tert-butyl)-6-(6-(((1S,3S)-3-((7-fluoro-[1,2,4]triazolo[1,5-a]pyridin-2-yl)amino)cyclopentyl)amino)pyridin-3-yl)-5,6-dihydro-7H-pyrrolo[3,4-b]pyridin-7-one

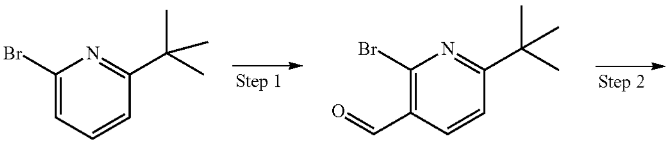

164a

164b

-continued

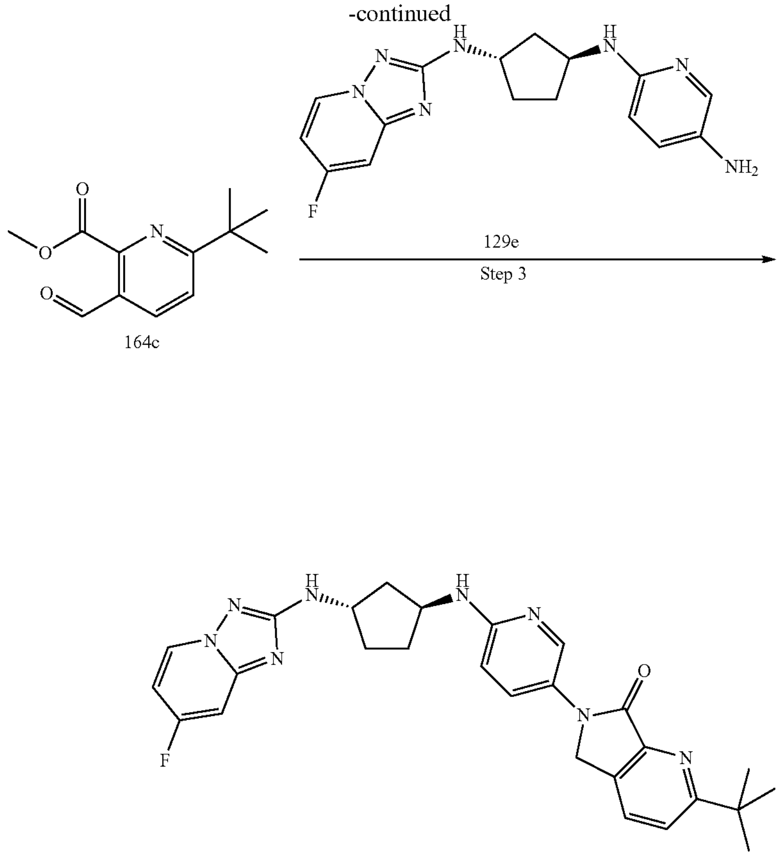

164c

164

Step 1

At −78° C., lithium diisopropylamide (2 M, 1.05 mL) was dropwise added to a solution of 2-bromo-6-tert-butylpyridine 164a (300 mg, 1.40 mmol) in tetrahydrofuran (5 mL). After the reaction was stirred at −78° C. for 1 hour, N,N-dimethylformamide (410 mg, 5.60 mmol) was dropwise added to the reaction liquid, and the reaction was slowly heated to room temperature and stirred for 1 hour. A saturated ammonium chloride solution was added to the reaction liquid, and the mixture was extracted with ethyl acetate (25 mL×2). The organic phases were combined, dried, and concentrated, and the residue was separated by silica gel column chromatography to obtain 2-bromo-6-(tert-butyl)nicotinaldehyde 164b (56 mg), yield: 16.51%.

MS m/z (ESI): 242.0 $[M+H]^+$.

Step 2

Under carbon monoxide protection, 164b (53 mg, 0.22 mmol), 1,1-bis(diphenylphosphino)ferrocene dichloropalladium (16 mg, 0.02 mmol), and triethylamine (44 mg, 0.44 mmol) were dissolved in a mixed solvent of N,N-dimethylformamide (1 mL) and methanol (2 mL), and the reaction was heated to 80° C. and stirred for 16 hours. A saturated sodium chloride solution was added to the reaction liquid, and the mixture was extracted with ethyl acetate (15 mL×2). The organic phases were combined, dried, and concentrated, and the residue was separated by silica gel column chromatography to obtain methyl 6-(tert-butyl)-3-formylpicolinate 164c (13 mg), yield: 26.84%.

MS m/z (ESI): 222.1 $[M+H]^+$.

Step 3

129e (23 mg, 0.07 mmol), 164c (13 mg, 0.06 mmol), and acetic acid (5 mg, 0.09 mmol) were dissolved in 1,2-dichloroethane (2 mL), and the reaction was heated to 60° C. and stirred for 1 hour. After the reaction liquid was brought back to room temperature, sodium triacetoxyborohydride (62 mg, 0.29 mmol) was added to the reaction liquid and stirred for 15 hours. A saturated ammonium chloride solution was added to the reaction liquid, and the mixture was extracted with dichloromethane (20 mL×2). The organic phases were combined, dried, and concentrated, and the residue was subjected to reversed-phase HPLC to prepare 2-(tert-butyl)-6-(6-(((1S,3S)-3-((7-fluoro-[1,2,4]triazolo[1,5-a]pyridin-2-yl)amino)cyclopentyl)amino)pyridin-3-yl)-5,6-dihydro-7H-pyrrolo[3,4-b]pyridin-7-one 164 (15.8 mg), yield: 53.72%.

MS m/z (ESI): 501.2 $[M+H]^+$.

$^1H$ NMR (400 MHz, DMSO-$d_6$) δ 8.70-8.62 (m, 1H), 8.34 (d, 1H), 8.02 (d, 1H), 7.89-7.80 (m, 1H), 7.68 (d, 1H), 7.31-7.22 (m, 1H), 6.90-6.82 (m, 1H), 6.75 (d, 1H), 6.68 (d, 1H), 6.56 (d, 1H), 4.86 (s, 2H), 4.35-4.23 (m, 1H), 4.22-4.08 (m, 1H), 2.22-2.07 (m, 2H), 2.03-1.81 (m, 2H), 1.63-1.42 (m, 2H), 1.37 (s, 9H).

For the synthesis method of the example, reference can be made to the above examples.

| Examples | Structure | MS m/z (ESI) |
| --- | --- | --- |
| 1 | 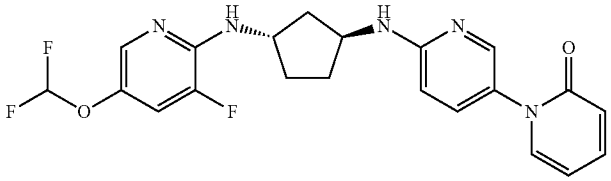 [SMILES: O=c1ccccn1-c1ccc(N[C@H]2CC[C@H](Nc3ncc(OC(F)F)cc3F)C2)nc1] | 432.2 [M + H]$^+$ |
| 2 | 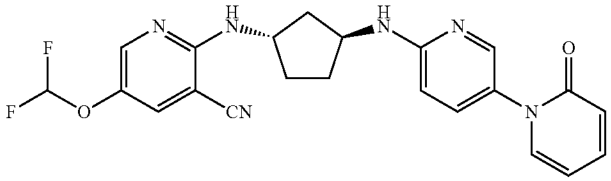 [SMILES: N#Cc1cc(OC(F)F)cnc1N[C@H]1CC[C@H](Nc2ccc(-n3ccccc3=O)cn2)C1] | 439.2 [M + H]$^+$ |
| 3 | 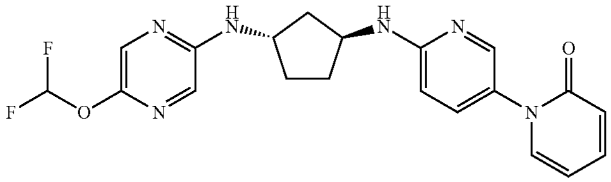 [SMILES: O=c1ccccn1-c1ccc(N[C@H]2CC[C@H](Nc3cnc(OC(F)F)cn3)C2)nc1] | 415.2 [M + H]$^+$ |
| 5 | 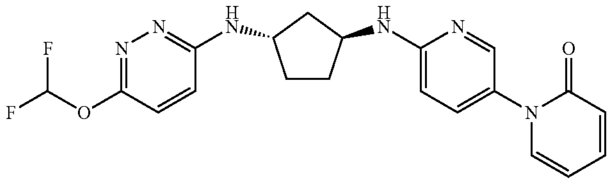 [SMILES: O=c1ccccn1-c1ccc(N[C@H]2CC[C@H](Nc3ccc(OC(F)F)nn3)C2)nc1] | 415.2 [M + H]$^+$ |
| 6 | 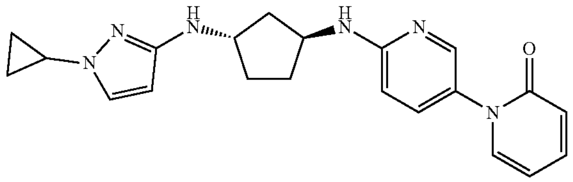 [SMILES: O=c1ccccn1-c1ccc(N[C@H]2CC[C@H](Nc3ccn(C4CC4)n3)C2)nc1] | 377.2 [M + H]$^+$ |
| 7 | 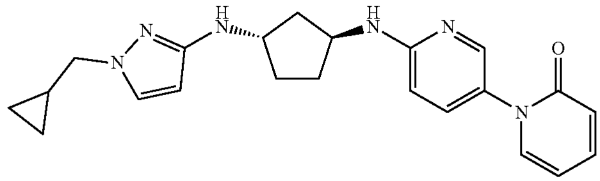 [SMILES: O=c1ccccn1-c1ccc(N[C@H]2CC[C@H](Nc3ccn(CC4CC4)n3)C2)nc1] | 391.2 [M + H]$^+$ |
| 8 | 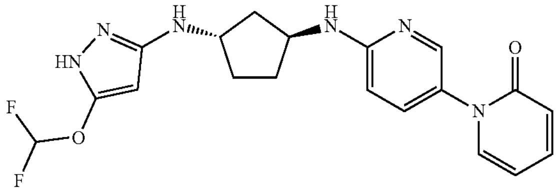 [SMILES: O=c1ccccn1-c1ccc(N[C@H]2CC[C@H](Nc3cc(OC(F)F)[nH]n3)C2)nc1] | 403.2 [M + H]$^+$ |
| 9 | 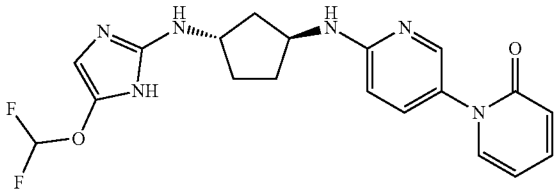 [SMILES: O=c1ccccn1-c1ccc(N[C@H]2CC[C@H](Nc3ncc(OC(F)F)[nH]3)C2)nc1] | 403.2 [M + H]$^+$ |

-continued
| Examples | Structure | MS m/z (ESI) |
|---|---|---|
| 10 | 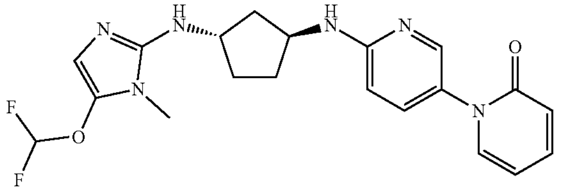 [SMILES: Cn1c(OC(F)F)cnc1N[C@H]1CC[C@H](Nc2ccc(-n3ccccc3=O)cn2)C1] | 417.2 [M + H]+ |
| 11 | 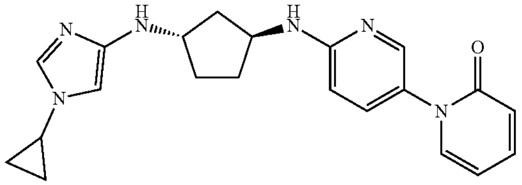 [SMILES: O=c1ccccn1-c1ccc(N[C@H]2CC[C@H](Nc3cn(C4CC4)cn3)C2)nc1] | 377.2 [M + H]+ |
| 13 | 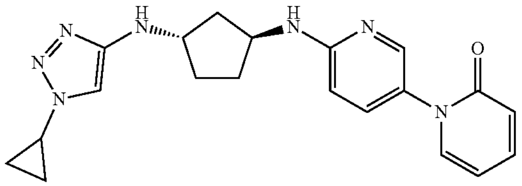 [SMILES: O=c1ccccn1-c1ccc(N[C@H]2CC[C@H](Nc3cn(C4CC4)nn3)C2)nc1] | 378.2 [M + H]+ |
| 14 | 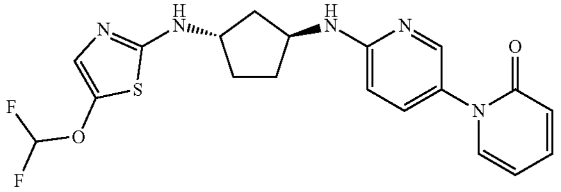 [SMILES: O=c1ccccn1-c1ccc(N[C@H]2CC[C@H](Nc3ncc(OC(F)F)s3)C2)nc1] | 420.1 [M + H]+ |
| 16 | 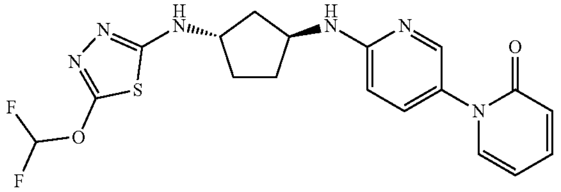 [SMILES: O=c1ccccn1-c1ccc(N[C@H]2CC[C@H](Nc3nnc(OC(F)F)s3)C2)nc1] | 421.1 [M + H]+ |
| 17 | 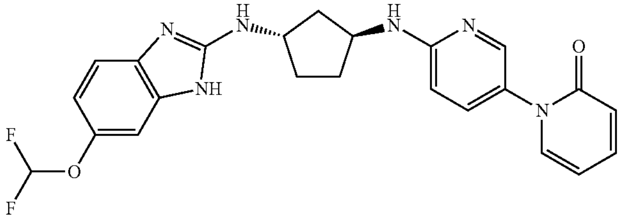 | 453.2 [M + H]+ |
| 18 | 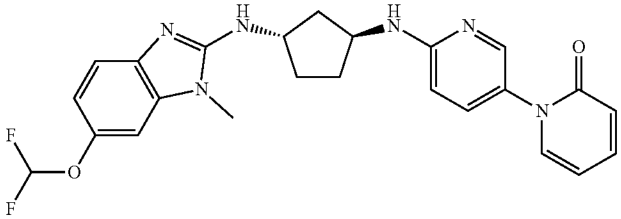 [SMILES: Cn1c(N[C@H]2CC[C@H](Nc3ccc(-n4ccccc4=O)cn3)C2)nc2ccc(OC(F)F)cc21] | 467.2 [M + H]+ |

-continued
| Examples | Structure | MS m/z (ESI) |
|---|---|---|
| 19 | 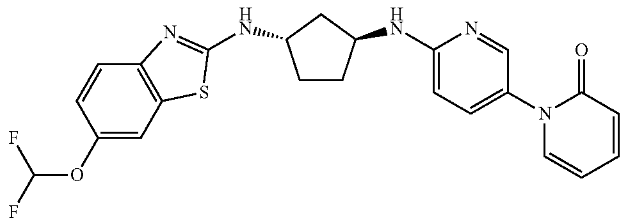 [SMILES: O=c1ccccn1-c1ccc(N[C@H]2CC[C@H](Nc3nc4ccc(OC(F)F)cc4s3)C2)nc1] | 470.1 [M + H]$^+$ |
| 21 | 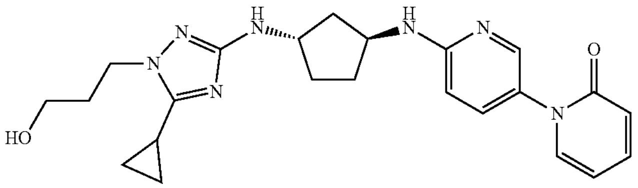 [SMILES: O=c1ccccn1-c1ccc(N[C@H]2CC[C@H](Nc3nc(C4CC4)n(CCCO)n3)C2)nc1] | 436.2 [M + H]$^+$ |
| 22 | 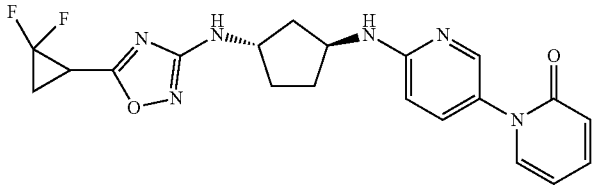 [SMILES: O=c1ccccn1-c1ccc(N[C@H]2CC[C@H](Nc3noc(C4CC4(F)F)n3)C2)nc1] | 415.2 [M + H]$^+$ |
| 23 | 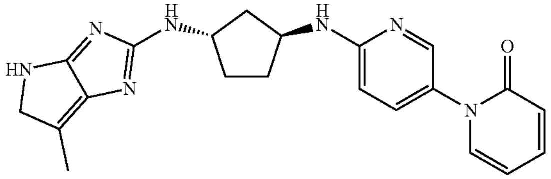 [SMILES: CC1=C2N=C(N[C@H]3CC[C@H](Nc4ccc(-n5ccccc5=O)cn4)C3)N=C2NC1] | 390.2 [M + H]$^+$ |
| 24 | 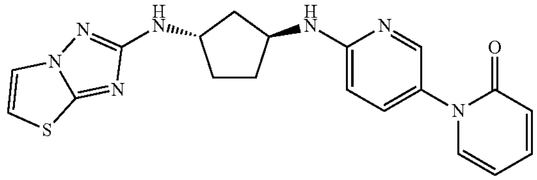 [SMILES: O=c1ccccn1-c1ccc(N[C@H]2CC[C@H](Nc3nc4sccn4n3)C2)nc1] | 394.1 [M + H]$^+$ |
| 25 | 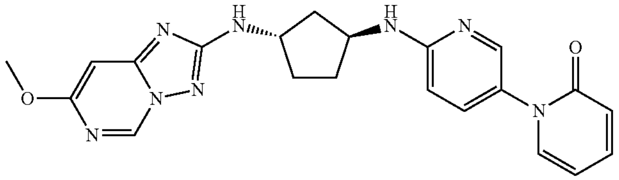 [SMILES: COc1cc2nc(N[C@H]3CC[C@H](Nc4ccc(-n5ccccc5=O)cn4)C3)nn2cn1] | 419.2 [M + H]$^+$ |
| 26 | 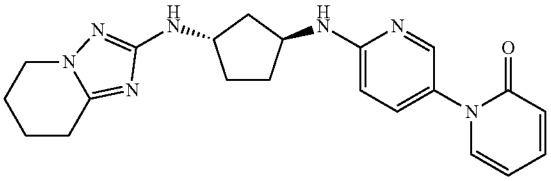 [SMILES: O=c1ccccn1-c1ccc(N[C@H]2CC[C@H](Nc3nc4n(n3)CCCC4)C2)nc1] | 392.2 [M + H]$^+$ |

-continued
| Examples | Structure | MS m/z (ESI) |
| --- | --- | --- |
| 28 | 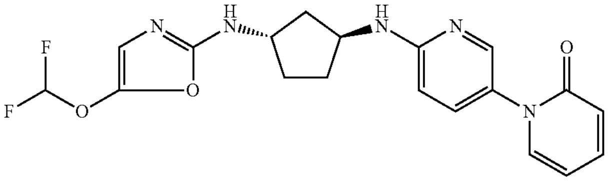 [SMILES: O=c1ccccn1-c1ccc(N[C@H]2CC[C@H](Nc3ncc(OC(F)F)o3)C2)nc1] | 404.2 [M + H]+ |
| 29 | 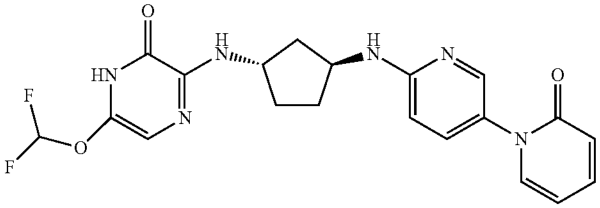 [SMILES: O=c1[nH]c(OC(F)F)cnc1N[C@H]1CC[C@H](Nc2ccc(-n3ccccc3=O)cn2)C1] | 431.2 [M + H]+ |
| 30 | 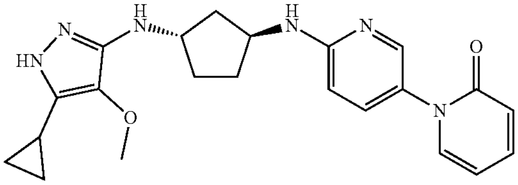 [SMILES: COc1c(N[C@H]2CC[C@H](Nc3ccc(-n4ccccc4=O)cn3)C2)n[nH]c1C1CC1] | 407.2 [M + H]+ |
| 31 | 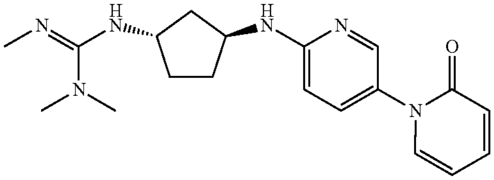 [SMILES: C/N=C(/N[C@H]1CC[C@H](Nc2ccc(-n3ccccc3=O)cn2)C1)N(C)C] | 355.2 [M + H]+ |
| 32 | 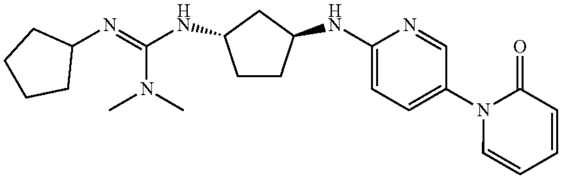 [SMILES: CN(C)/C(=N\C1CCCC1)N[C@H]1CC[C@H](Nc2ccc(-n3ccccc3=O)cn2)C1] | 409.3 [M + H]+ |
| 33 | 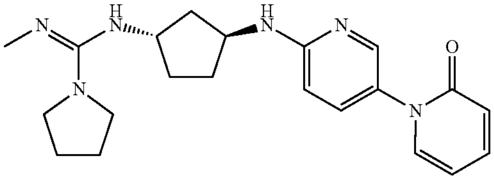 [SMILES: C/N=C(/N[C@H]1CC[C@H](Nc2ccc(-n3ccccc3=O)cn2)C1)N1CCCC1] | 381.2 [M + H]+ |
| 34 | 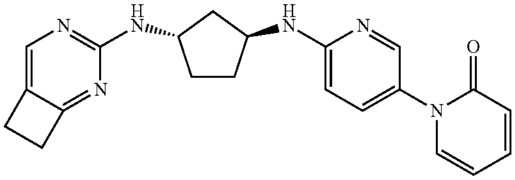 [SMILES: O=c1ccccn1-c1ccc(N[C@H]2CC[C@H](Nc3ncc4c(n3)CC4)C2)nc1] | 375.2 [M + H]+ |
| 35 | 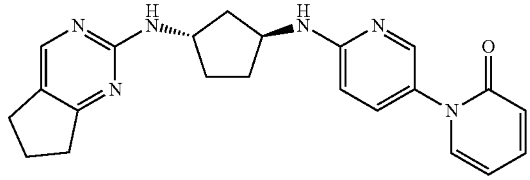 [SMILES: O=c1ccccn1-c1ccc(N[C@H]2CC[C@H](Nc3ncc4c(n3)CCC4)C2)nc1] | 389.2 [M + H]+ |

-continued
| Examples | Structure | MS m/z (ESI) |
|---|---|---|
| 36 | 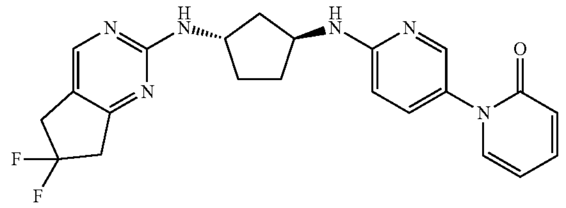 [SMILES: O=c1ccccn1-c1ccc(N[C@H]2CC[C@H](Nc3ncc4c(n3)CC(F)(F)C4)C2)nc1] | 425.2 [M + H]$^+$ |
| 37 | 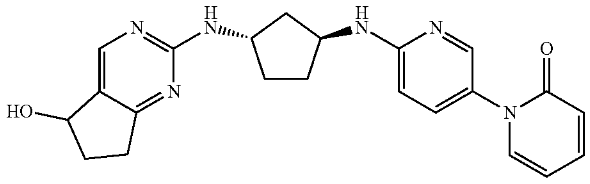 [SMILES: O=c1ccccn1-c1ccc(N[C@H]2CC[C@H](Nc3ncc4c(n3)CCC4O)C2)nc1] | 405.2 [M + H]$^+$ |
| 38 | 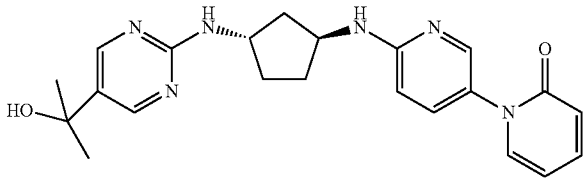 [SMILES: CC(C)(O)c1cnc(N[C@H]2CC[C@H](Nc3ccc(-n4ccccc4=O)cn3)C2)nc1] | 407.2 [M + H]$^+$ |
| 39 | 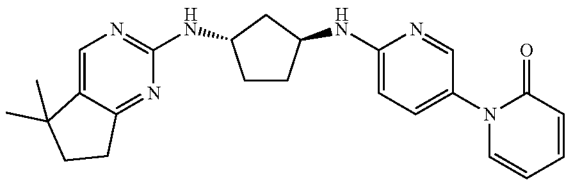 [SMILES: CC1(C)CCc2nc(N[C@H]3CC[C@H](Nc4ccc(-n5ccccc5=O)cn4)C3)ncc21] | 417.2 [M + H]$^+$ |
| 40 | 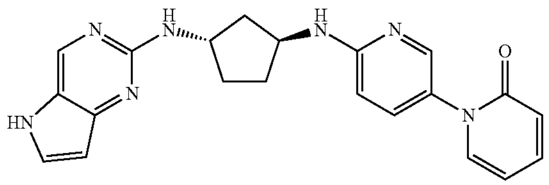 [SMILES: O=c1ccccn1-c1ccc(N[C@H]2CC[C@H](Nc3ncc4[nH]ccc4n3)C2)nc1] | 388.2 [M + H]$^+$ |
| 41 | 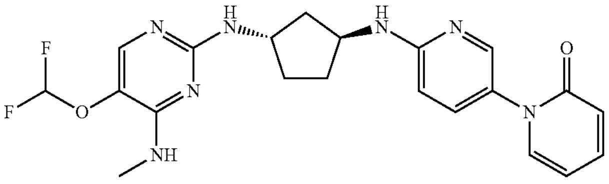 [SMILES: CNc1nc(N[C@H]2CC[C@H](Nc3ccc(-n4ccccc4=O)cn3)C2)ncc1OC(F)F] | 444.2 [M + H]$^+$ |
| 42 | 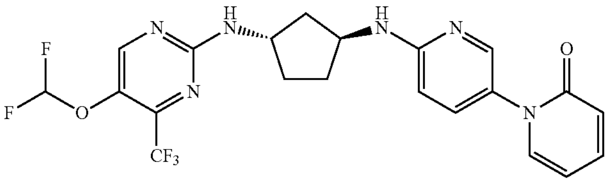 [SMILES: O=c1ccccn1-c1ccc(N[C@H]2CC[C@H](Nc3ncc(OC(F)F)c(C(F)(F)F)n3)C2)nc1] | 483.2 [M + H]$^+$ |

-continued
| Examples | Structure | MS m/z (ESI) |
|---|---|---|
| 43 | 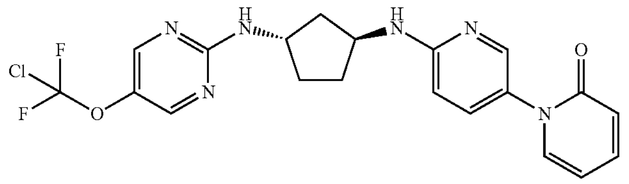 [SMILES: O=c1ccccn1-c1ccc(N[C@H]2CC[C@H](Nc3ncc(OC(F)(F)Cl)cn3)C2)nc1] | 449.1 [M + H]+ |
| 44 | 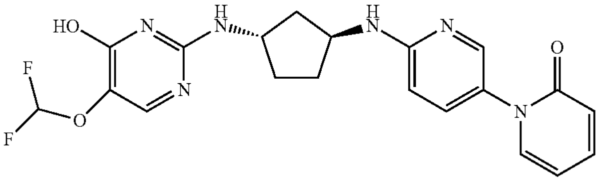 [SMILES: O=c1ccccn1-c1ccc(N[C@H]2CC[C@H](Nc3ncc(OC(F)F)c(O)n3)C2)nc1] | 431.2 [M + H]+ |
| 45 | 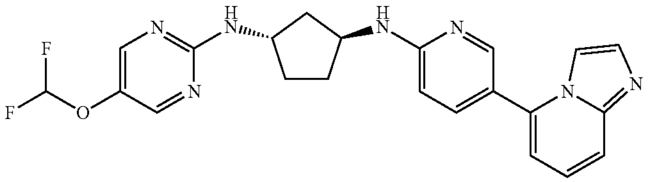 [SMILES: FC(F)Oc1cnc(N[C@H]2CC[C@H](Nc3ccc(-c4cccc5nccn45)cn3)C2)nc1] | 361.2 [M + H]+ |
| 46 | 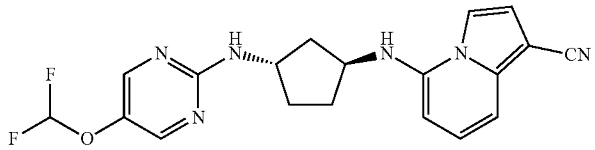 [SMILES: N#Cc1ccn2c(N[C@H]3CC[C@H](Nc4ncc(OC(F)F)cn4)C3)cccc12] | 385.2 [M + H]+ |
| 48 | 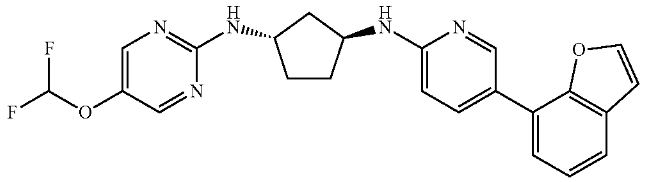 [SMILES: FC(F)Oc1cnc(N[C@H]2CC[C@H](Nc3ccc(-c4cccc5ccoc45)cn3)C2)nc1] | 438.2 [M + H]+ |
| 49 | 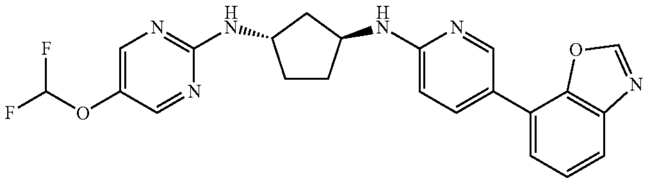 [SMILES: FC(F)Oc1cnc(N[C@H]2CC[C@H](Nc3ccc(-c4cccc5ncoc45)cn3)C2)nc1] | 439.2 [M + H]+ |
| 50 | 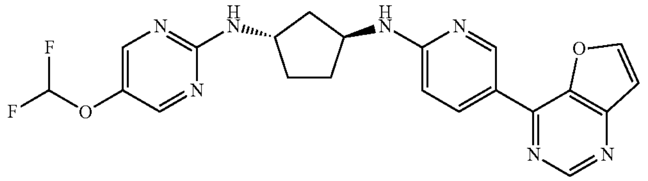 [SMILES: FC(F)Oc1cnc(N[C@H]2CC[C@H](Nc3ccc(-c4ncnc5ccoc45)cn3)C2)nc1] | 440.2 [M + H]+ |
| 51 | 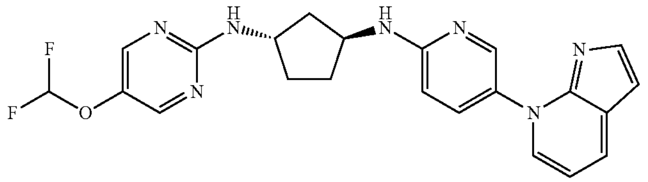 [SMILES: FC(F)Oc1cnc(N[C@H]2CC[C@H](Nc3ccc(-n4cccc5ccnc4-5)cn3)C2)nc1] | 438.2 [M + H]+ |

-continued
| Examples | Structure | MS m/z (ESI) |
| --- | --- | --- |
| 52 | 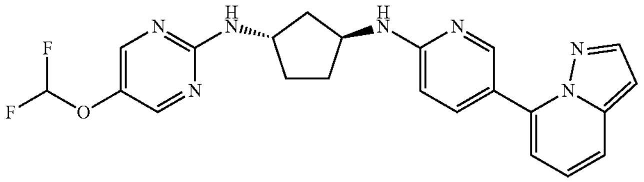 [SMILES: FC(F)Oc1cnc(N[C@H]2CC[C@H](Nc3ccc(-c4cccc5ccnn45)cn3)C2)nc1] | 438.2 [M + H]$^+$ |
| 54 | 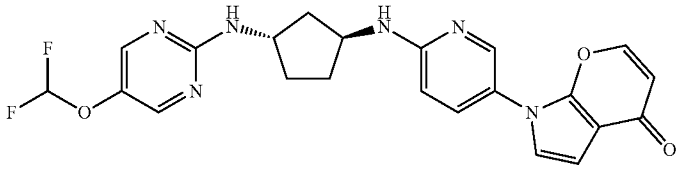 [SMILES: O=c1ccoc2c1ccn2-c1ccc(N[C@H]2CC[C@H](Nc3ncc(OC(F)F)cn3)C2)nc1] | 455.2 [M + H]$^+$ |
| 55 | 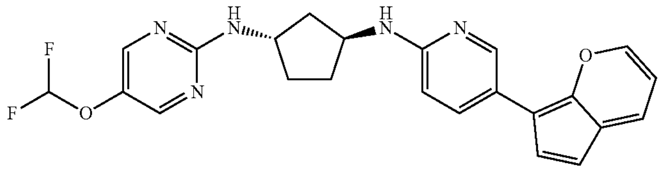 [SMILES: FC(F)Oc1cnc(N[C@H]2CC[C@H](Nc3ccc(-c4ccc5cccoc4-5)cn3)C2)nc1] | 438.2 [M + H]$^+$ |
| 58 | 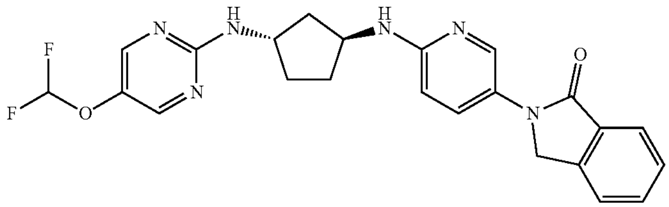 [SMILES: O=C1c2ccccc2CN1c1ccc(N[C@H]2CC[C@H](Nc3ncc(OC(F)F)cn3)C2)nc1] | 453.2 [M + H]$^+$ |
| 59 | 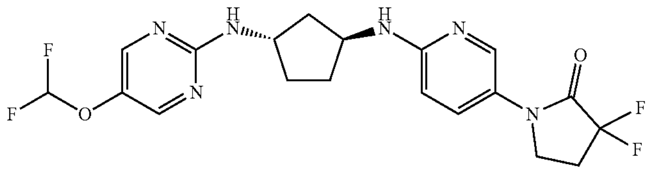 [SMILES: O=C1N(c2ccc(N[C@H]3CC[C@H](Nc4ncc(OC(F)F)cn4)C3)nc2)CCC1(F)F] | 441.2 [M + H]$^+$ |
| 60 | 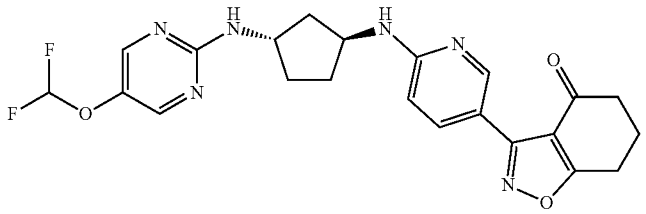 [SMILES: O=C1CCCc2onc(-c3ccc(N[C@H]4CC[C@H](Nc5ncc(OC(F)F)cn5)C4)nc3)c21] | 457.2 [M + H]$^+$ |
| 61 | 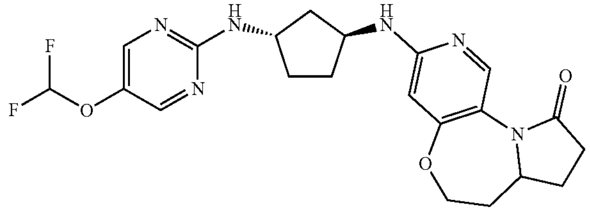 [SMILES: O=C1CCC2CCOc3cc(N[C@H]4CC[C@H](Nc5ncc(OC(F)F)cn5)C4)ncc3N12] | 447.2 [M + H]$^+$ |

-continued
| Examples | Structure | MS m/z (ESI) |
|---|---|---|
| 62 | 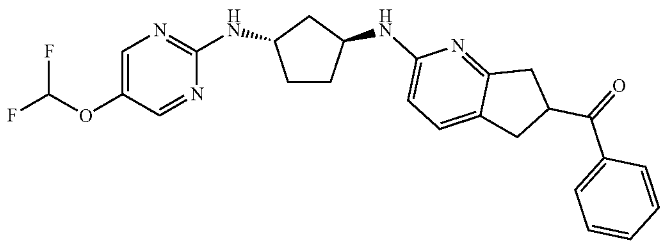 [SMILES: O=C(c1ccccc1)C1Cc2ccc(N[C@H]3CC[C@H](Nc4ncc(OC(F)F)cn4)C3)nc2C1] | 466.2 [M + H]+ |
| 63 | 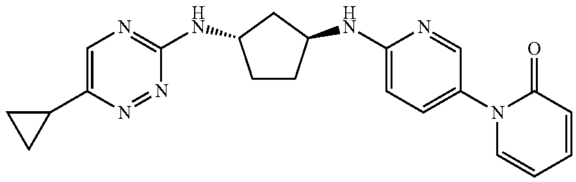 [SMILES: O=c1ccccn1-c1ccc(N[C@H]2CC[C@H](Nc3ncc(C4CC4)nn3)C2)nc1] | 390.2 [M + H]+ |
| 64 | 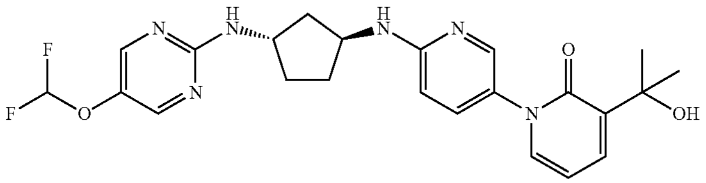 [SMILES: CC(C)(O)c1cccn(-c2ccc(N[C@H]3CC[C@H](Nc4ncc(OC(F)F)cn4)C3)nc2)c1=O] | 473.2 [M + H]+ |
| 65 | 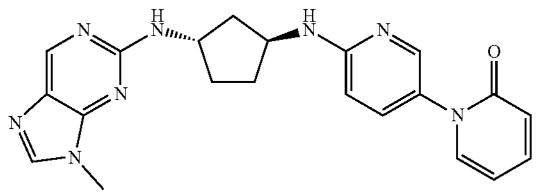 [SMILES: Cn1cnc2cnc(N[C@H]3CC[C@H](Nc4ccc(-n5ccccc5=O)cn4)C3)nc21] | 403.2 [M + H]+ |
| 66 | 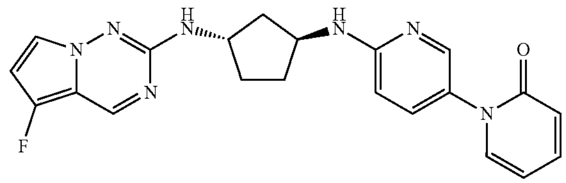 [SMILES: O=c1ccccn1-c1ccc(N[C@H]2CC[C@H](Nc3ncc4c(F)ccn4n3)C2)nc1] | 406.2 [M + H]+ |
| 67 | 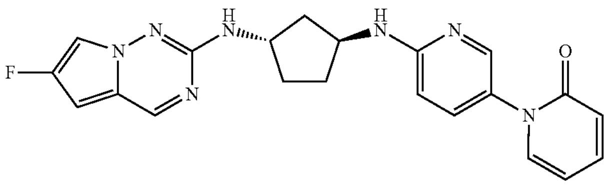 [SMILES: O=c1ccccn1-c1ccc(N[C@H]2CC[C@H](Nc3ncc4cc(F)cn4n3)C2)nc1] | 406.2 [M + H]+ |
| 68 | 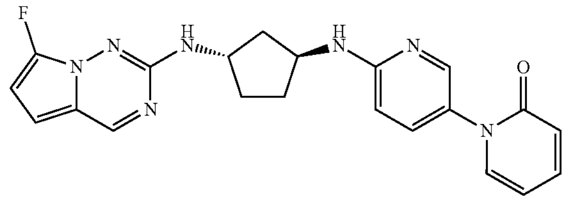 [SMILES: O=c1ccccn1-c1ccc(N[C@H]2CC[C@H](Nc3ncc4ccc(F)n4n3)C2)nc1] | 406.2 [M + H]+ |

-continued
| Examples | Structure | MS m/z (ESI) |
| --- | --- | --- |
| 69 | 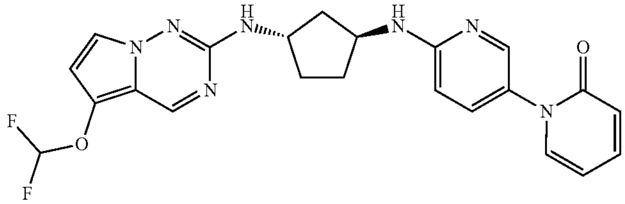 [SMILES: O=c1ccccn1-c1ccc(N[C@H]2CC[C@H](Nc3ncc4c(OC(F)F)ccn4n3)C2)nc1] | 454.2 [M + H]+ |
| 70 | 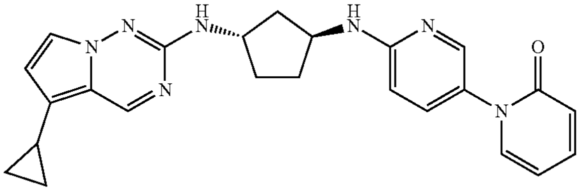 [SMILES: O=c1ccccn1-c1ccc(N[C@H]2CC[C@H](Nc3ncc4c(C5CC5)ccn4n3)C2)nc1] | 428.2 [M + H]+ |
| 71 | 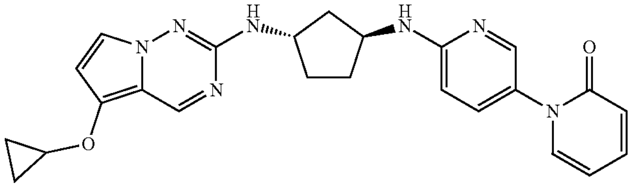 [SMILES: O=c1ccccn1-c1ccc(N[C@H]2CC[C@H](Nc3ncc4c(OC5CC5)ccn4n3)C2)nc1] | 444.2 [M + H]+ |
| 72 | 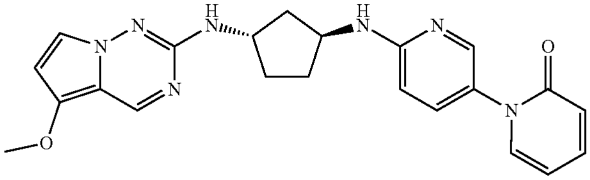 [SMILES: COc1ccn2nc(N[C@H]3CC[C@H](Nc4ccc(-n5ccccc5=O)cn4)C3)ncc12] | 418.2 [M + H]+ |
| 73 | 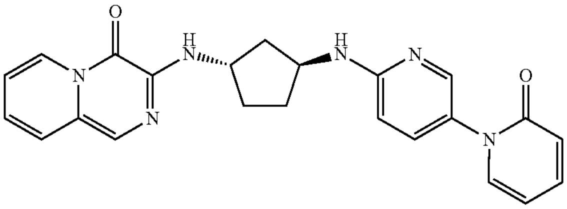 [SMILES: O=c1ccccn1-c1ccc(N[C@H]2CC[C@H](Nc3ncc4ccccn4c3=O)C2)nc1] | 415.2 [M + H]+ |
| 74 | 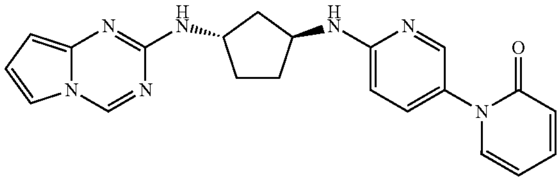 [SMILES: O=c1ccccn1-c1ccc(N[C@H]2CC[C@H](Nc3ncn4cccc4n3)C2)nc1] | 388.2 [M + H]+ |
| 75 | 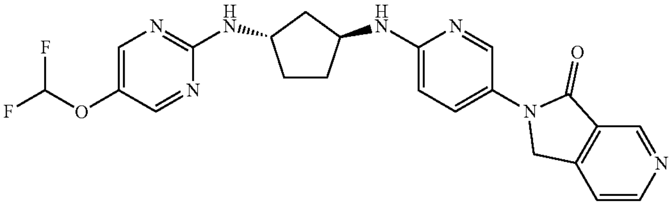 [SMILES: O=C1c2cnccc2CN1c1ccc(N[C@H]2CC[C@H](Nc3ncc(OC(F)F)cn3)C2)nc1] | 454.2 [M + H]+ |

-continued
| Examples | Structure | MS m/z (ESI) |
|---|---|---|
| 76 | 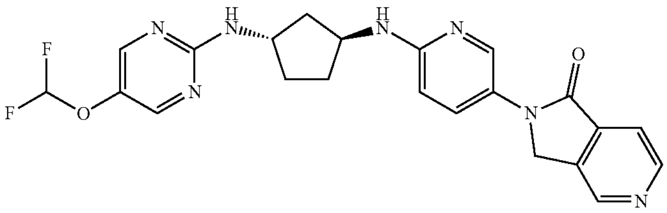 [SMILES: O=C1c2ccncc2CN1c1ccc(N[C@H]2CC[C@H](Nc3ncc(OC(F)F)cn3)C2)nc1] | 454.2 $[M + H]^+$ |
| 77 | 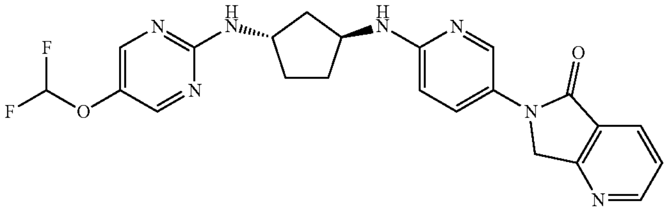 [SMILES: O=C1c2cccnc2CN1c1ccc(N[C@H]2CC[C@H](Nc3ncc(OC(F)F)cn3)C2)nc1] | 454.2 $[M + H]^+$ |
| 78 | 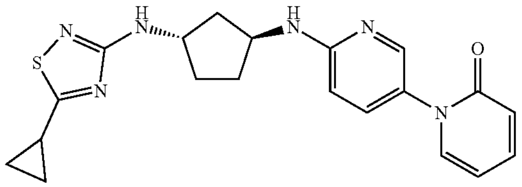 [SMILES: O=c1ccccn1-c1ccc(N[C@H]2CC[C@H](Nc3nsc(C4CC4)n3)C2)nc1] | 395.2 $[M + H]^+$ |
| 79 | 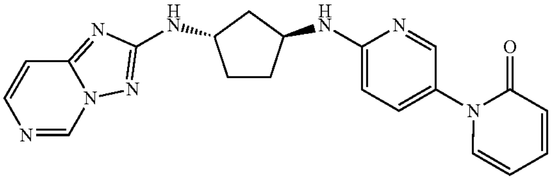 [SMILES: O=c1ccccn1-c1ccc(N[C@H]2CC[C@H](Nc3nc4ccncn4n3)C2)nc1] | 389.2 $[M + H]^+$ |
| 80 | 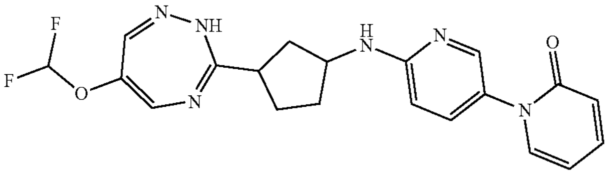 [SMILES: O=c1ccccn1-c1ccc(NC2CCC(C3=NC=C(OC(F)F)C=NN3)C2)nc1] | 415.2 $[M + H]^+$ |
| 81 | 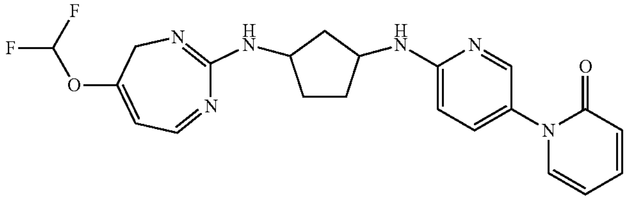 [SMILES: O=c1ccccn1-c1ccc(NC2CCC(NC3=NCC(OC(F)F)=CC=N3)C2)nc1] | 429.2 $[M + H]^+$ |
| 82 | 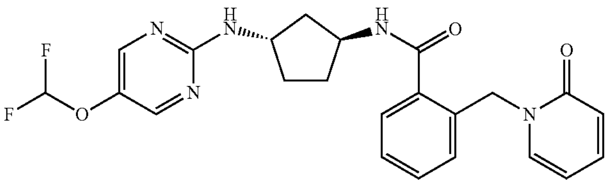 [SMILES: O=C(N[C@H]1CC[C@H](Nc2ncc(OC(F)F)cn2)C1)c1ccccc1Cn1ccccc1=O] | 456.2 $[M + H]^+$ |

-continued
| Examples | Structure | MS m/z (ESI) |
|---|---|---|
| 83 | 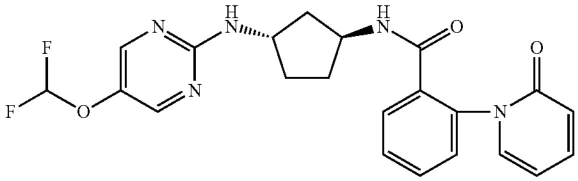 [SMILES: O=C(N[C@H]1CC[C@H](Nc2ncc(OC(F)F)cn2)C1)c1ccccc1-n1ccccc1=O] | 442.2 [M + H]+ |
| 84 | 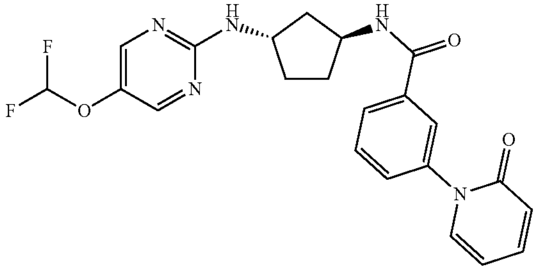 [SMILES: O=C(N[C@H]1CC[C@H](Nc2ncc(OC(F)F)cn2)C1)c1cccc(-n2ccccc2=O)c1] | 442.2 [M + H]+ |
| 85 | 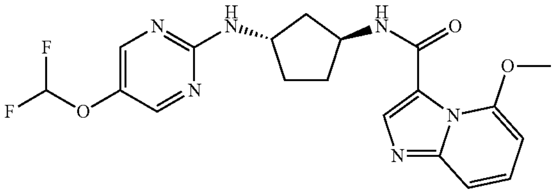 [SMILES: COc1cccc2ncc(C(=O)N[C@H]3CC[C@H](Nc4ncc(OC(F)F)cn4)C3)n12] | 419.2 [M + H]+ |
| 86 | 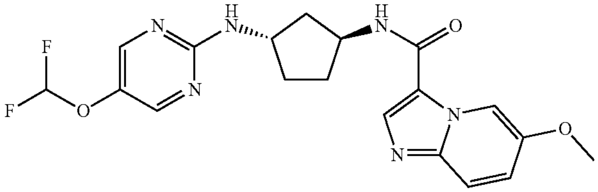 [SMILES: COc1ccc2ncc(C(=O)N[C@H]3CC[C@H](Nc4ncc(OC(F)F)cn4)C3)n2c1] | 419.2 [M + H]+ |
| 87 | 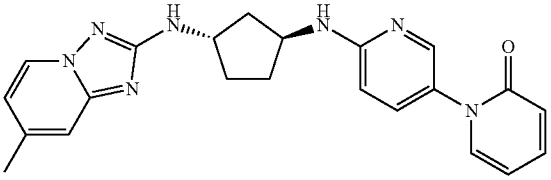 [SMILES: Cc1ccn2nc(N[C@H]3CC[C@H](Nc4ccc(-n5ccccc5=O)cn4)C3)nc2c1] | 402.2 [M + H]+ |
| 88 | 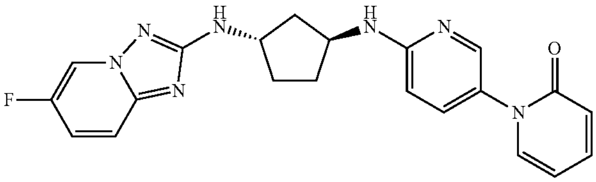 [SMILES: O=c1ccccn1-c1ccc(N[C@H]2CC[C@H](Nc3nc4ccc(F)cn4n3)C2)nc1] | 406.2 [M + H]+ |
| 89 | 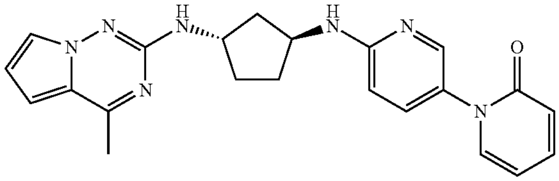 [SMILES: Cc1nc(N[C@H]2CC[C@H](Nc3ccc(-n4ccccc4=O)cn3)C2)nn2cccc12] | 402.2 [M + H]+ |

-continued
| Examples | Structure | MS m/z (ESI) |
|---|---|---|
| 90 | 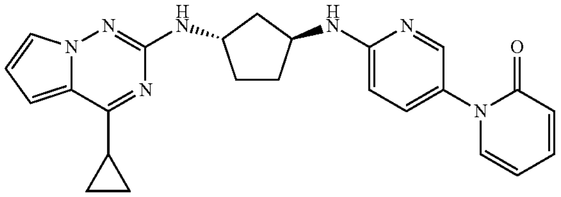 [SMILES: O=c1ccccn1-c1ccc(N[C@H]2CC[C@H](Nc3nc(C4CC4)c4cccn4n3)C2)nc1] | 428.2 [M + H]+ |
| 91 | 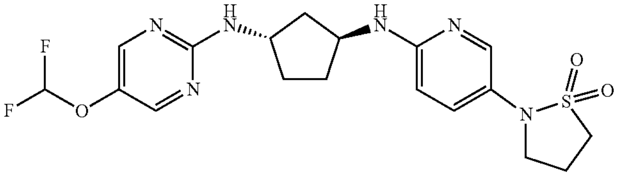 [SMILES: O=S1(=O)CCCN1c1ccc(N[C@H]2CC[C@H](Nc3ncc(OC(F)F)cn3)C2)nc1] | 441.1 [M + H]+ |
| 92 | 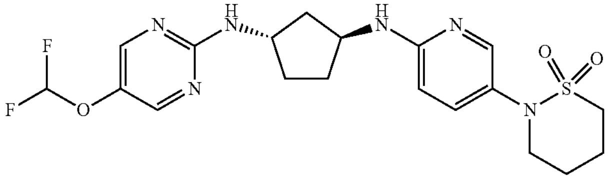 [SMILES: O=S1(=O)CCCCN1c1ccc(N[C@H]2CC[C@H](Nc3ncc(OC(F)F)cn3)C2)nc1] | 455.2 [M + H]+ |
| 93 | 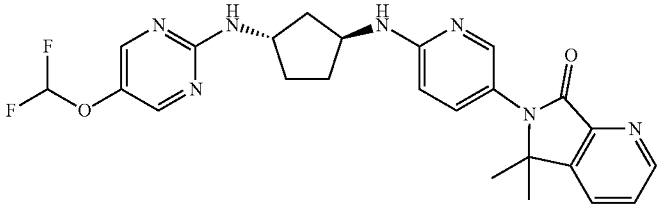 [SMILES: CC1(C)c2cccnc2C(=O)N1c1ccc(N[C@H]2CC[C@H](Nc3ncc(OC(F)F)cn3)C2)nc1] | 482.2 [M + H]+ |
| 94 | 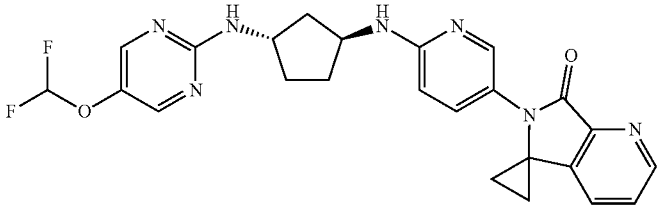 [SMILES: O=C1c2ncccc2C2(CC2)N1c1ccc(N[C@H]2CC[C@H](Nc3ncc(OC(F)F)cn3)C2)nc1] | 480.2 [M + H]+ |
| 95 | 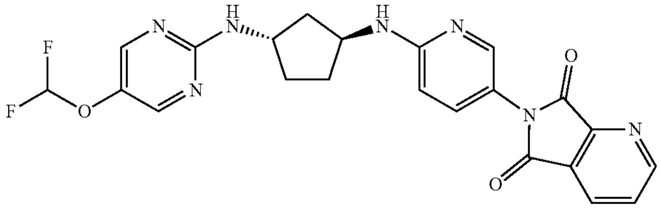 [SMILES: O=C1c2cccnc2C(=O)N1c1ccc(N[C@H]2CC[C@H](Nc3ncc(OC(F)F)cn3)C2)nc1] | 468.2 [M + H]+ |
| 96 | 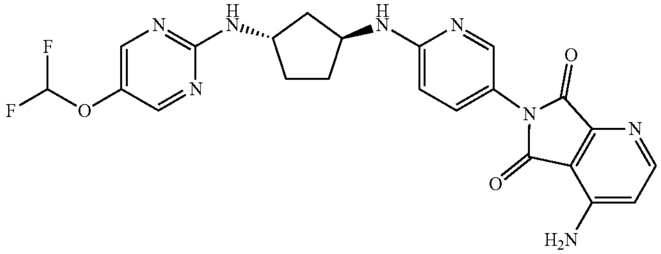 [SMILES: Nc1ccnc2c1C(=O)N(c1ccc(N[C@H]3CC[C@H](Nc4ncc(OC(F)F)cn4)C3)nc1)C2=O] | 483.2 [M + H]+ |

-continued
| Examples | Structure | MS m/z (ESI) |
|---|---|---|
| 97 | 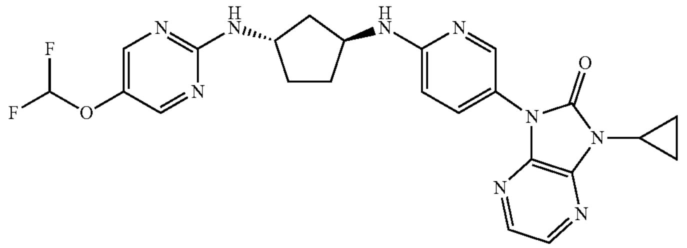 [SMILES: O=c1n(-c2ccc(N[C@H]3CC[C@H](Nc4ncc(OC(F)F)cn4)C3)nc2)c2nccnc2n1C1CC1] | 496.2 [M + H]+ |
| 98 | 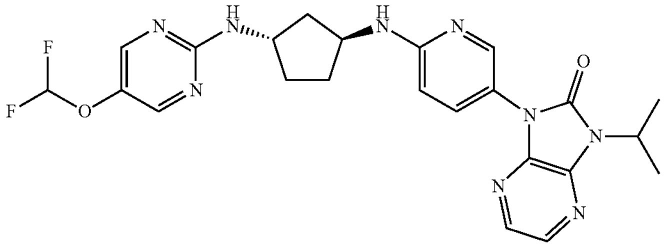 [SMILES: CC(C)n1c(=O)n(-c2ccc(N[C@H]3CC[C@H](Nc4ncc(OC(F)F)cn4)C3)nc2)c2nccnc21] | 498.2 [M + H]+ |
| 99 | 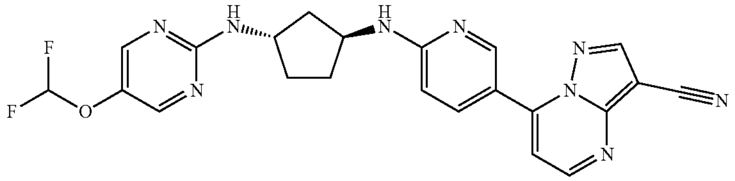 [SMILES: N#Cc1cnn2c(-c3ccc(N[C@H]4CC[C@H](Nc5ncc(OC(F)F)cn5)C4)nc3)ccnc12] | 463.2 [M + H]+ |
| 100 | 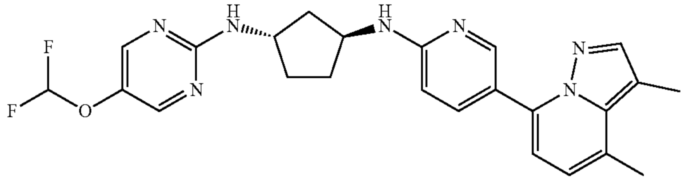 | 452.2 [M + H]+ |
| 101 | 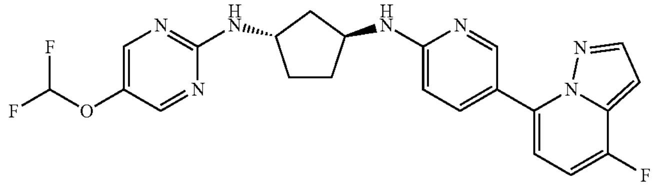 [SMILES: Fc1ccc(-c2ccc(N[C@H]3CC[C@H](Nc4ncc(OC(F)F)cn4)C3)nc2)n2nccc12] | 466.2 [M + H]+ |
| 102 | 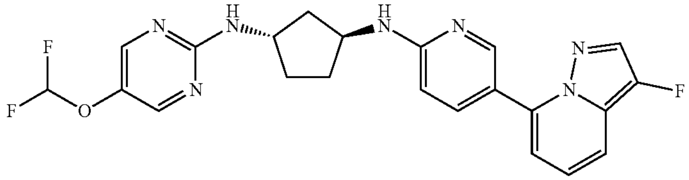 [SMILES: Fc1cnn2c(-c3ccc(N[C@H]4CC[C@H](Nc5ncc(OC(F)F)cn5)C4)nc3)cccc12] | 456.2 [M + H]+ |
| 103 | 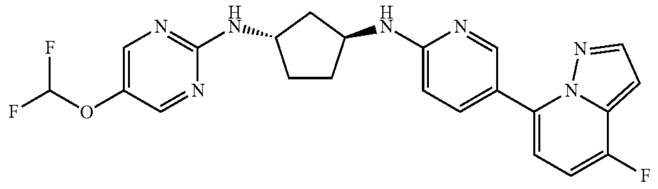 [SMILES: Fc1ccc(-c2ccc(N[C@H]3CC[C@H](Nc4ncc(OC(F)F)cn4)C3)nc2)n2nccc12] | 456.2 [M + H]+ |

-continued
| Examples | Structure | MS m/z (ESI) |
| --- | --- | --- |
| 104 | 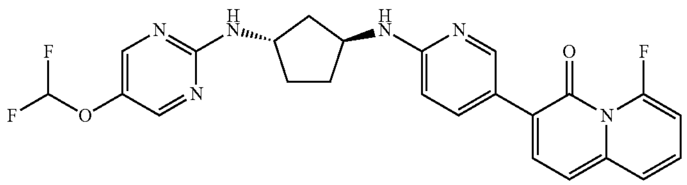 [SMILES: O=c1c(-c2ccc(N[C@H]3CC[C@H](Nc4ncc(OC(F)F)cn4)C3)nc2)ccc2cccc(F)n12] | 483.2 [M + H]+ |
| 105 | 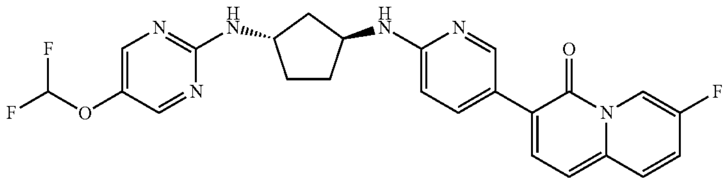 [SMILES: O=c1c(-c2ccc(N[C@H]3CC[C@H](Nc4ncc(OC(F)F)cn4)C3)nc2)ccc2ccc(F)cn12] | 483.2 [M + H]+ |
| 106 | 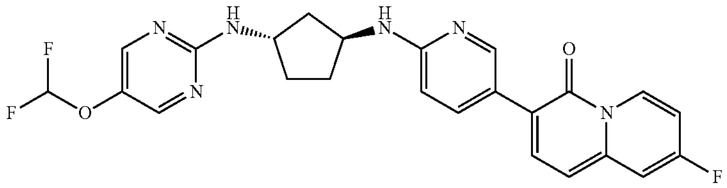 [SMILES: O=c1c(-c2ccc(N[C@H]3CC[C@H](Nc4ncc(OC(F)F)cn4)C3)nc2)ccc2cc(F)ccn12] | 483.2 [M + H]+ |
| 107 | 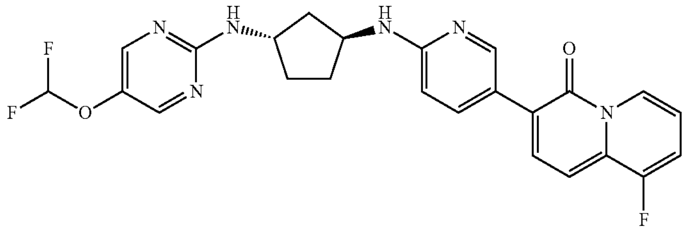 [SMILES: O=c1c(-c2ccc(N[C@H]3CC[C@H](Nc4ncc(OC(F)F)cn4)C3)nc2)ccc2c(F)cccn12] | 483.2 [M + H]+ |
| 108 | 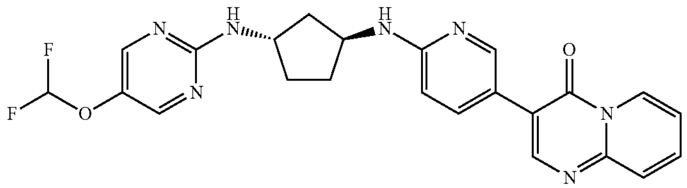 [SMILES: O=c1c(-c2ccc(N[C@H]3CC[C@H](Nc4ncc(OC(F)F)cn4)C3)nc2)cnc2ccccn12] | 466.2 [M + H]+ |
| 109 | 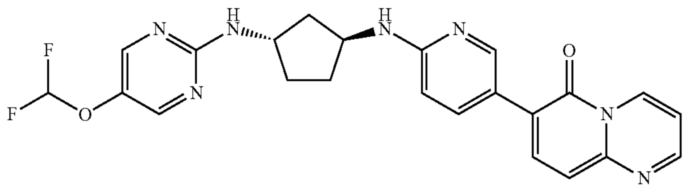 [SMILES: O=c1c(-c2ccc(N[C@H]3CC[C@H](Nc4ncc(OC(F)F)cn4)C3)nc2)ccc2ncccn12] | 466.2 [M + H]+ |
| 110 | 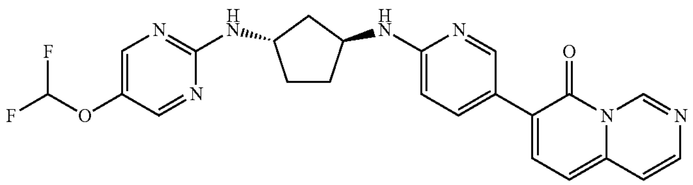 [SMILES: O=c1c(-c2ccc(N[C@H]3CC[C@H](Nc4ncc(OC(F)F)cn4)C3)nc2)ccc2ccncn12] | 466.2 [M + H]+ |

-continued
| Examples | Structure | MS m/z (ESI) |
| --- | --- | --- |
| 111 | 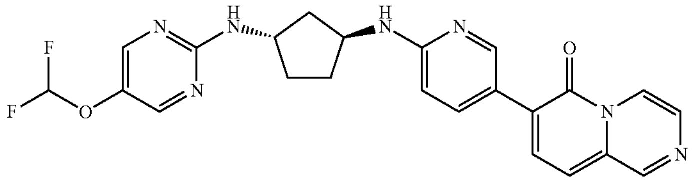 [SMILES: O=c1c(-c2ccc(N[C@H]3CC[C@H](Nc4ncc(OC(F)F)cn4)C3)nc2)ccc2cnccn12] | 466.2 [M + H]$^+$ |
| 112 | 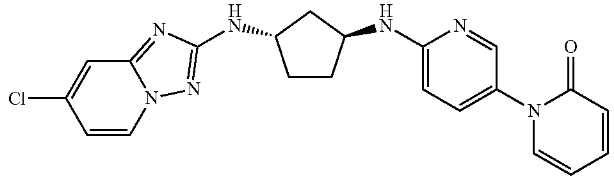 [SMILES: O=c1ccccn1-c1ccc(N[C@H]2CC[C@H](Nc3nc4cc(Cl)ccn4n3)C2)nc1] | 422.2 [M + H]$^+$ |
| 114 | 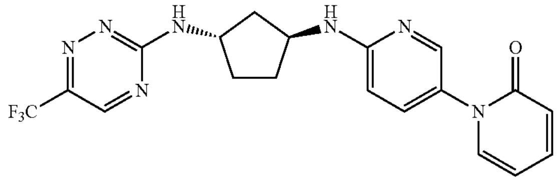 [SMILES: O=c1ccccn1-c1ccc(N[C@H]2CC[C@H](Nc3ncc(C(F)(F)F)nn3)C2)nc1] | 418.2 [M + H]$^+$ |
| 117 | 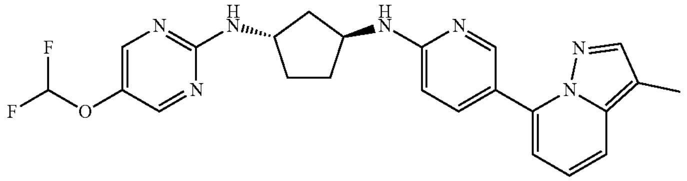 [SMILES: Cc1cnn2c(-c3ccc(N[C@H]4CC[C@H](Nc5ncc(OC(F)F)cn5)C4)nc3)cccc12] | 452.2 [M + H]$^+$ |
| 118 | 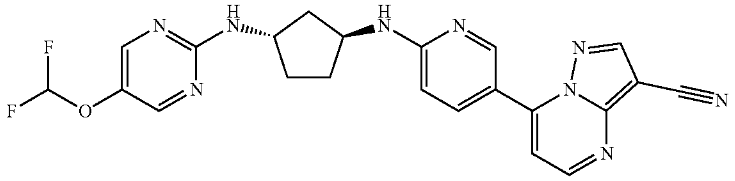 [SMILES: N#Cc1cnn2c(-c3ccc(N[C@H]4CC[C@H](Nc5ncc(OC(F)F)cn5)C4)nc3)ccnc12] | 464.2 [M + H]$^+$ |
| 119 | 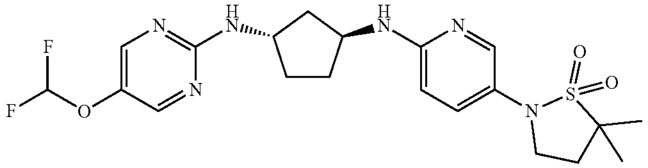 [SMILES: CC1(C)CCN(c2ccc(N[C@H]3CC[C@H](Nc4ncc(OC(F)F)cn4)C3)nc2)S1(=O)=O] | 469.2 [M + H]$^+$ |
| 120 | 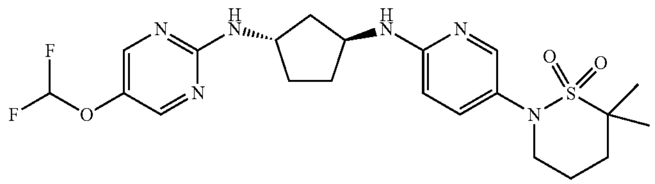 [SMILES: CC1(C)CCCN(c2ccc(N[C@H]3CC[C@H](Nc4ncc(OC(F)F)cn4)C3)nc2)S1(=O)=O] | 483.2 [M + H]$^+$ |
| 121 | 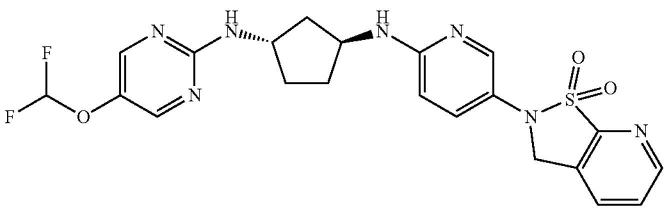 [SMILES: O=S1(=O)c2ncccc2CN1c1ccc(N[C@H]2CC[C@H](Nc3ncc(OC(F)F)cn3)C2)nc1] | 490.1 [M + H]$^+$ |

-continued
| Examples | Structure | MS m/z (ESI) |
|---|---|---|
| 126 | 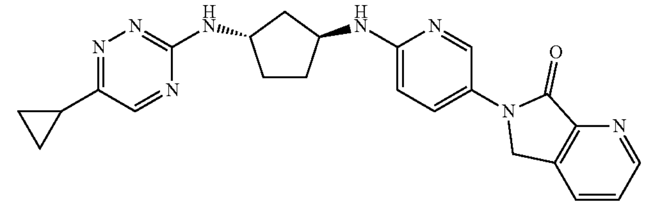 [SMILES: O=C1c2ncccc2CN1c1ccc(N[C@H]2CC[C@H](Nc3ncc(C4CC4)nn3)C2)nc1] | 429.2 [M + H]+ |
| 129-1 | 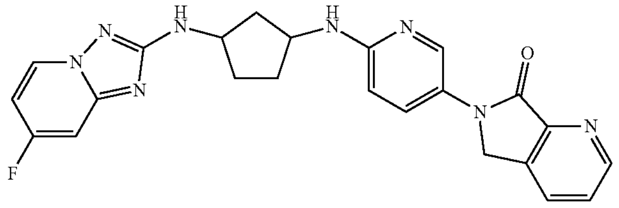 [SMILES: O=C1c2ncccc2CN1c1ccc(NC2CCC(Nc3nc4cc(F)ccn4n3)C2)nc1] | 445.2 [M + H]+ |
| 132 | 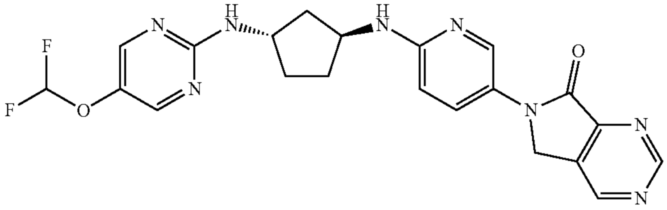 [SMILES: O=C1c2ncncc2CN1c1ccc(N[C@H]2CC[C@H](Nc3ncc(OC(F)F)cn3)C2)nc1] | 455.2 [M + H]+ |
| 133 | 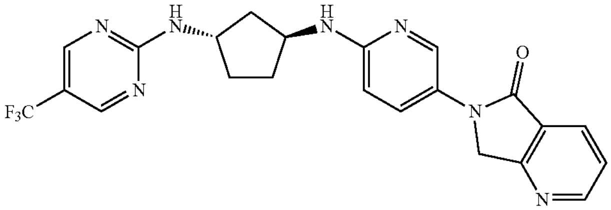 [SMILES: O=C1c2cccnc2CN1c1ccc(N[C@H]2CC[C@H](Nc3ncc(C(F)(F)F)cn3)C2)nc1] | 456.2 [M + H]+ |
| 134 | 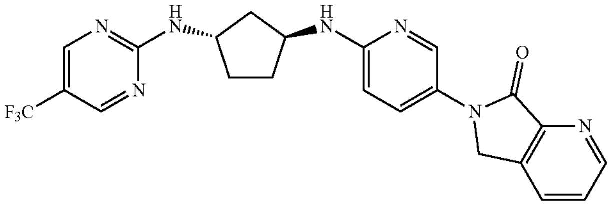 [SMILES: O=C1c2ncccc2CN1c1ccc(N[C@H]2CC[C@H](Nc3ncc(C(F)(F)F)cn3)C2)nc1] | 456.2 [M + H]+ |
| 135 | 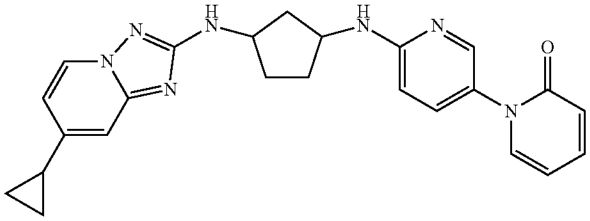 [SMILES: O=c1ccccn1-c1ccc(NC2CCC(Nc3nc4cc(C5CC5)ccn4n3)C2)nc1] | 428.2 [M + H]+ |

-continued
| Examples | Structure | MS m/z (ESI) |
|---|---|---|
| 136 | 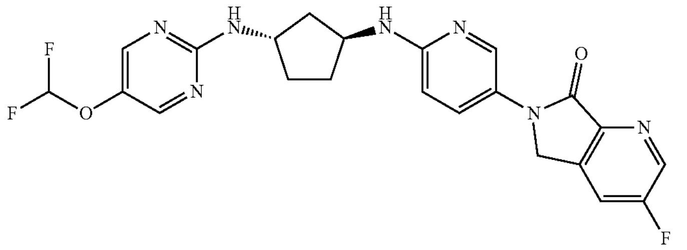 [SMILES: O=C1c2ncc(F)cc2CN1c1ccc(N[C@H]2CC[C@H](Nc3ncc(OC(F)F)cn3)C2)nc1] | 472.2 [M + H]$^+$ |
| 137 | 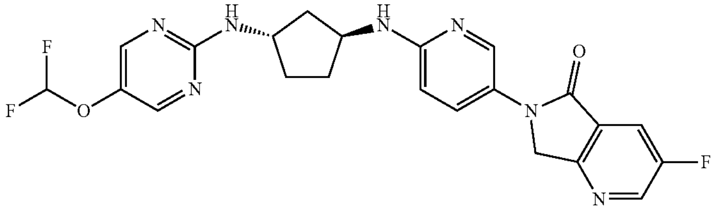 [SMILES: O=C1c2cc(F)cnc2CN1c1ccc(N[C@H]2CC[C@H](Nc3ncc(OC(F)F)cn3)C2)nc1] | 472.2 [M + H]$^+$ |
| 138 | 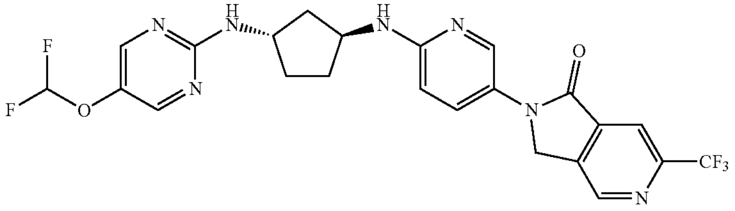 [SMILES: O=C1c2cc(C(F)(F)F)ncc2CN1c1ccc(N[C@H]2CC[C@H](Nc3ncc(OC(F)F)cn3)C2)nc1] | 522.2 [M + H]$^+$ |
| 141 | 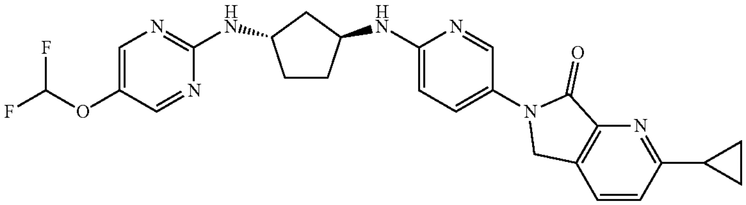 [SMILES: O=C1c2nc(C3CC3)ccc2CN1c1ccc(N[C@H]2CC[C@H](Nc3ncc(OC(F)F)cn3)C2)nc1] | 494.2 [M + H]$^+$ |
| 143-1 | 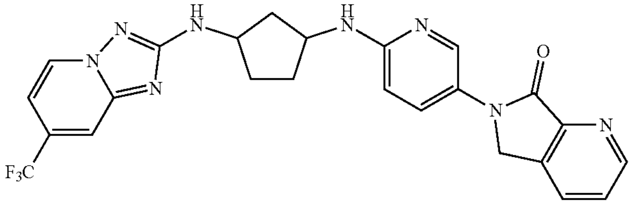 [SMILES: O=C1c2ncccc2CN1c1ccc(NC2CCC(Nc3nc4cc(C(F)(F)F)ccn4n3)C2)nc1] | 495.2 [M + H]$^+$ |
| 143 | 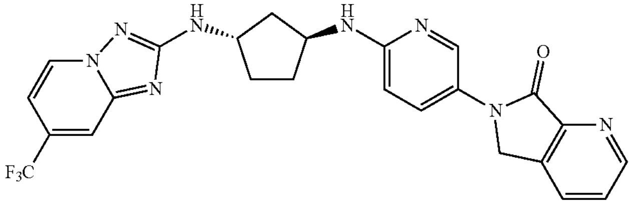 [SMILES: O=C1c2ncccc2CN1c1ccc(N[C@H]2CC[C@H](Nc3nc4cc(C(F)(F)F)ccn4n3)C2)nc1] | 495.2 [M + H]$^+$ |
| 144-1 | 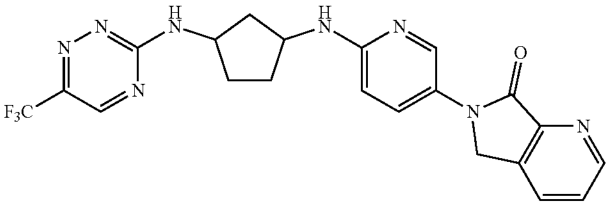 [SMILES: O=C1c2ncccc2CN1c1ccc(NC2CCC(Nc3ncc(C(F)(F)F)nn3)C2)nc1] | 457.2 [M + H]$^+$ |

-continued
| Examples | Structure | MS m/z (ESI) |
| --- | --- | --- |
| 144 | 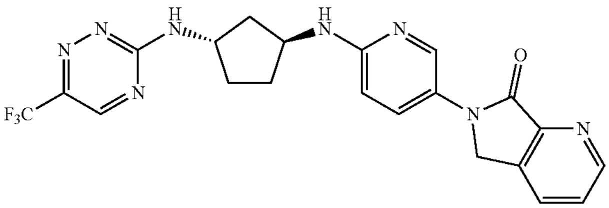 [SMILES: O=C1c2ncccc2CN1c1ccc(N[C@H]2CC[C@H](Nc3ncc(C(F)(F)F)nn3)C2)nc1] | 457.2 [M + H]+ |
| 145 | 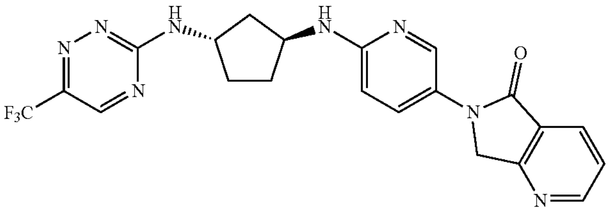 [SMILES: O=C1c2cccnc2CN1c1ccc(N[C@H]2CC[C@H](Nc3ncc(C(F)(F)F)nn3)C2)nc1] | 457.2 [M + H]+ |
| 146 | 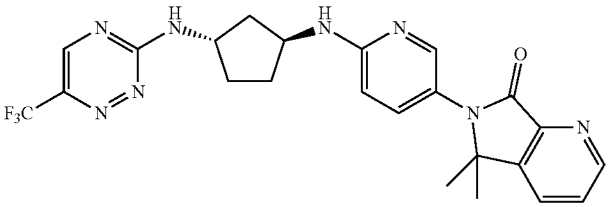 [SMILES: CC1(C)c2cccnc2C(=O)N1c1ccc(N[C@H]2CC[C@H](Nc3ncc(C(F)(F)F)nn3)C2)nc1] | 485.2 [M + H]+ |
| 147-1 | 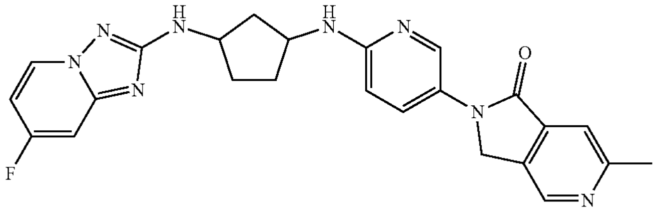 [SMILES: Cc1cc2c(cn1)CN(c1ccc(NC3CCC(Nc4nc5cc(F)ccn5n4)C3)nc1)C2=O] | 459.2 [M + H]+ |
| 148-1 | 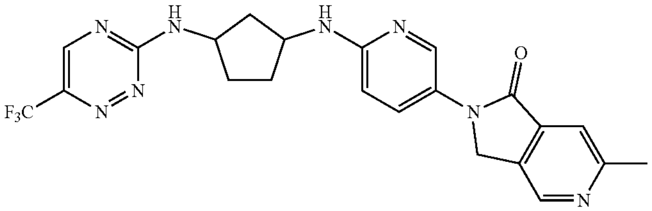 [SMILES: Cc1cc2c(cn1)CN(c1ccc(NC3CCC(Nc4ncc(C(F)(F)F)nn4)C3)nc1)C2=O] | 471.2 [M + H]+ |
| 149-1 | 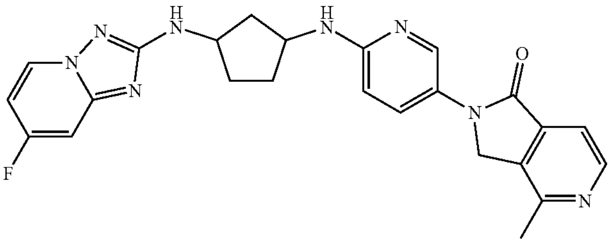 [SMILES: Cc1nccc2c1CN(c1ccc(NC3CCC(Nc4nc5cc(F)ccn5n4)C3)nc1)C2=O] | 459.2 [M + H]+ |

-continued
| Examples | Structure | MS m/z (ESI) |
| --- | --- | --- |
| 149 | 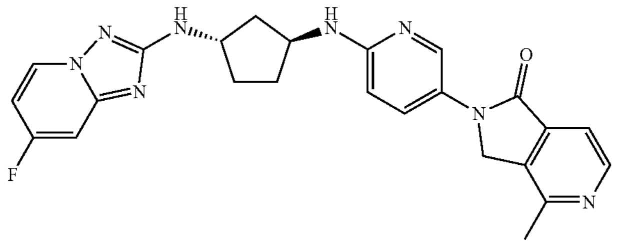 [SMILES: Cc1nccc2c1CN(c1ccc(N[C@H]3CC[C@H](Nc4nc5cc(F)ccn5n4)C3)nc1)C2=O] | 459.2 $[M + H]^+$ |
| 150 | 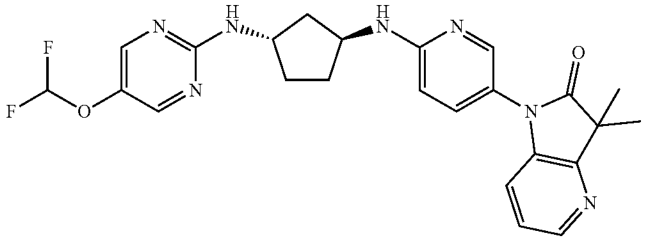 [SMILES: CC1(C)C(=O)N(c2ccc(N[C@H]3CC[C@H](Nc4ncc(OC(F)F)cn4)C3)nc2)c2cccnc21] | 482.2 $[M + H]^+$ |
| 151 | 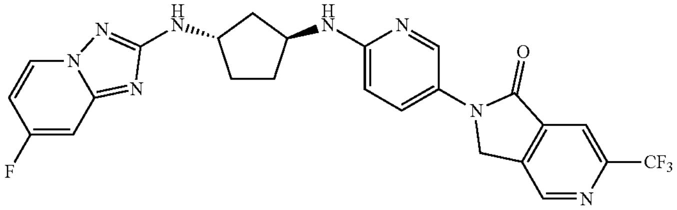 [SMILES: O=C1c2cc(C(F)(F)F)ncc2CN1c1ccc(N[C@H]2CC[C@H](Nc3nc4cc(F)ccn4n3)C2)nc1] | 513.2 $[M + H]^+$ |
| 152 | 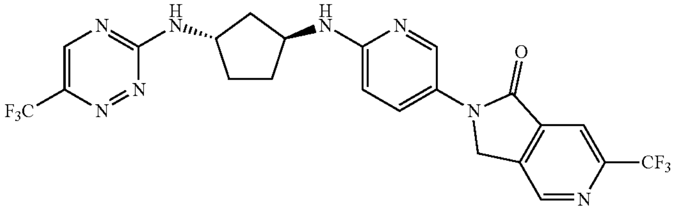 [SMILES: O=C1c2cc(C(F)(F)F)ncc2CN1c1ccc(N[C@H]2CC[C@H](Nc3ncc(C(F)(F)F)nn3)C2)nc1] | 525.2 $[M + H]^+$ |
| 153 | 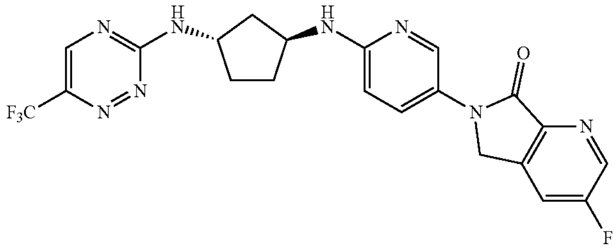 [SMILES: O=C1c2ncc(F)cc2CN1c1ccc(N[C@H]2CC[C@H](Nc3ncc(C(F)(F)F)nn3)C2)nc1] | 475.2 $[M + H]^+$ |
| 160 | 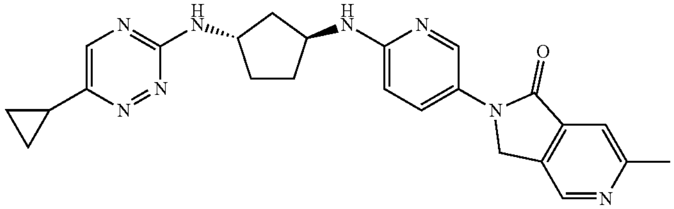 [SMILES: Cc1cc2c(cn1)CN(c1ccc(N[C@H]3CC[C@H](Nc4ncc(C5CC5)nn4)C3)nc1)C2=O] | 443.2 $[M + H]^+$ |

Biological Test and Evaluation

The present disclosure will be further described and explained below in Conjunction with test examples, but these examples are not meant to limit the scope of the present disclosure.

I. Binding Experiment

1. Experimental Objective

To detect the action of compounds to bind PCSK9 protein by a conventional surface plasmon resonance (SPR) method.

2. Experimental Results

| Examples | $K_D$ (nM) | $K_{off}$ |
|---|---|---|
| 20 | 2.4 | 1.32E−04 |
| 27 | 2.6 | 1.11E−04 |
| 77 | 1.5 | 1.60E−04 |
| 93 | 2.9 | 2.88E−04 |
| 112 | 2.7 | 1.9SE−04 |
| 113 | 4.2 | 2.40E−04 |
| 115 | 3.1 | 3.00E−04 |
| 122 | 2.2 | 2.28E−04 |
| 124 | 0.8 | 1.60E−04 |
| 126 | 1.2 | 2.40E−04 |
| 127 | 1.8 | 2.76E−04 |
| 130 | 1.2 | 1.97E−04 |
| 132 | 1.1 | 9.52E−05 |
| 135 | 4.9 | 1.79E−04 |
| 143 | 1.2 | 2.02E−04 |
| 145 | 3.2 | 2.89E−04 |
| 146 | 2.5 | 1.11E−04 |
| 149 | 1.4 | 2.00E−04 |
| 155 | 2.8 | 2.04E−04 |
| 156 | 4.8 | 2.17E−04 |
| 161 | 2.6 | 1.85E−04 |
| 162 | 3.0 | 1.97E−04 |

Note:
E−04: $\times 10^{-4}$

3. Experimental Conclusion

The compounds of the examples shown in the present disclosure had a good action of binding PCSK-9 protein, and the dissociation rate of the compounds on PCSK-9 protein was slow.

II. Cell Function Experiment

Test Example 1. Determination of the Effect of the Compounds of the Present Disclosure on the Concentration of PCSK9 Secreted by HepG2 Cells

1. Experimental Objective

To detect the inhibitory effect of the compounds on PCSK9.

2. Experimental Instruments and Reagents 2.1 Instruments:

Envision (PE-Cisbio: 2105-0020), centrifuge (Eppendorf: 5810R), water purifier (THERMO: Pacific T II+Micropure), plate washer (Thermo: WELLWASH VERSA), and micro-plate shaker (Thermo: 88882006)

2.2 Reagents:

CircuLex Human PCSK9 ELISA kit (MBL: CY-8079);
DMEM (Gibco: 31966-021)
FBS (Sigma: S5394)
Compound plate (Thermo: 1353506)
Complete culture medium: DMEM+10% FBS+1× P/S;
Experimental culture medium: DMEM+10% FBS
Cell strain: HepG2 (ATCC: HB-8065)

3. Experimental Method

1) HepG2 cell strain was cultured in the complete culture medium at 37° C., 5% $CO_2$ to 70-90% confluence.

2) The cells were digested and resuspended in the experimental culture medium, inoculation was performed at 25,000 cells/well/200 μL in a 96-well cell culture plate, and the cells were cultured at 37° C., 5% $CO_2$ for 20-24 hours.

3) The culture medium was removed from the cell culture plate, and the cell culture plate was washed once by adding 200 ul of the experimental culture medium to each well.

4) Preparation of positive control compound and compound to be tested: the positive control compound and the compound to be tested were diluted on the compound plate.

5) The diluted compound was added to the cell culture plate at 250 μL per well and incubated at 37° C. and 5% $CO_2$ for 48 hours.

6) The cell culture medium was collected at 200 μL per well and cryopreserved at −80° C. for later use.

7) A sample of the cell culture medium was taken from the −80° C. cryopreservation condition, dissolved, vortexed, and centrifuged for later use.

8) Preparation of standard curve: corresponding volumes of Dilution buffer were successively added to respective standard tubes, and in the order of the concentrations of 10, 5, 2.5, 1.25, 0.625, 0.313, 0.16, 0 ng/mL, the standard was diluted in series by taking the corresponding volume from the original tube or the last concentration tube.

9) Preparation of washing liquid: 10× Wash buffer was diluted into 1× with Milli-Q for later use.

10) According to the standard curve wells and sample wells set according to a plate map, 100 L/well of the corresponding standards and culture medium samples were added to the wells, with 2 replicate wells. A self-adhesive seal was applied, the plate was placed on a plate shaker at room temperature, gently shaken, uniformly mixed, and incubated for 1 hour.

11) The plate was placed on the plate washer, the washing liquid was set to 350 μL per well, and the plate was washed 4 times repeatedly.

12) 100 μL/well of an HRP-conjugated detection antibody was added, a self-adhesive seal was applied, and the plate was placed on the plate shaker, well mixed uniformly, and incubated for 1 hour.

13) The plate was placed on the plate washer, the washing liquid was set to 350 μL per well, and the plate was washed 4 times repeatedly.

14) 100 μL/well of Substrate reagent was added, and the plate was placed in the dark, applied with a self-adhesive seal, placed on the plate shaker, well mixed uniformly, and incubated for 10-20 minutes.

15) 100 μL/well of Stop solution (1N $H_2SO_4$) was added and mixed uniformly.

16) The optical density (OD) value in each well was measured in sequence at a wavelength of 450 nm by the microplate reader. Detection was carried out within 30 min after the reaction was stopped.

4. Experimental Data Processing Method

After the OD values were read by the microplate reader, the OD value of the 0-concentration standard in the standard group was subtracted from the OD values of the standards, control group, and samples to obtain the actual OD values for these wells. A standard curve was plotted with Graphpad and the concentration of the sample was calculated. If the dilution was performed during the sample detection, the calculated sample concentration was necessarily multiplied by the corresponding dilution ratio in the final calculation, which was the actual concentration of the sample. Inhibition rate=(actual concentration in control−actual concentration in sample)/actual concentration in control*100. According to the inhibition rates corresponding to the different concentrations, $IC_{50}$ was derived by Graphpad.

5. Experimental Results

| Examples | Inhibitory activity on PCSK9, $IC_{50}$ (μM) |
|---|---|
| 20 | 14.0 |
| 47 | 18.0 |
| 52 | 11.0 |
| 53 | 24.1 |
| 57 | 22.0 |
| 63 | 10.5 |
| 64 | 10.0 |
| 75 | 9.0 |
| 76 | 12.1 |
| 78 | 14.2 |
| 91 | 21.8 |
| 92 | 16.3 |
| 97 | 11.6 |
| 99 | 2.6 |
| 102 | 6.3 |
| 108 | 3.8 |
| 113 | 14.0 |
| 115 | 3.8 |
| 116 | 2.6 |
| 117 | 3.6 |
| 118 | 0.5 |
| 119 | 17.4 |
| 120 | 13.5 |
| 121 | 27.3 |
| 122 | 1.2 |
| 123 | 3.3 |
| 124 | 16.8 |
| 125 | 17.3 |
| 126 | 0.5 |
| 127 | 11.8 |
| 128 | 7.9 |
| 129 | 7.4 |
| 130 | 9.9 |
| 131 | 2.0 |
| 132 | 12 |
| 133 | 1.1 |
| 134 | 2.2 |
| 135 | 22.3 |
| 136 | 9.6 |
| 137 | 7.4 |
| 138 | 0.5 |
| 139 | 10.4 |
| 140 | 8.0 |
| 141 | 1.8 |
| 142 | 2.4 |
| 144 | 27.5 |
| 145 | 24.5 |
| 147 | 24.1 |
| 148 | 9.4 |
| 149 | 15.5 |
| 150 | 14.4 |
| 151 | 1.3 |
| 152 | 1.5 |
| 153 | 26.4 |
| 154 | 13.2 |
| 155 | 19.9 |
| 156 | 2.1 |
| 157 | 4.2 |
| 158 | 1.9 |

-continued

| Examples | Inhibitory activity on PCSK9, $IC_{50}$ (μM) |
|---|---|
| 159 | 5.9 |
| 160 | 6.2 |
| 161 | 17.6 |
| 162 | 22.8 |
| 163 | 12.0 |
| 164 | 2.8 |

6. Experimental Conclusion

The compounds of the examples shown in the present disclosure showed a good inhibitory effect in the experiment of the effect on the concentration of PCSK9 secreted by HepG2 cells.

Test Example 2. Determination of the Effect of the Compounds of the Present Disclosure on the LDLR Level in HepG2 Cells 1. Experimental Objective To detect the effect of the compounds on the LDLR protein level.

2. Experimental Instruments and Reagents 2.1 Instruments:

Envision (PE-Cisbio: 2105-0020), centrifuge (Eppendorf: 5810R), water purifier (THERMO: Pacific T II+Micropure), plate washer (Thermo: WELLWASH VERSA), and microplate shaker (Thermo: 88882006)

2.2 Reagents:

Human LDL R Quantikine ELISA Kit (R&D: DLDLR0)
DMEM (Gibco: 31966-021)
FBS (Sigma: S5394)
PBS
Cell lysis buffer (Thermo: 78503)
Protease inhibitor (Pierce: 78430)
Compound plate (Thermo: 1353506)
Complete culture medium: DMEM+10% FBS+1×P/S
Experimental culture medium: DMEM+10% FBS
Cell strain: HepG2 (ATCC: HB-8065)

3. Experimental Method

1) HepG2 cell strain was cultured in the complete culture medium at 37° C., 5% $CO_2$ to 70-90% confluence.

2) The cells were digested and resuspended in the experimental culture medium, inoculation was performed at 25,000 cells/well/200 μL in a 96-well cell culture plate, and the cells were cultured at 37° C., 5% $CO_2$ for 20-24 hours.

3) The culture medium was removed from the cell culture plate, and the cell culture plate was washed once by adding 200 ul of the experimental culture medium to each well.

4) Preparation of positive control compound and compound to be tested: the positive control compound and the compound to be tested were diluted on the compound plate.

5) The diluted compound was added to the cell culture plate at 250 μL per well and incubated at 37° C. and 5% $CO_2$ for 48 hours.

6) The cell culture medium was removed, the cells were washed with PBS, and 50 μL of the cell lysis buffer and the protein inhibitor were added.

7) After centrifugation, the lysate was removed and the sample was stored for later use.

8) Preparation of standard curve: corresponding volumes of Dilution buffer were successively added to respective standard tubes, and the standard was diluted in series by taking the corresponding volume from the original tube or the last concentration tube.

9) Preparation of washing liquid: 10× Wash buffer was diluted into 1× with Milli-Q for later use.

10) According to the standard curve wells and sample wells set according to a plate map, 80 μL/well of the corresponding standards and samples were added to the wells, with 2 replicate wells. A well in which no standard was added was used as a background value well. A self-adhesive seal was applied, the plate was placed on a plate shaker at room temperature, gently shaken, uniformly mixed, and incubated for 2 hours.

11) The plate was placed on the plate washer, the washing liquid was set to 350 μL per well, and the plate was washed 4 times repeatedly.

12) 200 μL of Human LDLR conjugate was added, a self-adhesive seal was applied, and the plate was placed on the plate shaker, well mixed uniformly, and incubated for 2 hours.

13) The plate was placed on the plate washer, the washing liquid was set to 350 μL per well, and the plate was washed 4 times repeatedly.

14) 200 μL/well of Substrate solution was added, and the plate was placed in the dark, applied with a self-adhesive seal, placed on the plate shaker, well mixed uniformly, and incubated for 20 minutes.

15) 50 μL/well of Stop solution was added and mixed uniformly over 20 min.

16) The optical density (OD) value in each well was measured in sequence at a wavelength of 450 nm by the microplate reader.

4. Experimental Data Processing Method

After the OD values were read by the microplate reader, the OD value of the 0-concentration standard in the standard group was subtracted from the OD values of the standards, control group, and samples to obtain the actual OD values for these wells. A standard curve was plotted with Graphpad and the concentration of the sample was calculated. If the dilution was performed during the sample detection, the calculated sample concentration was necessarily multiplied by the corresponding dilution ratio in the final calculation, which was the actual concentration of the sample. Concentration increase %=(actual concentration in control−actual concentration in sample)/actual concentration in control*100.

5. Experimental Results

| Examples | LDLR expression level |
|---|---|
| 20 | 302% |
| 47 | 859% |
| 52 | 278% |
| 53 | 175% |
| 76 | 156% |
| 77 | 117% |
| 92 | 105% |
| 99 | 274% |
| 102 | 215% |

-continued

| Examples | LDLR expression level |
|---|---|
| 144 | 117% |
| 148 | 121% |
| 151 | 138% |
| 157 | 129% |
| 159 | 105% |
| 164 | 254% |
| 165 | 224% |
| 206 | 206% |

6. Experimental Conclusion

The compounds of the examples shown in the present disclosure showed an effect of increasing the LDLR concentration in the experiment of the effect on the concentration of LDLR on HepG2 cells.

III. Pharmacokinetic Experiment

Test Example 1. Pharmacokinetic Determination in Mice

1. Experimental Objective

C57BL/6J mice were used as test animals to study the pharmacokinetic behavior of the compounds of the present disclosure in mice (plasma) after oral and intravenous administration.

2. Experimental Scheme 2.1 Test Drugs:

the compounds of the present disclosure, made in house;

2.2 Test Animals:

C57 mice, male, purchased from Shanghai Bk Lab Animal Co., Ltd., with animal production license number (SCXK (Shanghai) 2013-0006 N0.311620400001794).

2.3 Drug Preparation:

Preparation of oral drug: 10% Solutol HS15

10 g of Solutol HS15 solid was weighed, dissolved in 90 mL of pure water, uniformly mixed, stirred, and ultrasonically treated to form a clear solution.

The compound of the present disclosure was weighed and dissolved in this solution, uniformly shaken, and ultrasonically treated for 15 minutes to obtain a colorless clear solution with a concentration of 0.5 mg/mL.

Preparation of intravenous drug: 5% DMSO+10% Solutol HS15+85% PBS

The compound of the present disclosure was weighed, 5% DMSO was first added on the basis of the proportion relative to the total volume of dosage, and the mixture was vortexed and ultrasonically treated for 2 min until it was completely dissolved; 10% of Solutol HS15 was then added, and the mixture was vortexed and ultrasonically treated for 2 min until it was completely dissolved; and finally, 85% of PBS was added, and the mixture was vortexed, ultrasonically treated for 5 min, and filtered through a 0.22 um filter membrane to obtain a colorless and transparent clear solution with a concentration of 0.2 mg/mL.

2.4 Administration:

3 male C57 mice were fasted overnight and then respectively administered PO at a dose of 5 mg/kg and a volume of 10 mL/kg.

3 male C57 mice were fasted overnight and then respectively administered IV at a dose of 1 mg/kg and a volume of 5 mL/kg.

2.5 Sample Collection:

Before and after administration of mice, 0.04 mL of blood was collected from the orbit at 0.083 (iv), 0.25, 0.5, 1, 2, 4, 8, and 24 hours, and placed in EDTA-$K_2$ test tubes, which was centrifuged at 6000 rpm at 4° C. for 6 min to separate plasma which was stored at −80° C., and the rats were fed 4 h after administration.

2.6 Determination Results:

The final determination results were obtained by using an LCMS/MS method.

3. Experimental Results

The main pharmacokinetic parameters were calculated using WinNonlin 6.1.

| | Pharmacokinetic experiment (PO administration, 5 mpk) | | | | |
|---|---|---|---|---|---|
| Examples | Time to peak $t_{max}$ (ng/mL) | Plasma concentration $C_{max}$ (ng/ml) | Area under the curve $AUC_{0-\infty}$ (ng/ml × h) | Half-life $t_{1/2}$ (h) | Mean residence time MRT (h) |
| 57 | 1 | 9963 | 41462 | 5.9 | 4.8 |
| 77 | 0.25 | 4717 | 8075 | 4.3 | 2.1 |
| 87 | 0.25 | 5510 | 10718 | 4.7 | 3.1 |
| 115 | 0.5 | 4293 | 20937 | 5.8 | 5.3 |
| 116 | 1 | 4057 | 42511 | 5.1 | 7.2 |
| 122 | 0.5 | 2333 | 13239 | 3.2 | 4.5 |
| 125 | 1 | 8545 | 24298 | 7.7 | 4.0 |
| 128 | 0.5 | 4307 | 10873 | 4.0 | 3.7 |
| 129 | 0.5 | 4880 | 9641 | 3.9 | 1.5 |
| 133 | 0.25 | 7533 | 36786 | 6.7 | 6.2 |
| 134 | 2 | 9360 | 76650 | 4.1 | 5.8 |
| 142 | 2 | 5933 | 50798 | 6.5 | 8.1 |
| 143 | 1 | 3870 | 11579 | 3.9 | 2.2 |
| 144 | 1 | 2817 | 15047 | 2.8 | 4.0 |
| 145 | 0.5 | 2367 | 12221 | 3.8 | 4.6 |
| 147 | 2 | 8227 | 51978 | 4.4 | 4.8 |
| 148 | 1 | 13467 | 59788 | 3.4 | 4.3 |
| 149 | 0.5 | 12333 | 24191 | 4.8 | 2.4 |
| 151 | 2 | 7417 | 97699 | 15.1 | 19.0 |
| 152 | 2 | 5290 | 65471 | 9.6 | 12.1 |
| 153 | 2 | 6310 | 34638 | 2.9 | 4.4 |
| 155 | 0.5 | 10043 | 25472 | 5.9 | 1.9 |
| 156 | 1 | 5007 | 19724 | 3.6 | 3.2 |
| 157 | 0.5 | 2187 | 6197 | 3.1 | 2.6 |
| 158 | 4 | 2317 | 22402 | 16.2 | 19.5 |

4. Experimental Conclusion

The pharmacokinetic determination results in the C57BL/6J mice showed that the compounds of the present disclosure exhibited significant PK advantages.

IV. Pharmacodynamic Experiment

Test Example 1. In Vivo Pharmacodynamic Study of the Compounds of the Present Disclosure in a Hyperlipidemia Animal Model of B6-hPCSK9 Transgenic Mice

1. Experimental Objective

The compounds of the present disclosure were evaluated for in vivo pharmacodynamics in a hyperlipidemia animal model of B6-hPCSK9 transgenic mice.

2. Experimental Instruments and Reagents 2.1 Instruments

- Refrigerator (BCD-268TN, Haier)
- Biological safety cabinet (BSC-1300II A2, Shanghai Boxun Industrial Co., Ltd. Medical Equipment Factory)
- Ultra-clean workbench (CJ-2F, Suzhou Fengshi Experimental Animal Equipment Co., Ltd.)
- 5 mL pipettor (Research Plus, Eppendorf)
- 1 mL pipettor (Research Plus, Eppendorf)
- Thermostat water bath (HWS-12, Shanghai Yiheng Science)
- Centrifuge (Centrifuge 5720R, Eppendorf)
- Electronic balance (CPA2202S, Sartorius)
- Electronic balance (BSA2202S-CW, Sartorius)
- Ultrasonic cleaner (115F0032, Shanghai Kudos)
- Water purifier (Pacific TII, Thermo)
- Magnetic stirrer (08-2G, Chijiu)
- Fully automatic blood biochemical analyzer (HITACHI Model 7180, HITACHI)

2.2 Reagents

- High-fat feed (Western Diet, D12079B)
- Normal saline (MA0083-D, meilunbio)
- Solutol HS 15 (102483882, Sigma)

2.3 Test Drug: Compounds of the Present Disclosure, Made in House

3 Experimental Operations and Data Processing 3.1 Animals

B6-hPCSK9 transgenic C57 mice, 6-8 weeks old, male, purchased from Jiangsu GemPharmatech Co., Ltd.

3.2 Animal Model

After delivery to a barrier system, the animals were given one week for acclimatization and began to feed on the high-fat feed. The body weight and feed weight were weighed once a week, and the body weight and food intake thereof were recorded.

3.3 Grouping and Administration a. The animals were grouped by a random grouping method.

c. According to the grouping results, administration with the test drug was started (mode of administration: oral administration; administration volume: 10 mL/kg; frequency of administration: once/day or single administration; administration cycle: 21 days; vehicle: 10% Solutol HS 15/90% Saline).

d. After the test drug was administered, the body weight and feed weight were weighed twice a week and blood was taken once a week.

e. The data was processed with software such as Excel. Body weight change rate BWC (%)=(body weight at the end of animal treatment−body weight at the beginning of animal treatment)/body weight at the beginning of animal treatment×100%; food intake (g/mice/day)=(previous feed addition+previous feed residue−current feed residue)/number of animals/number of feeding days; and calculation of blood biochemical inhibition rate: with the blood biochemical results of the vehicle group detected in the same batch as the baseline, the data of each administration group were normalized, and the percentages of TC and LDL-C were then calculated according to the formulas: TC change percentage (%)=(TC value after administration−TC value before administration)/TC value before administration*100%; LDL-C change percentage (%)=(LDL-C value after administration−LDL-C value before administration)/LDL-C value before administration*100%. PCSK9 in plasma was detected by ELISA.

4 Experimental Results

| | | Pharmacodynamic experiment (PO administration) |
|---|---|---|
| Examples | Dosage | LDL-C reduction rate (%), Day 14 |
| 27 | 6 mpk | −31.52 |
| 57 | 3 mpk | −46.22 |
| 129 | 5 mpk | −21.98 |
| 134 | 5 mpk | −60.65 |
| 143 | 10 mpk | −34.97 |
| 144 | 10 mpk | −30.39 |
| 147 | 3 mpk | −23.20 |
| 148 | 10 mpk | −24.61 |
| 149 | 10 mpk | −41.65 |
| 156 | 10 mpk | −25.97 |
| 157 | 10 mpk | −28.99 |
| 158 | 10 mpk | −28.97 |

5. Experimental Conclusion

The compounds of the examples shown in the present disclosure can effectively reduce LDL-C in the hyperlipidemia animal model of B6-hPCSK9 transgenic mice.

The invention claimed is:

1. A compound represented by general formula (I-1'), or a stereoisomer or pharmaceutically acceptable salt thereof:

(I-1')

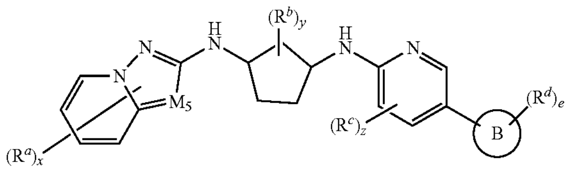

wherein ring B is selected from cycloalkyl, heterocyclyl, aryl, or heteroaryl;

$M_5$ is selected from N or $CR_5$;

$R_5$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, or $C_{1-6}$ hydroxyalkyl;

$R^a$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, or $C_{3-8}$ cycloalkyl;

$R^b$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl;

$R^c$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, or $C_{1-6}$ hydroxyalkyl;

$R^d$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, or $C_{3-8}$ cycloalkyl;

x is 0, 1, 2, or 3;

y is 0, 1, 2, or 3;

z is 0, 1, 2, or 3; and e is 0, 1, 2, or 3.

2. The compound or the stereoisomer or pharmaceutically acceptable salt thereof according to claim 1, wherein ring B is selected from cycloalkyl, heterocyclyl, aryl, or heteroaryl; further wherein the cycloalkyl contains 3 to 6 carbon atoms;

the heterocyclyl consists of 3 to 12 ring atoms, wherein one or more ring atoms are heteroatoms selected from nitrogen, oxygen or $S(O)_m$, wherein m is an integer from 0 to 2, but excluding ring moieties of —O—O—, —O—S— or —S—S—, and the remaining ring atoms are carbon;

the aryl is a 6- to 14-membered all-carbon monocyclic or fused polycyclic group having a conjugated π electron system;

and the heteroaryl consists of 1 to 4 heteroatoms and 5 to 14 ring atoms, wherein the heteroatoms are selected from oxygen, sulfur and nitrogen.

3. The compound or the stereoisomer or pharmaceutically acceptable salt thereof according to claim 1, wherein ring B is selected from $C_{3-6}$ cycloalkyl, phenyl, 3- to 8-membered heterocyclyl, 7- to 10-membered bicyclic heterocyclyl, 5-membered heteroaryl, 6-membered heteroaryl, 5-membered fused 5-membered bicyclic heteroaryl, 5-membered fused 6-membered bicyclic heteroaryl, 5-membered fused 6-membered bicyclic heterocyclyl, 6-membered fused 5-membered bicyclic heteroaryl, or 6-membered fused 6-membered bicyclic heteroaryl.

4. The compound or the stereoisomer or pharmaceutically acceptable salt thereof according to claim 1, wherein ring B is selected from C, cycloalkyl, phenyl, 5-membered nitrogen-containing heterocyclyl, 6-membered nitrogen-containing heterocyclyl, 7- to 10-membered bicyclic heterocyclyl, 5-membered nitrogen-containing heteroaryl, 6-membered nitrogen-containing heteroaryl, 5-membered fused 5-membered bicyclic nitrogen-containing heteroaryl, 5-membered fused 6-membered bicyclic nitrogen-containing heteroaryl, 6-membered fused 5-membered bicyclic nitrogen-containing heteroaryl, or 6-membered fused 6-membered bicyclic nitrogen-containing heteroaryl.

5. The compound or the stereoisomer or pharmaceutically acceptable salt thereof according to claim 1, wherein the compound is further represented by general formula (I-1), or (I-2):

(I-1)

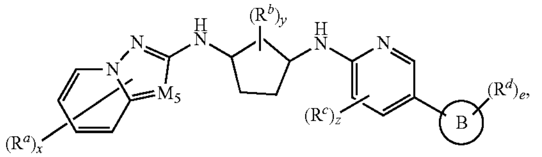

or

-continued (I-2)

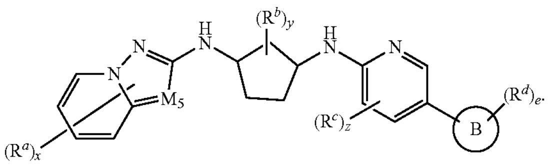

6. The compound or the stereoisomer or pharmaceutically acceptable salt thereof according to claim 1, wherein ring B is selected from

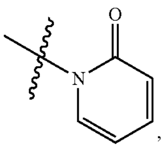,
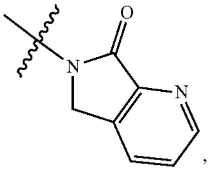,
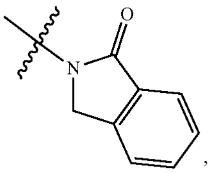,
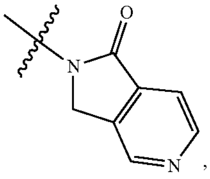,
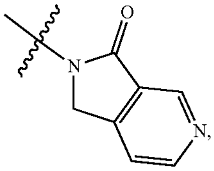, or
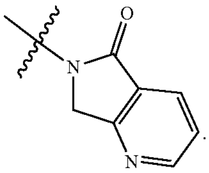.

7. The compound or the stereoisomer or pharmaceutically acceptable salt thereof according to claim 1, wherein ring B is selected from pyridine, pyrimidine, benzene,

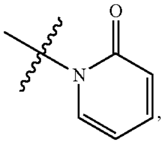,
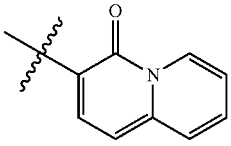,
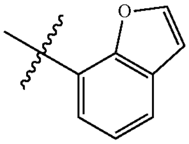,
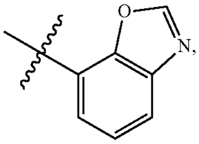,
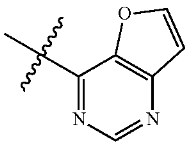,
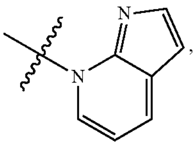,
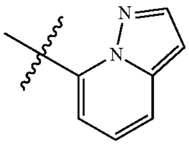,
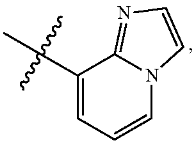, -continued

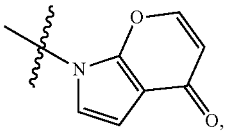,
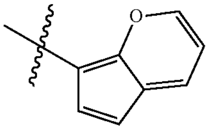,
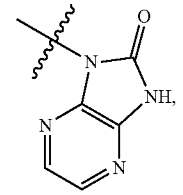,
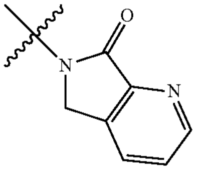,
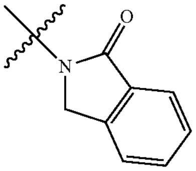,
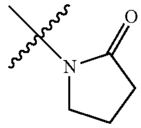,
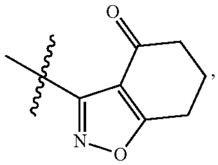,
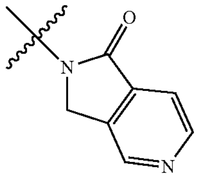,
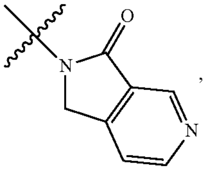,
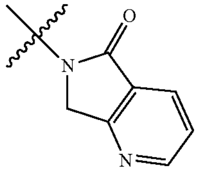,
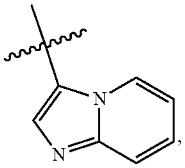,
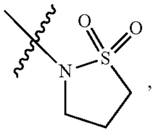,
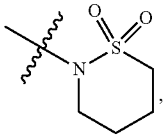,
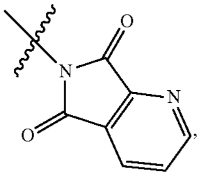,
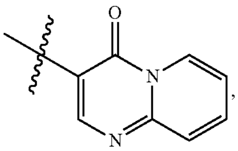,
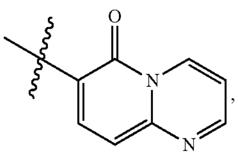,
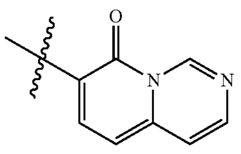 or
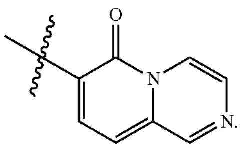.

8. The compound or the stereoisomer or pharmaceutically acceptable salt thereof according to claim 1, wherein ring B is selected from pyridine, pyrimidine, benzene, -continued
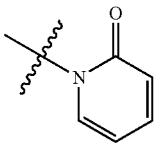, 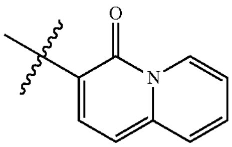,
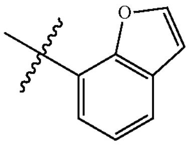, 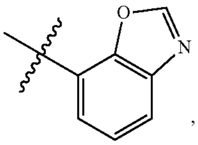,
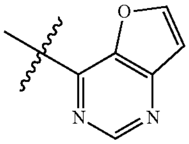, 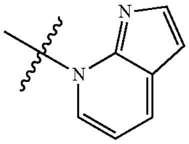,
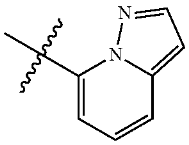, 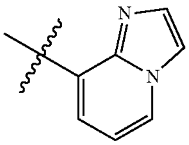,
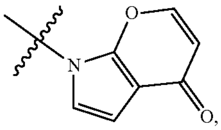, 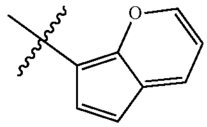,
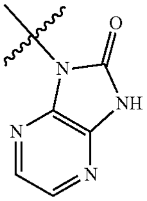, 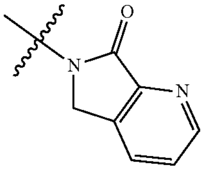,
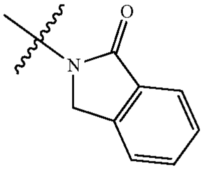, 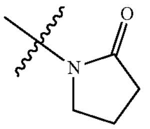,
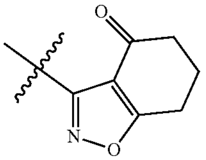, 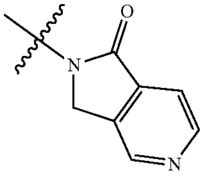,
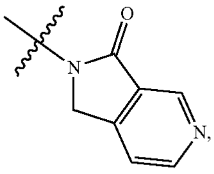, 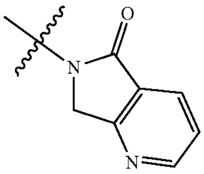,
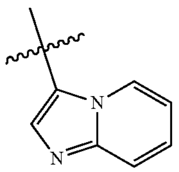, 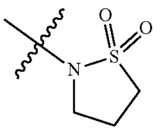,
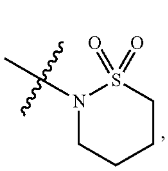, 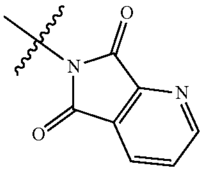,
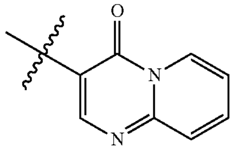, 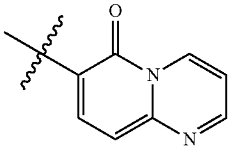,
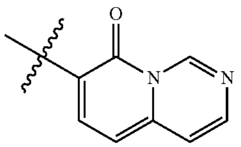, 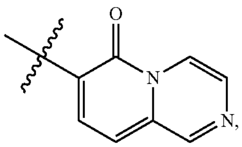,
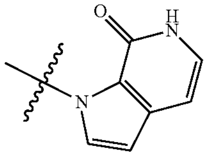, 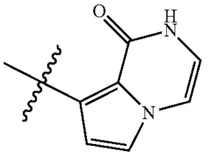,
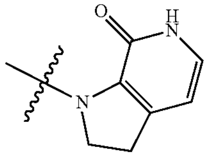, 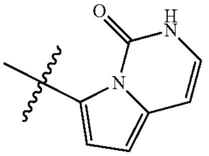,
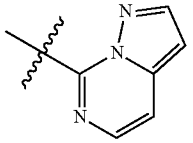, 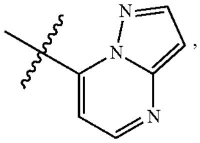,
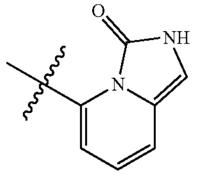, 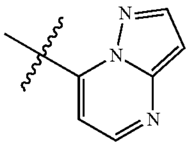,
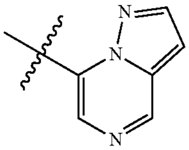, 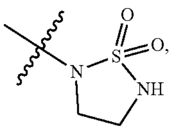,
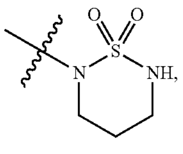, 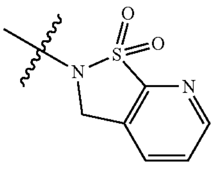,
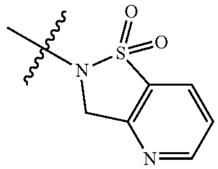, 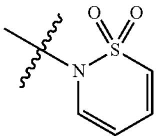, -continued

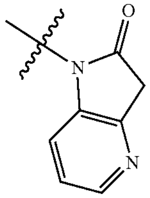
,
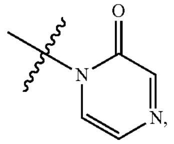

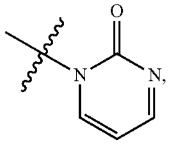
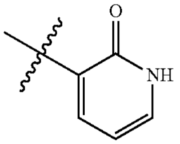
or
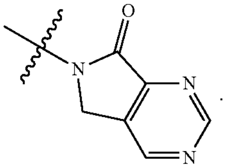
.

9. The compound or the stereoisomer or pharmaceutically acceptable salt thereof according to claim 1, wherein ring B is selected from

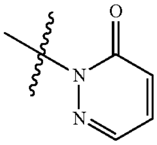
,
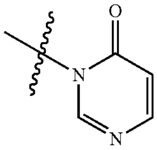
,
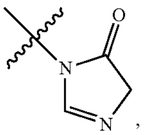
,
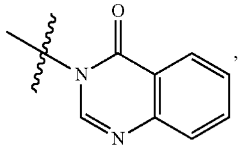
,
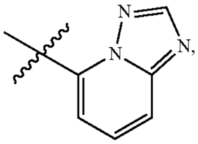
or
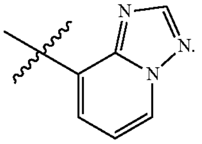

10. The compound or the stereoisomer or pharmaceutically acceptable salt thereof according to claim 1, wherein the compound is further represented by general formula (V):

(V)

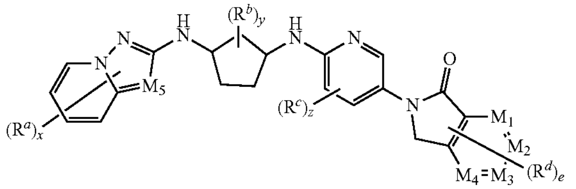

wherein $M_1$ is selected from N or CH; $M_2$ is selected from N or CH; $M_3$ is selected from N or CH; and $M_4$ is selected from N or CH.

11. The compound or the stereoisomer or pharmaceutically acceptable salt thereof according to claim 1, wherein $R^a$ is selected from hydrogen, deuterium, halogen, amino, hydroxyl, cyano, nitro, $C_{1-3}$ alkyl, $C_{2-4}$ alkenyl, $C_{2-4}$ alkynyl, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, or $C_{3-8}$ cycloalkyl;

$R^b$ is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, or cyano-substituted $C_{1-3}$ alkyl;

$R^c$ is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, or $C_{1-3}$ hydroxyalkyl; and $R^d$ is selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ alkylthio, $C_{1-3}$ deuteroalkyl, $C_{1-3}$ haloalkyl, $C_{1-3}$ alkoxy, halo $C_{1-3}$ alkoxy, $C_{1-3}$ hydroxyalkyl, cyano-substituted $C_{1-3}$ alkyl, or $C_{3-8}$ cycloalkyl.

12. The compound or the stereoisomer or pharmaceutically acceptable salt thereof according to claim 1, wherein the compound is selected from the following compounds:

27

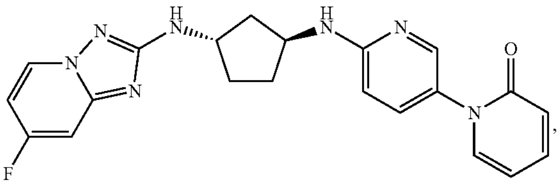
,
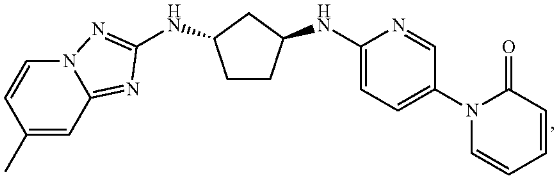
,
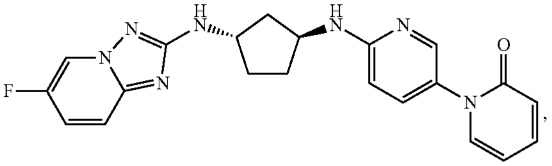
,
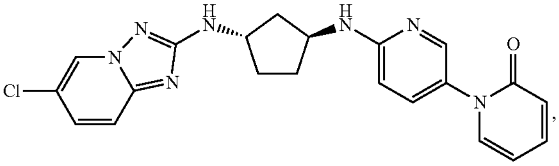
,
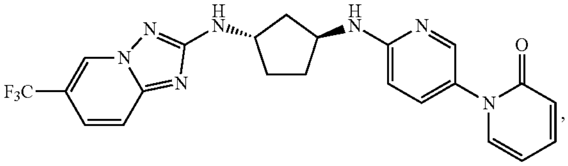
,
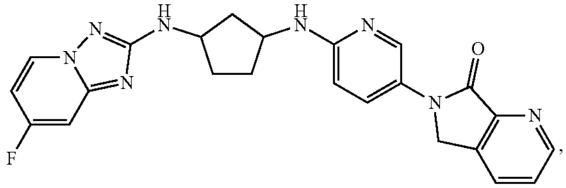
, -continued
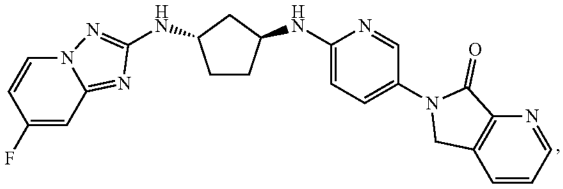
,
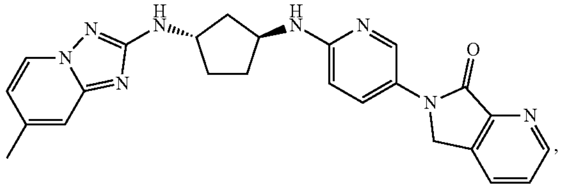
,
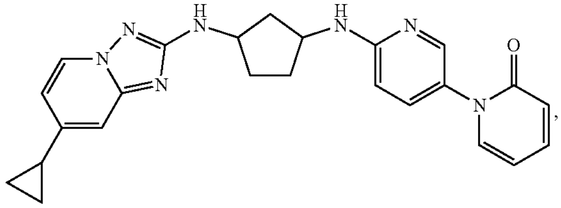
,
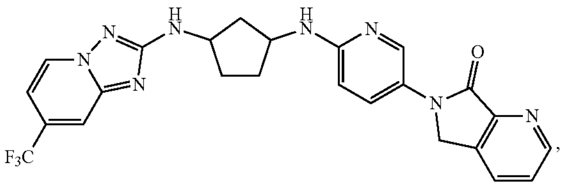
,
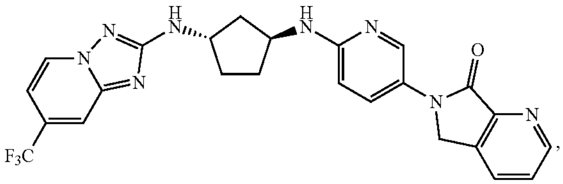
,
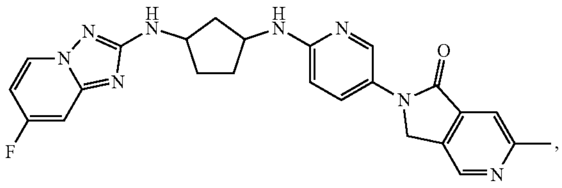
,
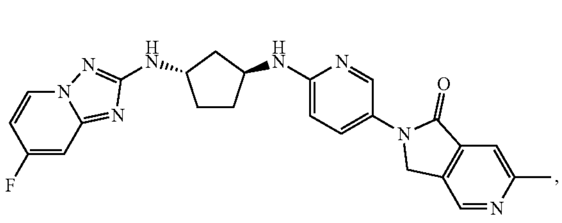
,
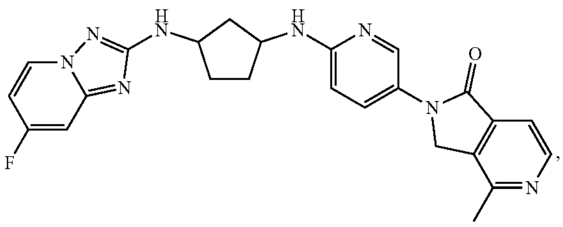
,
-continued
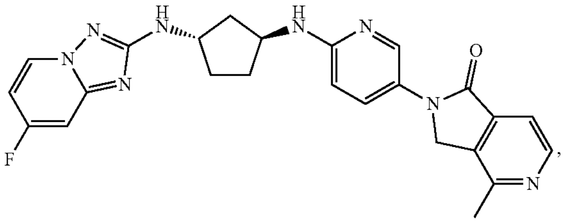
,
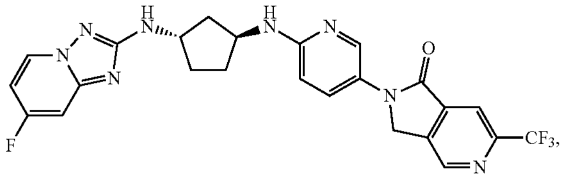
,
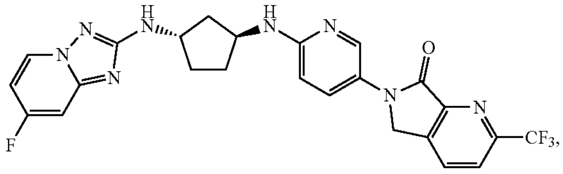
,
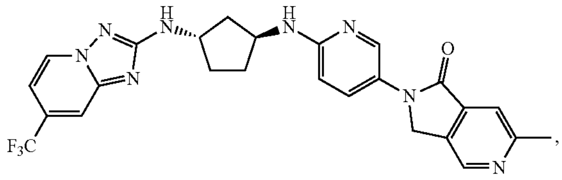
,
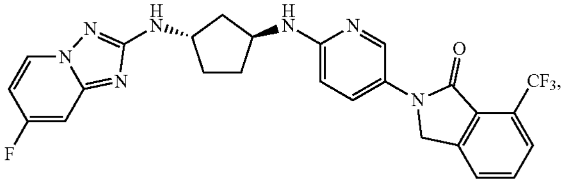
,
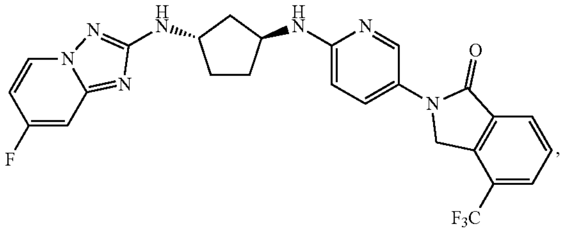
,
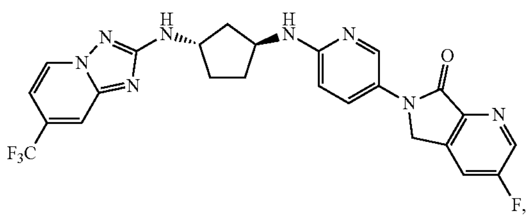
, or
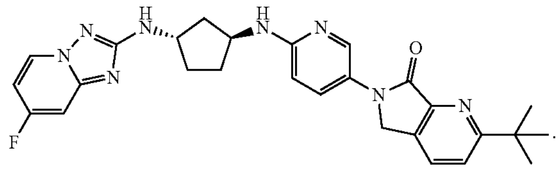
.
13. A compound represented by general formula (VI-2) or a stereoisomer or pharmaceutically acceptable salt thereof, (VI-2)

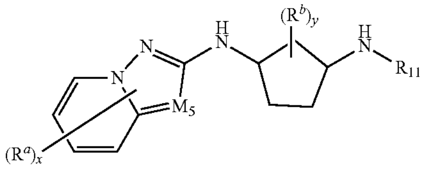

wherein $R_{11}$ is selected from an amino protecting group, 5- to 6-membered heteroaryl, and 5- to 6-membered heterocyclyl, wherein the 5- to 6-membered heteroaryl and 5- to 6-membered heterocyclyl are optionally further substituted with one or more substituents selected from deuterium, halogen, nitro, hydroxyl, mercapto, cyano, amino, oxo, thio, carboxyl, $C_{1-6}$ alkyl, $C_{1-6}$ deuteroalkyl, $C_{1-6}$ haloalkyl, $C_{1-6}$ hydroxyalkyl, $C_{1-6}$ alkoxy, $C_{1-6}$ deuteroalkoxy, $C_{1-6}$ haloalkoxy, $C_{2-6}$ alkenyl, $C_{2-6}$ alkynyl, $C_{3-12}$ cycloalkyl, 3- to 12-membered heterocyclyl, $C_{6-14}$ aryl, or 5- to 14-membered heteroaryl, further wherein the amino protecting group is selected from allyloxycarbonyl, trifluoroacetyl, tert-butylsulfinyl, 2,4-dimethoxybenzyl, nitrobenzenesulfonyl, triphenylmethyl, fluorenylmethoxycarbonyl, 9-fluorenylmethoxycarbonyl, benzyl, p-toluenesulfonyl, p-methoxybenzyl, formate, acetyl, benzyloxycarbonyl, phthaloyl, tert-butyloxycarbonyl, benzyl, or p-methoxyphenyl;

$M_5$ is selected from N or $CR_5$;

$R_5$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, or $C_{1-6}$ hydroxyalkyl;

$R^a$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, or $C_{3-8}$ cycloalkyl;

$R^b$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, or cyano-substituted $C_{1-6}$ alkyl;

x is 0, 1, 2, or 3; and y is 0, 1, 2, or 3.

14. A compound represented by general formula (VI-3) or a stereoisomer or pharmaceutically acceptable salt thereof, (VI-3)

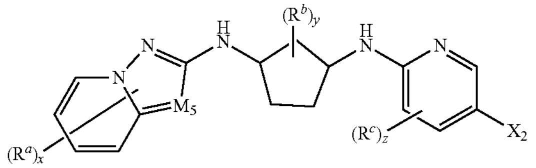

wherein $X_2$ is amino, halogen, boronic acid, or a boronate;

$M_5$ is selected from N or $CR_5$;

$R_5$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, or $C_{1-6}$ hydroxyalkyl;

$R^a$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, cyano-substituted $C_{1-6}$ alkyl, or $C_{3-8}$ cycloalkyl;

$R^b$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ alkylthio, $C_{1-6}$ deuteroalkyl, $C_{1-6}$ haloalkyl, $C_{1-6}$ alkoxy, halo $C_{1-6}$ alkoxy, $C_{1-6}$ hydroxyalkyl, or cyano-substituted $C_{1-6}$ alkyl;

$R^c$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ alkylthio, $C_{1-6}$ deuteroalkyl, $C_{1-6}$ haloalkyl, $C_{1-6}$ alkoxy, halo $C_{1-6}$ alkoxy, or $C_{1-6}$ hydroxyalkyl;

x is 0, 1, 2, or 3;

y is 0, 1, 2, or 3; and z is 0, 1, 2, or 3.

15. A pharmaceutical composition comprising a therapeutically effective dose of the general formula (I-1') or the stereoisomer or pharmaceutically acceptable salt thereof according to claim 1, and one or more pharmaceutically acceptable carriers, diluents, or excipients.

* * * * *